US011246922B1

United States Patent
Cruz Rodriguez (12)

(10) Patent No.: US 11,246,922 B1
(45) Date of Patent: Feb. 15, 2022

(54) VACCINE RNA-PEPTIDE AGAINST SARS-COV-2 WITH ENDOGENOUS EXOSOMES AS CARRIER

(71) Applicant: Elidan America, LLC., Miami, FL (US)

(72) Inventor: Luis Cruz Rodriguez, Tampa, FL (US)

(73) Assignee: Elidan America, LLC., Miami, FL (US)

( * ) Notice: Subject to any disclaimer, the term of this patent is extended or adjusted under 35 U.S.C. 154(b) by 0 days.

(21) Appl. No.: 17/245,535

(22) Filed: Apr. 30, 2021

(51) Int. Cl.
*A61K 39/215* (2006.01)
*A61P 31/14* (2006.01)
*A61K 38/45* (2006.01)
*A61K 39/00* (2006.01)

(52) U.S. Cl.
CPC ............ *A61K 39/215* (2013.01); *A61K 38/45* (2013.01); *A61P 31/14* (2018.01); *A61K 2039/6018* (2013.01); *A61K 2039/6031* (2013.01)

(58) Field of Classification Search
None
See application file for complete search history.

(56) References Cited

PUBLICATIONS

Cruz-Rodriguez et al., Journal of Diabetes and Endocrinology Research, Apr. 10, 2020, 2(1):6 pages. (Year: 2020).*
Sabanovic et al., Biology, Jan. 27, 2021, 10(94), 14 pages. (Year: 2021).*
Cruz-Rodriguez et al., Journal of Bioscience & Biomedical Engineering, May 25, 2020, 1(1):11 pages. (Year: 2020).*
Madhavan et al., Journal of Infection and Public Health, 2021, 14:1106-1119. (Year: 2021).*

* cited by examiner

*Primary Examiner* — Stacy B Chen
(74) *Attorney, Agent, or Firm* — Albert Bordas, P.A.

(57) ABSTRACT

A vaccine RNA-peptide against SARS-CoV-2, which has a messenger ribonucleic acid (mRNA) having an open reading frame encoding a peptide of a Severe Acute Respiratory Syndrome Coronavirus 2 (SARS-CoV-2) surface protein. The peptide of the severe Acute Respiratory Syndrome Coronavirus 2 (SARS-CoV-2) surface protein is fused to a synthetic poly ADP-ribose polymerase peptide. The vaccine RNA-peptide against SARS-CoV-2 has endogenous exosomes as carrier.

14 Claims, 92 Drawing Sheets

Specification includes a Sequence Listing.

Fig. 2

HPLC REPORT

Sample Description:

| | |
|---|---|
| Structure | : #2 LCR_2020_B9 CK-28 |
| Number | : 0200046 |
| Lot # | : LT201117-LT847361 |
| Column | : 4.6×250mm,Sinochrom ODS-BP 5 |
| Mobile Phase | : A=0.1% TFA/Acetonitrile, |
| | : B=0.1%TFA/water, |
| Gradient | :    A      B |
| 0.01min | 19%    81% |
| 25min | 44%    56% |
| 25.1min | 100%   0% |
| 30.0min | STOP |
| Flow rate | : 1.0ml/min |
| Wavelength | : 220nm |
| Volume | : 5ul |

| Peak No. | Ret Time | Height | Area | Conc. |
|---|---|---|---|---|
| 1 | 12.492 | 561.944 | 3252.297 | 0.0810 |
| 2 | 12.700 | 3533.503 | 25264.738 | 0.6292 |
| 3 | 12.932 | 343201.031 | 3945083.750 | 98.2564 |
| 4 | 13.287 | 5388.146 | 32790.266 | 0.8167 |
| 5 | 13.685 | 1279.338 | 8700.799 | 0.2167 |
| Total | | | 100.0000 | |

SEQUENCE LISTING

<160> NUMBER OF SEQ ID NOS: 6

<210> SEQ ID NO 1
<211> LENGTH: 34
<212> TYPE: RNA
<213> ORGANISM: Artificial Sequence
<220> FEATURE:
<223> OTHER INFORMATION: Synthetic Polynucleotide

<400> SEQUENCE: 1
aaaaaaaaaa cuccuagaac uagcauuaca gaug 34

<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 2

Cys Val Asn Asp Thr Phe Ala Gly Ser Thr Phe Ile Ser Asp Glu Val
1 5 10 15

Asp

<210> SEQ ID NO 3
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 3

Gly Val Asp Glu Val Ala Lys Lys Lys Ser Lys
1 5 10

<210> SEQ ID NO 4
<211> LENGTH: 28
<212> TYPE: PRT
<213> ORGANISM: Artificial Sequence

```
<220> FEATURE:
<223> OTHER INFORMATION: Synthetic Polypeptide

<400> SEQUENCE: 4

Cys Val Asn Asp Thr Phe Ala Gly Ser Thr Phe Ile Ser Asp Glu Val
1               5                   10                  15

Asp Gly Val Asp Glu Val Ala Lys Lys Lys Ser Lys
            20                  25

<210> SEQ ID NO 5
<211> LENGTH: 7101
<212> TYPE: PRT
<213> ORGANISM: Severe Acute Respiratory Syndrome-related coronavirus

<400> SEQUENCE: 5

Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
            35                  40                  45

Gly Thr Cys Gly Leu Val Glu Val Glu Lys Gly Val Leu Pro Gln Leu
50                  55                  60

Glu Gln Pro Tyr Val Phe Ile Lys Arg Ser Asp Ala Arg Thr Ala Pro
65                  70                  75                  80

His Gly His Val Met Val Glu Leu Val Ala Glu Leu Glu Gly Ile Gln
                85                  90                  95

Tyr Gly Arg Ser Gly Glu Thr Leu Gly Val Leu Val Pro His Val Gly
            100                 105                 110

Glu Ile Pro Val Ala Tyr Arg Lys Val Leu Leu Arg Lys Asn Gly Asn
            115                 120                 125

Lys Gly Ala Gly Gly His Ser Tyr Gly Ala Asp Leu Lys Ser Phe Asp
130                 135                 140

Leu Gly Asp Glu Leu Gly Thr Asp Pro Tyr Glu Asp Phe Gln Glu Asn
145                 150                 155                 160

Trp Asn Thr Lys His Ser Ser Gly Val Thr Arg Glu Leu Met Arg Glu
                165                 170                 175

Leu Asn Gly Gly Ala Tyr Thr Arg Tyr Val Asp Asn Asn Phe Cys Gly
            180                 185                 190

Pro Asp Gly Tyr Pro Leu Glu Cys Ile Lys Asp Leu Leu Ala Arg Ala
            195                 200                 205

Gly Lys Ala Ser Cys Thr Leu Ser Glu Gln Leu Asp Phe Ile Asp Thr
210                 215                 220

Lys Arg Gly Val Tyr Cys Cys Arg Glu His Glu His Glu Ile Ala Trp
225                 230                 235                 240

Tyr Thr Glu Arg Ser Glu Lys Ser Tyr Glu Leu Gln Thr Pro Phe Glu
                245                 250                 255

Ile Lys Leu Ala Lys Lys Phe Asp Ile Phe Asn Gly Glu Cys Pro Asn
            260                 265                 270

Phe Val Phe Pro Leu Asn Ser Ile Ile Lys Thr Ile Gln Pro Arg Val
            275                 280                 285

Glu Lys Lys Lys Leu Asp Gly Phe Met Gly Arg Ile Arg Ser Val Tyr
            290                 295                 300

Pro Val Ala Ser Pro Asn Glu Cys Asn Gln Met Cys Leu Ser Thr Leu
305                 310                 315                 320
```

```
Met Lys Cys Asp His Cys Gly Glu Thr Ser Trp Gln Thr Gly Asp Phe
            325                 330                 335

Val Lys Ala Thr Cys Glu Phe Cys Gly Thr Glu Asn Leu Thr Lys Glu
            340                 345                 350

Gly Ala Thr Thr Cys Gly Tyr Leu Pro Gln Asn Ala Val Val Lys Ile
            355                 360                 365

Tyr Cys Pro Ala Cys His Asn Ser Glu Val Gly Pro Glu His Ser Leu
370                 375                 380

Ala Glu Tyr His Asn Glu Ser Gly Leu Lys Thr Ile Leu Arg Lys Gly
385                 390                 395                 400

Gly Arg Thr Ile Ala Phe Gly Gly Cys Val Phe Ser Tyr Val Gly Cys
                405                 410                 415

His Asn Lys Cys Ala Tyr Trp Val Pro Arg Ala Ser Ala Asn Ile Gly
            420                 425                 430

Cys Asn His Thr Gly Val Val Gly Glu Gly Ser Glu Gly Leu Asn Asp
            435                 440                 445

Asn Leu Leu Glu Ile Leu Gln Lys Glu Lys Val Asn Ile Asn Ile Val
            450                 455                 460

Gly Asp Phe Lys Leu Asn Glu Glu Ile Ala Ile Ile Leu Ala Ser Phe
465                 470                 475                 480

Ser Ala Ser Thr Ser Ala Phe Val Glu Thr Val Lys Gly Leu Asp Tyr
                485                 490                 495

Lys Ala Phe Lys Gln Ile Val Glu Ser Cys Gly Asn Phe Lys Val Thr
            500                 505                 510

Lys Gly Lys Ala Lys Lys Gly Ala Trp Asn Ile Gly Glu Gln Lys Ser
            515                 520                 525

Ile Leu Ser Pro Leu Tyr Ala Phe Ala Ser Glu Ala Ala Arg Val Val
530                 535                 540

Arg Ser Ile Phe Ser Arg Thr Leu Glu Thr Ala Gln Asn Ser Val Arg
545                 550                 555                 560

Val Leu Gln Lys Ala Ala Ile Thr Ile Leu Asp Gly Ile Ser Gln Tyr
                565                 570                 575

Ser Leu Arg Leu Ile Asp Ala Met Met Phe Thr Ser Asp Leu Ala Thr
            580                 585                 590

Asn Asn Leu Val Val Met Ala Tyr Ile Thr Gly Gly Val Val Gln Leu
            595                 600                 605

Thr Ser Gln Trp Leu Thr Asn Ile Phe Gly Thr Val Tyr Glu Lys Leu
            610                 615                 620

Lys Pro Val Leu Asp Trp Leu Glu Glu Lys Phe Lys Glu Gly Val Glu
625                 630                 635                 640

Phe Leu Arg Asp Gly Trp Glu Ile Val Lys Phe Ile Ser Thr Cys Ala
                645                 650                 655

Cys Glu Ile Val Gly Gly Gln Ile Val Thr Cys Ala Lys Glu Ile Lys
            660                 665                 670

Glu Ser Val Gln Thr Phe Phe Lys Leu Val Asn Lys Phe Leu Ala Leu
            675                 680                 685

Cys Ala Asp Ser Ile Ile Ile Gly Gly Ala Lys Leu Lys Ala Leu Asn
            690                 695                 700

Leu Gly Glu Thr Phe Val Thr His Ser Lys Gly Leu Tyr Arg Lys Cys
705                 710                 715                 720

Val Lys Ser Arg Glu Glu Thr Gly Leu Leu Met Pro Leu Lys Ala Pro
                725                 730                 735

Lys Glu Ile Ile Phe Leu Glu Gly Glu Thr Leu Pro Thr Glu Val Leu
```

-continued

```
            740                 745                 750
Thr Glu Glu Val Val Leu Lys Thr Gly Asp Leu Gln Pro Leu Glu Gln
            755                 760                 765
Pro Thr Ser Glu Ala Val Glu Ala Pro Leu Val Gly Thr Pro Val Cys
            770                 775                 780
Ile Asn Gly Leu Met Leu Glu Ile Lys Asp Thr Glu Lys Tyr Cys
785                 790                 795                 800
Ala Leu Ala Pro Asn Met Met Val Thr Asn Asn Thr Phe Thr Leu Lys
                    805                 810                 815
Gly Gly Ala Pro Thr Lys Val Thr Phe Gly Asp Asp Thr Val Ile Glu
                    820                 825                 830
Val Gln Gly Tyr Lys Ser Val Asn Ile Thr Phe Glu Leu Asp Glu Arg
                    835                 840                 845
Ile Asp Lys Val Leu Asn Glu Lys Cys Ser Ala Tyr Thr Val Glu Leu
                    850                 855                 860
Gly Thr Glu Val Asn Glu Phe Ala Cys Val Val Ala Asp Ala Val Ile
865                 870                 875                 880
Lys Thr Leu Gln Pro Val Ser Glu Leu Leu Thr Pro Leu Gly Ile Asp
                    885                 890                 895
Leu Asp Glu Trp Ser Met Ala Thr Tyr Tyr Leu Phe Asp Glu Ser Gly
                    900                 905                 910
Glu Phe Lys Leu Ala Ser His Met Tyr Cys Ser Phe Tyr Pro Pro Asp
                    915                 920                 925
Glu Asp Glu Glu Glu Gly Asp Cys Glu Glu Glu Phe Glu Pro Ser
                    930                 935                 940
Thr Gln Tyr Glu Tyr Gly Thr Glu Asp Asp Tyr Gln Gly Lys Pro Leu
945                 950                 955                 960
Glu Phe Gly Ala Thr Ser Ala Ala Leu Gln Pro Glu Asn Pro His Leu
                    965                 970                 975
Glu Glu Glu Gln Glu Glu Asp Trp Leu Asp Asp Ser Gln Gln Thr
                    980                 985                 990
Val Gly Gln Gln Asp Gly Ser Glu  Asp Asn Gln Thr Thr  Thr Ile Gln
            995                 1000                1005
Thr Ile  Val Glu Val Gln Pro  Gln Leu Glu Met Glu   Leu Thr Pro
    1010                1015                1020
Val Val  Gln Thr Ile Glu Val  Asn Ser Phe Ser Gly  Tyr Leu Lys
    1025                1030                1035
Leu Thr  Asp Asn Val Tyr Ile  Lys Asn Ala Asp Ile  Val Glu Glu
    1040                1045                1050
Ala Lys  Lys Val Lys Pro Thr  Val Val Asn Ala  Ala Asn Val
    1055                1060                1065
Tyr Leu  Lys His Gly Gly  Val Ala Gly Ala Leu  Asn Lys Ala
    1070                1075                1080
Thr Asn  Asn Ala Met Gln Val  Glu Ser Asp Asp Tyr  Ile Ala Thr
    1085                1090                1095
Asn Gly  Pro Leu Lys Val Gly  Gly Ser Cys Val Leu  Ser Gly His
    1100                1105                1110
Asn Leu  Ala Lys His Cys Leu  His Val Val Gly Pro  Asn Val Asn
    1115                1120                1125
Lys Gly  Glu Asp Ile Gln Leu  Leu Lys Ser Ala Tyr  Glu Asn Phe
    1130                1135                1140
Asn Gln  His Glu Val Leu Leu  Ala Pro Leu Leu Ser  Ala Gly Ile
    1145                1150                1155
```

```
Phe Gly Ala Asp Pro Ile His Ser Leu Arg Val Cys Val Asp Thr
    1160            1165            1170

Val Arg Thr Asn Val Tyr Leu Ala Val Phe Asp Lys Asn Leu Tyr
    1175            1180            1185

Asp Lys Leu Val Ser Ser Phe Leu Glu Met Lys Ser Glu Lys Gln
    1190            1195            1200

Val Glu Gln Lys Ile Ala Glu Ile Pro Lys Glu Val Lys Pro
    1205            1210            1215

Phe Ile Thr Glu Ser Lys Pro Ser Val Glu Gln Arg Lys Gln Asp
    1220            1225            1230

Asp Lys Lys Ile Lys Ala Cys Val Glu Glu Val Thr Thr Thr Leu
    1235            1240            1245

Glu Glu Thr Lys Phe Leu Thr Glu Asn Leu Leu Leu Tyr Ile Asp
    1250            1255            1260

Ile Asn Gly Asn Leu His Pro Asp Ser Ala Thr Leu Val Ser Asp
    1265            1270            1275

Ile Asp Ile Thr Phe Leu Lys Lys Asp Ala Pro Tyr Ile Val Gly
    1280            1285            1290

Asp Val Val Gln Glu Gly Val Leu Thr Ala Val Val Ile Pro Thr
    1295            1300            1305

Lys Lys Ala Gly Gly Thr Thr Glu Met Leu Ala Lys Ala Leu Arg
    1310            1315            1320

Lys Val Pro Thr Asp Asn Tyr Ile Thr Thr Tyr Pro Gly Gln Gly
    1325            1330            1335

Leu Asn Gly Tyr Thr Val Glu Glu Ala Lys Thr Val Leu Lys Lys
    1340            1345            1350

Cys Lys Ser Ala Phe Tyr Ile Leu Pro Ser Ile Ile Ser Asn Glu
    1355            1360            1365

Lys Gln Glu Ile Leu Gly Thr Val Ser Trp Asn Leu Arg Glu Met
    1370            1375            1380

Leu Ala His Ala Glu Glu Thr Arg Lys Leu Met Pro Val Cys Val
    1385            1390            1395

Glu Thr Lys Ala Ile Val Ser Thr Ile Gln Arg Lys Tyr Lys Gly
    1400            1405            1410

Ile Lys Ile Gln Glu Gly Val Val Asp Tyr Gly Ala Arg Phe Tyr
    1415            1420            1425

Phe Tyr Thr Ser Lys Thr Thr Val Ala Ser Leu Ile Asn Thr Leu
    1430            1435            1440

Asn Asp Leu Asn Glu Thr Leu Val Thr Met Pro Leu Gly Tyr Val
    1445            1450            1455

Thr His Gly Leu Asn Leu Glu Glu Ala Ala Arg Tyr Met Arg Ser
    1460            1465            1470

Leu Lys Val Pro Ala Thr Val Ser Val Ser Ser Pro Asp Ala Val
    1475            1480            1485

Thr Ala Tyr Asn Gly Tyr Leu Thr Ser Ser Ser Lys Thr Pro Glu
    1490            1495            1500

Glu His Phe Ile Glu Thr Ile Ser Leu Ala Gly Ser Tyr Lys Asp
    1505            1510            1515

Trp Ser Tyr Ser Gly Gln Ser Thr Gln Leu Gly Ile Glu Phe Leu
    1520            1525            1530

Lys Arg Gly Asp Lys Ser Val Tyr Tyr Thr Ser Asn Pro Thr Thr
    1535            1540            1545
```

-continued

```
Phe His Leu Asp Gly Glu Val Ile Thr Phe Asp Asn Leu Lys Thr
1550                1555                1560

Leu Leu Ser Leu Arg Glu Val Arg Thr Ile Lys Val Phe Thr Thr
1565                1570                1575

Val Asp Asn Ile Asn Leu His Thr Gln Val Val Asp Met Ser Met
1580                1585                1590

Thr Tyr Gly Gln Gln Phe Gly Pro Thr Tyr Leu Asp Gly Ala Asp
1595                1600                1605

Val Thr Lys Ile Lys Pro His Asn Ser His Glu Gly Lys Thr Phe
1610                1615                1620

Tyr Val Leu Pro Asn Asp Asp Thr Leu Arg Val Glu Ala Phe Glu
1625                1630                1635

Tyr Tyr His Thr Thr Asp Pro Ser Phe Leu Gly Arg Tyr Met Ser
1640                1645                1650

Ala Leu Asn His Thr Lys Lys Trp Lys Tyr Pro Gln Val Asn Gly
1655                1660                1665

Leu Thr Ser Ile Lys Trp Ala Asp Asn Asn Cys Tyr Leu Ala Thr
1670                1675                1680

Ala Leu Leu Thr Leu Gln Gln Ile Glu Leu Lys Phe Asn Pro Pro
1685                1690                1695

Ala Leu Gln Asp Ala Tyr Tyr Arg Ala Arg Ala Gly Glu Ala Ala
1700                1705                1710

Asn Phe Cys Ala Leu Ile Leu Ala Tyr Cys Asn Lys Thr Val Gly
1715                1720                1725

Glu Leu Gly Asp Val Arg Glu Thr Met Ser Tyr Leu Phe Gln His
1730                1735                1740

Ala Asn Leu Asp Ser Cys Lys Arg Val Leu Asn Val Val Cys Lys
1745                1750                1755

Thr Cys Gly Gln Gln Gln Thr Thr Leu Lys Gly Val Glu Ala Val
1760                1765                1770

Met Tyr Met Gly Thr Leu Ser Tyr Glu Gln Phe Lys Lys Gly Val
1775                1780                1785

Gln Ile Pro Cys Thr Cys Gly Lys Gln Ala Thr Lys Tyr Leu Val
1790                1795                1800

Gln Gln Glu Ser Pro Phe Val Met Met Ser Ala Pro Pro Ala Gln
1805                1810                1815

Tyr Glu Leu Lys His Gly Thr Phe Thr Cys Ala Ser Glu Tyr Thr
1820                1825                1830

Gly Asn Tyr Gln Cys Gly His Tyr Lys His Ile Thr Ser Lys Glu
1835                1840                1845

Thr Leu Tyr Cys Ile Asp Gly Ala Leu Leu Thr Lys Ser Ser Glu
1850                1855                1860

Tyr Lys Gly Pro Ile Thr Asp Val Phe Tyr Lys Glu Asn Ser Tyr
1865                1870                1875

Thr Thr Thr Ile Lys Pro Val Thr Tyr Lys Leu Asp Gly Val Val
1880                1885                1890

Cys Thr Glu Ile Asp Pro Lys Leu Asp Asn Tyr Tyr Lys Lys Asp
1895                1900                1905

Asn Ser Tyr Phe Thr Glu Gln Pro Ile Asp Leu Val Pro Asn Gln
1910                1915                1920

Pro Tyr Pro Asn Ala Ser Phe Asp Asn Phe Lys Phe Val Cys Asp
1925                1930                1935

Asn Ile Lys Phe Ala Asp Asp Leu Asn Gln Leu Thr Gly Tyr Lys
```

-continued

```
                1940                1945                1950
Lys Pro Ala Ser Arg Glu Leu Lys Val Thr Phe Phe Pro Asp Leu
    1955                1960                1965
Asn Gly Asp Val Val Ala Ile Asp Tyr Lys His Tyr Thr Pro Ser
    1970                1975                1980
Phe Lys Lys Gly Ala Lys Leu Leu His Lys Pro Ile Val Trp His
    1985                1990                1995
Val Asn Asn Ala Thr Asn Lys Ala Thr Tyr Lys Pro Asn Thr Trp
    2000                2005                2010
Cys Ile Arg Cys Leu Trp Ser Thr Lys Pro Val Glu Thr Ser Asn
    2015                2020                2025
Ser Phe Asp Val Leu Lys Ser Glu Asp Ala Gln Gly Met Asp Asn
    2030                2035                2040
Leu Ala Cys Glu Asp Leu Lys Pro Val Ser Glu Glu Val Val Glu
    2045                2050                2055
Asn Pro Thr Ile Gln Lys Asp Val Leu Glu Cys Asn Val Lys Thr
    2060                2065                2070
Thr Glu Val Val Gly Asp Ile Ile Leu Lys Pro Ala Asn Asn Ser
    2075                2080                2085
Leu Lys Ile Thr Glu Glu Val Gly His Thr Asp Leu Met Ala Ala
    2090                2095                2100
Tyr Val Asp Asn Ser Ser Leu Thr Ile Lys Lys Pro Asn Glu Leu
    2105                2110                2115
Ser Arg Val Leu Gly Leu Lys Thr Leu Ala Thr His Gly Leu Ala
    2120                2125                2130
Ala Val Asn Ser Val Pro Trp Asp Thr Ile Ala Asn Tyr Ala Lys
    2135                2140                2145
Pro Phe Leu Asn Lys Val Val Ser Thr Thr Thr Asn Ile Val Thr
    2150                2155                2160
Arg Cys Leu Asn Arg Val Cys Thr Asn Tyr Met Pro Tyr Phe Phe
    2165                2170                2175
Thr Leu Leu Leu Gln Leu Cys Thr Phe Thr Arg Ser Thr Asn Ser
    2180                2185                2190
Arg Ile Lys Ala Ser Met Pro Thr Thr Ile Ala Lys Asn Thr Val
    2195                2200                2205
Lys Ser Val Gly Lys Phe Cys Leu Glu Ala Ser Phe Asn Tyr Leu
    2210                2215                2220
Lys Ser Pro Asn Phe Ser Lys Leu Ile Asn Ile Ile Trp Phe
    2225                2230                2235
Leu Leu Leu Ser Val Cys Leu Gly Ser Leu Ile Tyr Ser Thr Ala
    2240                2245                2250
Ala Leu Gly Val Leu Met Ser Asn Leu Gly Met Pro Ser Tyr Cys
    2255                2260                2265
Thr Gly Tyr Arg Glu Gly Tyr Leu Asn Ser Thr Asn Val Thr Ile
    2270                2275                2280
Ala Thr Tyr Cys Thr Gly Ser Ile Pro Cys Ser Val Cys Leu Ser
    2285                2290                2295
Gly Leu Asp Ser Leu Asp Thr Tyr Pro Ser Leu Glu Thr Ile Gln
    2300                2305                2310
Ile Thr Ile Ser Ser Phe Lys Trp Asp Leu Thr Ala Phe Gly Leu
    2315                2320                2325
Val Ala Glu Trp Phe Leu Ala Tyr Ile Leu Phe Thr Arg Phe Phe
    2330                2335                2340
```

```
Tyr Val Leu Gly Leu Ala Ala Ile Met Gln Leu Phe Phe Ser Tyr
2345                2350                2355

Phe Ala Val His Phe Ile Ser Asn Ser Trp Leu Met Trp Leu Ile
2360                2365                2370

Ile Asn Leu Val Gln Met Ala Pro Ile Ser Ala Met Val Arg Met
2375                2380                2385

Tyr Ile Phe Phe Ala Ser Phe Tyr Tyr Val Trp Lys Ser Tyr Val
2390                2395                2400

His Val Val Asp Gly Cys Asn Ser Ser Thr Cys Met Met Cys Tyr
2405                2410                2415

Lys Arg Asn Arg Ala Thr Arg Val Glu Cys Thr Thr Ile Val Asn
2420                2425                2430

Gly Val Arg Arg Ser Phe Tyr Val Tyr Ala Asn Gly Gly Lys Gly
2435                2440                2445

Phe Cys Lys Leu His Asn Trp Asn Cys Val Asn Cys Asp Thr Phe
2450                2455                2460

Cys Ala Gly Ser Thr Phe Ile Ser Asp Glu Val Ala Arg Asp Leu
2465                2470                2475

Ser Leu Gln Phe Lys Arg Pro Ile Asn Pro Thr Asp Gln Ser Ser
2480                2485                2490

Tyr Ile Val Asp Ser Val Thr Val Lys Asn Gly Ser Ile His Leu
2495                2500                2505

Tyr Phe Asp Lys Ala Gly Gln Lys Thr Tyr Glu Arg His Ser Leu
2510                2515                2520

Ser His Phe Val Asn Leu Asp Asn Leu Arg Ala Asn Asn Thr Lys
2525                2530                2535

Gly Ser Leu Pro Ile Asn Val Ile Val Phe Asp Gly Lys Ser Lys
2540                2545                2550

Cys Glu Glu Ser Ser Ala Lys Ser Ala Ser Val Tyr Tyr Ser Gln
2555                2560                2565

Leu Met Cys Gln Pro Ile Leu Leu Leu Asp Gln Ala Leu Val Ser
2570                2575                2580

Asp Val Gly Asp Ser Ala Glu Val Ala Val Lys Met Phe Asp Ala
2585                2590                2595

Tyr Val Asn Thr Phe Ser Ser Thr Phe Asn Val Pro Met Glu Lys
2600                2605                2610

Leu Lys Thr Leu Val Ala Thr Ala Glu Ala Glu Leu Ala Lys Asn
2615                2620                2625

Val Ser Leu Asp Asn Val Leu Ser Thr Phe Ile Ser Ala Ala Arg
2630                2635                2640

Gln Gly Phe Val Asp Ser Asp Val Glu Thr Lys Asp Val Val Glu
2645                2650                2655

Cys Leu Lys Leu Ser His Gln Ser Asp Ile Glu Val Thr Gly Asp
2660                2665                2670

Ser Cys Asn Asn Tyr Met Leu Thr Tyr Asn Lys Val Glu Asn Met
2675                2680                2685

Thr Pro Arg Asp Leu Gly Ala Cys Ile Asp Cys Ser Ala Arg His
2690                2695                2700

Ile Asn Ala Gln Val Ala Lys Ser His Asn Ile Ala Leu Ile Trp
2705                2710                2715

Asn Val Lys Asp Phe Met Ser Leu Ser Glu Gln Leu Arg Lys Gln
2720                2725                2730
```

-continued

```
Ile Arg Ser Ala Ala Lys Lys Asn Asn Leu Pro Phe Lys Leu Thr
2735                2740                2745

Cys Ala Thr Thr Arg Gln Val Val Asn Val Val Thr Thr Lys Ile
2750                2755                2760

Ala Leu Lys Gly Gly Lys Ile Val Asn Asn Trp Leu Lys Gln Leu
2765                2770                2775

Ile Lys Val Thr Leu Val Phe Leu Phe Val Ala Ala Ile Phe Tyr
2780                2785                2790

Leu Ile Ile Pro Val His Val Met Ser Lys His Thr Asp Phe Ser
2795                2800                2805

Ser Glu Ile Ile Gly Tyr Lys Ala Ile Asp Gly Gly Val Thr Arg
2810                2815                2820

Asp Ile Ala Ser Thr Asp Thr Cys Phe Ala Asn Lys His Ala Asp
2825                2830                2835

Phe Asp Thr Trp Phe Ser Gln Arg Gly Gly Ser Tyr Thr Asn Asp
2840                2845                2850

Lys Ala Cys Pro Leu Ile Ala Ala Val Ile Thr Arg Glu Val Gly
2855                2860                2865

Phe Val Val Pro Gly Leu Pro Gly Thr Ile Leu Arg Thr Thr Asn
2870                2875                2880

Gly Asp Phe Leu His Phe Leu Pro Arg Val Phe Ser Ala Val Gly
2885                2890                2895

Asn Ile Cys Tyr Thr Pro Ser Lys Leu Ile Glu Tyr Thr Asp Phe
2900                2905                2910

Ala Thr Ser Ala Cys Val Leu Ala Ala Glu Cys Thr Ile Phe Lys
2915                2920                2925

Asp Ala Ser Gly Lys Pro Val Pro Tyr Cys Tyr Asp Thr Asn Val
2930                2935                2940

Leu Glu Gly Ser Val Ala Tyr Glu Ser Leu Arg Pro Asp Thr Arg
2945                2950                2955

Tyr Val Leu Met Asp Gly Ser Ile Ile Gln Phe Pro Asn Thr Tyr
2960                2965                2970

Leu Glu Gly Ser Val Arg Val Val Thr Thr Phe Asp Ser Glu Tyr
2975                2980                2985

Cys Arg His Gly Thr Cys Glu Arg Ser Glu Ala Gly Val Cys Val
2990                2995                3000

Ser Thr Ser Gly Arg Trp Val Leu Asn Asn Asp Tyr Tyr Arg Ser
3005                3010                3015

Leu Pro Gly Val Phe Cys Gly Val Asp Ala Val Asn Leu Leu Thr
3020                3025                3030

Asn Met Phe Thr Pro Leu Ile Gln Pro Ile Gly Ala Leu Asp Ile
3035                3040                3045

Ser Ala Ser Ile Val Ala Gly Gly Ile Val Ala Ile Val Val Thr
3050                3055                3060

Cys Leu Ala Tyr Tyr Phe Met Arg Phe Arg Arg Ala Phe Gly Glu
3065                3070                3075

Tyr Ser His Val Val Ala Phe Asn Thr Leu Leu Phe Leu Met Ser
3080                3085                3090

Phe Thr Val Leu Cys Leu Thr Pro Val Tyr Ser Phe Leu Pro Gly
3095                3100                3105

Val Tyr Ser Val Ile Tyr Leu Tyr Leu Thr Phe Tyr Leu Thr Asn
3110                3115                3120

Asp Val Ser Phe Leu Ala His Ile Gln Trp Met Val Met Phe Thr
```

```
                3125                3130                3135

Pro Leu Val Pro Phe Trp Ile Thr Ile Ala Tyr Ile Ile Cys Ile
    3140                3145                3150

Ser Thr Lys His Phe Tyr Trp Phe Phe Ser Asn Tyr Leu Lys Arg
    3155                3160                3165

Arg Val Val Phe Asn Gly Val Ser Phe Ser Thr Phe Glu Glu Ala
    3170                3175                3180

Ala Leu Cys Thr Phe Leu Leu Asn Lys Glu Met Tyr Leu Lys Leu
    3185                3190                3195

Arg Ser Asp Val Leu Leu Pro Leu Thr Gln Tyr Asn Arg Tyr Leu
    3200                3205                3210

Ala Leu Tyr Asn Lys Tyr Lys Tyr Phe Ser Gly Ala Met Asp Thr
    3215                3220                3225

Thr Ser Tyr Arg Glu Ala Ala Cys Cys His Leu Ala Lys Ala Leu
    3230                3235                3240

Asn Asp Phe Ser Asn Ser Gly Ser Asp Val Leu Tyr Gln Pro Pro
    3245                3250                3255

Gln Thr Ser Ile Thr Ser Ala Val Leu Gln Ser Gly Phe Arg Lys
    3260                3265                3270

Met Ala Phe Pro Ser Gly Lys Val Glu Gly Cys Met Val Gln Val
    3275                3280                3285

Thr Cys Gly Thr Thr Thr Leu Asn Gly Leu Trp Leu Asp Asp Val
    3290                3295                3300

Val Tyr Cys Pro Arg His Val Ile Cys Thr Ser Glu Asp Met Leu
    3305                3310                3315

Asn Pro Asn Tyr Glu Asp Leu Leu Ile Arg Lys Ser Asn His Asn
    3320                3325                3330

Phe Leu Val Gln Ala Gly Asn Val Gln Leu Arg Val Ile Gly His
    3335                3340                3345

Ser Met Gln Asn Cys Val Leu Lys Phe Lys Val Asp Thr Ala Asn
    3350                3355                3360

Pro Lys Thr Pro Lys Tyr Lys Phe Val Arg Ile Gln Pro Gly Gln
    3365                3370                3375

Thr Phe Ser Val Leu Ala Cys Tyr Asn Gly Ser Pro Ser Gly Val
    3380                3385                3390

Tyr Gln Cys Ala Met Arg Pro Asn Phe Thr Ile Lys Gly Ser Phe
    3395                3400                3405

Leu Asn Gly Ser Cys Gly Ser Val Gly Phe Asn Ile Asp Tyr Asp
    3410                3415                3420

Cys Val Ser Phe Cys Tyr Met His His Met Glu Leu Pro Thr Gly
    3425                3430                3435

Val His Ala Gly Thr Asp Leu Glu Gly Asn Phe Tyr Gly Pro Phe
    3440                3445                3450

Val Asp Arg Gln Thr Ala Gln Ala Ala Gly Thr Asp Thr Thr Ile
    3455                3460                3465

Thr Val Asn Val Leu Ala Trp Leu Tyr Ala Ala Val Ile Asn Gly
    3470                3475                3480

Asp Arg Trp Phe Leu Asn Arg Phe Thr Thr Thr Leu Asn Asp Phe
    3485                3490                3495

Asn Leu Val Ala Met Lys Tyr Asn Tyr Glu Pro Leu Thr Gln Asp
    3500                3505                3510

His Val Asp Ile Leu Gly Pro Leu Ser Ala Gln Thr Gly Ile Ala
    3515                3520                3525
```

```
Val Leu Asp Met Cys Ala Ser Leu Lys Glu Leu Leu Gln Asn Gly
3530                3535                3540

Met Asn Gly Arg Thr Ile Leu Gly Ser Ala Leu Leu Glu Asp Glu
3545                3550                3555

Phe Thr Pro Phe Asp Val Val Arg Gln Cys Ser Gly Val Thr Phe
3560                3565                3570

Gln Ser Ala Val Lys Arg Thr Ile Lys Gly Thr His His Trp Leu
3575                3580                3585

Leu Leu Thr Ile Leu Thr Ser Leu Leu Val Leu Val Gln Ser Thr
3590                3595                3600

Gln Trp Ser Leu Phe Phe Leu Tyr Glu Asn Ala Phe Leu Pro
3605                3610                3615

Phe Ala Met Gly Ile Ile Ala Met Ser Ala Phe Ala Met Met Phe
3620                3625                3630

Val Lys His Lys His Ala Phe Leu Cys Leu Phe Leu Leu Pro Ser
3635                3640                3645

Leu Ala Thr Val Ala Tyr Phe Asn Met Val Tyr Met Pro Ala Ser
3650                3655                3660

Trp Val Met Arg Ile Met Thr Trp Leu Asp Met Val Asp Thr Ser
3665                3670                3675

Leu Ser Gly Phe Lys Leu Lys Asp Cys Val Met Tyr Ala Ser Ala
3680                3685                3690

Val Val Leu Leu Ile Leu Met Thr Ala Arg Thr Val Tyr Asp Asp
3695                3700                3705

Gly Ala Arg Arg Val Trp Thr Leu Met Asn Val Leu Thr Leu Val
3710                3715                3720

Tyr Lys Val Tyr Tyr Gly Asn Ala Leu Asp Gln Ala Ile Ser Met
3725                3730                3735

Trp Ala Leu Ile Ile Ser Val Thr Ser Asn Tyr Ser Gly Val Val
3740                3745                3750

Thr Thr Val Met Phe Leu Ala Arg Gly Ile Val Phe Met Cys Val
3755                3760                3765

Glu Tyr Cys Pro Ile Phe Phe Ile Thr Gly Asn Thr Leu Gln Cys
3770                3775                3780

Ile Met Leu Val Tyr Cys Phe Leu Gly Tyr Phe Cys Thr Cys Tyr
3785                3790                3795

Phe Gly Leu Phe Cys Leu Leu Asn Arg Tyr Phe Arg Leu Thr Leu
3800                3805                3810

Gly Val Tyr Asp Tyr Leu Val Ser Thr Gln Glu Phe Arg Tyr Met
3815                3820                3825

Asn Ser Gln Gly Leu Leu Pro Pro Lys Asn Ser Ile Asp Ala Phe
3830                3835                3840

Lys Leu Asn Ile Lys Leu Leu Gly Val Gly Gly Lys Pro Cys Ile
3845                3850                3855

Lys Val Ala Thr Val Gln Ser Lys Met Ser Asp Val Lys Cys Thr
3860                3865                3870

Ser Val Val Leu Leu Ser Val Leu Gln Gln Leu Arg Val Glu Ser
3875                3880                3885

Ser Ser Lys Leu Trp Ala Gln Cys Val Gln Leu His Asn Asp Ile
3890                3895                3900

Leu Leu Ala Lys Asp Thr Thr Glu Ala Phe Glu Lys Met Val Ser
3905                3910                3915
```

| | | | | | | | | | | | |
|---|---|---|---|---|---|---|---|---|---|---|---|
|Leu|Leu|Ser|Val|Leu|Leu|Ser|Met|Gln|Gly|Ala|Val|
| | |3920| | | |3925| | | |3930| |
|Asp|Ile|Asn| | | | | | | | | |

Lys Leu Cys Glu Glu Met Leu Asp Asn Arg Ala Thr Leu Gln Ala
  3935               3940                 3945

Ile Ala Ser Glu Phe Ser Ser Leu Pro Ser Tyr Ala Ala Phe Ala
  3950               3955                 3960

Thr Ala Gln Glu Ala Tyr Glu Gln Ala Val Ala Asn Gly Asp Ser
  3965               3970                 3975

Glu Val Val Leu Lys Lys Leu Lys Lys Ser Leu Asn Val Ala Lys
  3980               3985                 3990

Ser Glu Phe Asp Arg Asp Ala Ala Met Gln Arg Lys Leu Glu Lys
  3995               4000                 4005

Met Ala Asp Gln Ala Met Thr Gln Met Tyr Lys Gln Ala Arg Ser
  4010               4015                 4020

Glu Asp Lys Arg Ala Lys Val Thr Ser Ala Met Gln Ile Met Leu
  4025               4030                 4035

Phe Thr Met Leu Arg Lys Leu Asp Asn Asp Ala Leu Asn Asn Ile
  4040               4045                 4050

Ile Asn Asn Ala Arg Asp Gly Cys Val Pro Leu Asn Ile Ile Pro
  4055               4060                 4065

Leu Thr Thr Ala Ala Lys Leu Met Val Val Ile Pro Asp Tyr Asn
  4070               4075                 4080

Thr Tyr Lys Asn Thr Cys Asp Gly Thr Thr Phe Thr Tyr Ala Ser
  4085               4090                 4095

Ala Leu Trp Glu Ile Gln Gln Val Val Asp Ala Asp Ser Lys Ile
  4100               4105                 4110

Val Gln Leu Ser Glu Ile Ser Met Asp Asn Ser Pro Asn Leu Ala
  4115               4120                 4125

Trp Pro Leu Ile Val Thr Ala Leu Arg Ala Asn Ser Ala Val Lys
  4130               4135                 4140

Leu Gln Asn Asn Glu Leu Ser Pro Val Ala Leu Arg Gln Met Ser
  4145               4150                 4155

Cys Ala Ala Gly Thr Thr Gln Thr Ala Cys Thr Asp Asp Asn Ala
  4160               4165                 4170

Leu Ala Tyr Tyr Asn Thr Thr Lys Gly Gly Arg Phe Val Leu Ala
  4175               4180                 4185

Leu Leu Ser Asp Leu Gln Asp Leu Lys Trp Ala Arg Phe Pro Lys
  4190               4195                 4200

Ser Asp Gly Thr Gly Thr Ile Tyr Thr Glu Leu Glu Pro Pro Cys
  4205               4210                 4215

Arg Phe Val Thr Asp Thr Pro Lys Gly Pro Lys Val Lys Tyr Leu
  4220               4225                 4230

Tyr Phe Ile Lys Gly Leu Asn Asn Leu Asn Arg Gly Met Val Leu
  4235               4240                 4245

Gly Ser Leu Ala Ala Thr Val Arg Leu Gln Ala Gly Asn Ala Thr
  4250               4255                 4260

Glu Val Pro Ala Asn Ser Thr Val Leu Ser Phe Cys Ala Phe Ala
  4265               4270                 4275

Val Asp Ala Ala Lys Ala Tyr Lys Asp Tyr Leu Ala Ser Gly Gly
  4280               4285                 4290

Gln Pro Ile Thr Asn Cys Val Lys Met Leu Cys Thr His Thr Gly
  4295               4300                 4305

Thr Gly Gln Ala Ile Thr Val Thr Pro Glu Ala Asn Met Asp Gln

```
           4310            4315            4320
Glu Ser Phe Gly Gly Ala Ser Cys Cys Leu Tyr Cys Arg Cys His
        4325            4330            4335
Ile Asp His Pro Asn Pro Lys Gly Phe Cys Asp Leu Lys Gly Lys
        4340            4345            4350
Tyr Val Gln Ile Pro Thr Thr Cys Ala Asn Asp Pro Val Gly Phe
        4355            4360            4365
Thr Leu Lys Asn Thr Val Cys Thr Val Cys Gly Met Trp Lys Gly
        4370            4375            4380
Tyr Gly Cys Ser Cys Asp Gln Leu Arg Glu Pro Met Leu Gln Ser
        4385            4390            4395
Ala Asp Ala Gln Ser Phe Leu Asn Arg Val Cys Gly Val Ser Ala
        4400            4405            4410
Ala Arg Leu Thr Pro Cys Gly Thr Gly Thr Ser Thr Asp Val Val
        4415            4420            4425
Tyr Arg Ala Phe Asp Ile Tyr Asn Asp Lys Val Ala Gly Phe Ala
        4430            4435            4440
Lys Phe Leu Lys Thr Asn Cys Cys Arg Phe Gln Glu Lys Asp Glu
        4445            4450            4455
Asp Asp Asn Leu Ile Asp Ser Tyr Phe Val Val Lys Arg His Thr
        4460            4465            4470
Phe Ser Asn Tyr Gln His Glu Glu Thr Ile Tyr Asn Leu Leu Lys
        4475            4480            4485
Asp Cys Pro Ala Val Ala Lys His Asp Phe Phe Lys Phe Arg Ile
        4490            4495            4500
Asp Gly Asp Met Val Pro His Ile Ser Arg Gln Arg Leu Thr Lys
        4505            4510            4515
Tyr Thr Met Ala Asp Leu Val Tyr Ala Leu Arg His Phe Asp Glu
        4520            4525            4530
Gly Asn Cys Asp Thr Leu Lys Glu Ile Leu Val Thr Tyr Asn Cys
        4535            4540            4545
Cys Asp Asp Asp Tyr Phe Asn Lys Lys Asp Trp Tyr Asp Phe Val
        4550            4555            4560
Glu Asn Pro Asp Ile Leu Arg Val Tyr Ala Asn Leu Gly Glu Arg
        4565            4570            4575
Val Arg Gln Ala Leu Leu Lys Thr Val Gln Phe Cys Asp Ala Met
        4580            4585            4590
Arg Asn Ala Gly Ile Val Gly Val Leu Thr Leu Asp Asn Gln Asp
        4595            4600            4605
Leu Asn Gly Asn Trp Tyr Asp Phe Gly Asp Phe Ile Gln Thr Thr
        4610            4615            4620
Pro Gly Ser Gly Val Pro Val Val Asp Ser Tyr Tyr Ser Leu Leu
        4625            4630            4635
Met Pro Ile Leu Thr Leu Thr Arg Ala Leu Thr Ala Glu Ser His
        4640            4645            4650
Val Asp Thr Asp Leu Thr Lys Pro Tyr Ile Lys Trp Asp Leu Leu
        4655            4660            4665
Lys Tyr Asp Phe Thr Glu Glu Arg Leu Lys Leu Phe Asp Arg Tyr
        4670            4675            4680
Phe Lys Tyr Trp Asp Gln Thr Tyr His Pro Asn Cys Val Asn Cys
        4685            4690            4695
Leu Asp Asp Arg Cys Ile Leu His Cys Ala Asn Phe Asn Val Leu
        4700            4705            4710
```

-continued

```
Phe Ser Thr Val Phe Pro Leu Thr Ser Phe Gly Pro Leu Val Arg
4715                4720                4725

Lys Ile Phe Val Asp Gly Val Pro Phe Val Val Ser Thr Gly Tyr
4730                4735                4740

His Phe Arg Glu Leu Gly Val Val His Asn Gln Asp Val Asn Leu
4745                4750                4755

His Ser Ser Arg Leu Ser Phe Lys Glu Leu Leu Val Tyr Ala Ala
4760                4765                4770

Asp Pro Ala Met His Ala Ala Ser Gly Asn Leu Leu Leu Asp Lys
4775                4780                4785

Arg Thr Thr Cys Phe Ser Val Ala Ala Leu Thr Asn Asn Val Ala
4790                4795                4800

Phe Gln Thr Val Lys Pro Gly Asn Phe Asn Lys Asp Phe Tyr Asp
4805                4810                4815

Phe Ala Val Ser Lys Gly Phe Phe Lys Glu Gly Ser Ser Val Glu
4820                4825                4830

Leu Lys His Phe Phe Phe Ala Gln Asp Gly Asn Ala Ala Ile Ser
4835                4840                4845

Asp Tyr Asp Tyr Tyr Arg Tyr Asn Leu Pro Thr Met Cys Asp Ile
4850                4855                4860

Arg Gln Leu Leu Phe Val Val Glu Val Val Asp Lys Tyr Phe Asp
4865                4870                4875

Cys Tyr Asp Gly Gly Cys Ile Asn Ala Asn Gln Val Ile Val Asn
4880                4885                4890

Asn Leu Asp Lys Ser Ala Gly Phe Pro Phe Asn Lys Trp Gly Lys
4895                4900                4905

Ala Arg Leu Tyr Tyr Asp Ser Met Ser Tyr Glu Asp Gln Asp Ala
4910                4915                4920

Leu Phe Ala Tyr Thr Lys Arg Asn Val Ile Pro Thr Ile Thr Gln
4925                4930                4935

Met Asn Leu Lys Tyr Ala Ile Ser Ala Lys Asn Arg Ala Arg Thr
4940                4945                4950

Val Ala Gly Val Ser Ile Cys Ser Thr Met Thr Asn Arg Gln Phe
4955                4960                4965

His Gln Lys Leu Leu Lys Ser Ile Ala Ala Thr Arg Gly Ala Thr
4970                4975                4980

Val Val Ile Gly Thr Ser Lys Phe Tyr Gly Gly Trp His Asn Met
4985                4990                4995

Leu Lys Thr Val Tyr Ser Asp Val Glu Asn Pro His Leu Met Gly
5000                5005                5010

Trp Asp Tyr Pro Lys Cys Asp Arg Ala Met Pro Asn Met Leu Arg
5015                5020                5025

Ile Met Ala Ser Leu Val Leu Ala Arg Lys His Thr Thr Cys Cys
5030                5035                5040

Ser Leu Ser His Arg Phe Tyr Arg Leu Ala Asn Glu Cys Ala Gln
5045                5050                5055

Val Leu Ser Glu Met Val Met Cys Gly Gly Ser Leu Tyr Val Lys
5060                5065                5070

Pro Gly Gly Thr Ser Ser Gly Asp Ala Thr Thr Ala Tyr Ala Asn
5075                5080                5085

Ser Val Phe Asn Ile Cys Gln Ala Val Thr Ala Asn Val Asn Ala
5090                5095                5100
```

```
Leu Leu Ser Thr Asp Gly Asn Lys Ile Ala Asp Lys Tyr Val Arg
    5105                5110                5115
Asn Leu Gln His Arg Leu Tyr Glu Cys Leu Tyr Arg Asn Arg Asp
    5120                5125                5130
Val Asp Thr Asp Phe Val Asn Glu Phe Tyr Ala Tyr Leu Arg Lys
    5135                5140                5145
His Phe Ser Met Met Ile Leu Ser Asp Asp Ala Val Val Cys Phe
    5150                5155                5160
Asn Ser Thr Tyr Ala Ser Gln Gly Leu Val Ala Ser Ile Lys Asn
    5165                5170                5175
Phe Lys Ser Val Leu Tyr Tyr Gln Asn Asn Val Phe Met Ser Glu
    5180                5185                5190
Ala Lys Cys Trp Thr Glu Thr Asp Leu Thr Lys Gly Pro His Glu
    5195                5200                5205
Phe Cys Ser Gln His Thr Met Leu Val Lys Gln Gly Asp Asp Tyr
    5210                5215                5220
Val Tyr Leu Pro Tyr Pro Asp Pro Ser Arg Ile Leu Gly Ala Gly
    5225                5230                5235
Cys Phe Val Asp Asp Ile Val Lys Thr Asp Gly Thr Leu Met Ile
    5240                5245                5250
Glu Arg Phe Val Ser Leu Ala Ile Asp Ala Tyr Pro Leu Thr Lys
    5255                5260                5265
His Pro Asn Gln Glu Tyr Ala Asp Val Phe His Leu Tyr Leu Gln
    5270                5275                5280
Tyr Ile Arg Lys Leu His Asp Glu Leu Thr Gly His Met Leu Asp
    5285                5290                5295
Met Tyr Ser Val Met Leu Thr Asn Asp Asn Thr Ser Arg Tyr Trp
    5300                5305                5310
Glu Pro Glu Phe Tyr Glu Ala Met Tyr Thr Pro His Thr Val Leu
    5315                5320                5325
Gln Ala Val Gly Ala Cys Val Leu Cys Asn Ser Gln Thr Ser Leu
    5330                5335                5340
Arg Cys Gly Ala Cys Ile Arg Arg Pro Phe Leu Cys Cys Lys Cys
    5345                5350                5355
Cys Tyr Asp His Val Ile Ser Thr Ser His Lys Leu Val Leu Ser
    5360                5365                5370
Val Asn Pro Tyr Val Cys Asn Ala Pro Gly Cys Asp Val Thr Asp
    5375                5380                5385
Val Thr Gln Leu Tyr Leu Gly Gly Met Ser Tyr Tyr Cys Lys Ser
    5390                5395                5400
His Lys Pro Pro Ile Ser Phe Pro Leu Cys Ala Asn Gly Gln Val
    5405                5410                5415
Phe Gly Leu Tyr Lys Asn Thr Cys Val Gly Ser Asp Asn Val Thr
    5420                5425                5430
Asp Phe Asn Ala Ile Ala Thr Cys Asp Trp Thr Asn Ala Gly Asp
    5435                5440                5445
Tyr Ile Leu Ala Asn Thr Cys Thr Glu Arg Leu Lys Leu Phe Ala
    5450                5455                5460
Ala Glu Thr Leu Lys Ala Thr Glu Glu Thr Phe Lys Leu Ser Tyr
    5465                5470                5475
Gly Ile Ala Thr Val Arg Glu Val Leu Ser Asp Arg Glu Leu His
    5480                5485                5490
Leu Ser Trp Glu Val Gly Lys Pro Arg Pro Pro Leu Asn Arg Asn
```

```
                5495                5500                5505
Tyr Val Phe Thr Gly Tyr Arg Val Thr Lys Asn Ser Lys Val Gln
            5510                5515                5520
Ile Gly Glu Tyr Thr Phe Glu Lys Gly Asp Tyr Gly Asp Ala Val
            5525                5530                5535
Val Tyr Arg Gly Thr Thr Thr Tyr Lys Leu Asn Val Gly Asp Tyr
            5540                5545                5550
Phe Val Leu Thr Ser His Thr Val Met Pro Leu Ser Ala Pro Thr
            5555                5560                5565
Leu Val Pro Gln Glu His Tyr Val Arg Ile Thr Gly Leu Tyr Pro
            5570                5575                5580
Thr Leu Asn Ile Ser Asp Glu Phe Ser Ser Asn Val Ala Asn Tyr
            5585                5590                5595
Gln Lys Val Gly Met Gln Lys Tyr Ser Thr Leu Gln Gly Pro Pro
            5600                5605                5610
Gly Thr Gly Lys Ser His Phe Ala Ile Gly Leu Ala Leu Tyr Tyr
            5615                5620                5625
Pro Ser Ala Arg Ile Val Tyr Thr Ala Cys Ser His Ala Ala Val
            5630                5635                5640
Asp Ala Leu Cys Glu Lys Ala Leu Lys Tyr Leu Pro Ile Asp Lys
            5645                5650                5655
Cys Ser Arg Ile Ile Pro Ala Arg Ala Arg Val Glu Cys Phe Asp
            5660                5665                5670
Lys Phe Lys Val Asn Ser Thr Leu Glu Gln Tyr Val Phe Cys Thr
            5675                5680                5685
Val Asn Ala Leu Pro Glu Thr Thr Ala Asp Ile Val Val Phe Asp
            5690                5695                5700
Glu Ile Ser Met Ala Thr Asn Tyr Asp Leu Ser Val Val Asn Ala
            5705                5710                5715
Arg Leu Arg Ala Lys His Tyr Val Tyr Ile Gly Asp Pro Ala Gln
            5720                5725                5730
Leu Pro Ala Pro Arg Thr Leu Leu Thr Lys Gly Thr Leu Glu Pro
            5735                5740                5745
Glu Tyr Phe Asn Ser Val Cys Arg Leu Met Lys Thr Ile Gly Pro
            5750                5755                5760
Asp Met Phe Leu Gly Thr Cys Arg Arg Cys Pro Ala Glu Ile Val
            5765                5770                5775
Asp Thr Val Ser Ala Leu Val Tyr Asp Asn Lys Leu Lys Ala His
            5780                5785                5790
Lys Asp Lys Ser Ala Gln Cys Phe Lys Met Phe Tyr Lys Gly Val
            5795                5800                5805
Ile Met His Asp Val Ser Ser Ala Ile Asn Arg Pro Gln Ile Gly
            5810                5815                5820
Val Val Arg Glu Phe Leu Thr Arg Asn Pro Ala Trp Arg Lys Ala
            5825                5830                5835
Val Phe Ile Ser Pro Tyr Asn Ser Gln Asn Ala Val Ala Ser Lys
            5840                5845                5850
Ile Leu Gly Leu Pro Thr Gln Thr Val Asp Ser Ser Gln Gly Ser
            5855                5860                5865
Glu Tyr Asp Tyr Val Ile Phe Thr Gln Thr Thr Glu Thr Ala His
            5870                5875                5880
Ser Cys Asn Val Asn Arg Phe Asn Val Ala Ile Thr Arg Ala Lys
            5885                5890                5895
```

-continued

```
Val Gly Ile Leu Cys Ile Met Ser Asp Arg Asp Leu Tyr Asp Lys
    5900                5905                5910

Leu Gln Phe Thr Ser Leu Glu Ile Pro Arg Arg Asn Val Ala Thr
    5915                5920                5925

Leu Gln Ala Glu Asn Val Thr Gly Leu Phe Lys Asp Cys Ser Lys
    5930                5935                5940

Val Ile Thr Gly Leu His Pro Thr Gln Ala Pro Thr His Leu Ser
    5945                5950                5955

Val Asp Thr Lys Phe Lys Thr Glu Gly Leu Cys Val Asp Ile Pro
    5960                5965                5970

Gly Ile Pro Lys Asp Met Thr Tyr Arg Arg Leu Ile Ser Met Met
    5975                5980                5985

Gly Phe Lys Met Asn Tyr Gln Val Asn Gly Tyr Pro Asn Met Phe
    5990                5995                6000

Ile Thr Arg Glu Glu Ala Ile Arg His Val Arg Ala Trp Ile Gly
    6005                6010                6015

Phe Asp Val Glu Gly Cys His Ala Thr Arg Glu Ala Val Gly Thr
    6020                6025                6030

Asn Leu Pro Leu Gln Leu Gly Phe Ser Thr Gly Val Asn Leu Val
    6035                6040                6045

Ala Val Pro Thr Gly Tyr Val Asp Thr Pro Asp Asn Thr Asp Phe
    6050                6055                6060

Ser Arg Val Ser Ala Lys Pro Pro Gly Asp Gln Phe Lys His
    6065                6070                6075

Leu Ile Pro Leu Met Tyr Lys Gly Leu Pro Trp Asn Val Val Arg
    6080                6085                6090

Ile Lys Ile Val Gln Met Leu Ser Asp Thr Leu Lys Asn Leu Ser
    6095                6100                6105

Asp Arg Val Val Phe Val Leu Trp Ala His Gly Phe Glu Leu Thr
    6110                6115                6120

Ser Met Lys Tyr Phe Val Lys Ile Gly Pro Glu Arg Thr Cys Cys
    6125                6130                6135

Leu Cys Asp Arg Arg Ala Thr Cys Phe Ser Thr Ala Ser Asp Thr
    6140                6145                6150

Tyr Ala Cys Trp His His Ser Ile Gly Phe Asp Tyr Val Tyr Asn
    6155                6160                6165

Pro Phe Met Ile Asp Val Gln Gln Trp Gly Phe Thr Gly Asn Leu
    6170                6175                6180

Gln Ser Asn His Asp Leu Tyr Cys Gln Val His Gly Asn Ala His
    6185                6190                6195

Val Ala Ser Cys Asp Ala Ile Met Thr Arg Cys Leu Ala Val His
    6200                6205                6210

Glu Cys Phe Val Lys Arg Val Asp Trp Thr Ile Glu Tyr Pro Ile
    6215                6220                6225

Ile Gly Asp Glu Leu Lys Ile Asn Ala Ala Cys Arg Lys Val Gln
    6230                6235                6240

His Met Val Val Lys Ala Ala Leu Leu Ala Asp Lys Phe Pro Val
    6245                6250                6255

Leu His Asp Ile Gly Asn Pro Lys Ala Ile Lys Cys Val Pro Gln
    6260                6265                6270

Ala Asp Val Glu Trp Lys Phe Tyr Asp Ala Gln Pro Cys Ser Asp
    6275                6280                6285
```

-continued

```
Lys Ala Tyr Lys Ile Glu Glu Leu Phe Tyr Ser Tyr Ala Thr His
6290            6295                6300

Ser Asp Lys Phe Thr Asp Gly Val Cys Leu Phe Trp Asn Cys Asn
6305            6310                6315

Val Asp Arg Tyr Pro Ala Asn Ser Ile Val Cys Arg Phe Asp Thr
6320            6325                6330

Arg Val Leu Ser Asn Leu Asn Leu Pro Gly Cys Asp Gly Gly Ser
6335            6340                6345

Leu Tyr Val Asn Lys His Ala Phe His Thr Pro Ala Phe Asp Lys
6350            6355                6360

Ser Ala Phe Val Asn Leu Lys Gln Leu Pro Phe Phe Tyr Tyr Ser
6365            6370                6375

Asp Ser Pro Cys Glu Ser His Gly Lys Gln Val Ser Asp Ile
6380            6385                6390

Asp Tyr Val Pro Leu Lys Ser Ala Thr Cys Ile Thr Arg Cys Asn
6395            6400                6405

Leu Gly Gly Ala Val Cys Arg His His Ala Asn Glu Tyr Arg Leu
6410            6415                6420

Tyr Leu Asp Ala Tyr Asn Met Met Ile Ser Ala Gly Phe Ser Leu
6425            6430                6435

Trp Val Tyr Lys Gln Phe Asp Thr Tyr Asn Leu Trp Asn Thr Phe
6440            6445                6450

Thr Arg Leu Gln Ser Leu Glu Asn Val Ala Phe Asn Val Val Asn
6455            6460                6465

Lys Gly His Phe Asp Gly Gln Gln Gly Glu Val Pro Val Ser Ile
6470            6475                6480

Ile Asn Asn Thr Val Tyr Thr Lys Val Asp Gly Val Asp Val Glu
6485            6490                6495

Leu Phe Glu Asn Lys Thr Thr Leu Pro Val Asn Val Ala Phe Glu
6500            6505                6510

Leu Trp Ala Lys Arg Asn Ile Lys Pro Val Pro Glu Val Lys Ile
6515            6520                6525

Leu Asn Asn Leu Gly Val Asp Ile Ala Ala Asn Thr Val Ile Trp
6530            6535                6540

Asp Tyr Lys Arg Asp Ala Pro Ala His Ile Ser Thr Ile Gly Val
6545            6550                6555

Cys Ser Met Thr Asp Ile Ala Lys Lys Pro Thr Glu Thr Ile Cys
6560            6565                6570

Ala Pro Leu Thr Val Phe Phe Asp Gly Arg Val Asp Gly Gln Val
6575            6580                6585

Asp Leu Phe Arg Asn Ala Arg Asn Gly Val Leu Ile Thr Glu Gly
6590            6595                6600

Ser Val Lys Gly Leu Gln Pro Ser Val Gly Pro Lys Gln Ala Ser
6605            6610                6615

Leu Asn Gly Val Thr Leu Ile Gly Glu Ala Val Lys Thr Gln Phe
6620            6625                6630

Asn Tyr Tyr Lys Lys Val Asp Gly Val Val Gln Gln Leu Pro Glu
6635            6640                6645

Thr Tyr Phe Thr Gln Ser Arg Asn Leu Gln Glu Phe Lys Pro Arg
6650            6655                6660

Ser Gln Met Glu Ile Asp Phe Leu Glu Leu Ala Met Asp Glu Phe
6665            6670                6675

Ile Glu Arg Tyr Lys Leu Glu Gly Tyr Ala Phe Glu His Ile Val
```

-continued

```
            6680                6685                 6690

Tyr Gly Asp Phe Ser His Ser Gln Leu Gly Gly Leu His Leu Leu
        6695                6700                6705

Ile Gly Leu Ala Lys Arg Phe Lys Glu Ser Pro Phe Glu Leu Glu
        6710                6715                6720

Asp Phe Ile Pro Met Asp Ser Thr Val Lys Asn Tyr Phe Ile Thr
        6725                6730                6735

Asp Ala Gln Thr Gly Ser Ser Lys Cys Val Cys Ser Val Ile Asp
        6740                6745                6750

Leu Leu Leu Asp Asp Phe Val Glu Ile Ile Lys Ser Gln Asp Leu
        6755                6760                6765

Ser Val Val Ser Lys Val Val Lys Val Thr Ile Asp Tyr Thr Glu
        6770                6775                6780

Ile Ser Phe Met Leu Trp Cys Lys Asp Gly His Val Glu Thr Phe
        6785                6790                6795

Tyr Pro Lys Leu Gln Ser Ser Gln Ala Trp Gln Pro Gly Val Ala
        6800                6805                6810

Met Pro Asn Leu Tyr Lys Met Gln Arg Met Leu Leu Glu Lys Cys
        6815                6820                6825

Asp Leu Gln Asn Tyr Gly Asp Ser Ala Thr Leu Pro Lys Gly Ile
        6830                6835                6840

Met Met Asn Val Ala Lys Tyr Thr Gln Leu Cys Gln Tyr Leu Asn
        6845                6850                6855

Thr Leu Thr Leu Ala Val Pro Tyr Asn Met Arg Val Ile His Phe
        6860                6865                6870

Gly Ala Gly Ser Asp Lys Gly Val Ala Pro Gly Thr Ala Val Leu
        6875                6880                6885

Arg Gln Trp Leu Pro Thr Gly Thr Leu Leu Val Asp Ser Asp Leu
        6890                6895                6900

Asn Asp Phe Val Ser Asp Ala Asp Ser Thr Leu Ile Gly Asp Cys
        6905                6910                6915

Ala Thr Val His Thr Ala Asn Lys Trp Asp Leu Ile Ile Ser Asp
        6920                6925                6930

Met Tyr Asp Pro Lys Thr Lys Asn Val Thr Lys Glu Asn Asp Ser
        6935                6940                6945

Lys Glu Gly Phe Phe Thr Tyr Ile Cys Gly Phe Ile Gln Gln Lys
        6950                6955                6960

Leu Ala Leu Gly Gly Ser Val Ala Ile Lys Ile Thr Glu His Ser
        6965                6970                6975

Trp Asn Ala Asp Leu Tyr Lys Leu Met Gly His Phe Ala Trp Trp
        6980                6985                6990

Thr Ala Phe Val Thr Asn Val Asn Ala Ser Ser Ser Glu Ala Phe
        6995                7000                7005

Leu Ile Gly Cys Asn Tyr Leu Gly Lys Pro Cys Glu Gln Ile Asp
        7010                7015                7020

Gly Tyr Val Met His Ala Asn Tyr Ile Phe Trp Arg Asn Thr Asn
        7025                7030                7035

Pro Ile Gln Leu Ser Ser Tyr Ser Leu Phe Asp Met Ser Lys Phe
        7040                7045                7050

Pro Leu Lys Leu Arg Gly Thr Ala Val Met Ser Leu Lys Glu Gly
        7055                7060                7065

Gln Ile Asn Asp Met Ile Leu Ser Leu Leu Ser Lys Gly Arg Leu
        7070                7075                7080
```

```
Ile Ile Arg Glu Asn Asn Arg Val Val Ile Ser Ser Asp Val Leu
    7085                7090                7095

Val Asn Asn
    7100

<210> SEQ ID NO 6
<211> LENGTH: 1014
<212> TYPE: PRT
<213> ORGANISM: Homo sapiens

<400> SEQUENCE: 6

Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
```

```
                    340                 345                 350
Gln Asp Arg Ile Phe Pro Pro Glu Thr Ser Ala Ser Val Ala Ala Thr
            355                 360                 365

Pro Pro Pro Ser Thr Ala Ser Ala Pro Ala Ala Val Asn Ser Ser Ala
            370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Met Glu Glu Val Lys Glu
            435                 440                 445

Ala Asn Ile Arg Val Val Ser Glu Asp Phe Leu Gln Asp Val Ser Ala
            450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
            515                 520                 525

Gly Gly Ala Ala Val Asp Pro Asp Ser Gly Leu Glu His Ser Ala His
            530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
            595                 600                 605

Asp Ala Ile Glu His Phe Met Lys Leu Tyr Glu Glu Lys Thr Gly Asn
            610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
            675                 680                 685

Tyr Glu Ile Asp Leu Gln Lys Met Pro Leu Gly Lys Leu Ser Lys Arg
            690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
            755                 760                 765
```

-continued

```
Leu Asp Ile Glu Val Ala Tyr Ser Leu Leu Arg Gly Gly Ser Asp Asp
    770             775             780

Ser Ser Lys Asp Pro Ile Asp Val Asn Tyr Glu Lys Leu Lys Thr Asp
785             790             795             800

Ile Lys Val Val Asp Arg Asp Ser Glu Glu Ala Glu Ile Ile Arg Lys
                805             810             815

Tyr Val Lys Asn Thr His Ala Thr Thr His Asn Ala Tyr Asp Leu Glu
            820             825             830

Val Ile Asp Ile Phe Lys Ile Glu Arg Glu Gly Glu Cys Gln Arg Tyr
        835             840             845

Lys Pro Phe Lys Gln Leu His Asn Arg Arg Leu Leu Trp His Gly Ser
    850             855             860

Arg Thr Thr Asn Phe Ala Gly Ile Leu Ser Gln Gly Leu Arg Ile Ala
865             870             875             880

Pro Pro Glu Ala Pro Val Thr Gly Tyr Met Phe Gly Lys Gly Ile Tyr
                885             890             895

Phe Ala Asp Met Val Ser Lys Ser Ala Asn Tyr Cys His Thr Ser Gln
            900             905             910

Gly Asp Pro Ile Gly Leu Ile Leu Leu Gly Glu Val Ala Leu Gly Asn
        915             920             925

Met Tyr Glu Leu Lys His Ala Ser His Ile Ser Lys Leu Pro Lys Gly
    930             935             940

Lys His Ser Val Lys Gly Leu Gly Lys Thr Thr Pro Asp Pro Ser Ala
945             950             955             960

Asn Ile Ser Leu Asp Gly Val Asp Val Pro Leu Gly Thr Gly Ile Ser
                965             970             975

Ser Gly Val Asn Asp Thr Ser Leu Leu Tyr Asn Glu Tyr Ile Val Tyr
            980             985             990

Asp Ile Ala Gln Val Asn Leu Lys  Tyr Leu Leu Lys Leu Lys Phe Asn
        995             1000            1005

Phe Lys  Thr Ser Leu Trp
    1010
```

VACCINE RNA-PEPTIDE AGAINST SARS-COV-2 WITH ENDOGENOUS EXOSOMES AS CARRIER

BACKGROUND OF THE INVENTION

1. Field of the Invention

The present invention relates to antiviral vaccines, and more particularly, to a vaccine RNA-peptide against coronavirus, specifically SARS-CoV-2 using endogenous exosomes as carrier.

This application contains a Sequence Listing which has been submitted electronically in ASCII format and is expressly incorporated by reference in its entirety as though fully set forth herein. Said ASCII copy is named "ST25SequenceListing200271.txt", created on Jul. 26, 2021 and having a size of 73 kilobytes.

2. Description of the Related Art

The new coronavirus formed a clade within the subgenus Orthocoronavirinae, sarbecovirus subfamily. The first time these cases were published, and they were classified as "pneumonia of unknown etiology." The Chinese Center for Disease Control and Prevention (CDC) and local CDCs organized an intensive outbreak investigation program. The etiology of this illness is now attributed to a novel virus belonging to the coronavirus (CoV) family, COVID-19. This disease has inflicted catastrophic damages in public health, economic and social stability—putting life globally on hold in 2020 and presumably a year more. Moreover, a solid second wave in some countries, in cases exceeding the first, ensures that from the clinical range details of the disease, new diagnostics, prevention and vaccination strategies remain in the process of development.

A vaccine for severe acute respiratory syndrome coronavirus-2 (SARS-CoV-2) is needed to control the coronavirus disease 2019 (COVID-19) global pandemic. Structural studies have led to the development of mutations that stabilize Beta-coronavirus spike proteins in the prefusion state, improving their expression and increasing immunogenicity. Vaccines of the art show that mRNA induces potent neutralizing antibody responses and protects against SARS-CoV-2 infection in the lungs and noses of mice without evidence of immunopathology.

1) mRNA Vaccines
  1.1 Recent improvements in mRNA vaccines act to increase protein translation, modulate innate and adaptive immunogenicity, and improve delivery.
  1.2 mRNA vaccines have elicited potent immunity against infectious disease targets in animal models of influenza virus, Zika virus, rabies virus and others, especially in recent years, using lipid-encapsulated or naked forms of sequence-optimized mRNA.
  1.3 Diverse approaches to mRNA cancer vaccines, including dendritic cell vaccines and various types of directly injectable mRNA, have been employed in numerous cancer clinical trials, with some promising results showing antigen-specific T cell responses and prolonged disease-free survival in some cases.
  1.4 Therapeutic considerations and challenges include scaling up good manufacturing practice (GMP) production, establishing regulations, further documenting safety and increasing efficacy.
  1.5 Important future directions of research will be to compare and elucidate the immune pathways activated by various mRNA vaccine platforms, to improve current approaches based on these mechanisms and to initiate new clinical trials against additional disease targets.

The mRNA vaccines represent a promising alternative to conventional vaccine approaches because of their high potency, capacity for rapid development and potential for low-cost manufacture and safe administration. However, their application has until recently been restricted by the instability and inefficient in vivo delivery of mRNA. Recent technological advances have now largely overcome these issues, and multiple mRNA vaccine platforms against Beta-coronavirus spike proteins in the prefusion state, improving their expression and increasing immunogenicity.

SUMMARY OF THE INVENTION

The present invention is a vaccine against SARS-CoV-2 with prophylactic and therapeutic actions, also useful in post-COVID-19 infection rehabilitation. This COVID-19 peptide vaccine projects involving RNA-peptide and endogenous exosomes have unique antiviral Strategic Duplicity Millstones, with outcomes of perpetuation research cycles to potentially diverse vaccine pathway.

Present invention proposes a mRNA-peptide as vaccine with therapeutic action to treatment of SARS-CoV-2 infection, using endogenous exosomes as carrier adjuvant.

In one embodiment, a vaccine RNA-peptide against SARS-CoV-2 comprises a micro ribonucleic acid (mRNA) fused to a peptide of a Severe Acute Respiratory Syndrome Coronavirus 2 (SARS-CoV-2) surface protein wherein endogenous exosomes act as carrier.

The mRNA comprises a poly-A sequence. In a preferred embodiment, the poly-A sequence is about 10 adenosine nucleotides.

In a preferred embodiment, the mRNA comprises the nucleic acid sequence of SEQ ID NO: 1.

The peptide of the SARS-CoV-2 surface protein (peptide SARS-CoV-2) is chemically modified.

In a preferred embodiment, the peptide of the SARS-CoV-2 surface protein comprises the amino acid sequence of SEQ ID NO: 2.

In another preferred embodiment, the peptide of the SARS-CoV-2 surface protein is fused to a synthetic poly ADP-ribose polymerase peptide (PARP1 peptide).

Present invention is also related with a method for stimulating an immune response against SARS-CoV-2 in a subject administering the vaccine RNA-peptide.

In another embodiment, present invention is referred to a vaccine RNA-peptide against SARS-CoV-2 comprising a micro ribonucleic acid (miRNA) fused to a peptide of a Severe Acute Respiratory Syndrome Coronavirus 2 (SARS-CoV-2) surface protein fused to a synthetic poly ADP-ribose polymerase peptide.

The mRNA comprises a poly-A sequence, wherein the poly-A sequence is about 10 adenosine nucleosides.

In a preferred embodiment, the mRNA comprises the nucleic acid sequence of SEQ ID NO: 1.

In a preferred embodiment, the peptide of the SARS-CoV-2 surface protein (SARS-CoV-2 peptide) comprises the amino acid sequence of SEQ ID NO: 2.

In a preferred embodiment, the synthetic poly ADP-ribose polymerase peptide comprises the amino acid sequence of SEQ ID NO: 3.

In a preferred embodiment, the open reading frame encoding the peptide comprises the amino acid sequence of SEQ ID NO: 4.

The vaccine RNA-peptide against SARS-CoV-2 comprises endogenous exosomes as carrier.

In one embodiment, a method for treating of SARS-CoV-2 in a subject in need thereof comprises administering an effective amount of the vaccine RNA-peptide.

In one embodiment, a method for treating SARS-CoV-2 in a subject in need thereof comprises administering to the subject an effective amount of a vaccine RNA-peptide against SARS-CoV-2 comprising a micro ribonucleic acid (mRNA) comprising an open reading frame encoding a peptide of a Severe Acute Respiratory Syndrome Coronavirus 2 (SARS-CoV-2) surface protein fused to a synthetic poly ADP-ribose polymerase peptide, wherein endogenous are the carrier.

In preferred embodiment, exosomes are endogenous exosomes nanoparticles. The vaccine composition RNA-peptide-AB has high affinity for intracellular exosomes, specifically endogenous exosomes, that are normally produced for carry it, facilitating the interaction between cells of the same and different phenotypes and biological action, such as epithelial tissue cells and lung cells.

In a preferred embodiment, the mRNA comprises the nucleic acid sequence of SEQ ID NO: 1 and the open reading frame encodes the peptide comprising the amino acid sequence of SEQ ID NO: 4.

MHC class I molecules bind the synthetic poly ADP-ribose polymerase peptide, also referred as peptide-B, with SEQ ID NO: 3 GVDEVAKKKSK (Size=11 aa) generated by hydrolysis of RNA-peptide after apoptosis induction for caspase 3 or caspase 7 in infected cell with SARS-CoV-2. The sequence of origin was from RNA-peptide-AB: (Size=34 nt; Size=28 aa)

SEQ ID NO: 1 and SEQ ID NO: 4
AAAAAAAAAACUCCUAGAACUAGCAUUACAGAUG-

CVNDTFAGSTFISDEVDGVDEVAKKKSK

It is therefore one of the main objects of the present invention to provide a vaccine RNA-peptide against SARS-CoV-2.

It is another object of this invention the algorithm to obtain a vaccine candidate against SARS-CoV-2.

It is another object of this invention to provide a vaccine RNA-peptide against SARS-CoV-2 having endogenous exosomes as carrier.

It is another object of this invention to provide a vaccine RNA-peptide against SARS-CoV-2, which induce an immune response against SARS-CoV-2.

It is another object of this invention to provide a vaccine RNA-peptide against SARS-CoV-2 useful in the treatment of SARS-CoV-2.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

Figure 2:
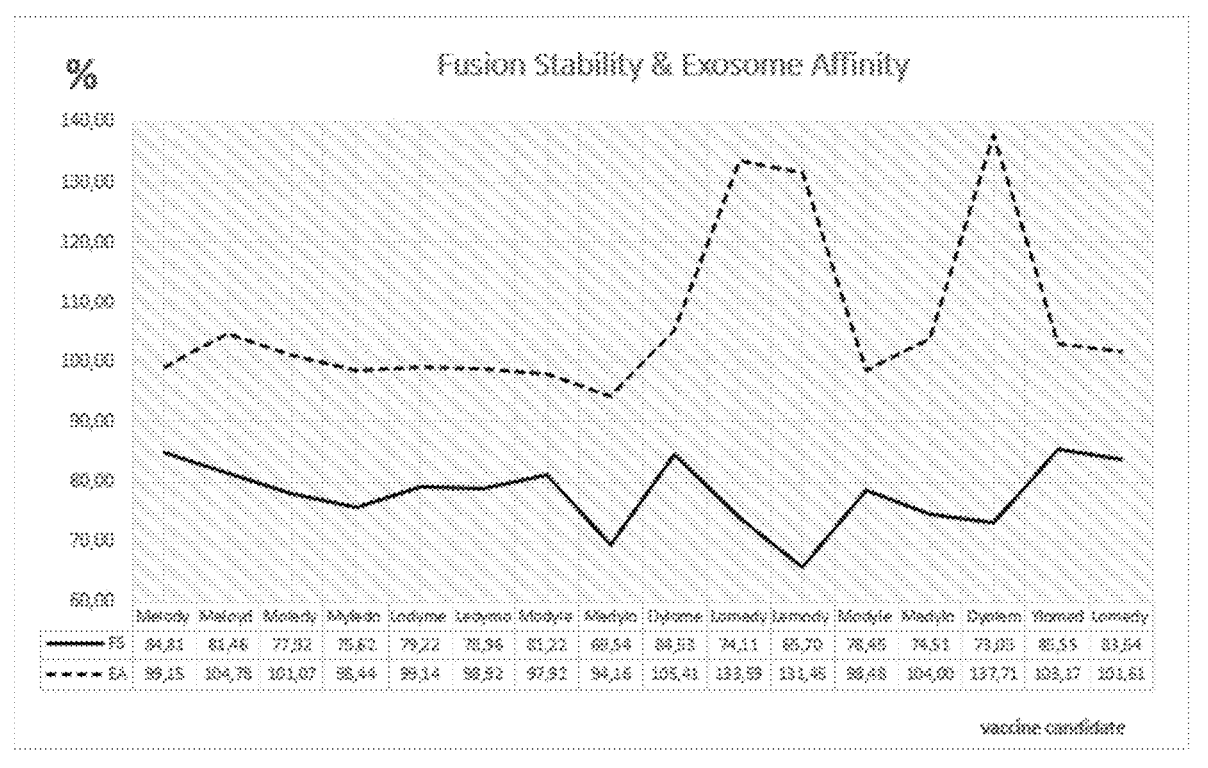

FIG. 2 is a graphic illustrating Fusion Stability against Exosome affinity in sixteen vaccines candidates.

DETAILED DESCRIPTION OF THE PREFERRED EMBODIMENT

Figure 1:
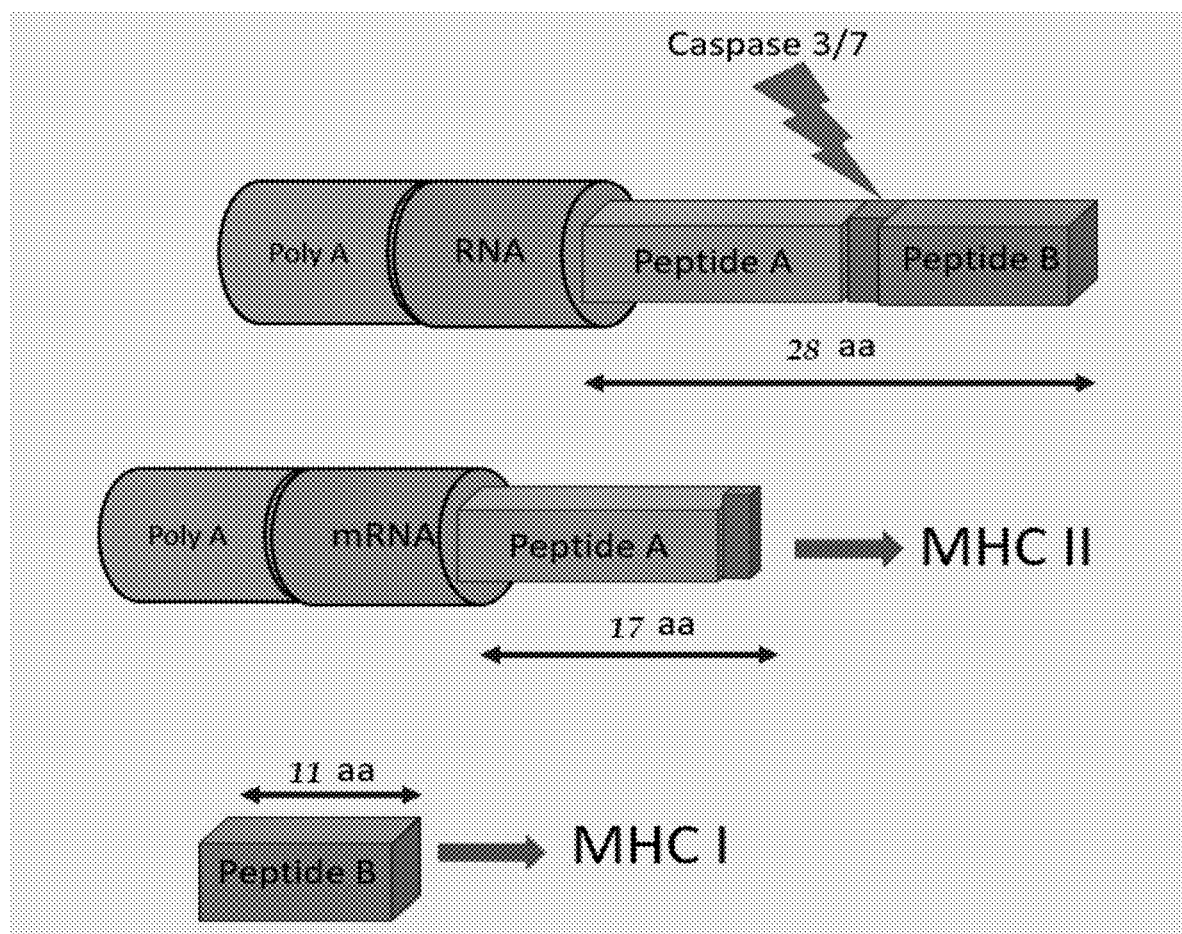
FIG. 1 is a Schema of structure of RNA-peptide vaccine.
Figure 3:
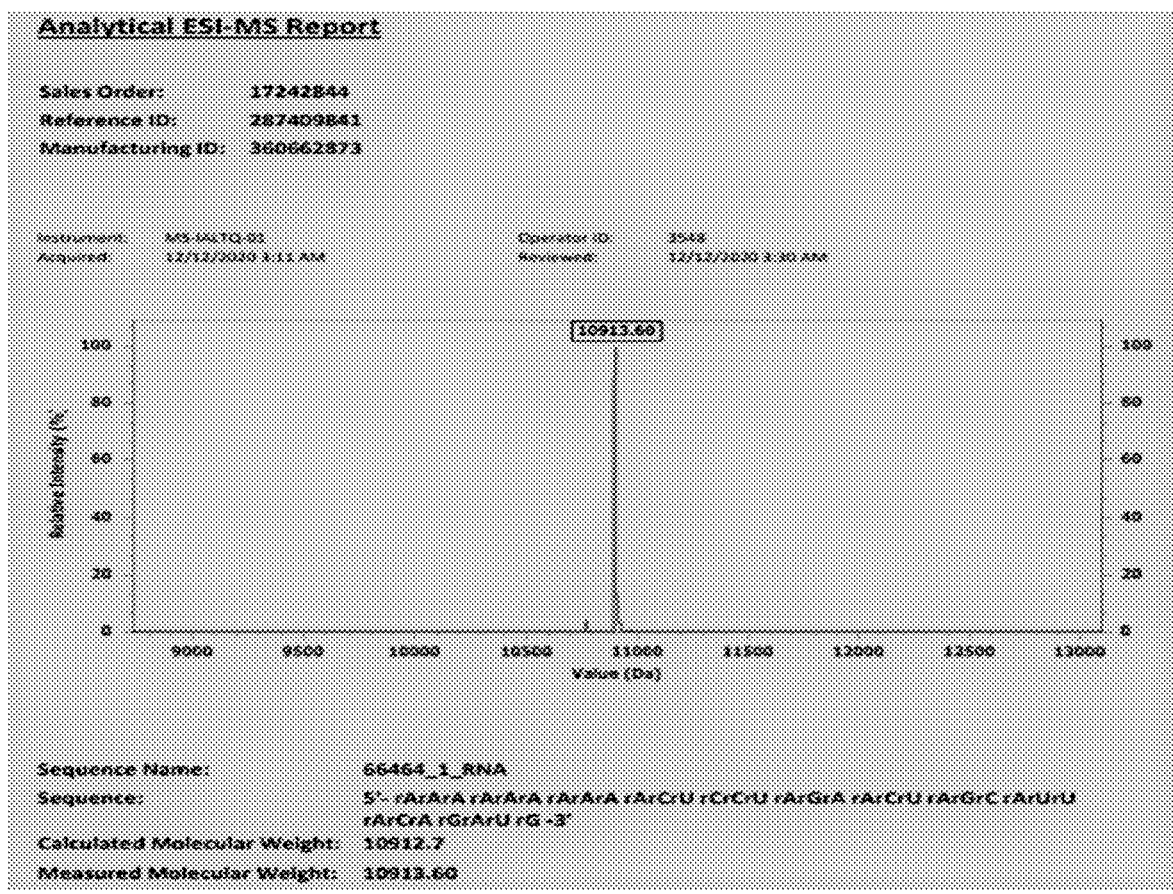
FIG. 3 is a graphic showing the Analytical ESI-MS report of SEQ ID No: 1.
Figure 4:
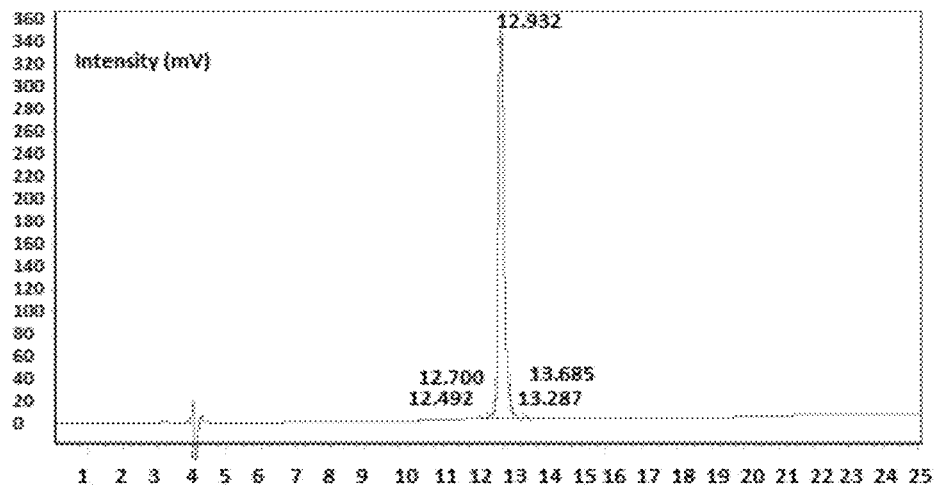
FIG. 4 is a graphic showing the HPLC report of the SEQ ID No 1.
Figure 5:
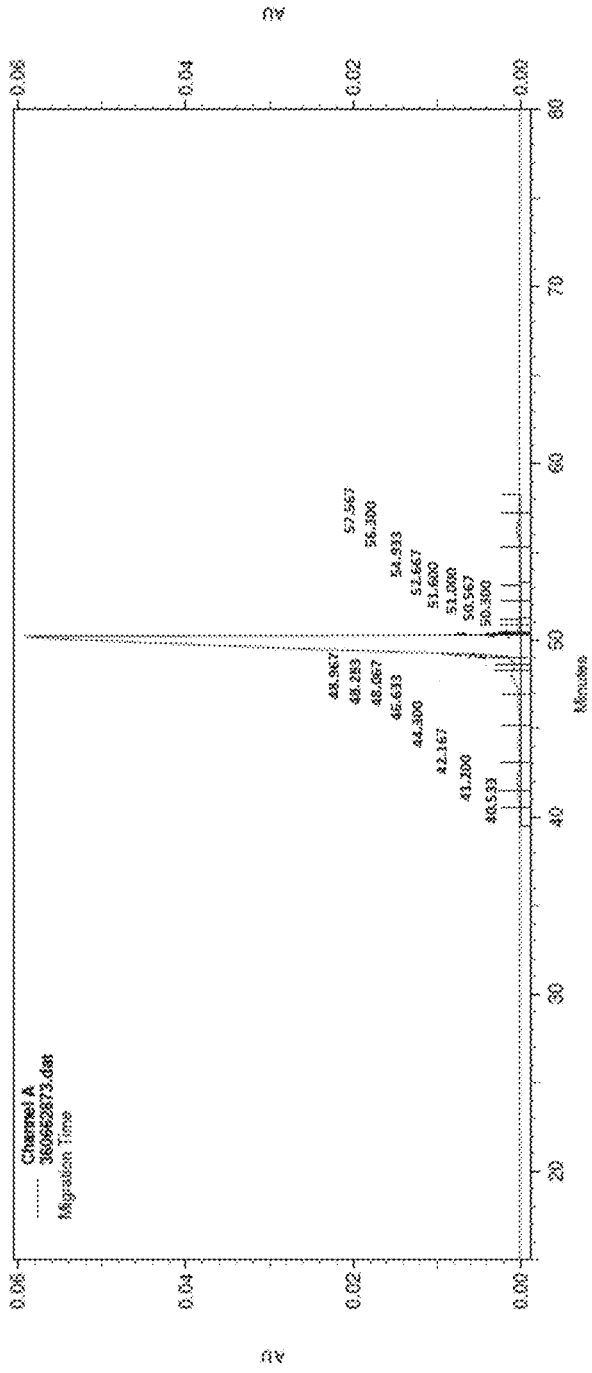
FIG. 5 is a graphic showing the Analytical OligoPro CE Report of #2 Peptide AB (SEQ ID NO: 4), MW=2990.25 Da.
Figure 6:
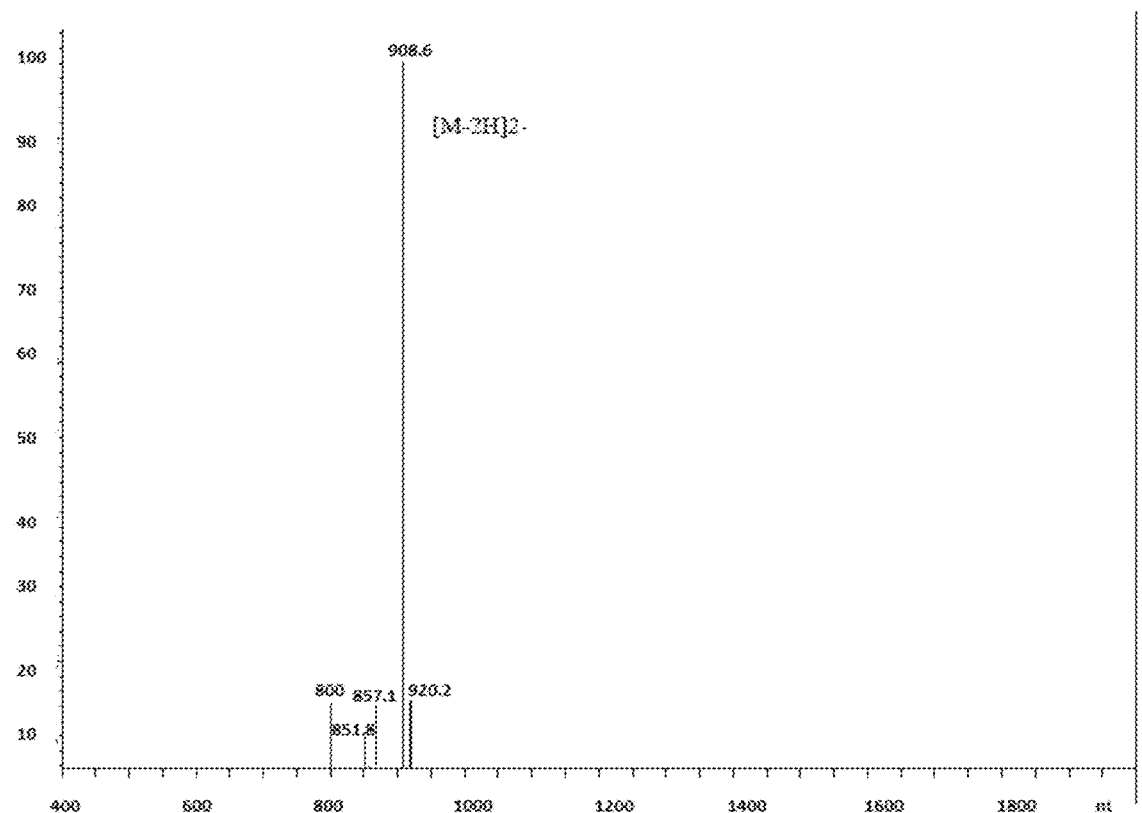
FIG. 6 is a graphic showing the Mass Spectrometry report #3 Peptide A (SEQ ID NO: 2), (MW=1819.89 Da).
Figure 7:
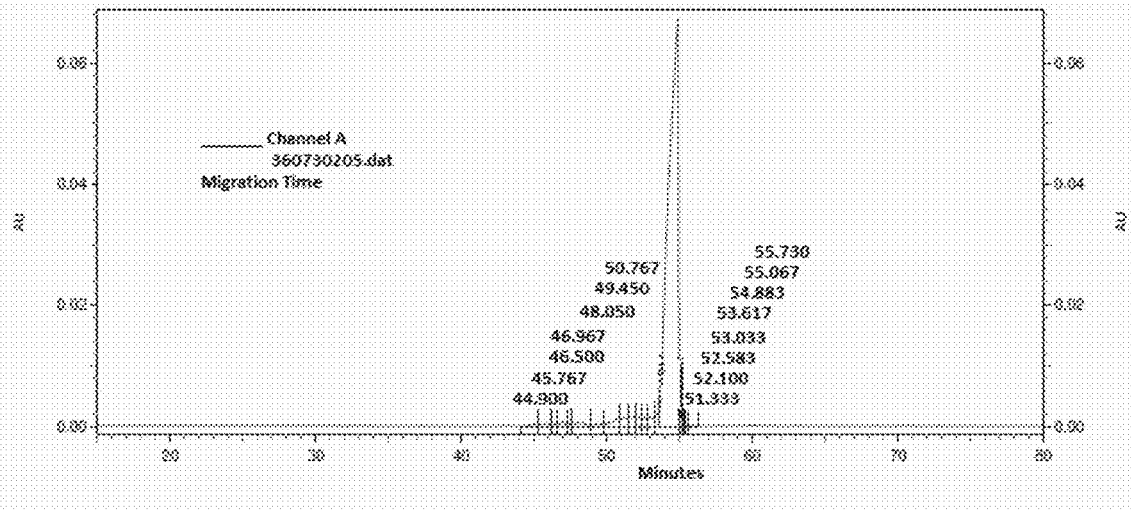
FIG. 7 is a graphic showing the Analytical OligoPro CE Report of #3 Peptide A (SEQ ID NO: 2), MW=1819.89 Da.
Figure 8:
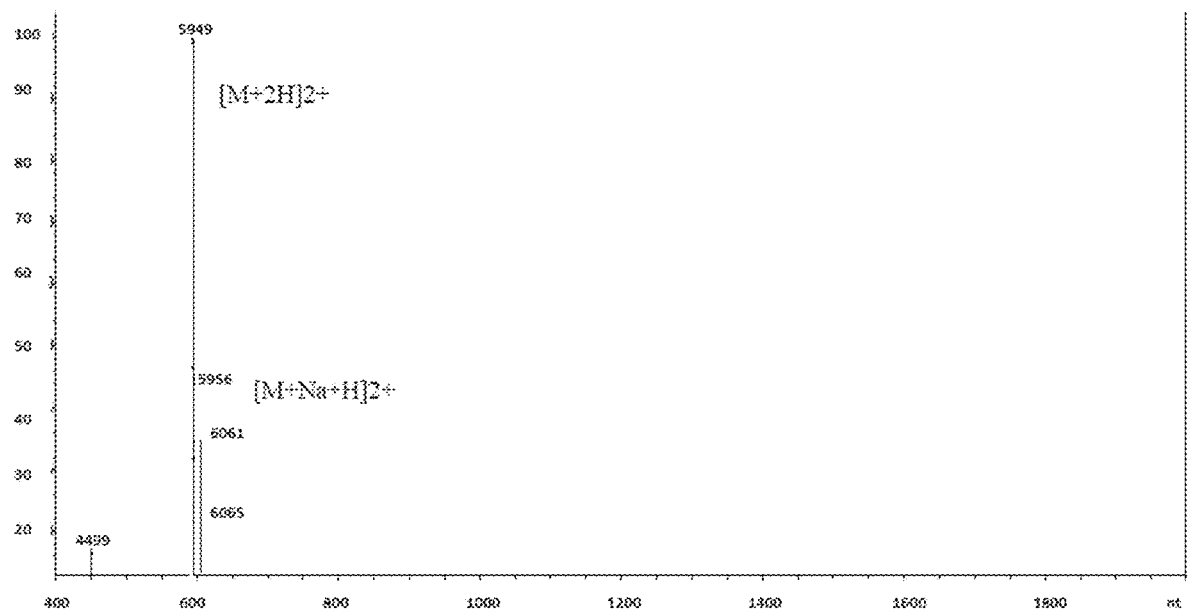
FIG. 8 is a graphic showing the Mass Spectrometry Report of #4 Peptide B (SEQ ID NO: 3), MW=1188.37 Da.
Figure 9:
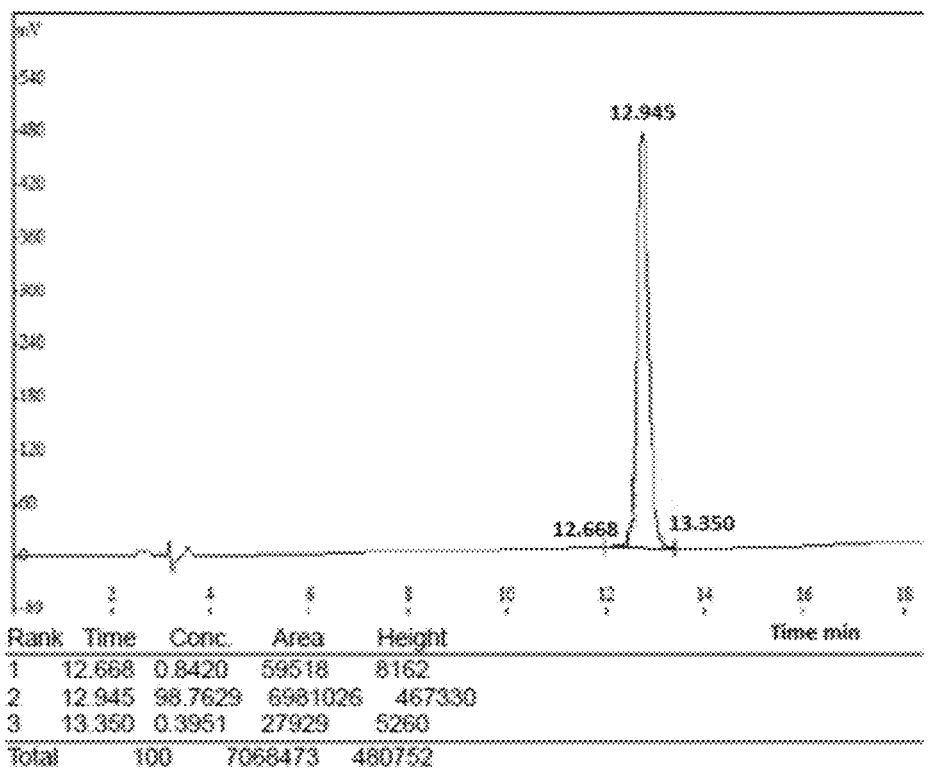
FIG. 9 is a graphic showing the HPLC Report of #5 primer-peptide AB (SEQ ID NO: 1-SEQ ID NO: 4), MW=14,680.75 Da.
Figure 10:
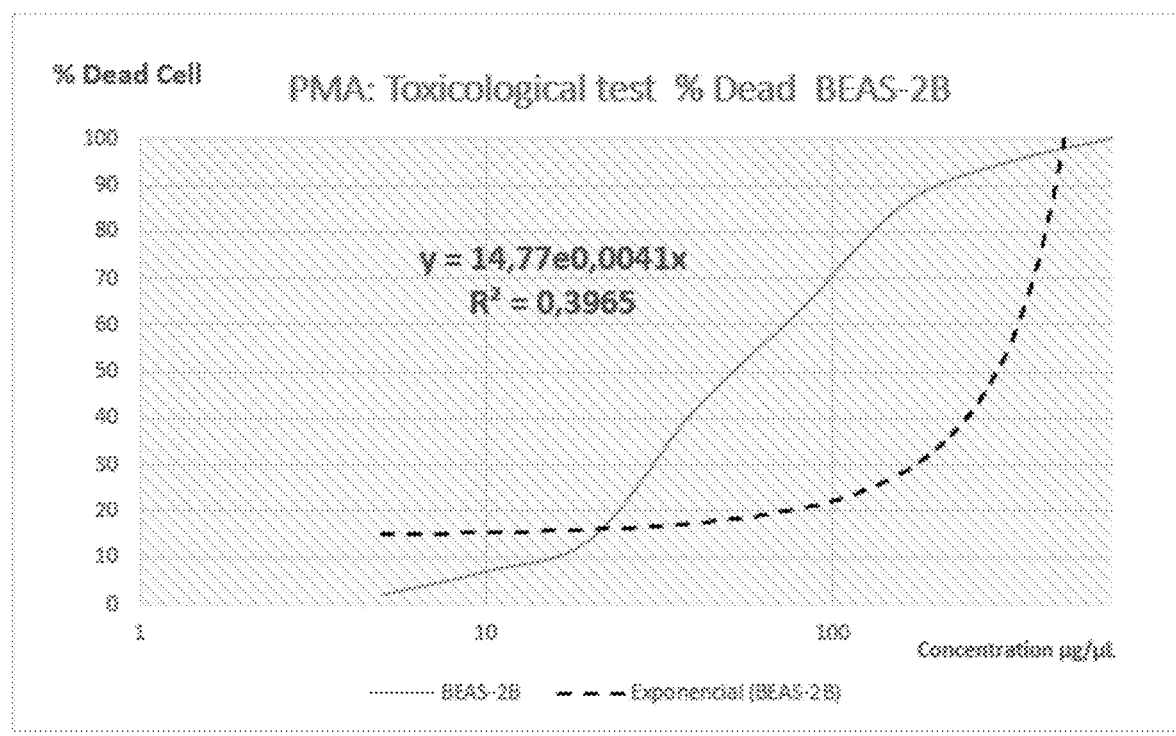
FIG. 10 is a graphic showing the PMA toxicological test in BEAS-2B cell line. The dashed curve represents the exponential dead cell according to serial concentration of PMA (5 µg/µL, 10 µg/µL, 20 µg/µL, 40 µg/µL, 80 µg/µL, 160 µg/µL, 320 µg/µL and 640 µg/µL).
Figure 11:
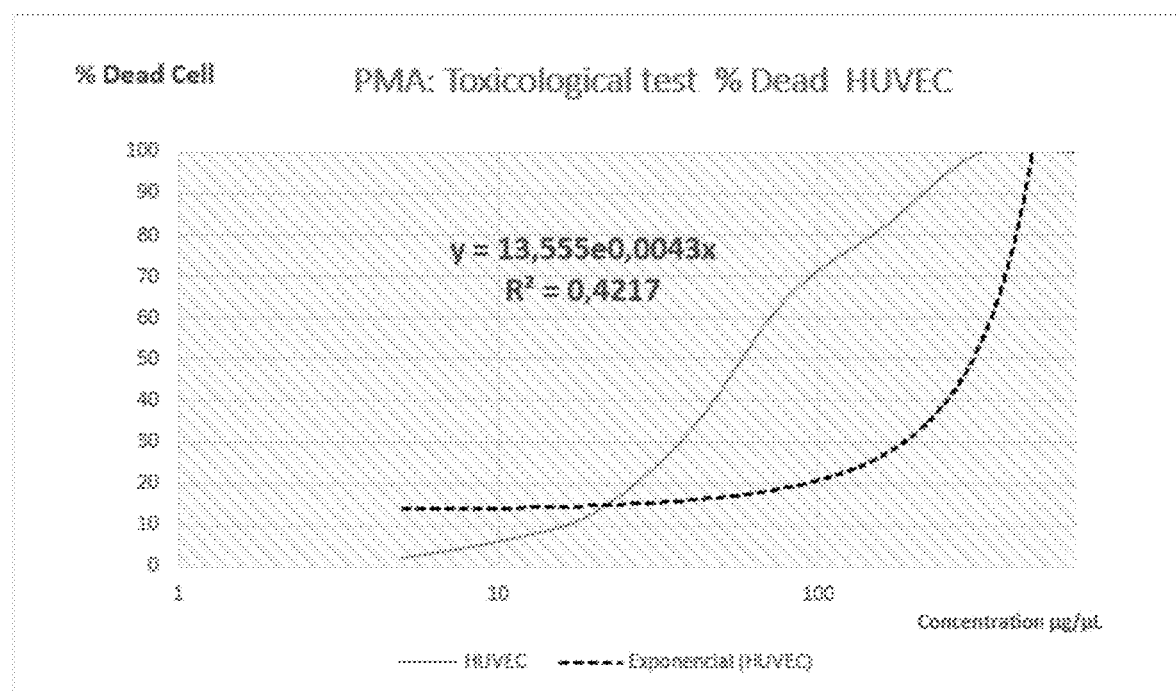
FIG. 11 is a graphic showing the PMA toxicological test in HUVEC cell line. The dashed curve represents the exponential dead cell according to serial concentration of PMA (5 µg/µL, 10 µg/µL, 20 µg/µL, 40 µg/µL, 80 µg/µL, 160 µg/µL, 320 µg/µL and 640 µg/µL).
Figure 12:
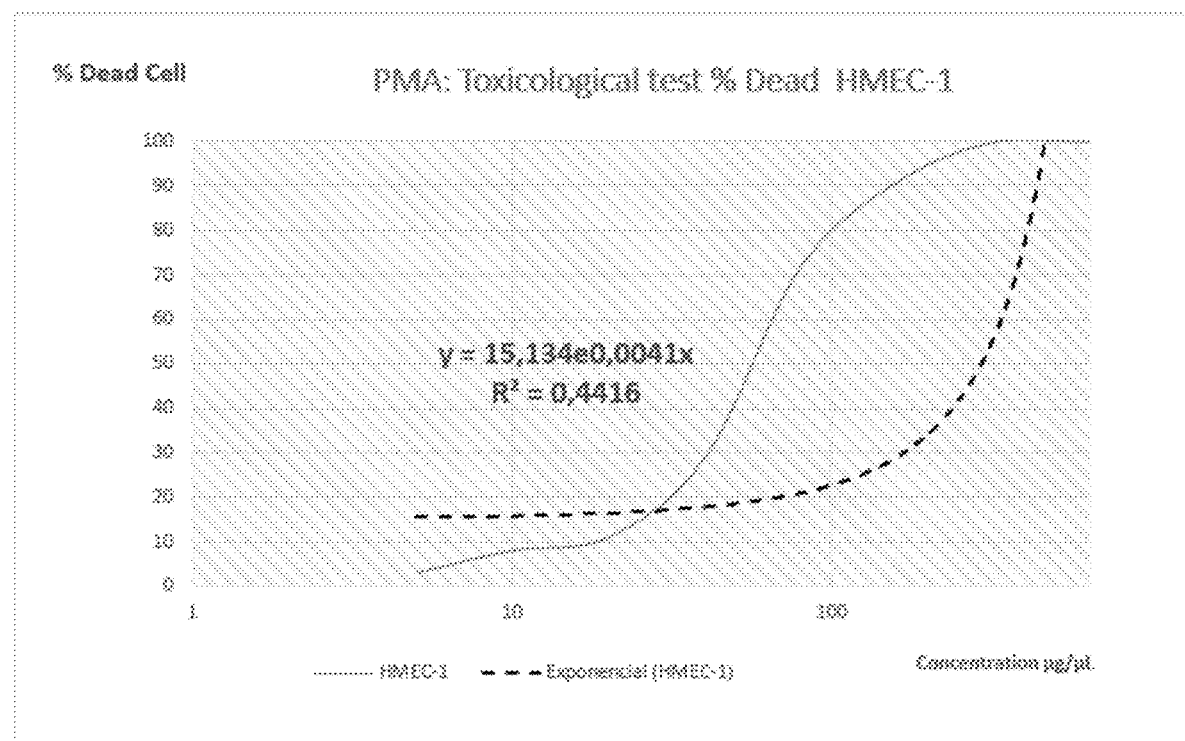
FIG. 12 is a graphic showing the PMA toxicological test in HMEC-1 cell line. The dashed curve represents the exponential dead cell according to serial concentration of PMA (5 µg/µL, 10 µg/µL, 20 µg/µL, 40 µg/µL, 80 µg/µL, 160 µg/µL, 320 µg/µL and 640 µg/µL).
Figure 13:
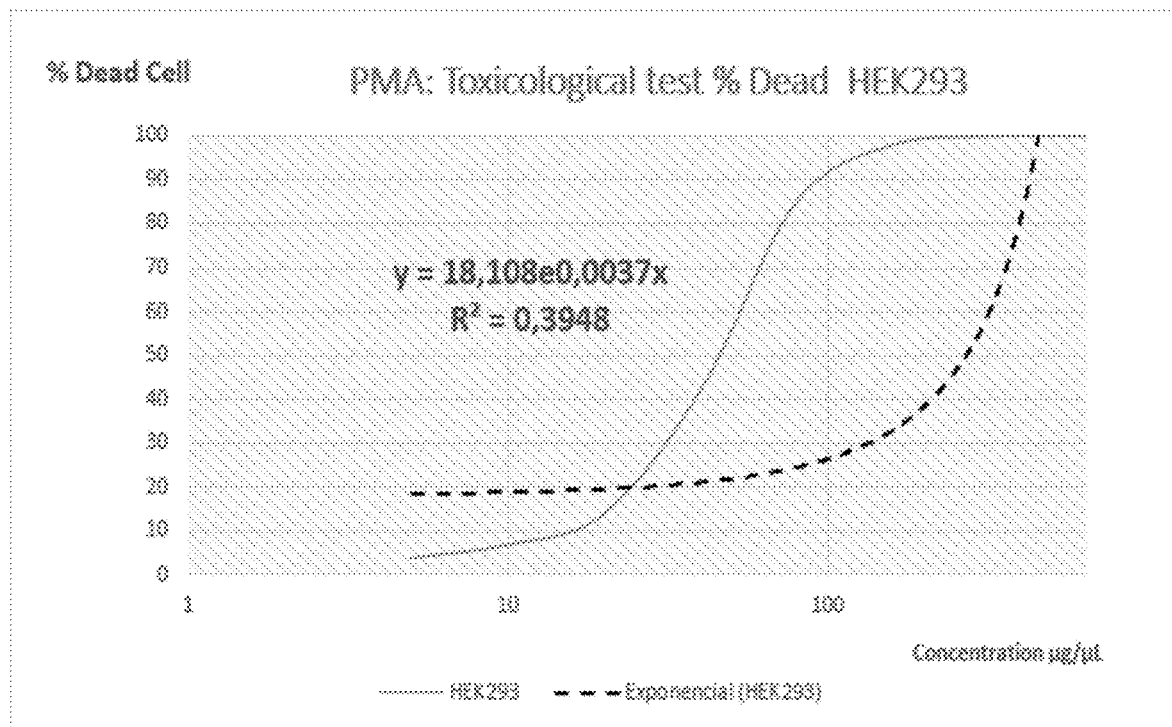
FIG. 13 is a graphic showing the PMA toxicological 1 test in HEK293 cell line. The dashed curve represents the exponential dead cell according to serial concentration of PMA (5 µg/µL, 10 µg/µL, 20 µg/µL, 40 µg/µL, 80 µg/µL, 160 µg/µL, 320 µg/µL and 640 µg/µL).
Figure 14:
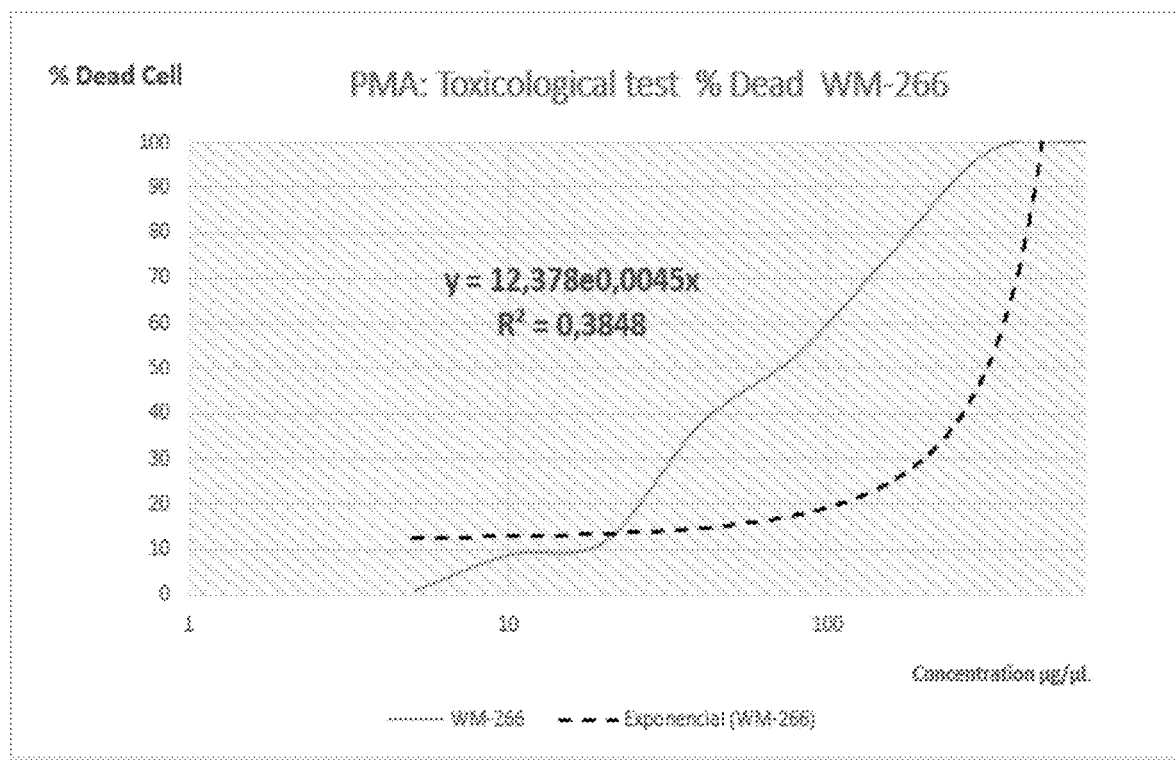
FIG. 14 is a graphic showing the PMA toxicological test in WM-266 cell line. The dashed curve represents the exponential dead cell according to serial concentration of PMA (5 µg/µL, 10 µg/µL, 20 µg/µL, 40 µg/µL, 80 µg/µL, 160 µg/µL, 320 µg/µL and 640 µg/µL).
Figure 15:
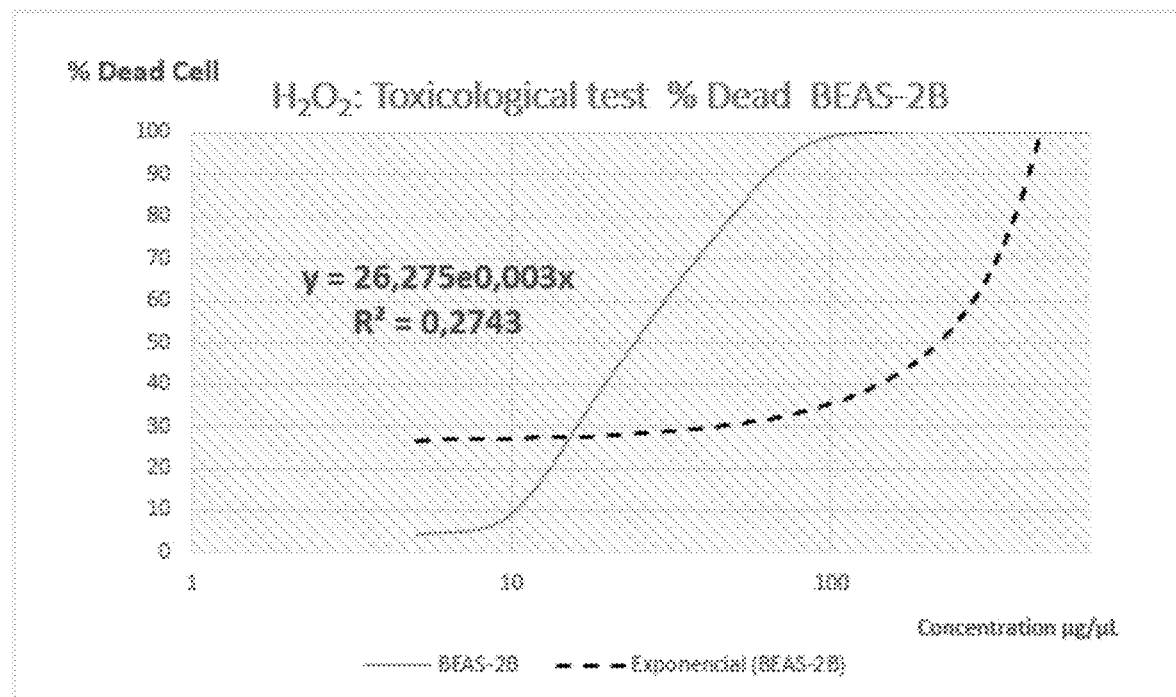
FIG. 15 is a graphic showing the $H_2O_2$ toxicological test in BEAS-2B cell line. The dashed curve represents the exponential dead cell according to serial concentration of $H_2O_2$ (5 µg/µL, 10 µg/µL, 20 µg/µL, 40 µg/µL, 80 µg/µL, 160 µg/µL, 320 µg/µL and 640 µg/µL).
Figure 16:
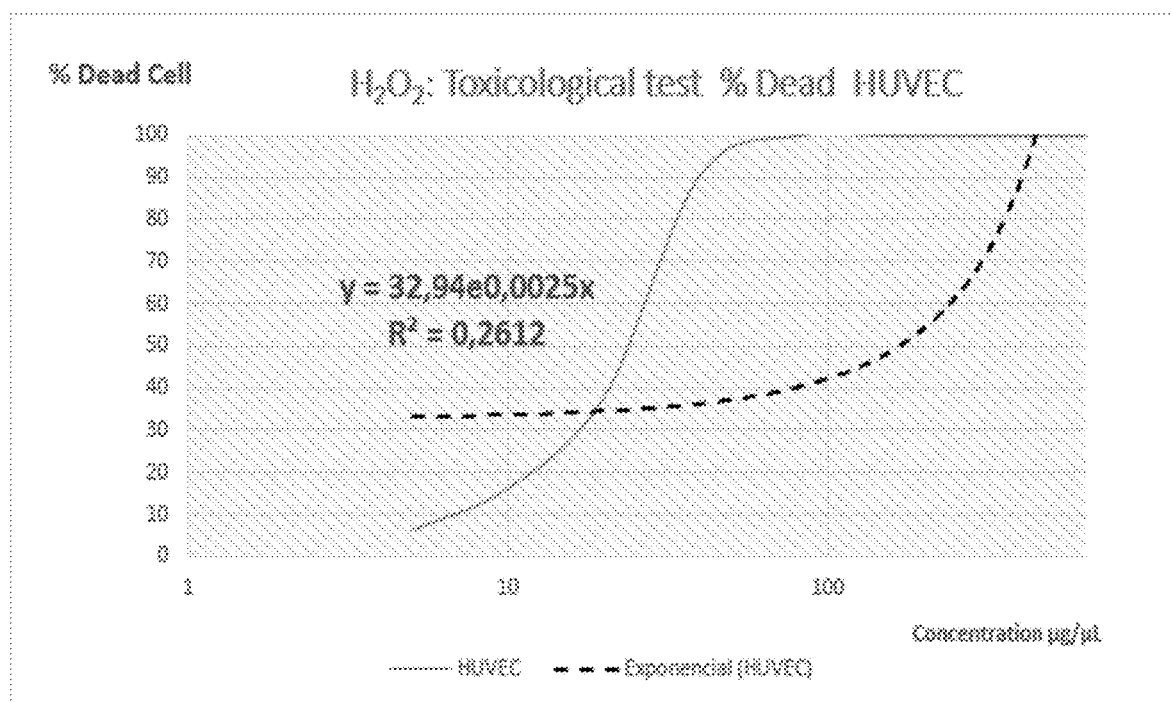
FIG. 16 is a graphic showing the $H_2O_2$ toxicological test in HUVEC cell line. The dashed curve represents the exponential dead cell according to serial concentration of $H_2O_2$ (5 µg/µL, 10 µg/µL, 20 µg/µL, 40 µg/µL, 80 µg/µL, 160 µg/µL, 320 µg/µL and 640 µg/µL).
Figure 17:
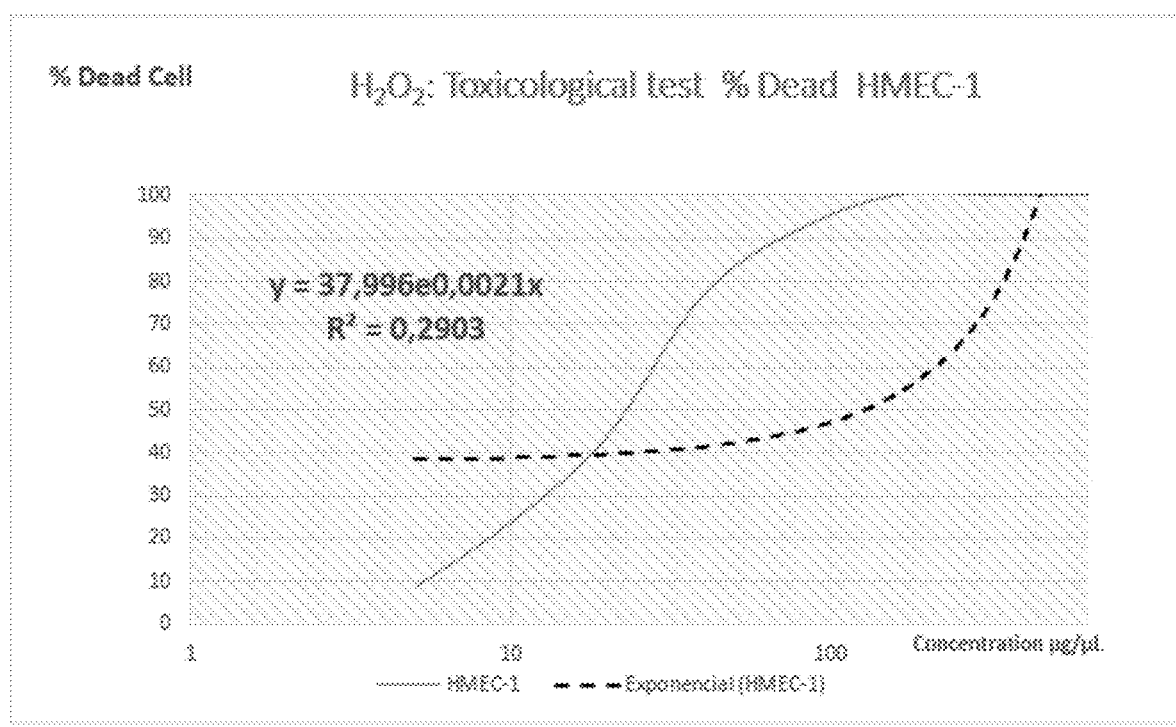
FIG. 17 is a graphic showing the $H_2O_2$ toxicological test in HMEC-1 cell line. The dashed curve represents the exponential dead cell according to serial concentration of $H_2O_2$ (5 µg/µL, 10 µg/µL, 20 µg/µL, 40 µg/µL, 80 µg/µL, 160 µg/µL, 320 µg/µL and 640 µg/µL).
Figure 18:
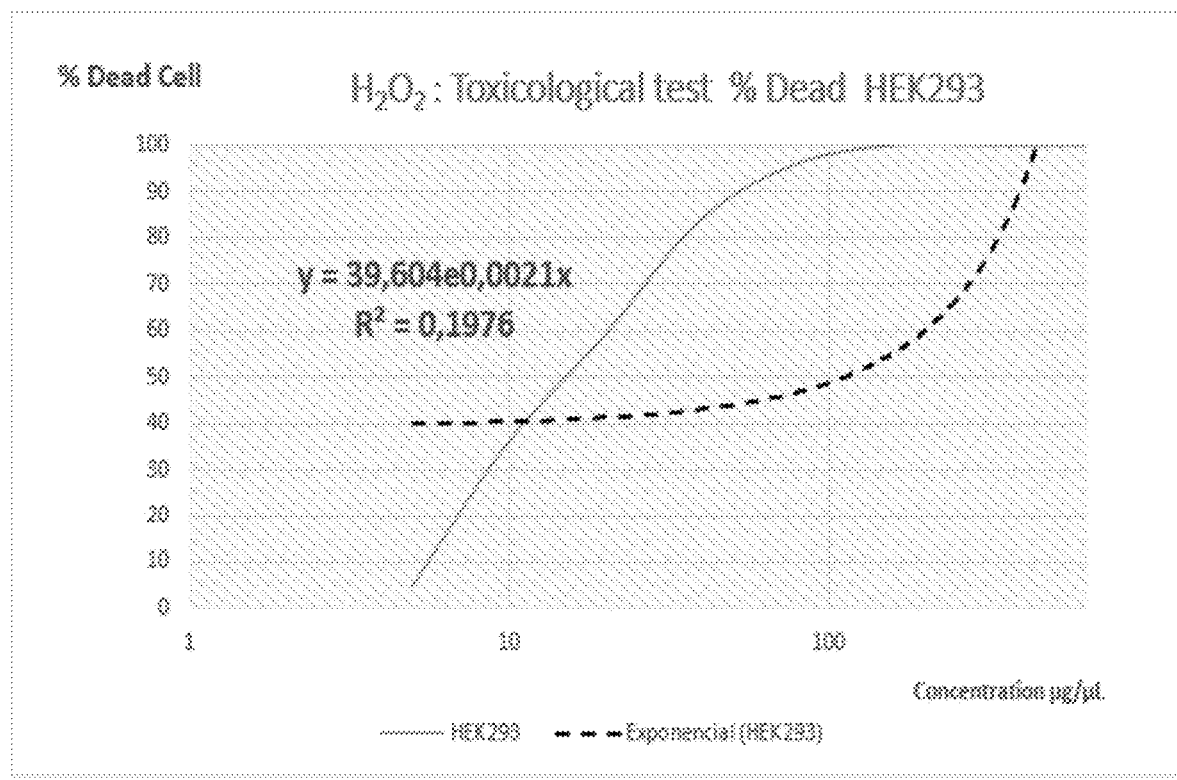
FIG. 18 is a graphic showing the $H_2O_2$ toxicological test in HEK293 cell line. The dashed curve represents the exponential dead cell according to serial concentration of $H_2O_2$ (5 µg/µL, 10 µg/µL, 20 µg/µL, 40 µg/µL, 80 µg/µL, 160 µg/µL, 320 µg/µL and 640 µg/µL).
Figure 19:
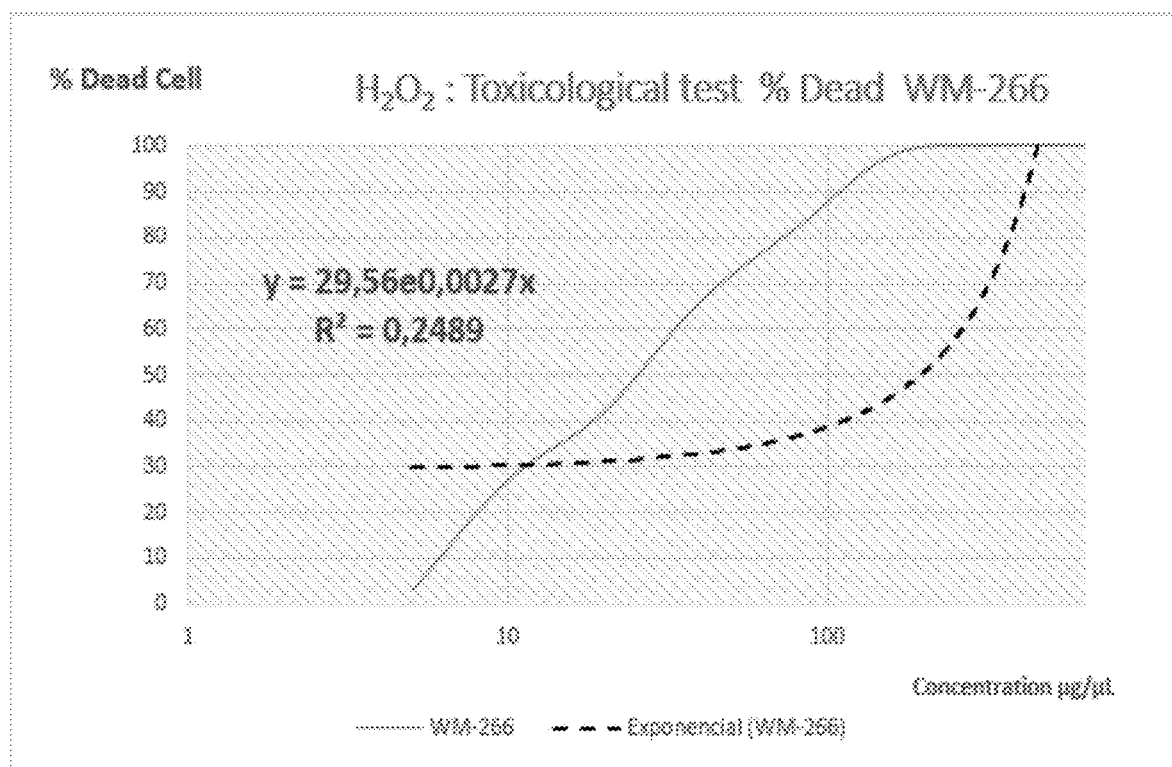
FIG. 19 is a graphic showing the $H_2O_2$ toxicological test in WM-266 cell line. The dashed curve represents the exponential dead cell according to serial concentration of $H_2O_2$ (5 µg/µL, 10 µg/µL, 20 µg/µL, 40 µg/µL, 80 µg/µL, 160 µg/µL, 320 µg/µL and 640 µg/µL).
Figure 20:
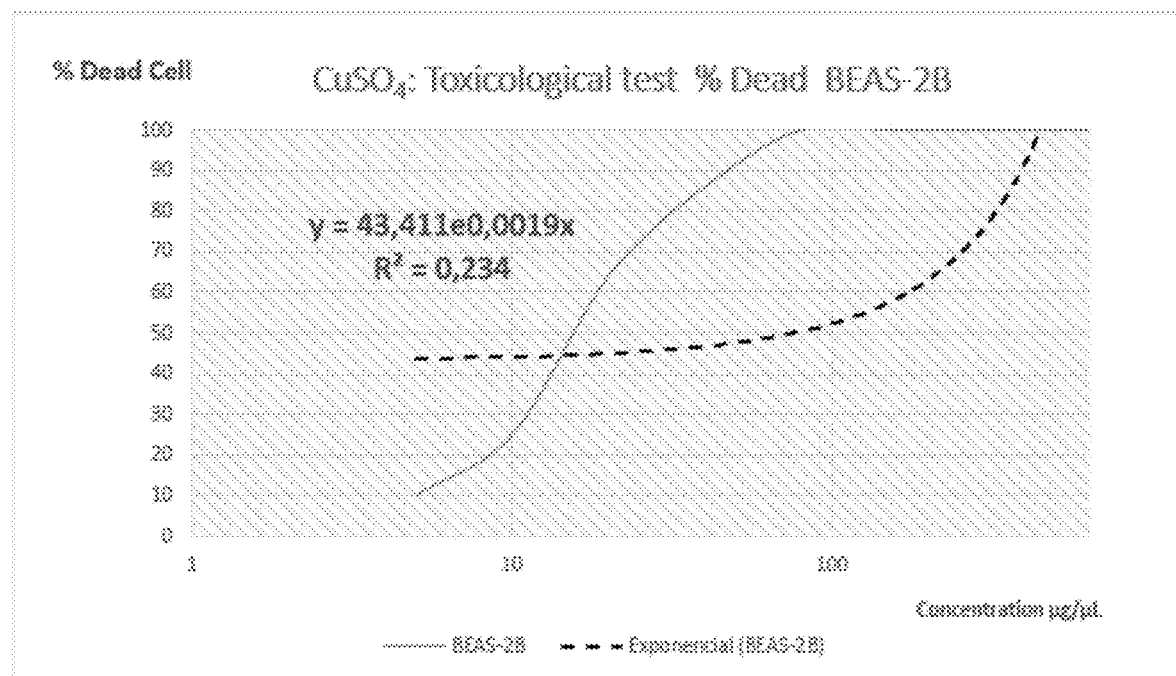
FIG. 20 is a graphic showing the $CuSO_4$ toxicological test in BEAS cell line. The dashed curve represents the exponential dead cell according to serial concentration of $CuSO_4$ (5 µg/µL, 10 µg/µL, 20 µg/µL, 40 µg/µL, 80 µg/µL, 160 µg/µL, 320 µg/µL and 640 µg/µL).
Figure 21:
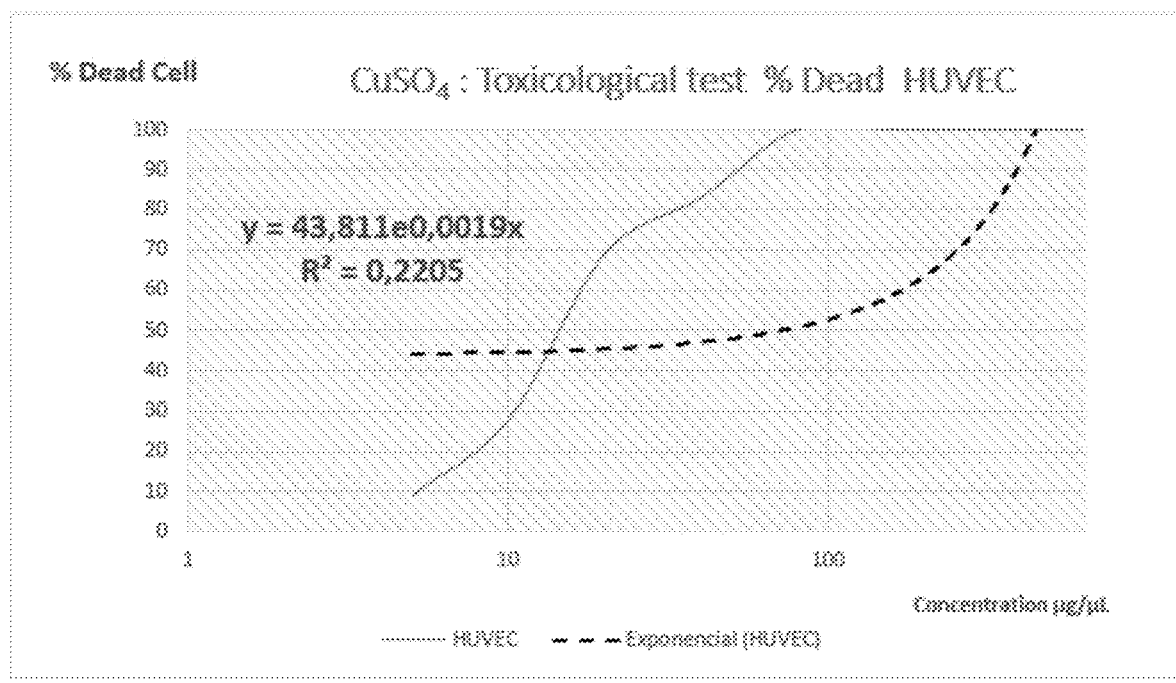
FIG. 21 is a graphic showing the $CuSO_4$ toxicological test in HUVEC cell line. The dashed curve represents the exponential dead cell according to serial concentration of $CuSO_4$ (5 µg/µL, 10 µg/µL, 20 µg/µL, 40 µg/µL, 80 µg/µL, 160 µg/µL, 320 µg/µL and 640 µg/µL).
Figure 22:
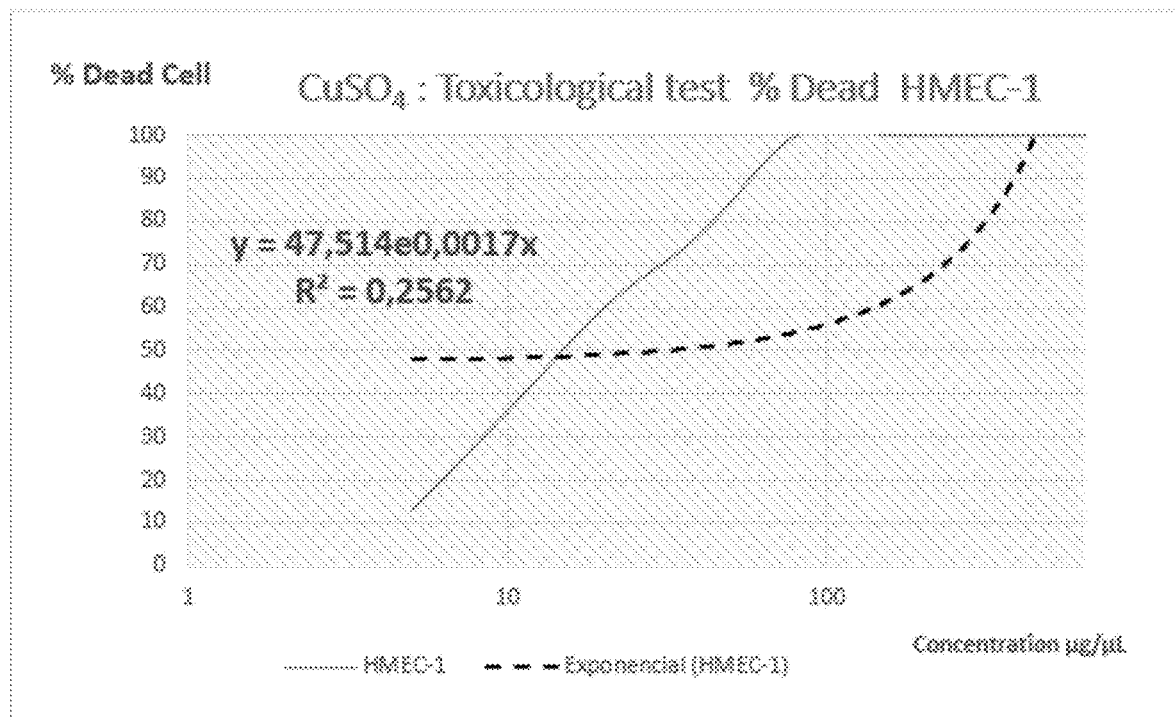
FIG. 22 is a graphic showing the $CuSO_4$ toxicological test in HMEC-1 cell line. The dashed curve represents the exponential dead cell according to serial concentration of $CuSO_4$ (5 µg/µL, 10 µg/µL, 20 µg/µL, 40 µg/µL, 80 µg/µL, 160 µg/µL, 320 µg/µL and 640 µg/µL).
Figure 23:
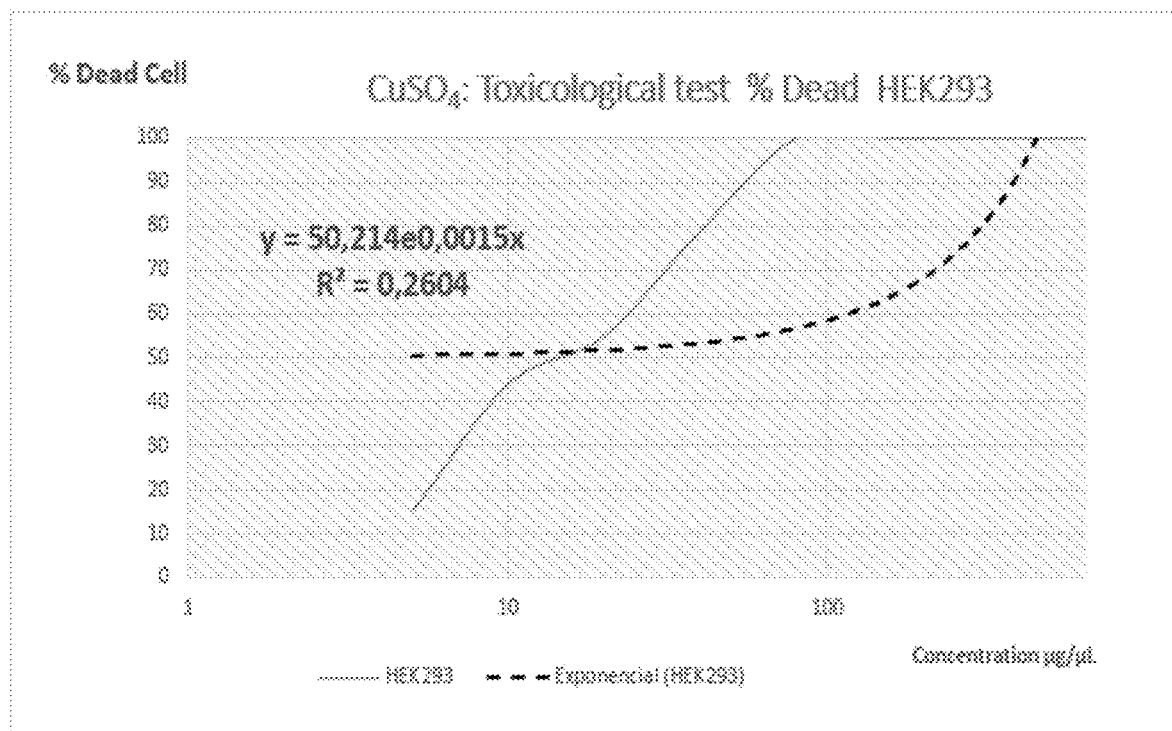
FIG. 23 is a graphic showing the $CuSO_4$ toxicological test in HEK293 cell line. The dashed curve represents the exponential dead cell according to serial concentration of $CuSO_4$ (5 µg/µL, 10 µg/µL, 20 µg/µL, 40 µg/µL, 80 µg/µL, 160 µg/µL, 320 µg/µL and 640 µg/µL).
Figure 24:
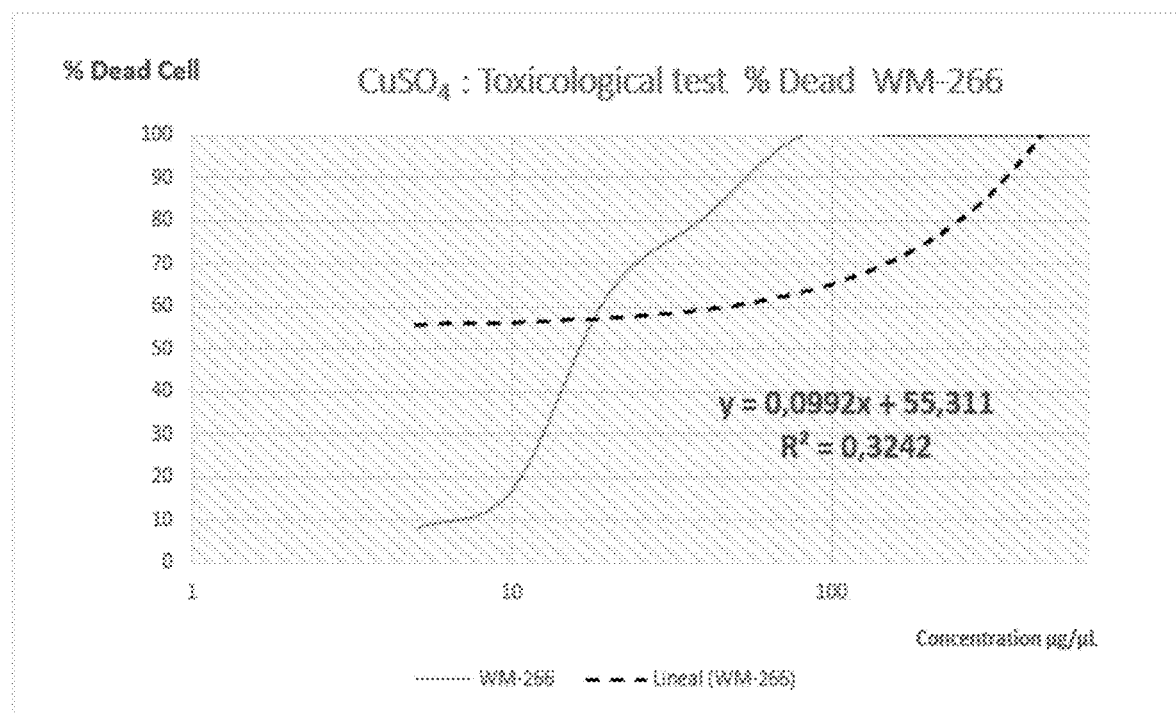
FIG. 24 is a graphic showing the $CuSO_4$ toxicological test in WM-266 cell line. The dashed curve represents the exponential dead cell according to serial concentration of $CuSO_4$ (5 µg/µL, 10 µg/µL, 20 µg/µL, 40 µg/µL, 80 µg/µL, 160 µg/µL, 320 µg/µL and 640 µg/µL).
Figure 25:
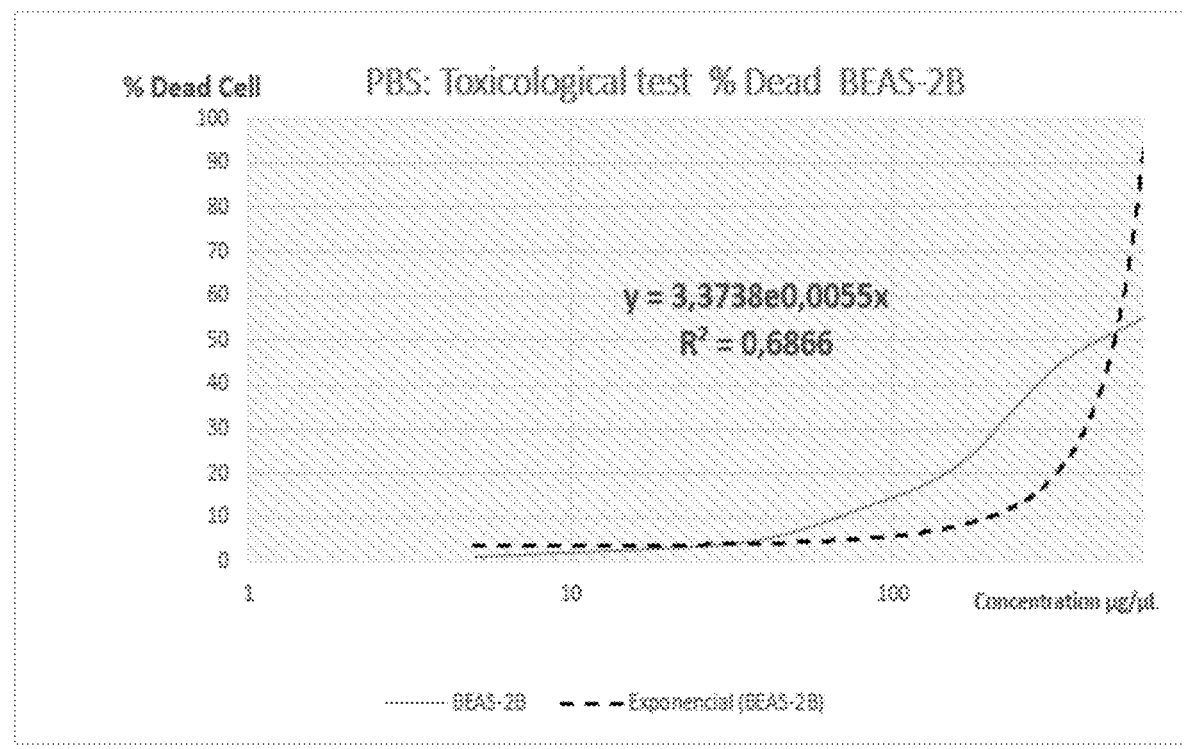
FIG. 25 is a graphic showing the PBS toxicological test in BEAS-2B cell line. The dashed curve represents the exponential dead cell according to serial concentration of PBS (5 µg/µL, 10 µg/µL, 20 µg/µL, 40 µg/µL, 80 µg/µL, 160 µg/µL, 320 µg/µL and 640 µg/µL).
Figure 26:
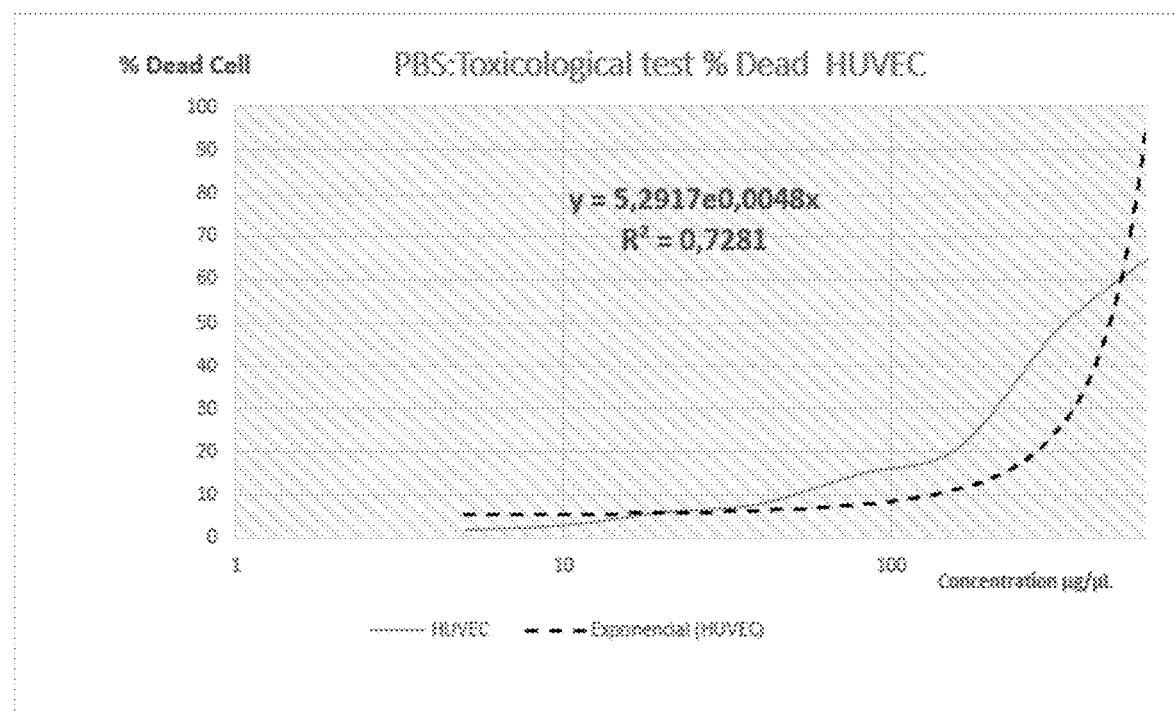
FIG. 26 is a graphic showing the PBS toxicological test in HUVEC cell line. The dashed curve represents the exponential dead cell according to serial concentration of PBS 1 (5 µg/µL, 10 µg/µL, 20 µg/µL, 40 µg/µL, 80 µg/µL, 160 µg/L, 320 µg/µL and 640 µg/µL).
Figure 27:
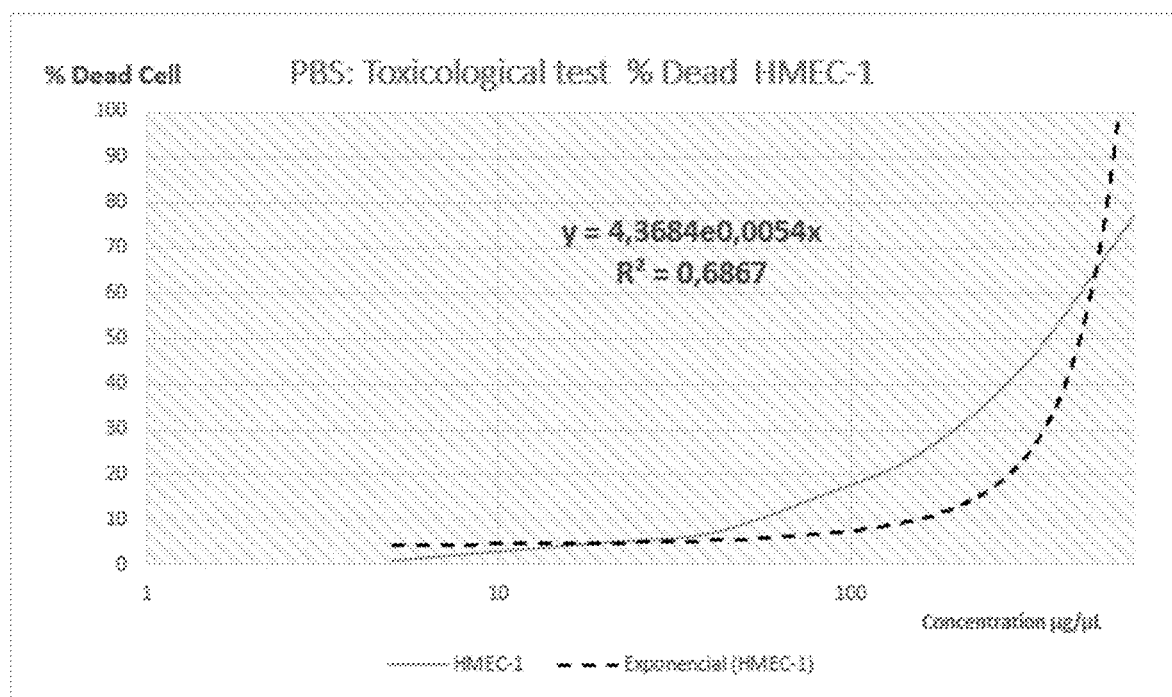
FIG. 27 is a graphic showing the PBS toxicological test in HMEC-1 cell line. The dashed curve represents the exponential dead cell according to serial concentration of PBS (5 µg/µL, 10 µg/µL, 20 µg/µL, 40 µg/µL, 80 µg/µL, 160 µg/µL, 320 µg/µL and 640 µg/µL).
Figure 28:
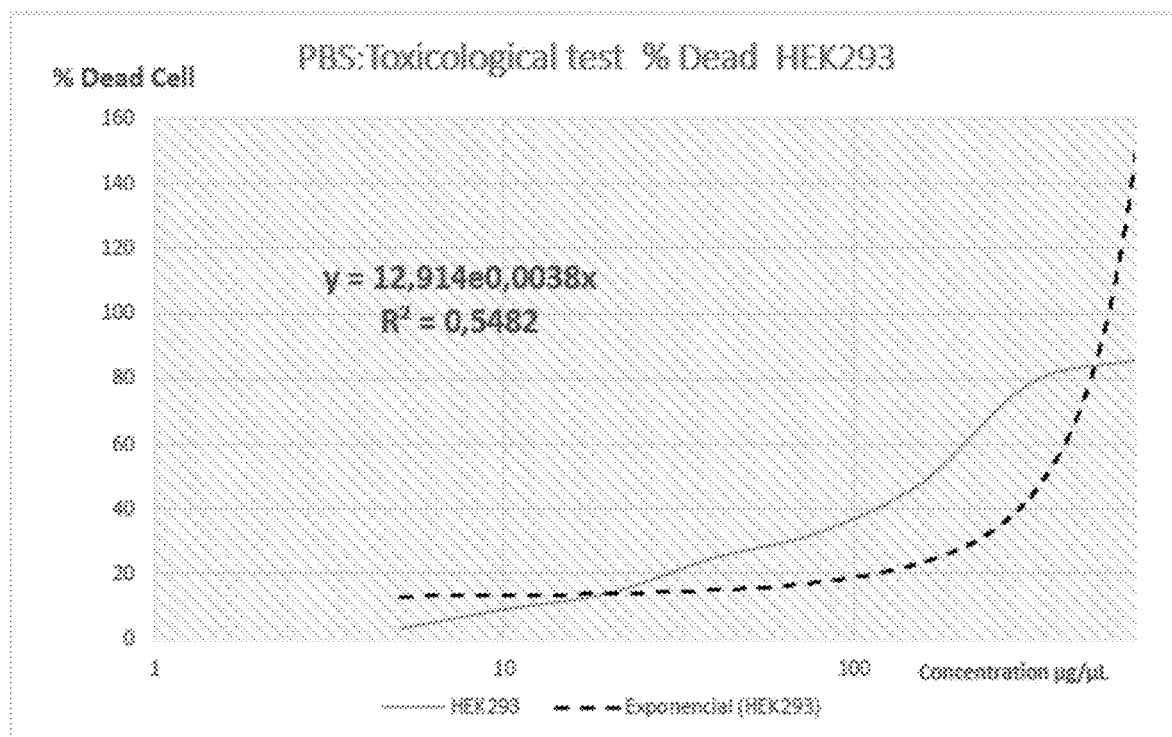
FIG. 28 is a graphic showing the PBS toxicological test in HEK293 cell line. The dashed curve represents the exponential dead cell according to serial concentration of PBS (5 µg/µL, 10 µg/µL, 20 µg/µL, 40 µg/µL, 80 µg/µL, 160 µg/µL, 320 µg/µL and 640 µg/µL).
Figure 29:
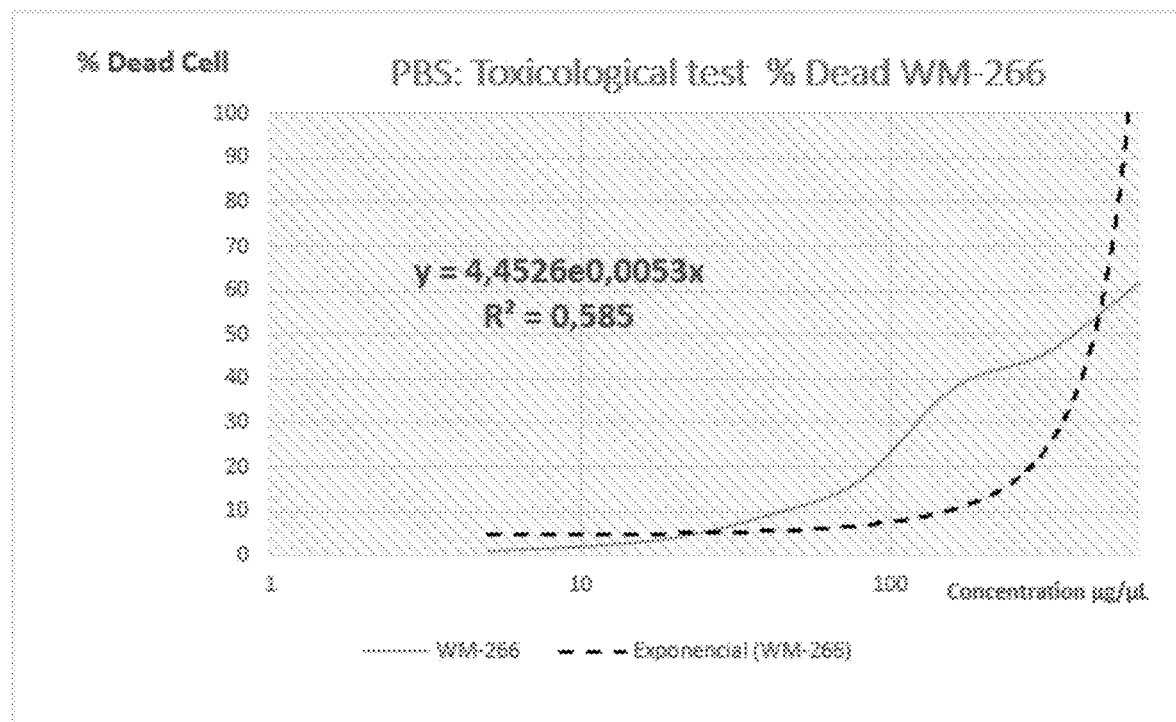
FIG. 29 is a graphic showing the PBS toxicological test in WM-266 cell line. The dashed curve represents the exponential dead cell according to serial concentration of PBS (5 µg/µL, 10 µg/µL, 20 µg/µL, 40 µg/µL, 80 µg/µL, 160 µg/µL, 320 µg/µL and 640 µg/µL).
Figure 30:
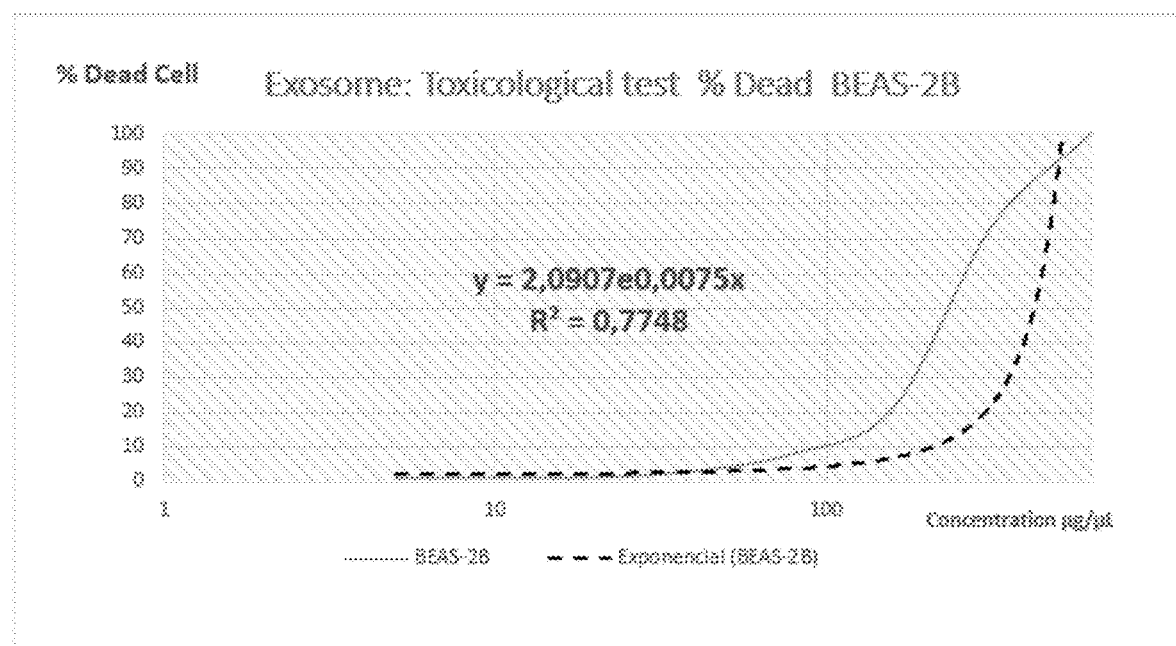
FIG. 30 is a graphic showing the exosome toxicological test in BEAS-2B cell line. The dashed curve represents the exponential dead cell according to serial concentration of exosome (5 µg/µL, 10 µg/µL, 20 µg/µL, 40 µg/µL, 80 µg/µL, 160 µg/µL, 320 µg/µL and 640 µg/µL).
Figure 31:
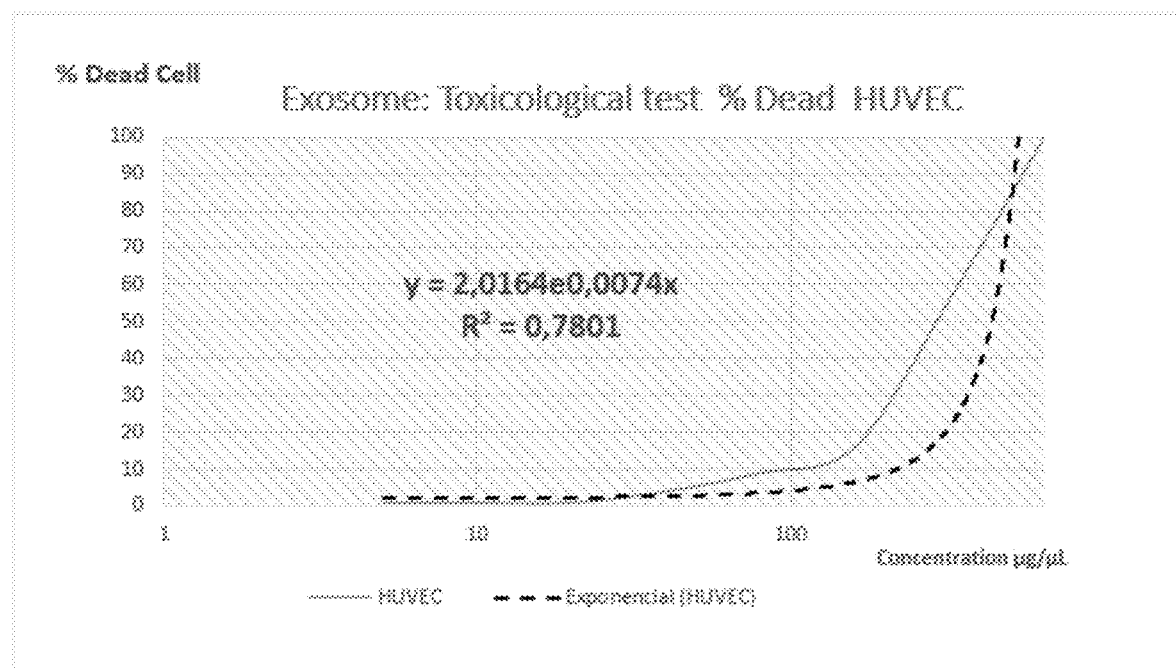
FIG. 31 is a graphic showing the exosome toxicological test in HUVEC cell line. The dashed curve represents the exponential dead cell according to serial concentration of exosome (5 µg/µL, 10 µg/µL, 20 µg/µL, 40 µg/µL, 80 µg/µL, 160 µg/µL, 320 µg/µL and 640 µg/µL).
Figure 32:
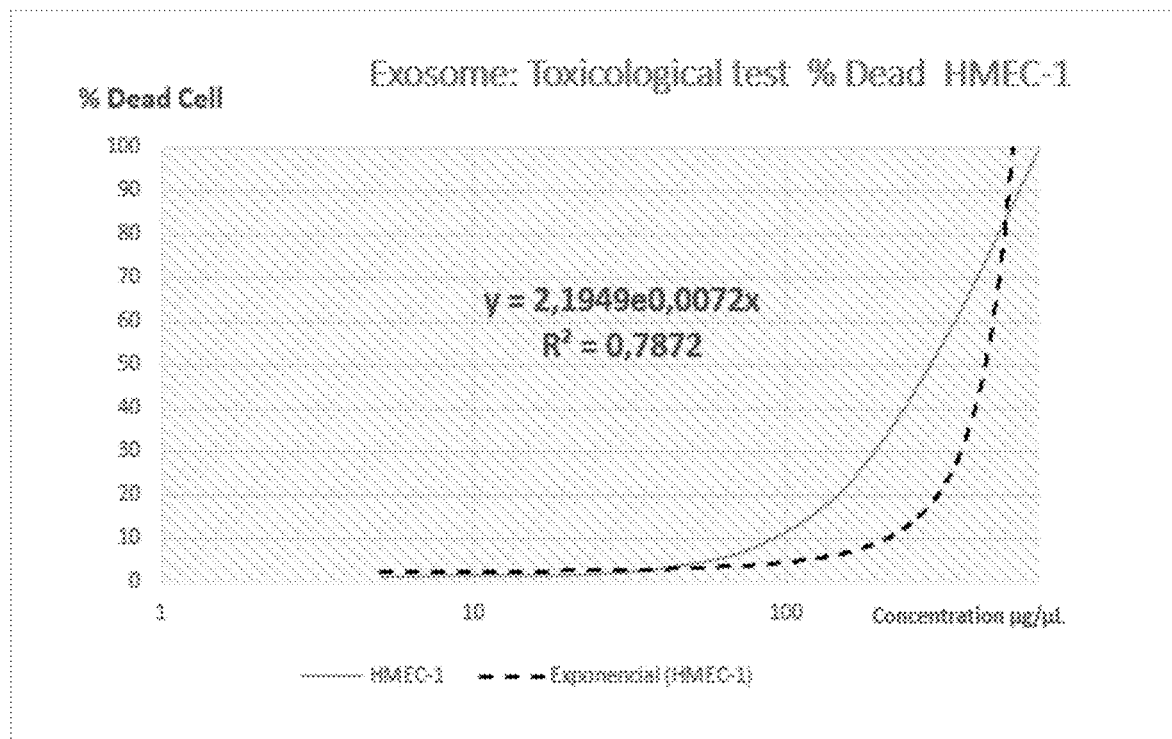
FIG. 32 is a graphic showing the exosome toxicological test in HMEC-1 cell line. The dashed curve represents the exponential dead cell according to serial concentration of exosome (5 µg/µL, 10 µg/µL, 20 µg/µL, 40 µg/µL, 80 µg/µL, 160 µg/µL, 320 µg/µL and 640 µg/µL).
Figure 33:
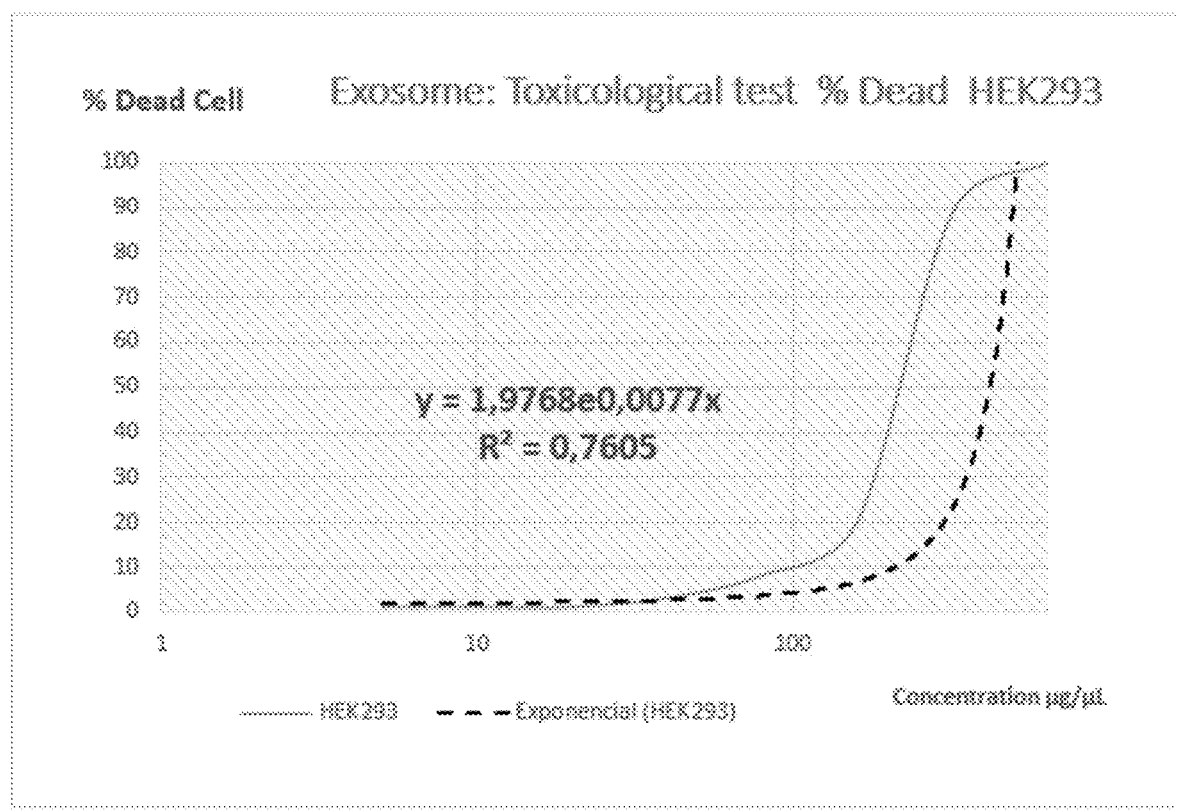
FIG. 33 is a graphic showing the exosome toxicological test in HEK293 cell line. The dashed curve represents the exponential dead cell according to serial concentration of exosome (5 µg/µL, 10 µg/µL, 20 µg/µL, 40 µg/µL, 80 µg/µL, 160 µg/µL, 320 µg/µL and 640 µg/µL).
Figure 34:
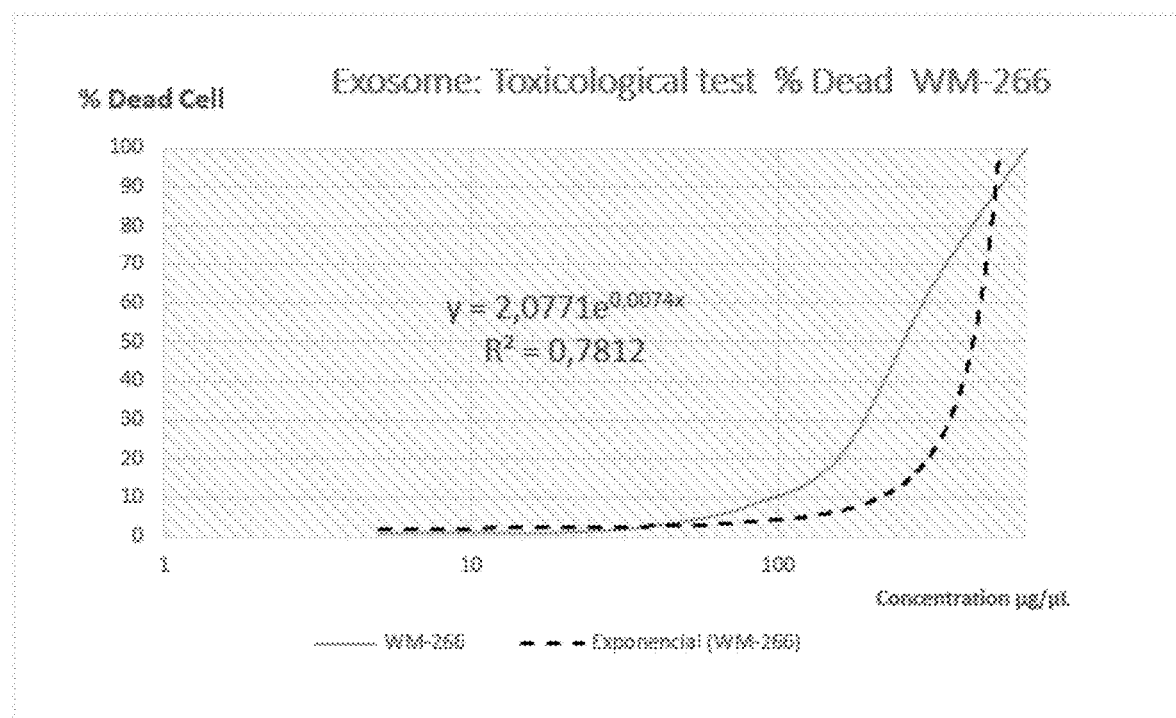
FIG. 34 is a graphic showing the exosome toxicological test in WM-266 cell line. The dashed curve represents the exponential dead cell according to serial concentration of exosome (5 µg/µL, 10 µg/µL, 20 µg/µL, 40 µg/µL, 80 µg/µL, 160 µg/µL, 320 µg/µL and 640 µg/µL).
Figure 35:
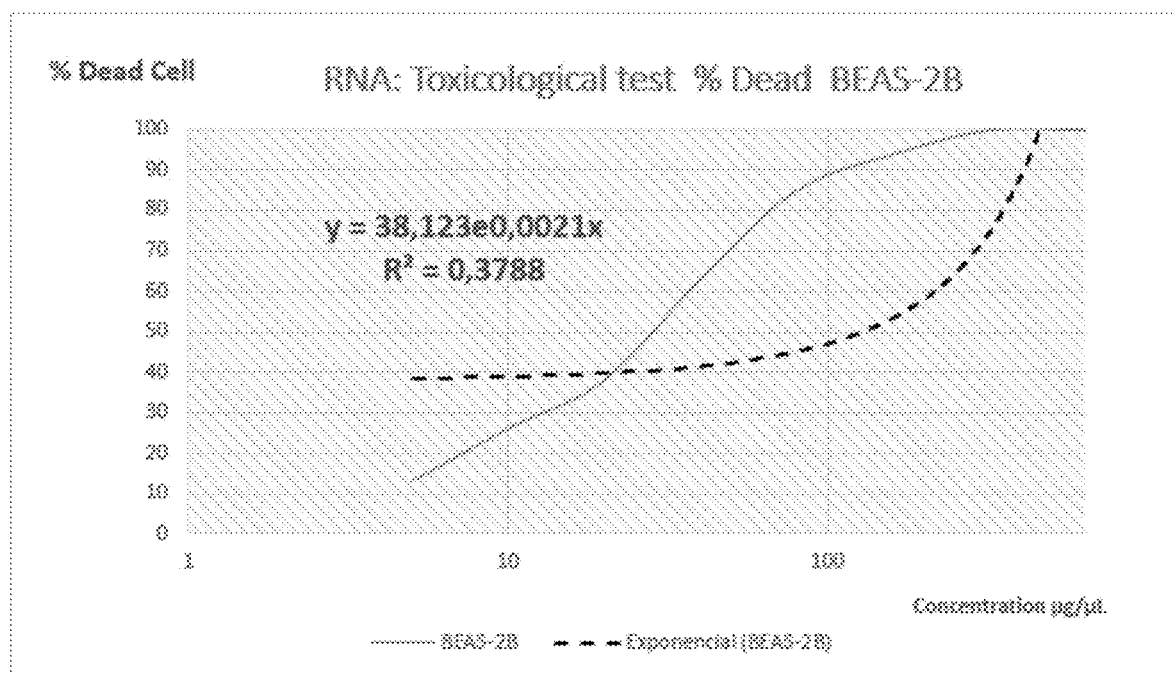
FIG. 35 is a graphic showing the RNA toxicological test in BEAS-2B cell line. The dashed curve represents the exponential dead cell according to serial concentration 1 of RNA (5 µg/µL, 10 µg/µL, 20 µg/µL, 40 µg/µL, 80 µg/µL, 160 µg/µL, 320 µg/µL and 640 µg/µL).
Figure 36:
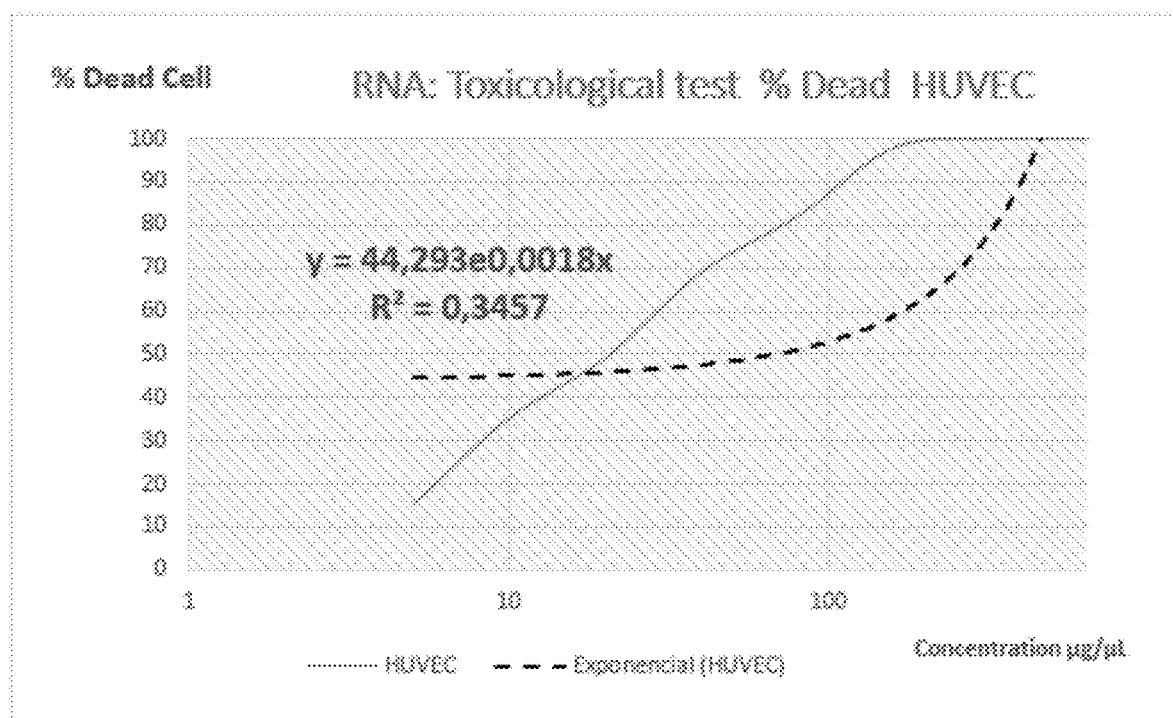
FIG. 36 is a graphic showing the RNA toxicological test in HUVEC cell line. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL).
Figure 37:
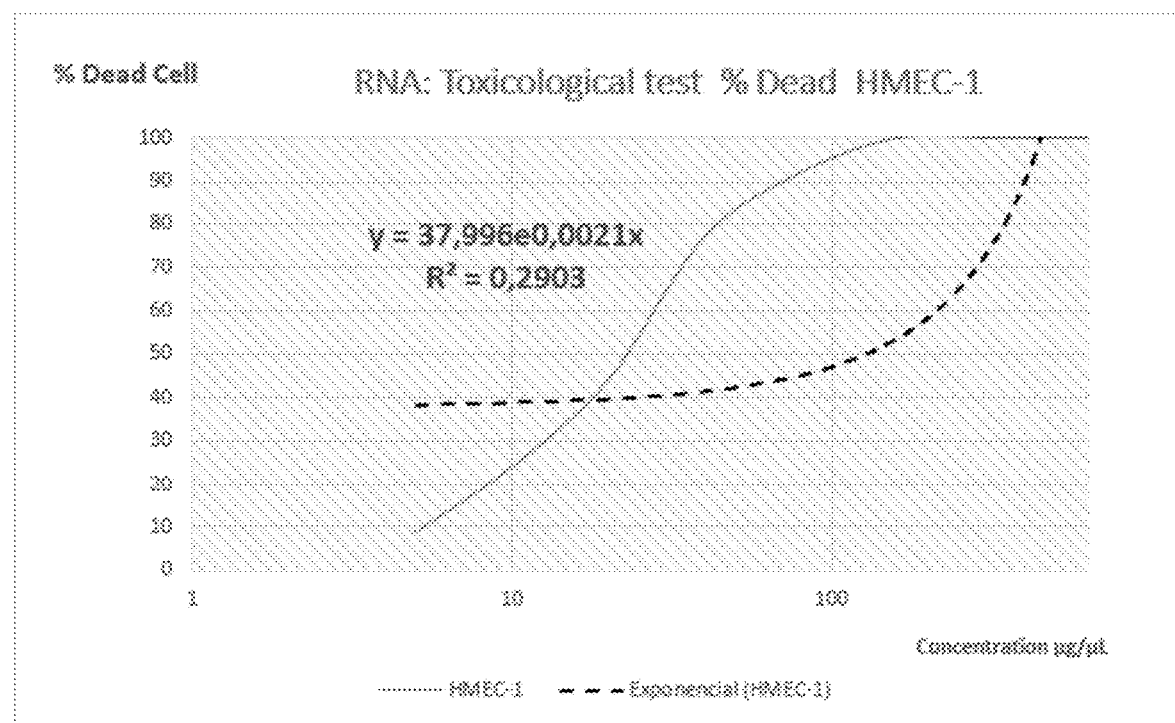
FIG. 37 is a graphic showing the RNA toxicological test in HMEC-1 cell line. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL).
Figure 38:
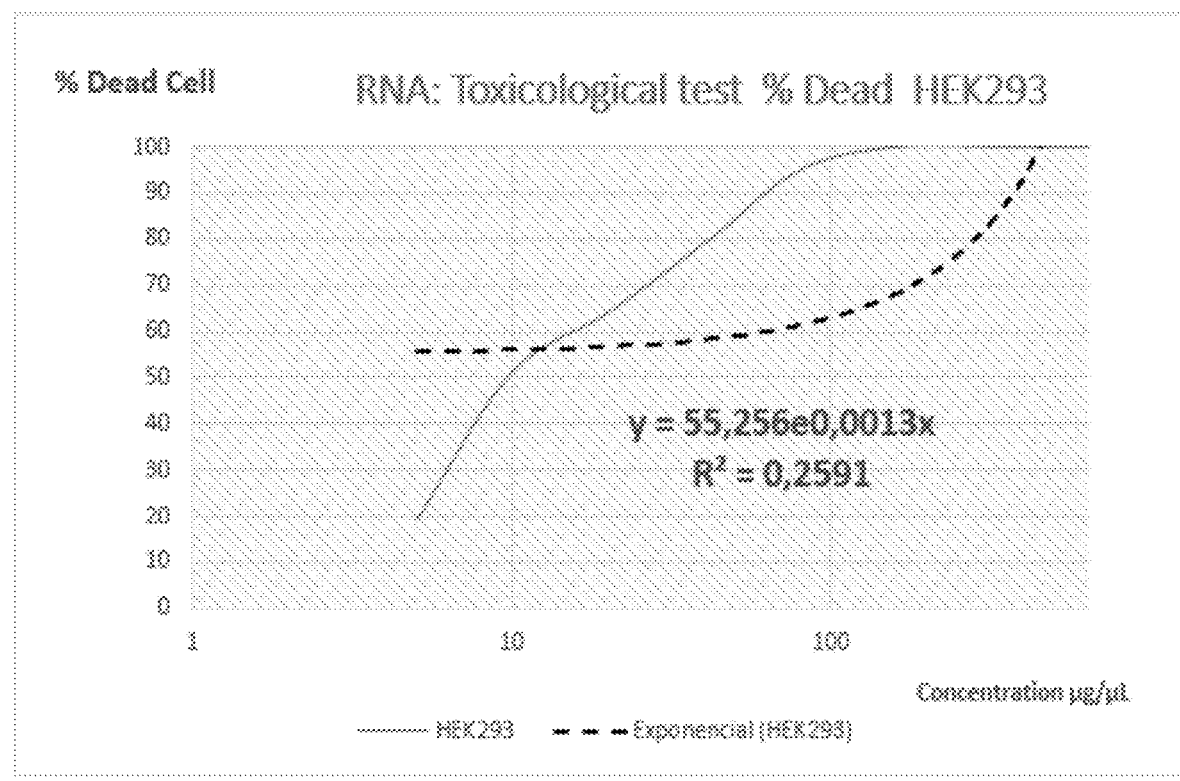
FIG. 38 is a graphic showing the RNA toxicological test in HEK293 cell lines. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 39:
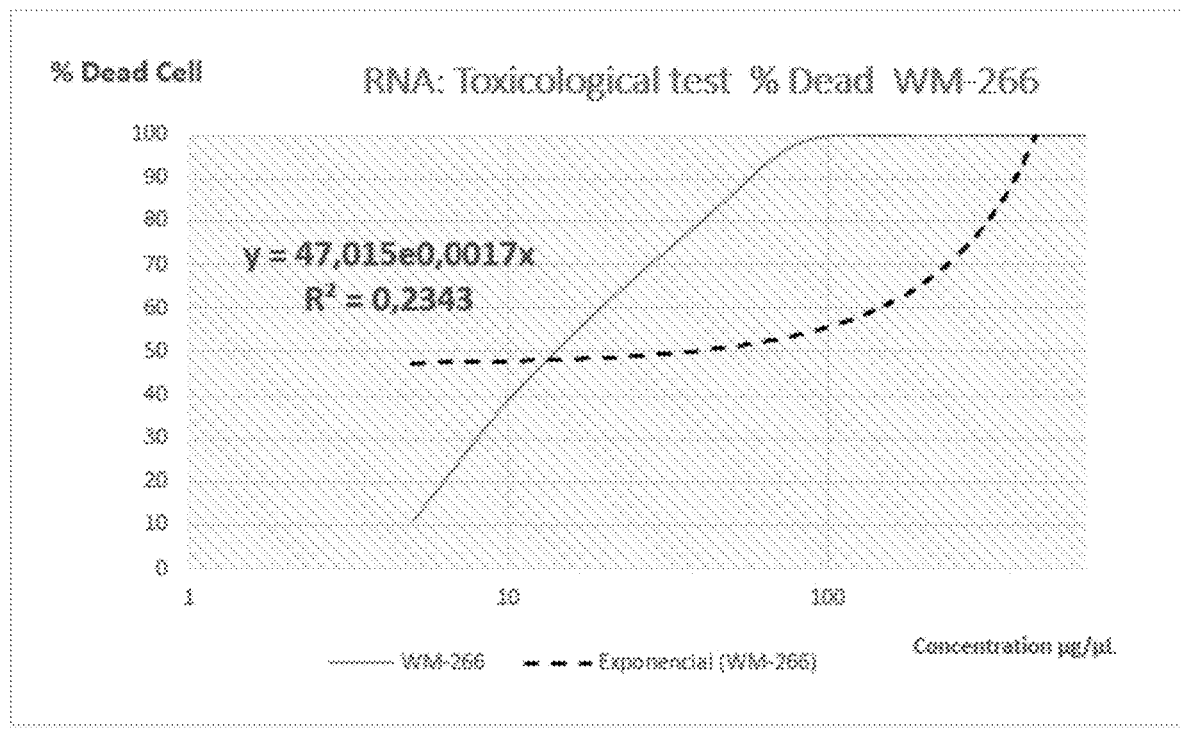
FIG. 39 is a graphic showing the RNA toxicological test in WM-266 cell lines. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 40:
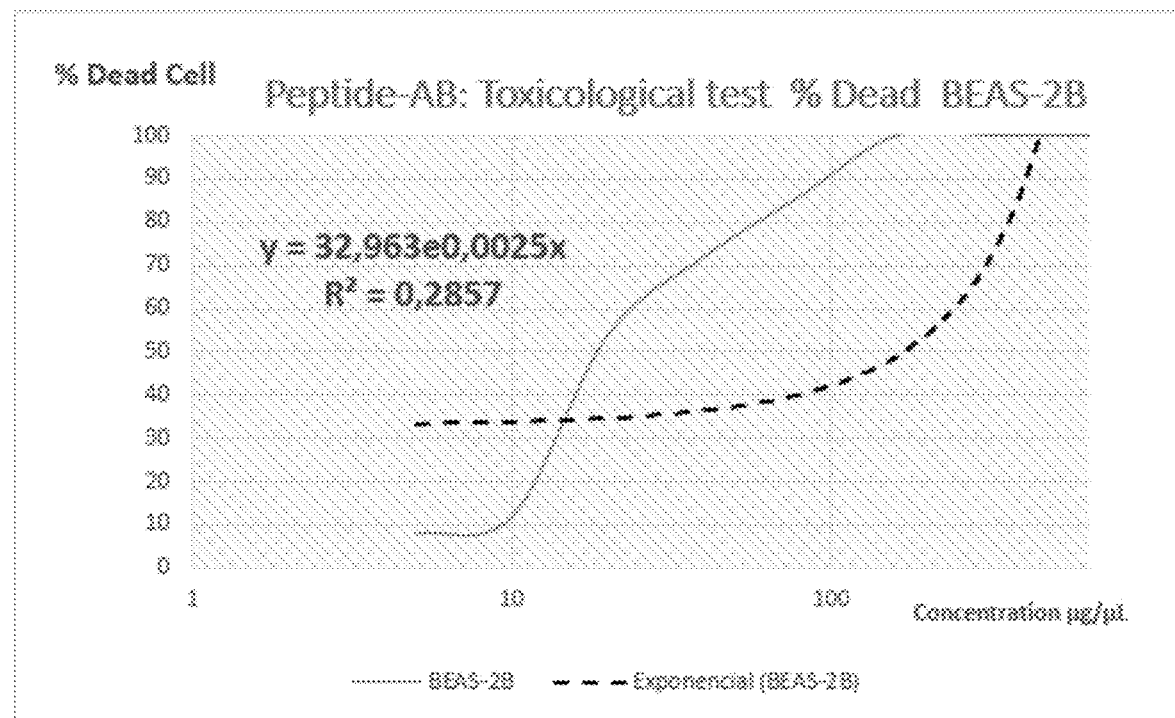
FIG. 40 is a graphic showing the Peptide-AB toxicological test in BEAR-2B cell lines. The dashed curve represents the exponential dead cell according to serial concentration of Peptide-AB (5 µg/µL, 10 µg/µL, 20 µg/µL, 40 µg/µL, 80 µg/µL, 160 µg/µL, 320 µg/µL and 640 µg/µL.
Figure 41:
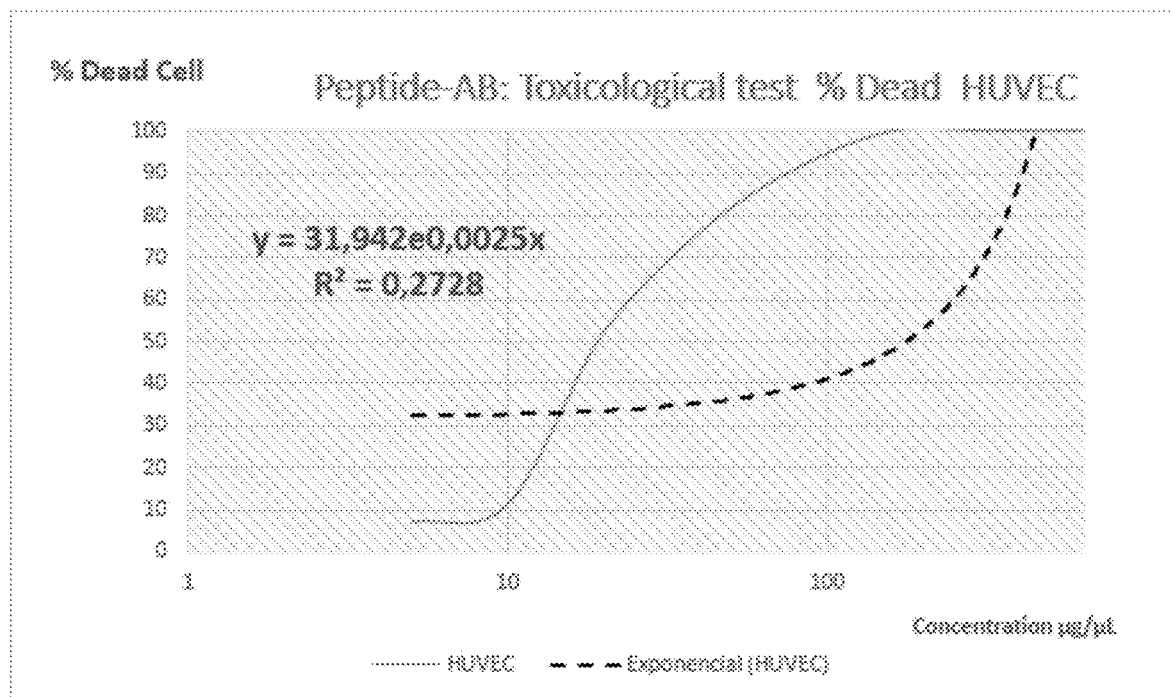
FIG. 41 is a graphic showing the Peptide-AB toxicological test in. HUVEC cell lines. The dashed curve represents the exponential dead cell according to serial concentration of Peptide-AB (5 µg/µL, 10 µg/µL, 20 µg/µL, 40 µg/µL, 80 µg/µL, 160 µg/µL, 320 µg/µL and 640 µg/µL.
Figure 42:
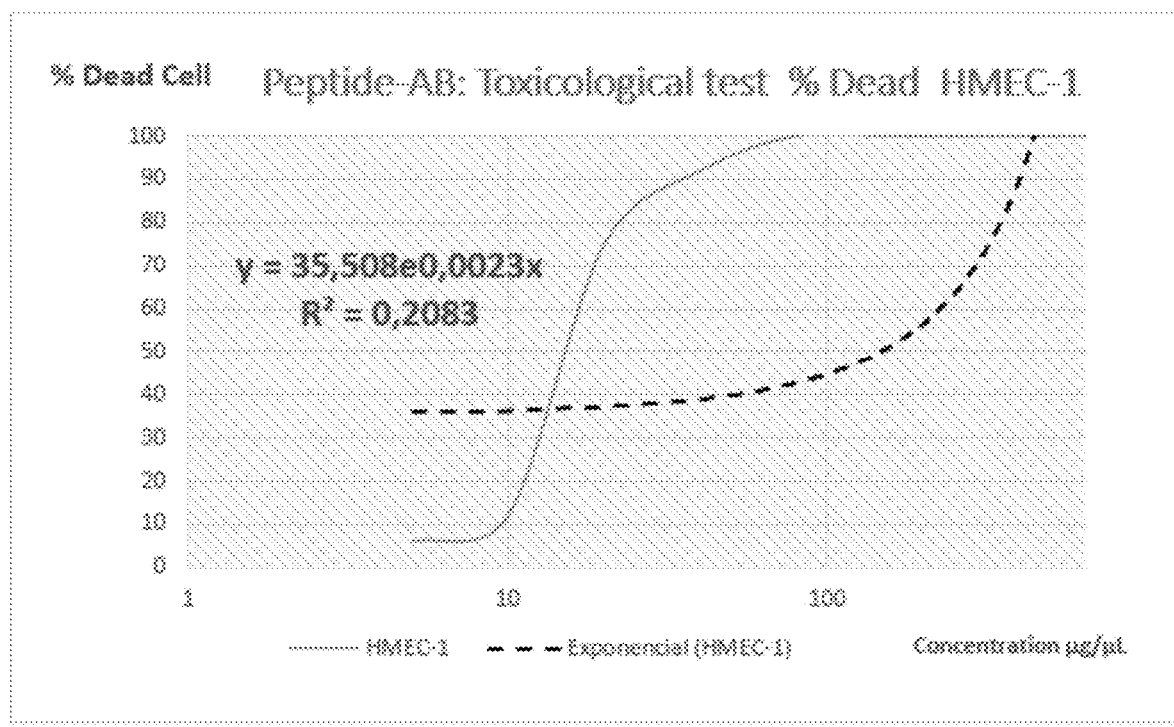
FIG. 42 is a graphic showing the Peptide-AB toxicological test in HMEC-1 cell lines. The dashed curve represents the exponential dead cell according to serial concentration of Peptide-AB (5 µg/µL, 10 µg/µL, 20 µg/µL, 40 µg/µL, 80 µg/µL, 160 µg/µL, 320 µg/µL and 640 µg/µL.
Figure 43:
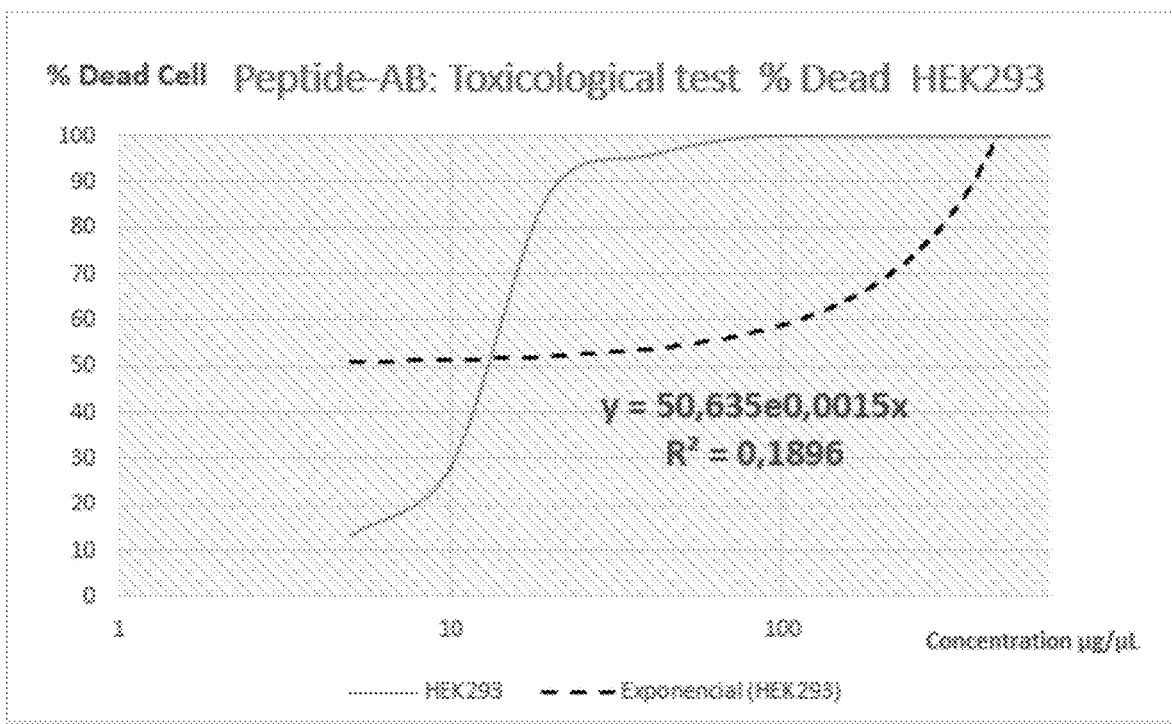
FIG. 43 is a graphic showing the Peptide-AB toxicological test in HEK293 cell lines. The dashed curve represents the exponential dead cell according to serial concentration of Peptide-AB (5 µg/µL, 10 µg/µL, 20 µg/µL, 40 µg/µL, 80 µg/µL, 160 µg/µL, 320 µg/µL and 640 µg/µL.
Figure 44:
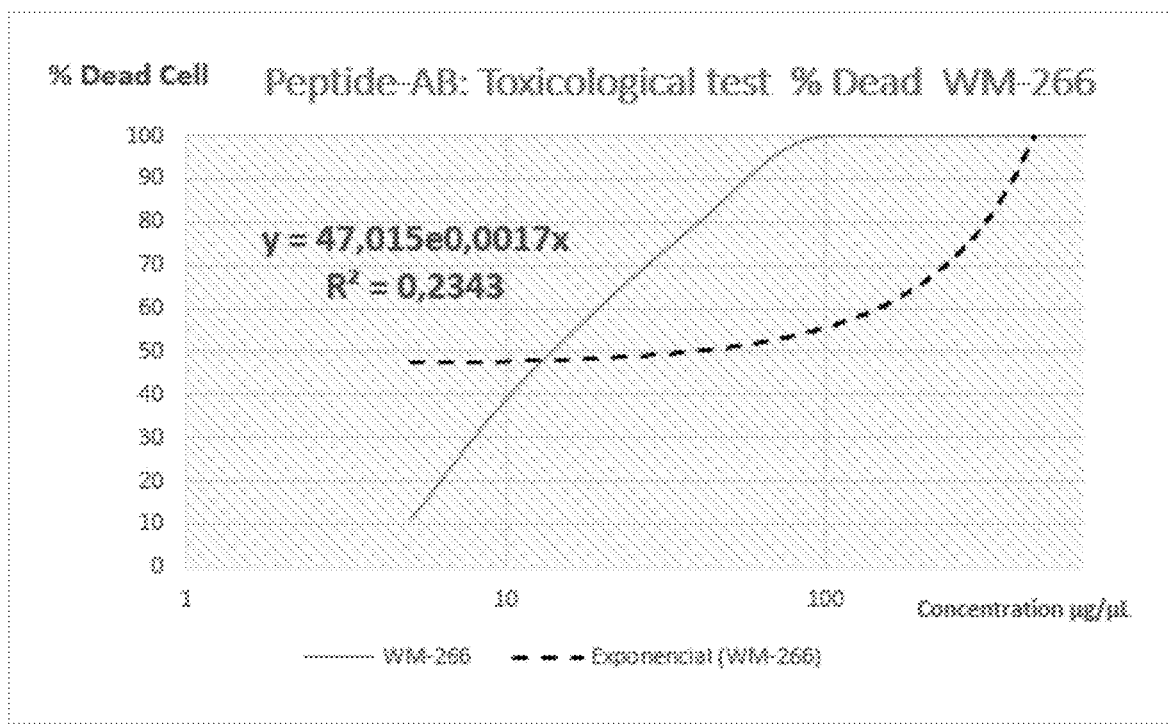
FIG. 44 is a graphic showing the Peptide-AB toxicological test in WM-266 cell lines. The dashed curve represents the exponential dead cell according to serial concentration of Peptide-AB (5 µg/µL, 10 µg/µL, 20 µg/L, 40 µg/L, 80 µg/µL, 160 µg/µL, 320 µg/µL and 640 µg/µL.
Figure 45:
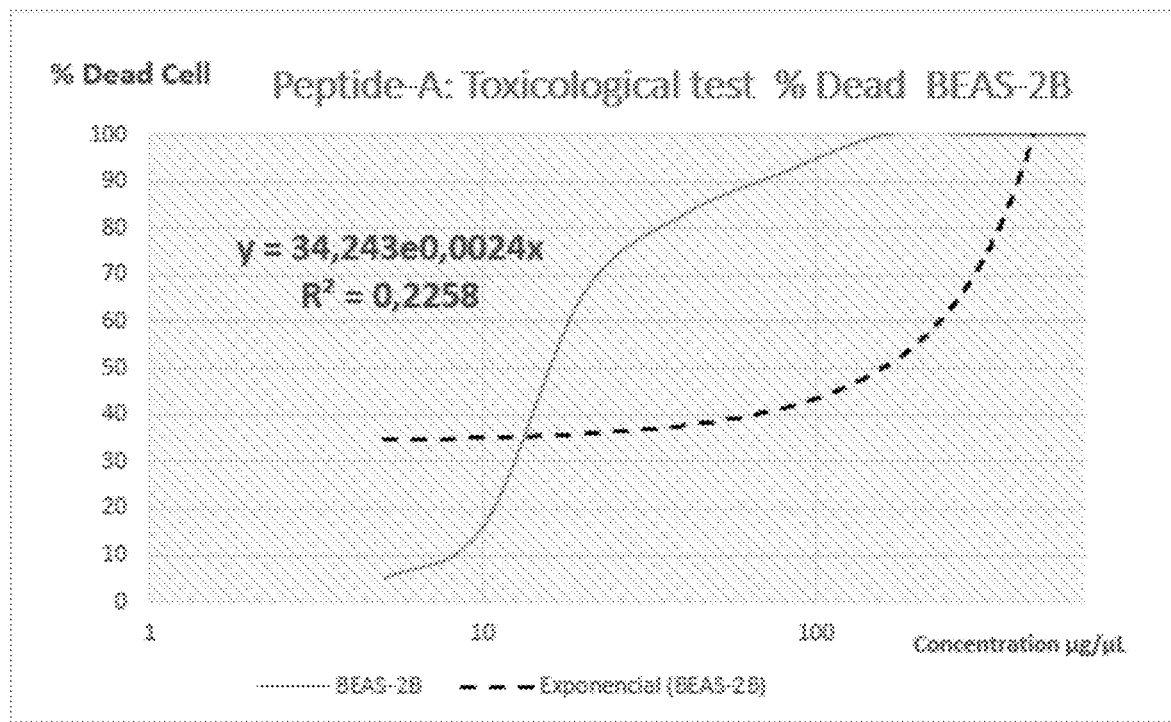
FIG. 45 is a graphic showing the Peptide-A toxicological test in BEAS-2B cell lines. The dashed curve represents the exponential dead cell according to serial concentration of Peptide-A (5 µg/µL, 10 µg/µL, 20 µg/µL, 40 µg/µL, 80 µg/µL, 160 µg/µL, 320 µg/µL and 640 µg/µL.
Figure 46:
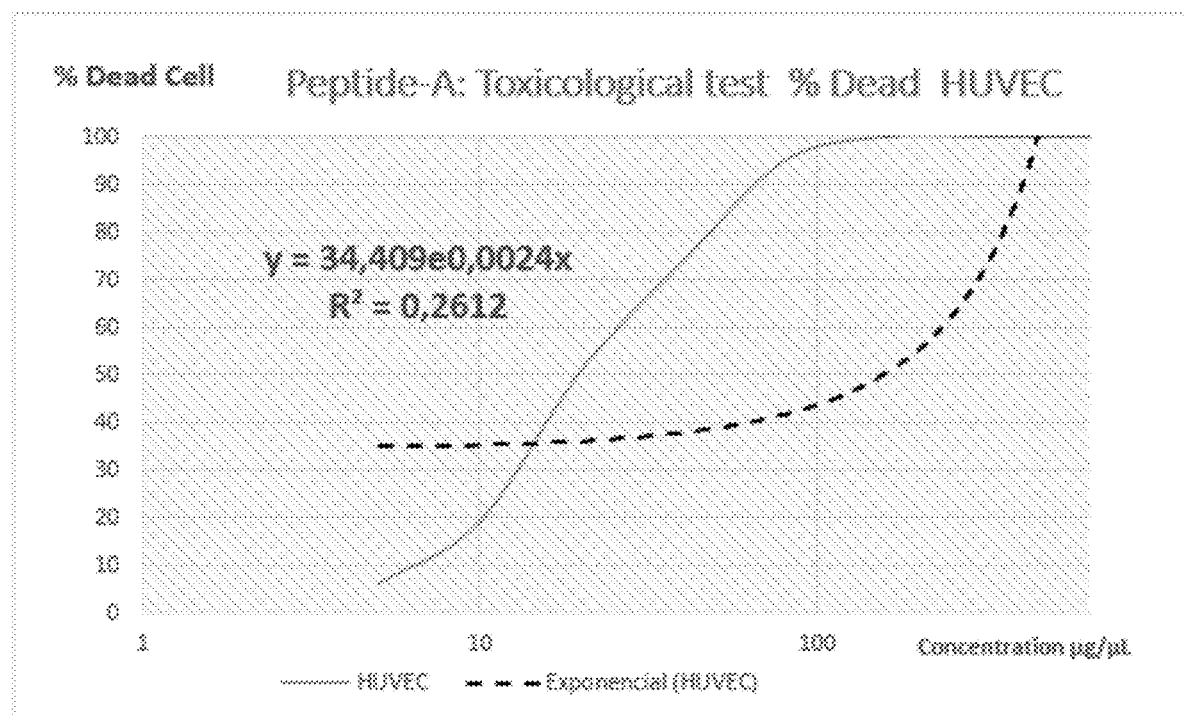
FIG. 46 is a graphic showing the Peptide-A toxicological test in HUVEC cell lines. The dashed curve represents the exponential dead cell according to serial concentration of Peptide-A (5 µg/µL, 10 µg/µL, 20 µg/µL, 40 µg/µL, 80 µg/µL, 160 µg/µL, 320 µg/µL and 640 µg/µL.
Figure 47:
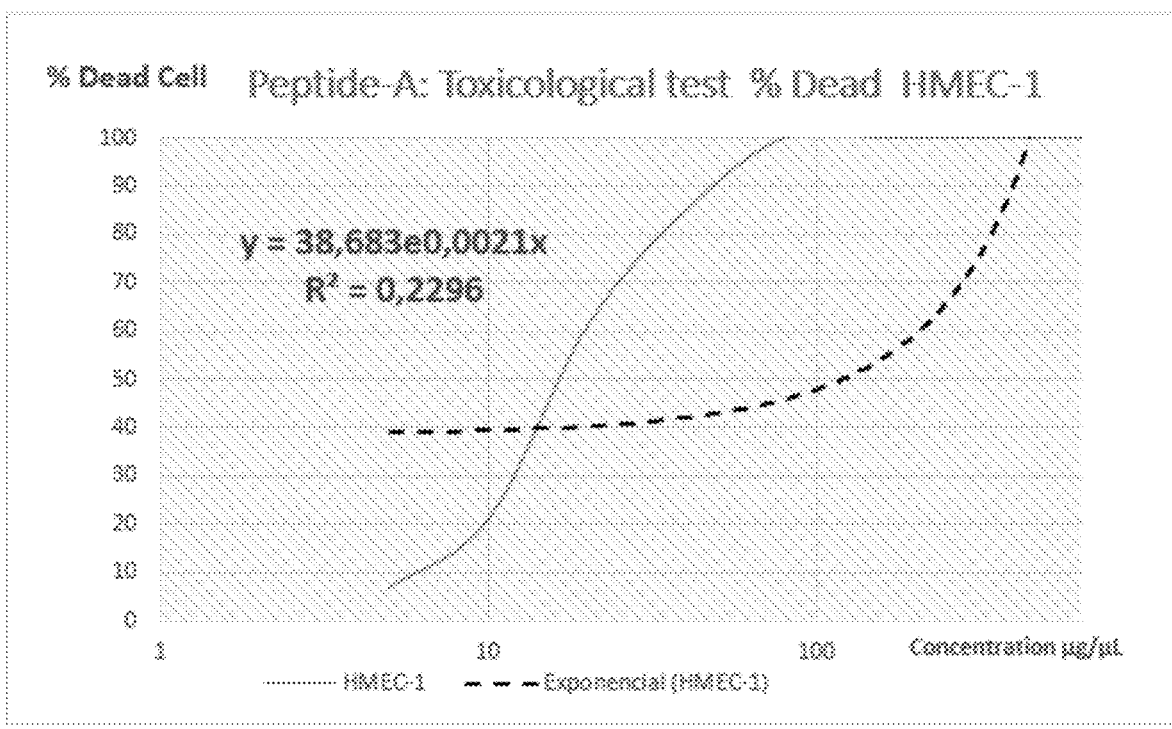
FIG. 47 is a graphic showing the Peptide-A toxicological test in HMEC-1 cell lines. The dashed curve represents the exponential dead cell according to serial concentration of Peptide-A (5 µg/µL, 10 µg/µL, 20 µg/µL, 40 µg/µL, 80 µg/µL, 160 µg/µL, 320 µg/µL and 640 µg/µL.
Figure 48:
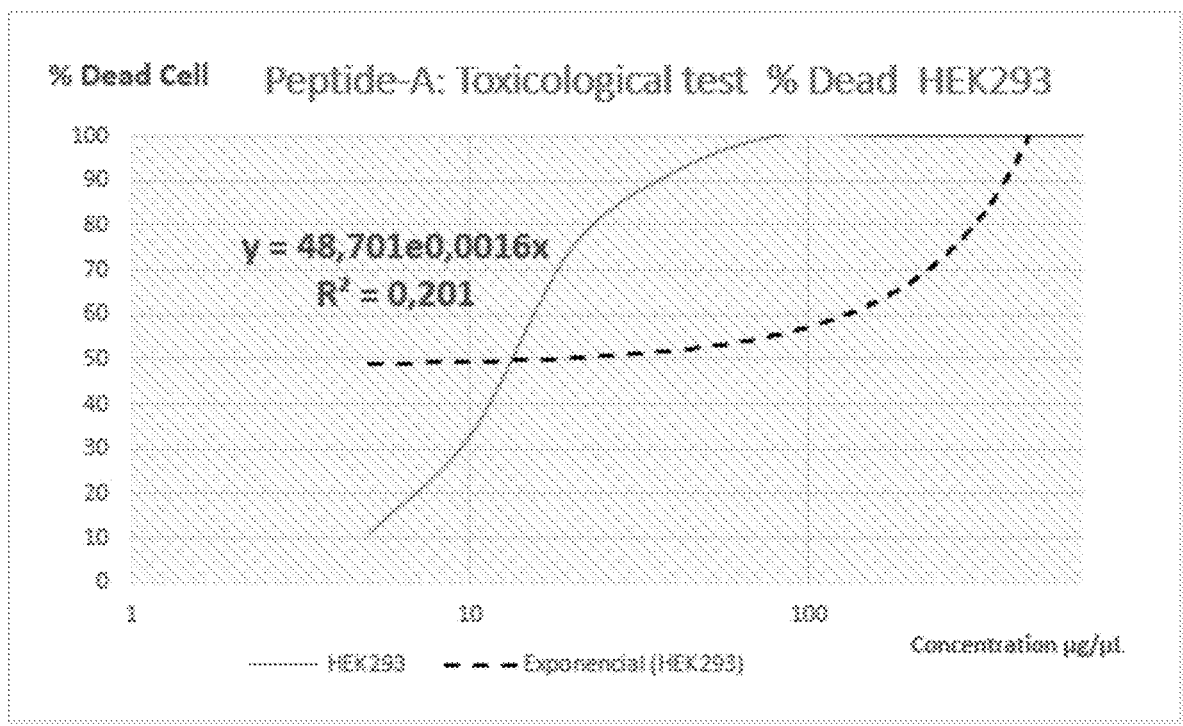
FIG. 48 is a graphic showing the Peptide-A toxicological test in HEK293 cell lines. The dashed curve represents the exponential dead cell according to serial concentration of Peptide-A (5 µg/µL, 10 µg/µL, 20 µg/µL, 40 µg/µL, 80 µg/µL, 160 µg/µL, 320 µg/µL and 640 µg/µL.
Figure 49:
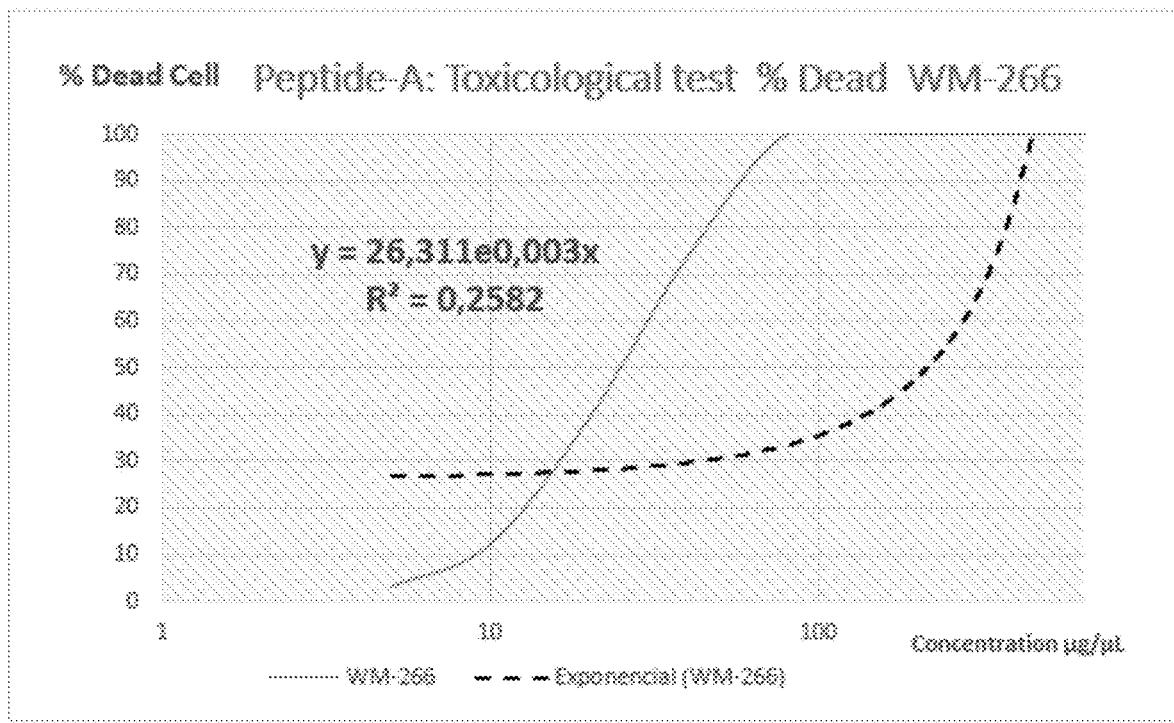
FIG. 49 is a graphic showing the Peptide-A toxicological test in WM-266 cell lines. The dashed curve represents the exponential dead cell according to serial concentration of Peptide-A (5 µg/µL, 10 µg/µL, 20 µg/µL, 40 µg/µL, 80 µg/µL, 160 µg/µL, 320 µg/µL and 640 µg/µL.
Figure 50:
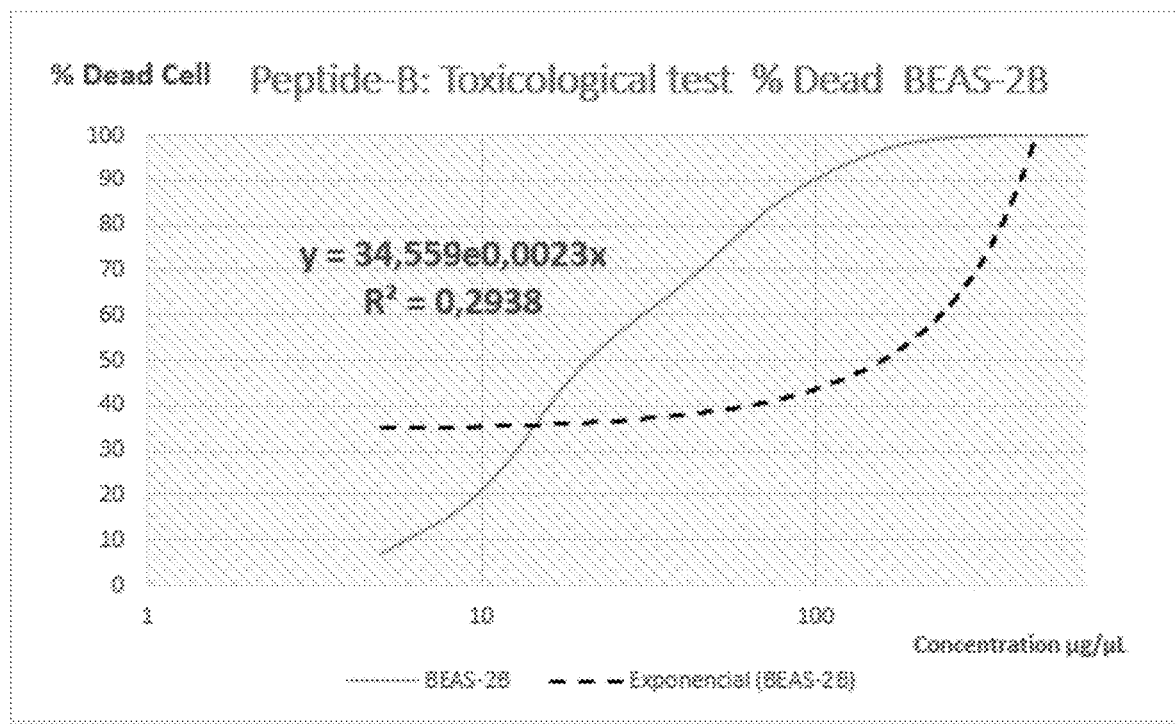
FIG. 50 is a graphic showing the Peptide-B toxicological test in BEAS-2B cell lines. The dashed curve represents the exponential dead cell according to serial concentration of Peptide-B (5 µg/µL, 10 µg/µL, 20 µg/µL, 40 µg/µL, 80 µg/µL, 160 µg/µL, 320 µg/µL and 640 µg/µL.
Figure 51:
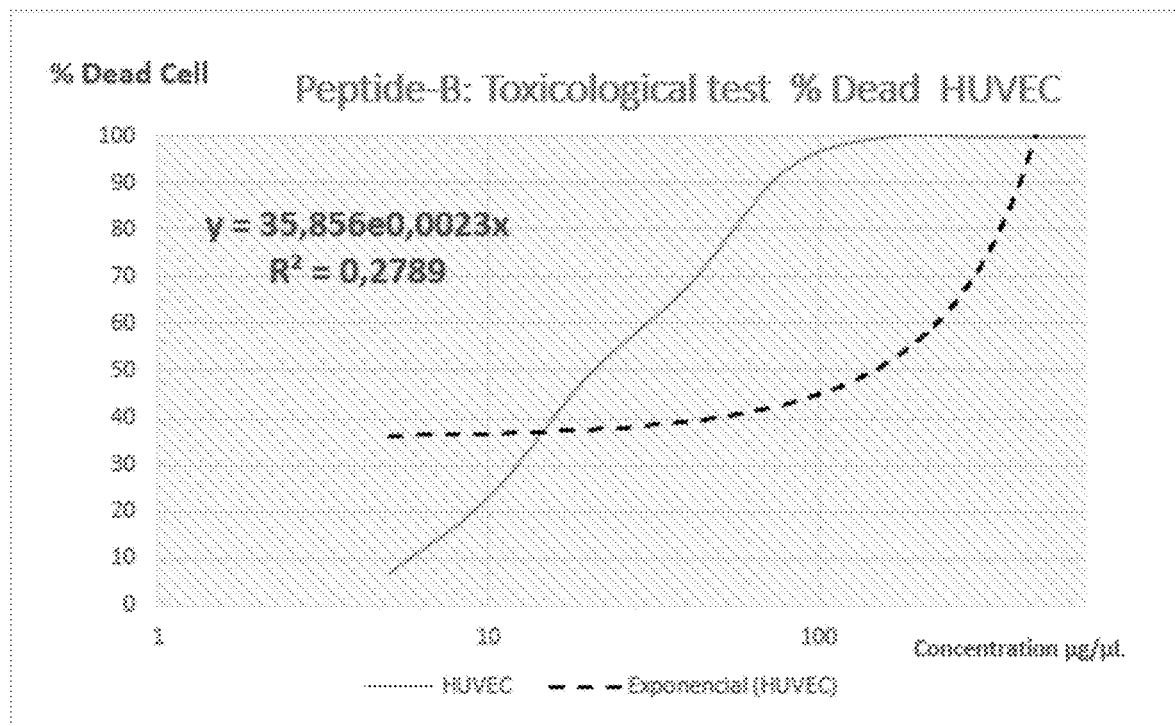
FIG. 51 is a graphic showing the Peptide-B toxicological test in HUVEC cell lines. The dashed curve represents the exponential dead cell according to serial concentration of Peptide-B (5 µg/µL, 10 µg/µL, 20 µg/µL, 40 µg/µL, 80 µg/µL, 160 µg/µL, 320 µg/µL and 640 µg/µL.
Figure 52:
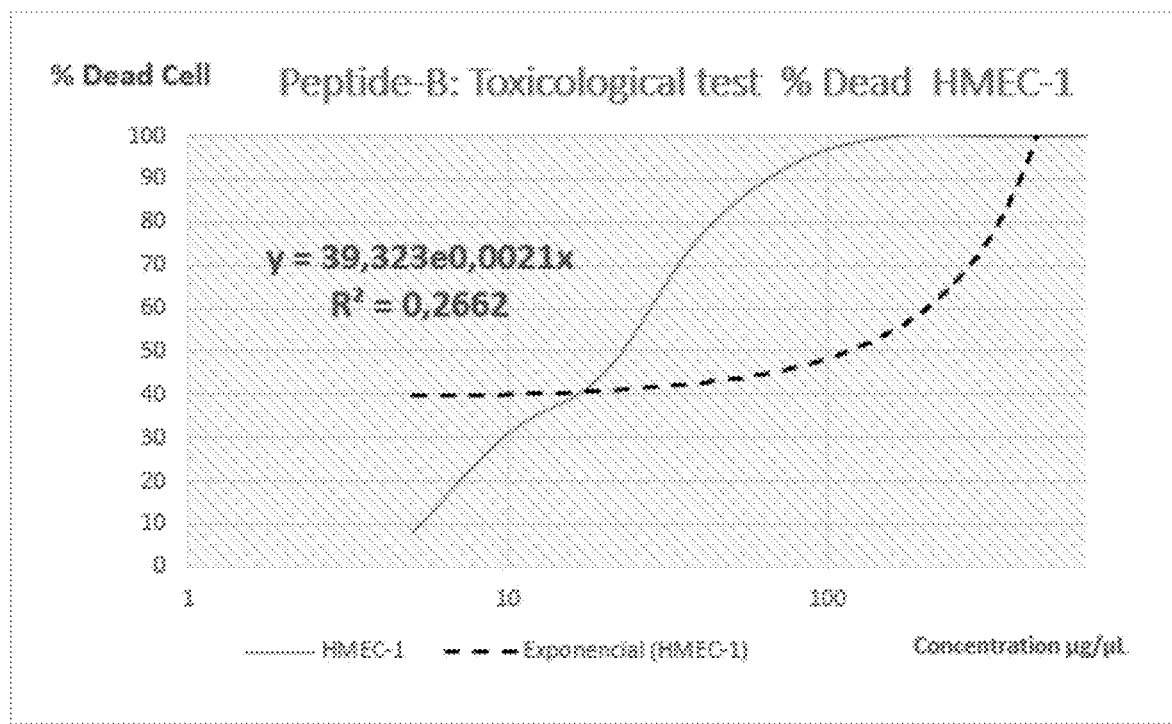
FIG. 52 is a graphic showing the Peptide-B toxicological test in HMEC-1 cell lines. The dashed curve represents the exponential dead cell according to serial concentration of Peptide-B (5 µg/µL, 10 µg/µL, 20 µg/µL, 40 µg/µL, 80 µg/µL, 160 µg/µL, 320 µg/µL and 640 µg/µL.
Figure 53:
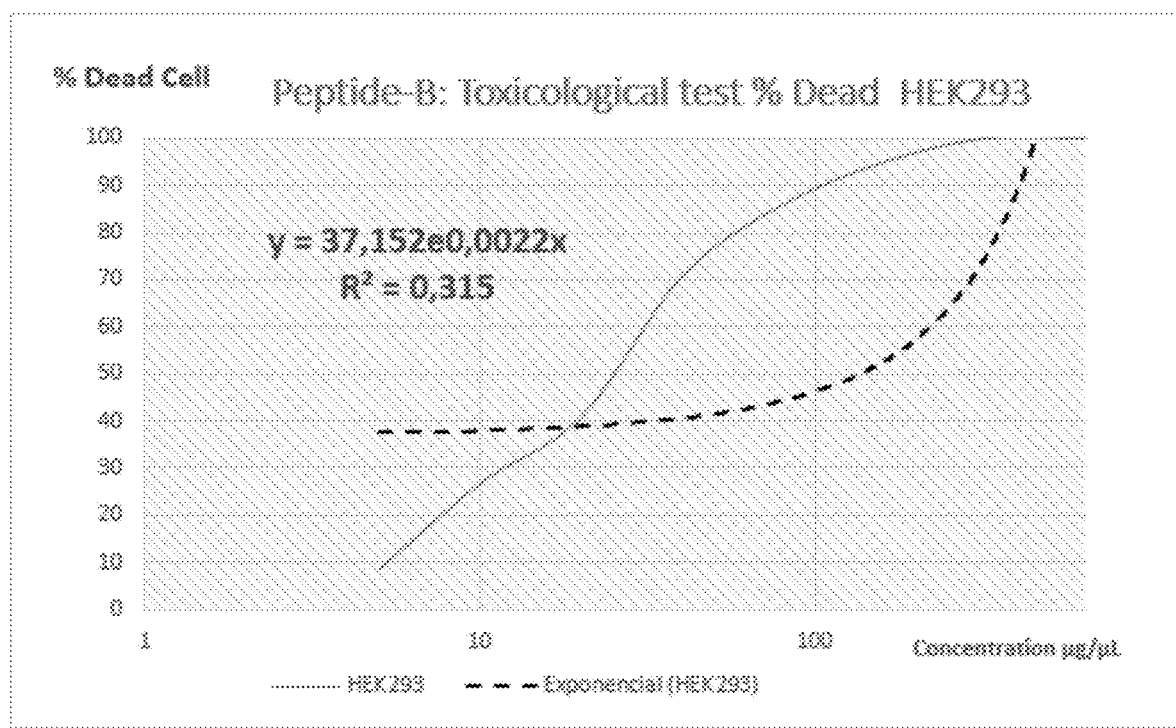
FIG. 53 is a graphic showing the Peptide-B toxicological test in HEK293 cell lines. The dashed curve represents the exponential dead cell according to serial concentration of Peptide-B (5 µg/µL, 10 µg/µL, 20 µg/µL, 40 µg/µL, 80 µg/µL, 160 µg/µL, 320 µg/µL and 640 µg/µL.
Figure 54:
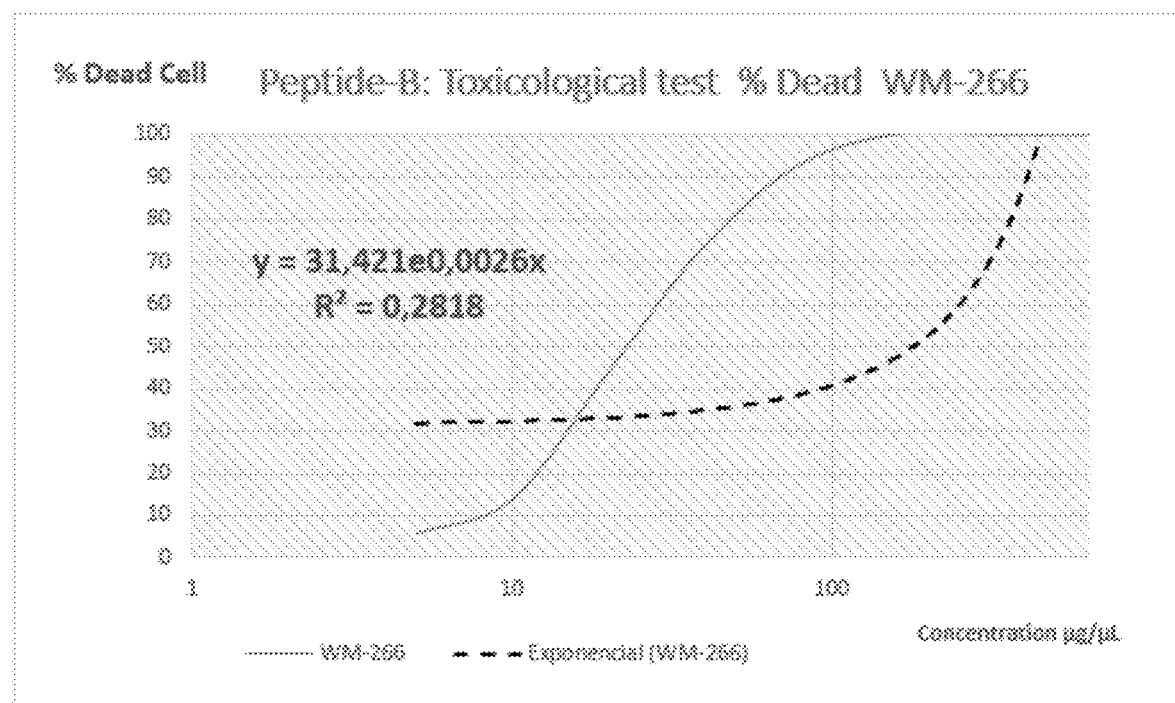
FIG. 54 is a graphic showing the Peptide-B toxicological test in WM-266 cell lines. The dashed curve represents the exponential dead cell according to serial concentration of Peptide-B (5 µg/µL, 10 µg/µL, 20 µg/µL, 40 µg/µL, 80 µg/µL, 160 µg/µL, 320 µg/µL and 640 µg/µL.
Figure 55:
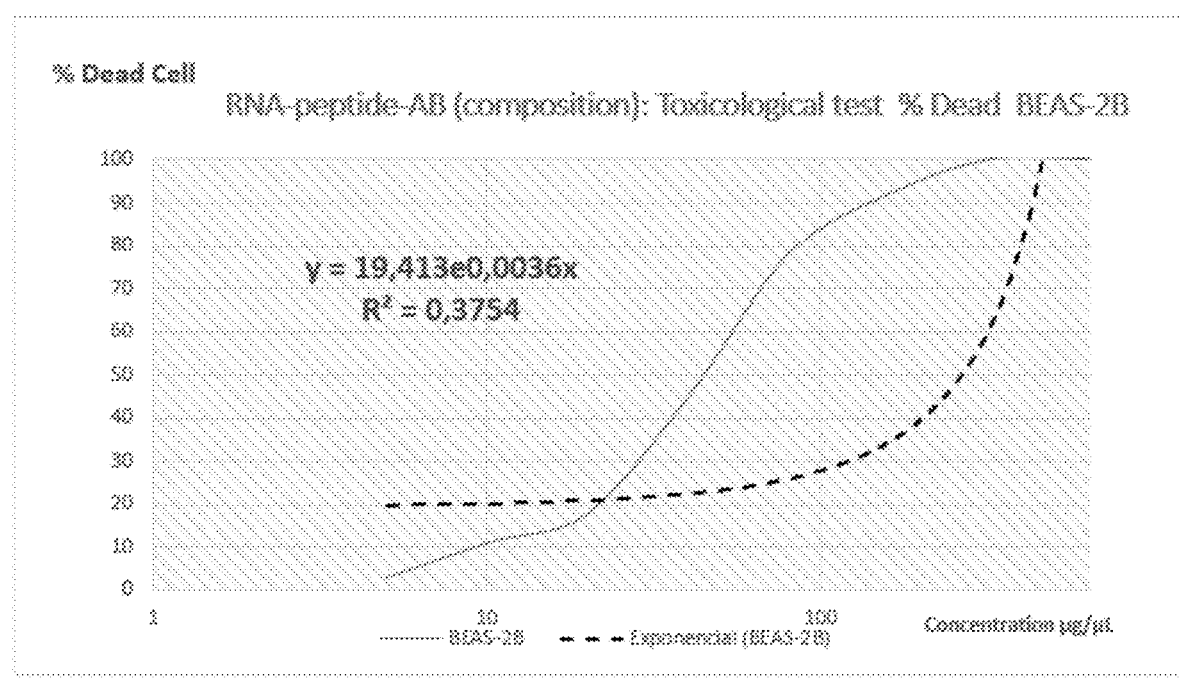
FIG. 55 is a graphic showing the vaccine toxicological test in BEAS-2B cell lines. The dashed curve represents the exponential dead cell according to serial concentration of vaccine (5 µg/µL, 10 µg/µL, 20 µg/µL, 40 µg/µL, 80 µg/µL, 160 µg/µL, 320 µg/µL and 640 µg/µL.
Figure 56:
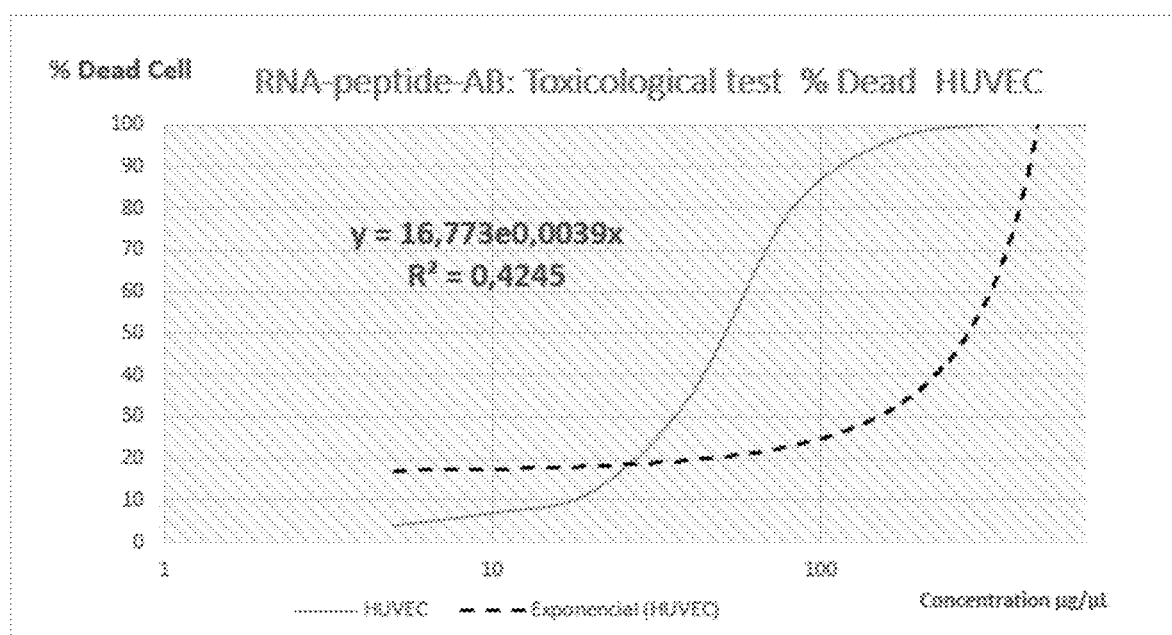
FIG. 56 is a graphic showing the vaccine toxicological test in HUVEC cell lines. The dashed curve represents the exponential dead cell according to serial concentration of vaccine (5 µg/µL, 10 µg/µL, 20 µg/µL, 40 µg/µL, 80 µg/µL, 160 µg/µL, 320 µg/µL and 640 µg/µL.
Figure 57:
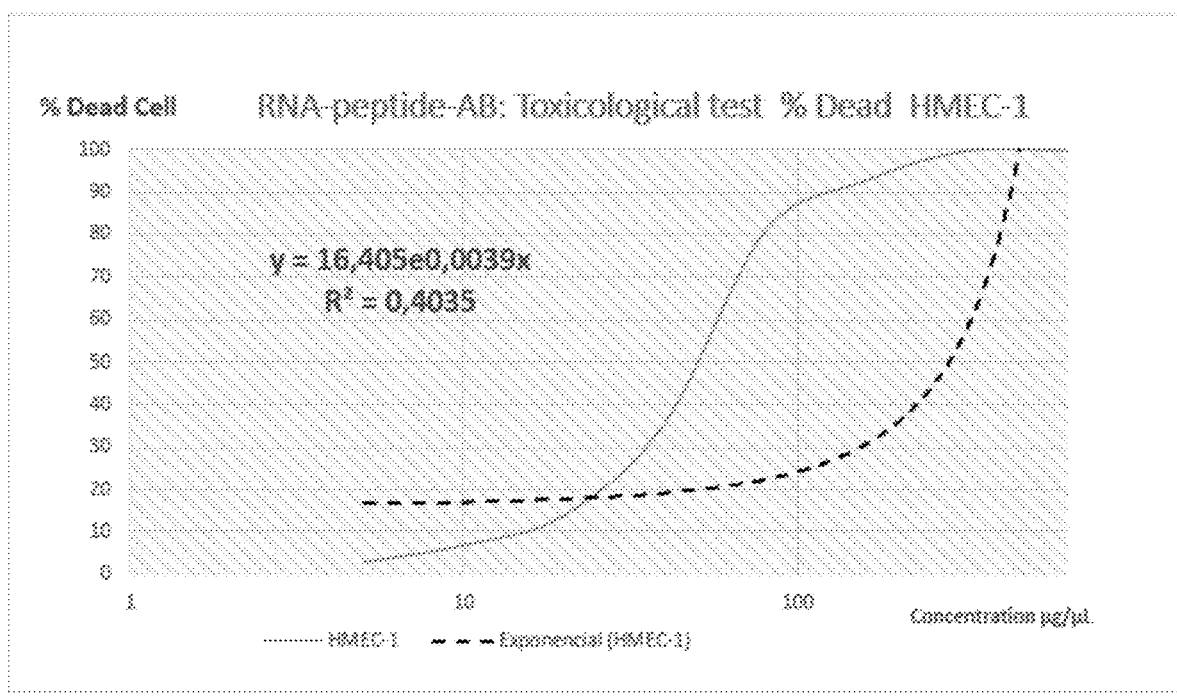
FIG. 57 is a graphic showing the vaccine toxicological test in HMEC-1 cell lines. The dashed curve represents the exponential dead cell according to serial concentration of vaccine (5 µg/µL, 10 µg/µL, 20 µg/µL, 40 µg/µL, 80 µg/µL, 160 µg/µL, 320 µg/µL and 640 µg/µL.
Figure 58:
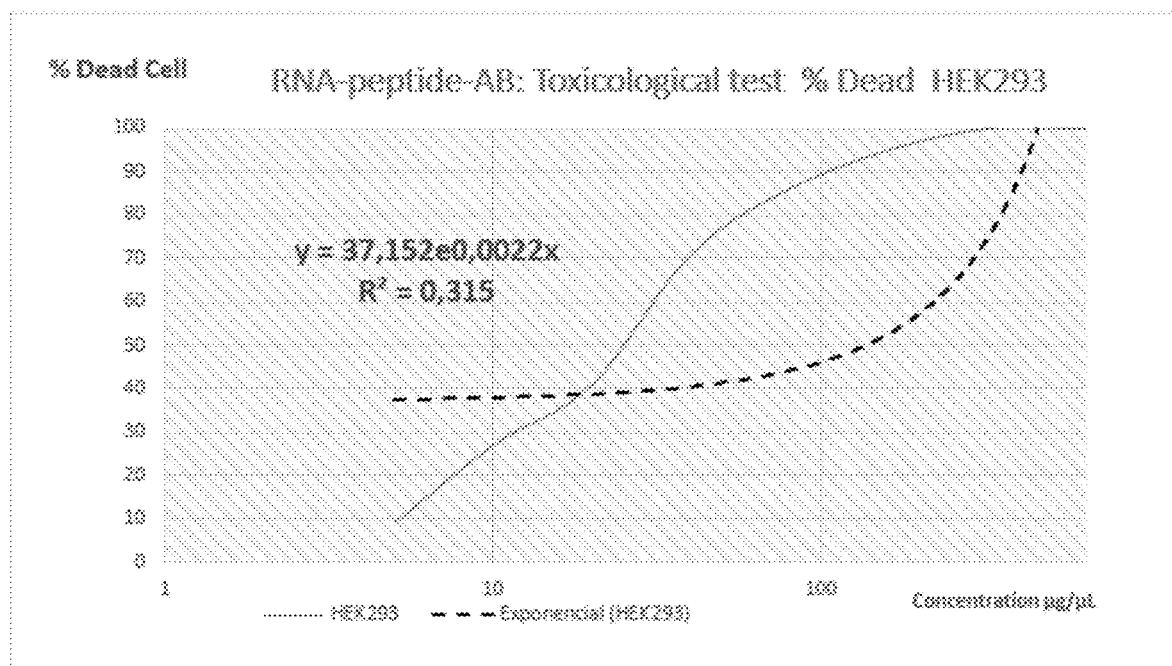
FIG. 58 is a graphic showing the vaccine toxicological test in HEK293 cell lines. The dashed curve represents the exponential dead cell according to serial concentration of vaccine (5 µg/µL, 10 µg/µL, 20 µg/µL, 40 µg/µL, 80 µg/µL, 160 µg/µL, 320 µg/µL and 640 µg/µL.
Figure 59:
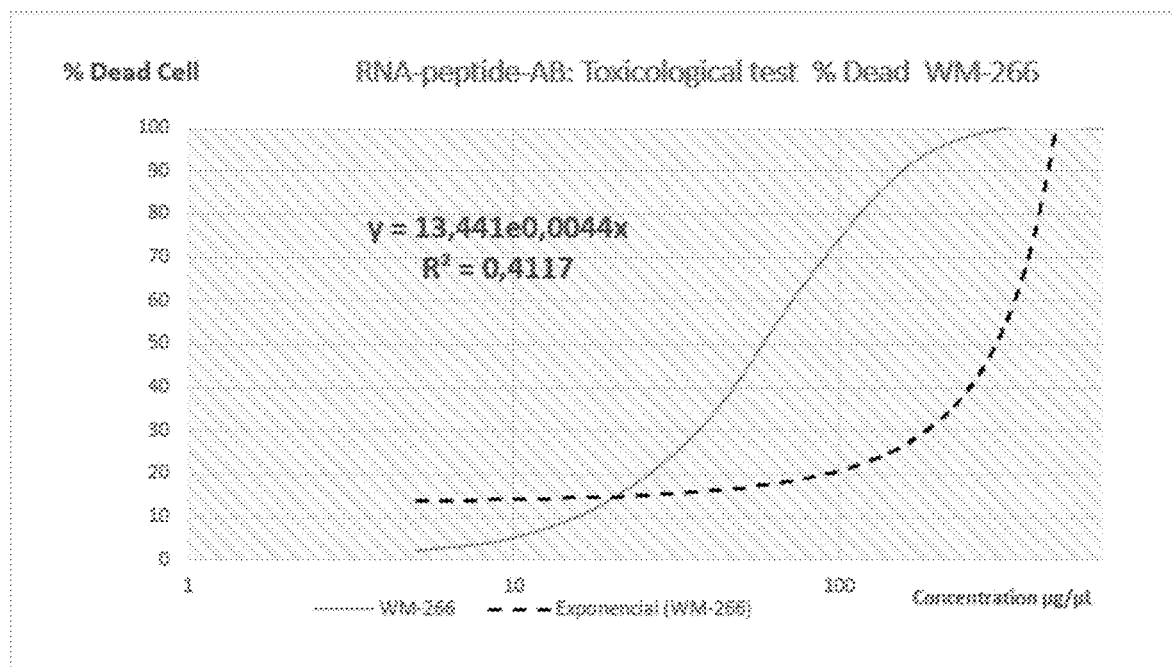
FIG. 59 is a graphic showing the vaccine toxicological test in WM-266 cell lines. The dashed curve represents the exponential dead cell according to serial concentration of vaccine (5 µg/µL, 10 µg/µL, 20 µg/µL, 40 µg/µL, 80 Mg/µL, 160 µg/µL, 320 µg/µL and 640 µg/µL.
Figure 60:
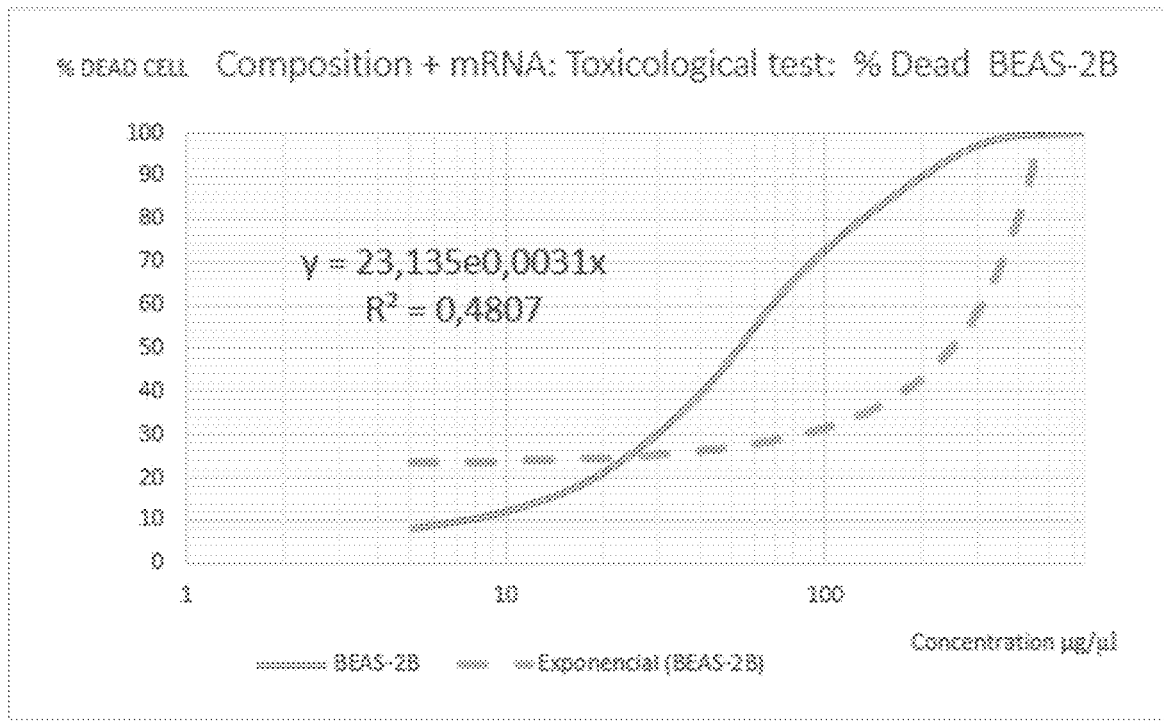
FIG. 60 is a graphic showing the RNA toxicological test in BEAS-2B cell lines after vaccine incubation of 16 hours. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 61:
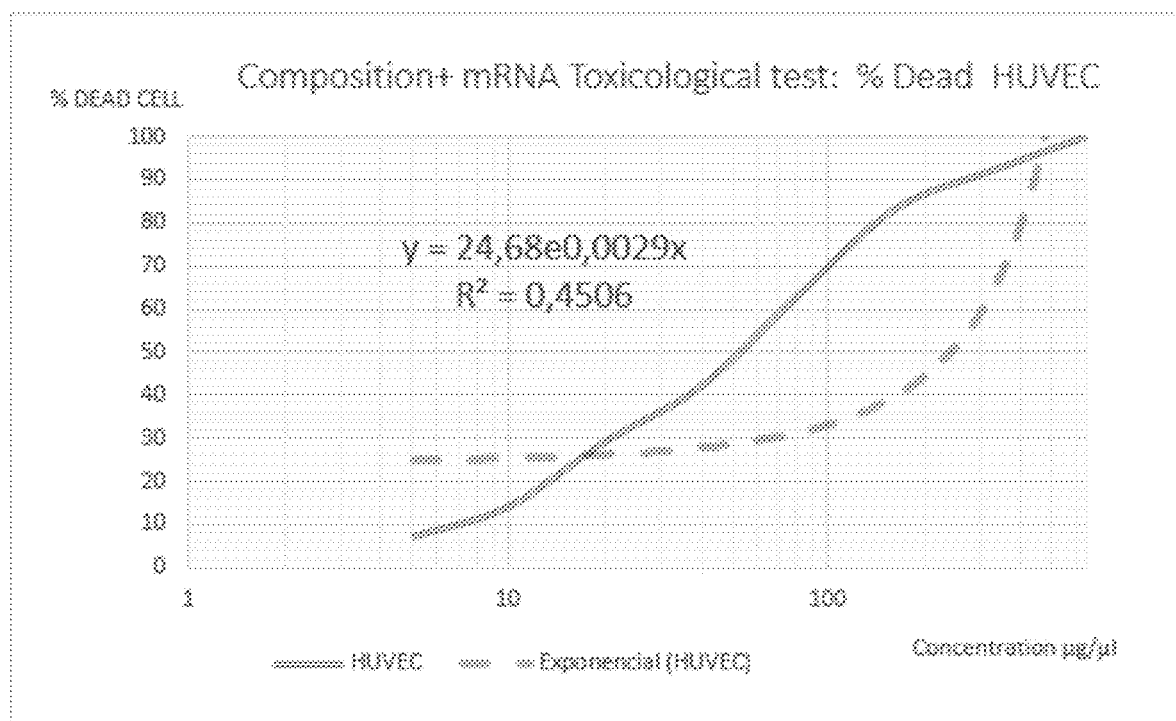
FIG. 61 is a graphic showing the RNA toxicological test in HUVEC cell lines after vaccine incubation of 16 hours. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 62:
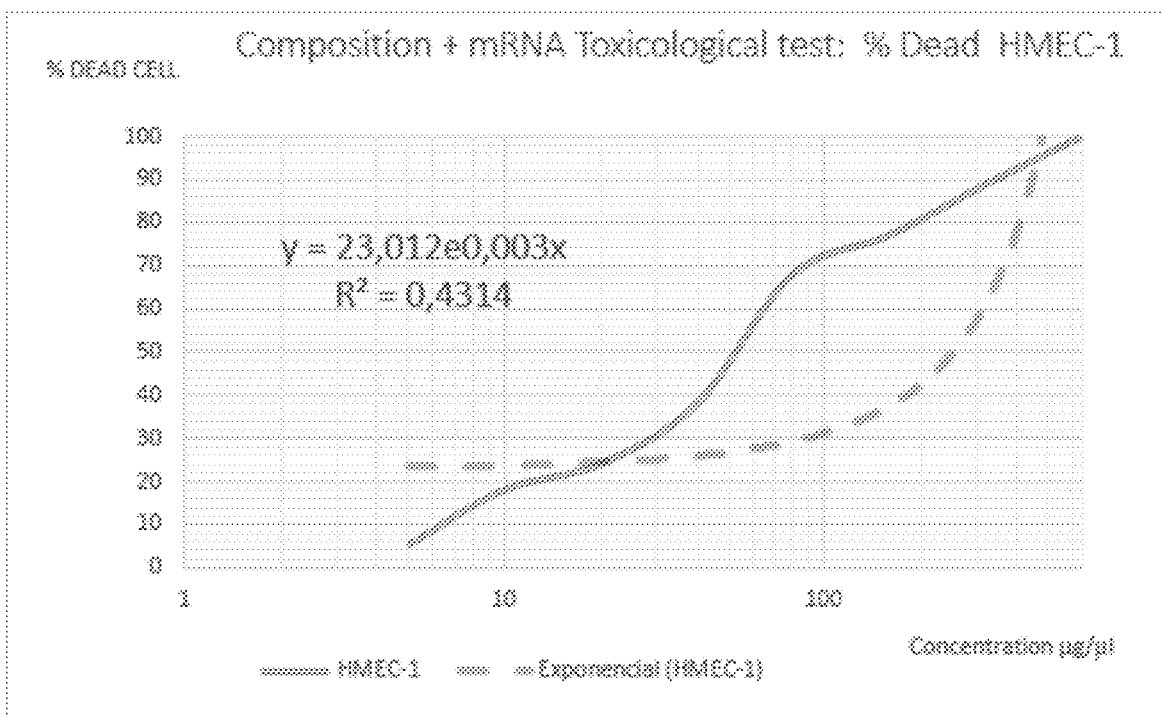
FIG. 62 is a graphic showing the RNA toxicological test in HMEC-1 cell lines after vaccine incubation of 16 hours. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 63:
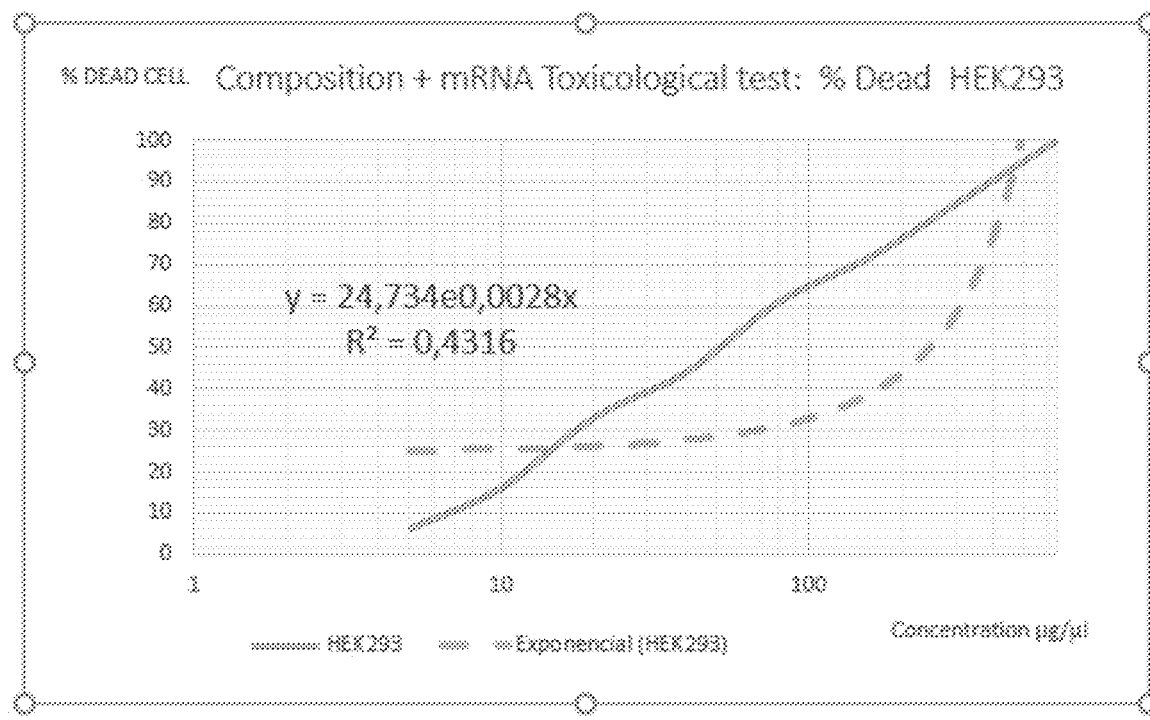
FIG. 63 is a graphic showing the RNA toxicological test in HEK293 cell lines after vaccine incubation of 16 hours. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 64:
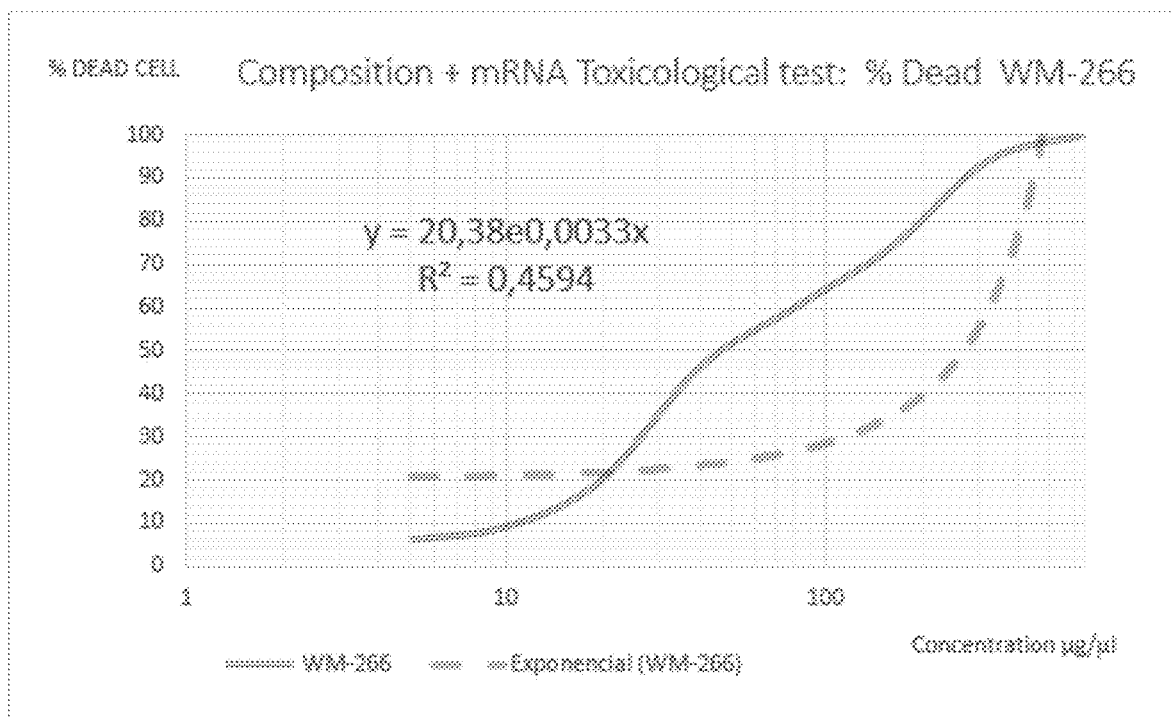
FIG. 64 is a graphic showing the RNA toxicological test in WM-266 cell lines after vaccine incubation of 16 hours. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 65:
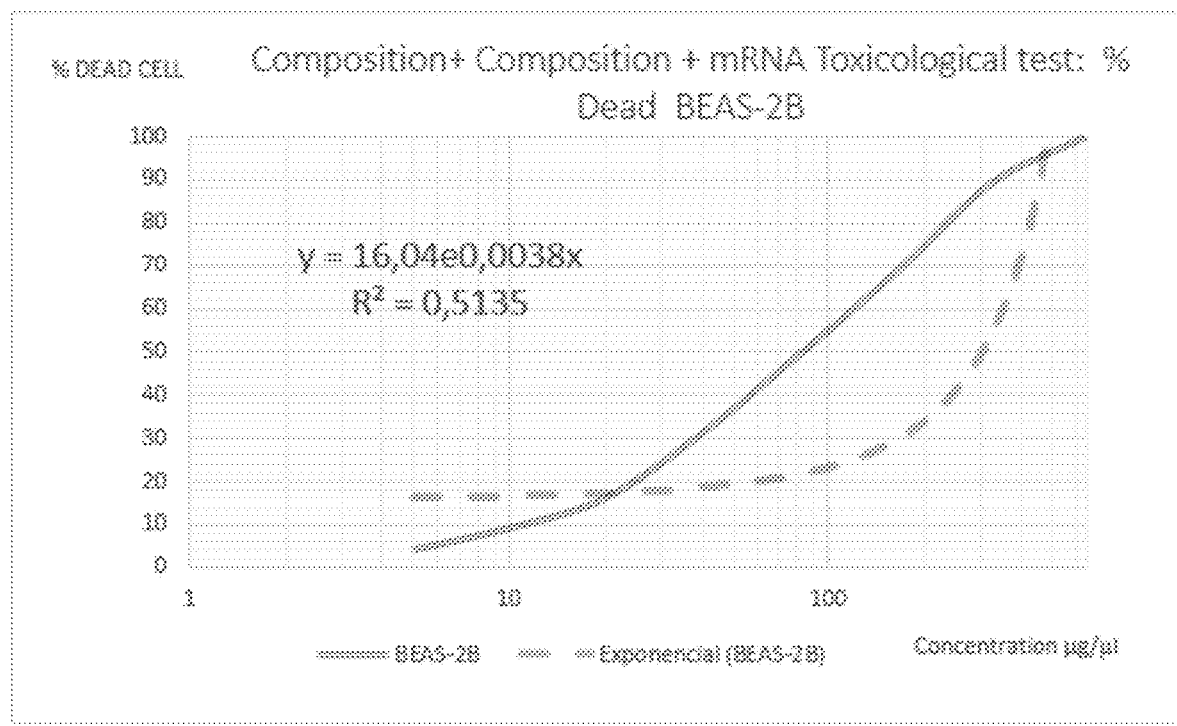
FIG. 65 is a graphic showing the RNA toxicological test in BEAS-2B cell lines after vaccine incubation of 16 hours two times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 66:
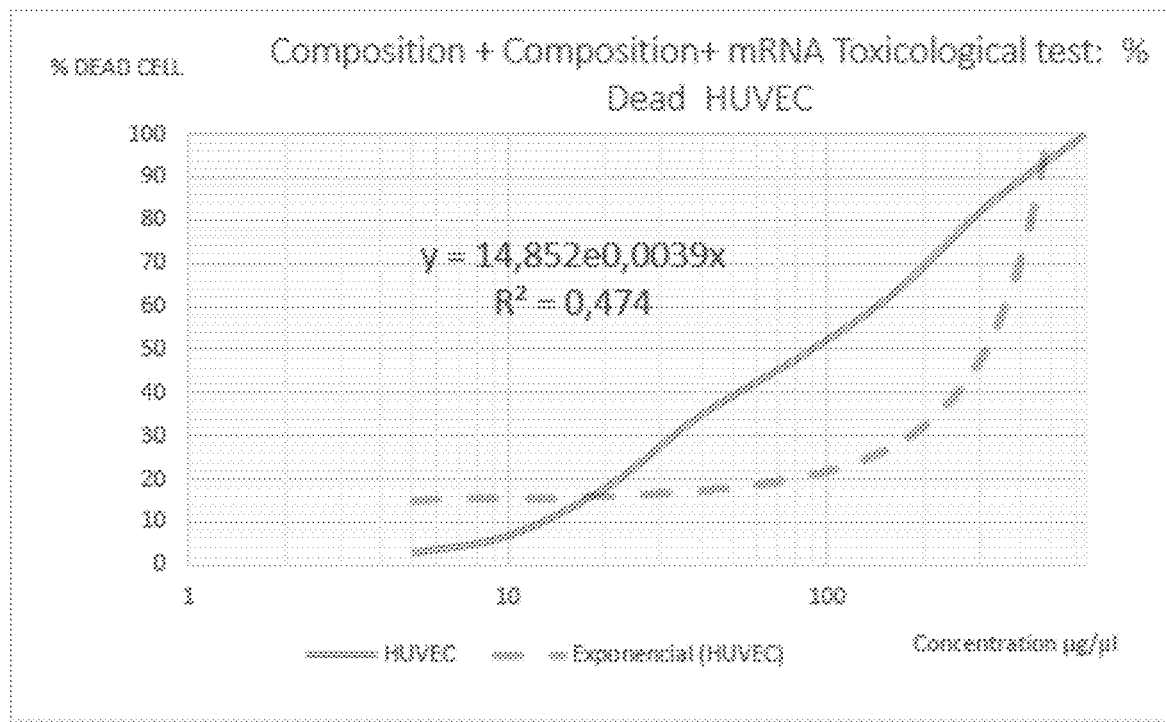
FIG. 66 is a graphic showing the RNA toxicological test in HUVEC cell lines after vaccine incubation of 16 hours two times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 67:
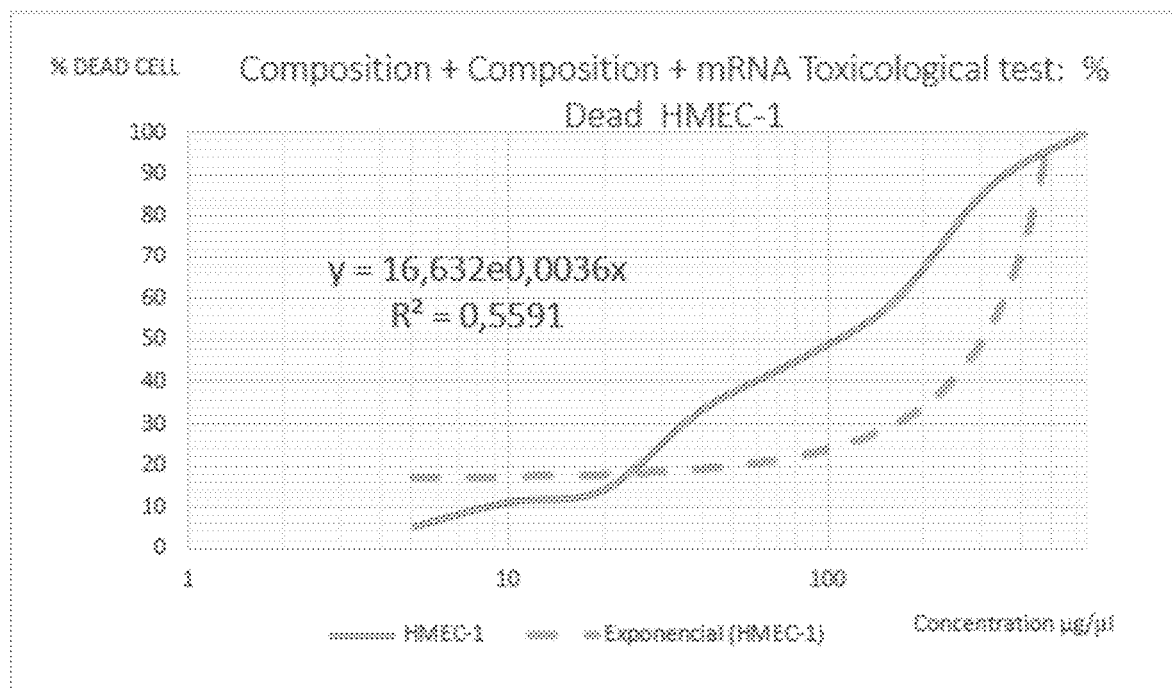
FIG. 67 is a graphic showing the RNA toxicological test in HMEC-1 cell lines after vaccine incubation of 16 hours two 20 times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 68:
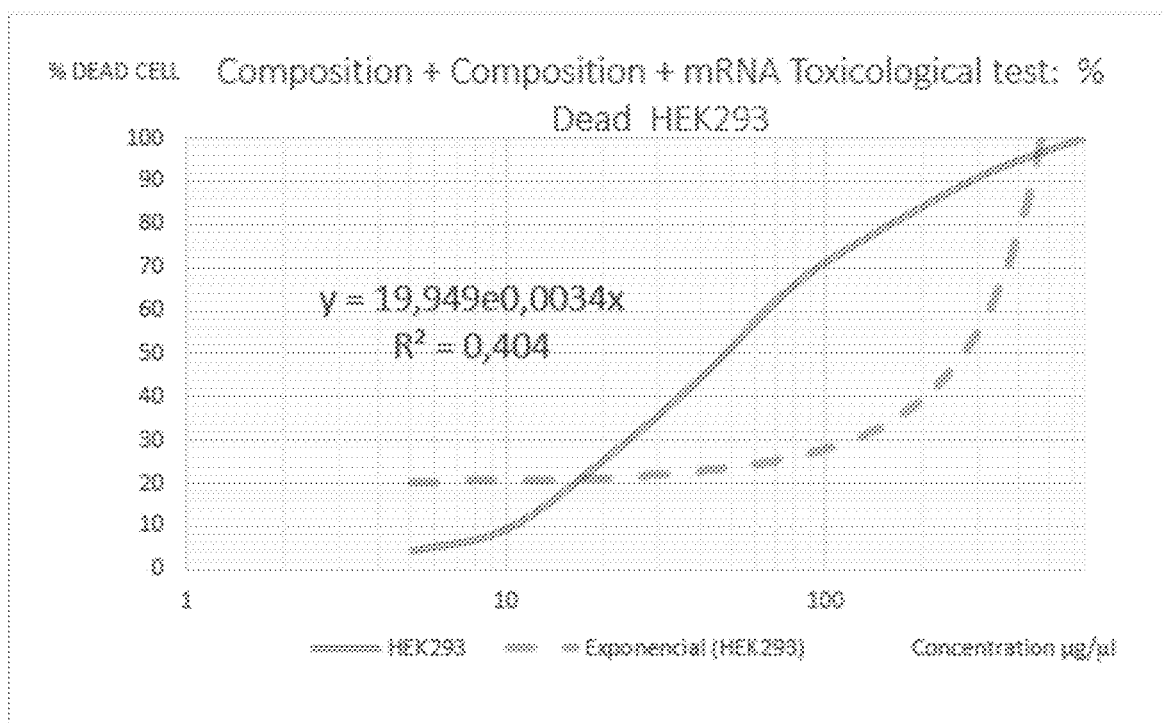
FIG. 68 is a graphic showing the RNA toxicological test in HEK293 cell lines after vaccine incubation of 16 hours two times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 69:
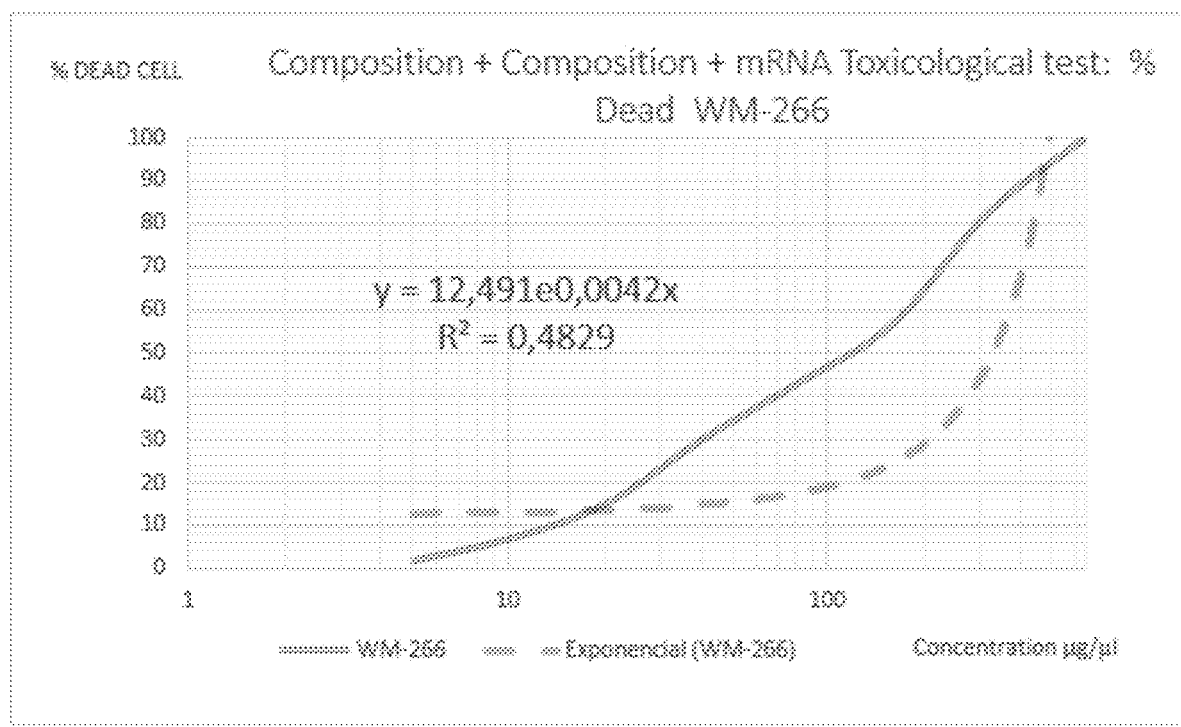
FIG. 69 is a graphic showing the RNA toxicological test in WM-266 cell lines after vaccine incubation of 16 hours two times. The dashed curve represents the exponential dead cell according to serial concentration of RNA (5 µg/µL, 1020 µg/µL, 40 µg/µL, 80 µg/µL, 160 µg/µL, 320 µg/µL and 640 µg/µL.
Figure 70:
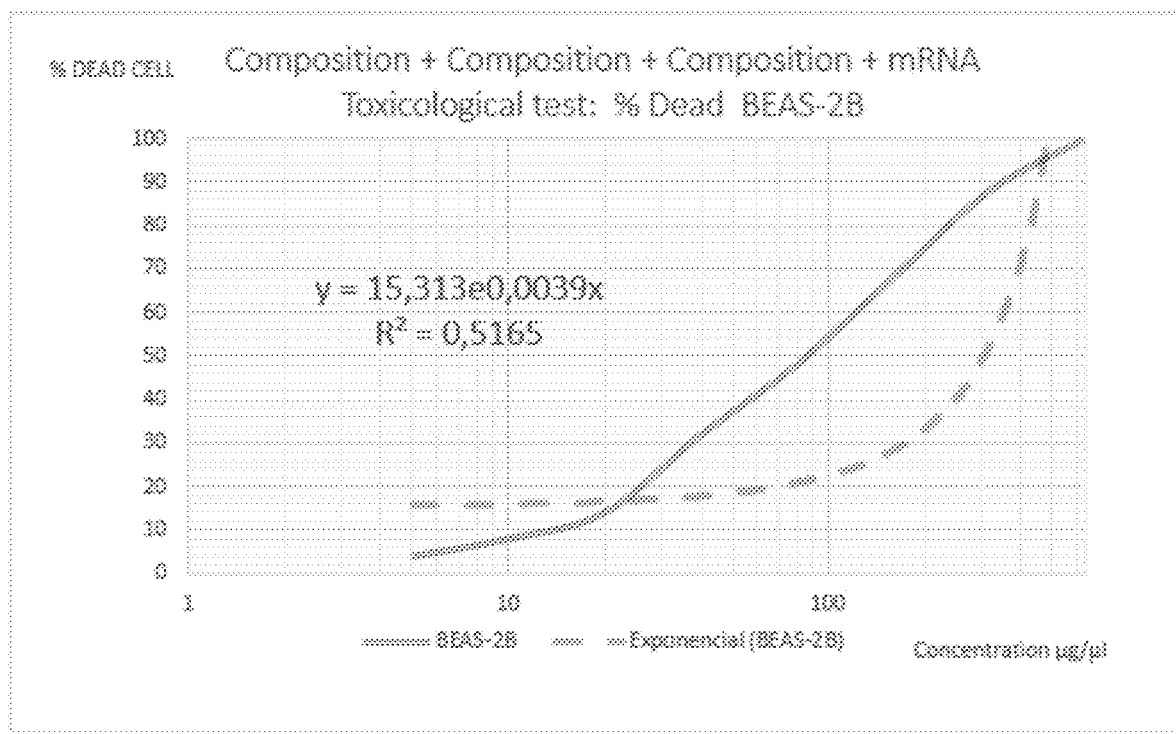
FIG. 70 is a graphic showing the RNA toxicological test in BEAS-2B cell lines after vaccine incubation of 16 hours three times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 71:
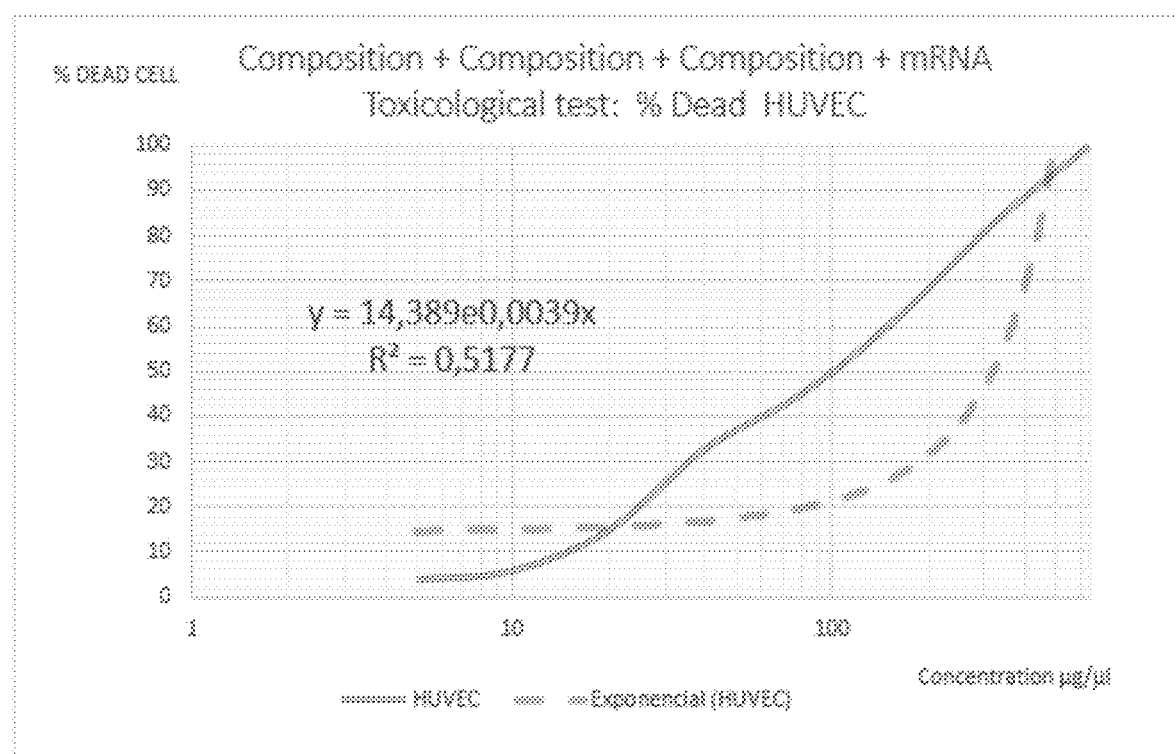
FIG. 71 is a graphic showing the RNA toxicological test in HUVEC cell lines after vaccine incubation of 16 hours three times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 72:
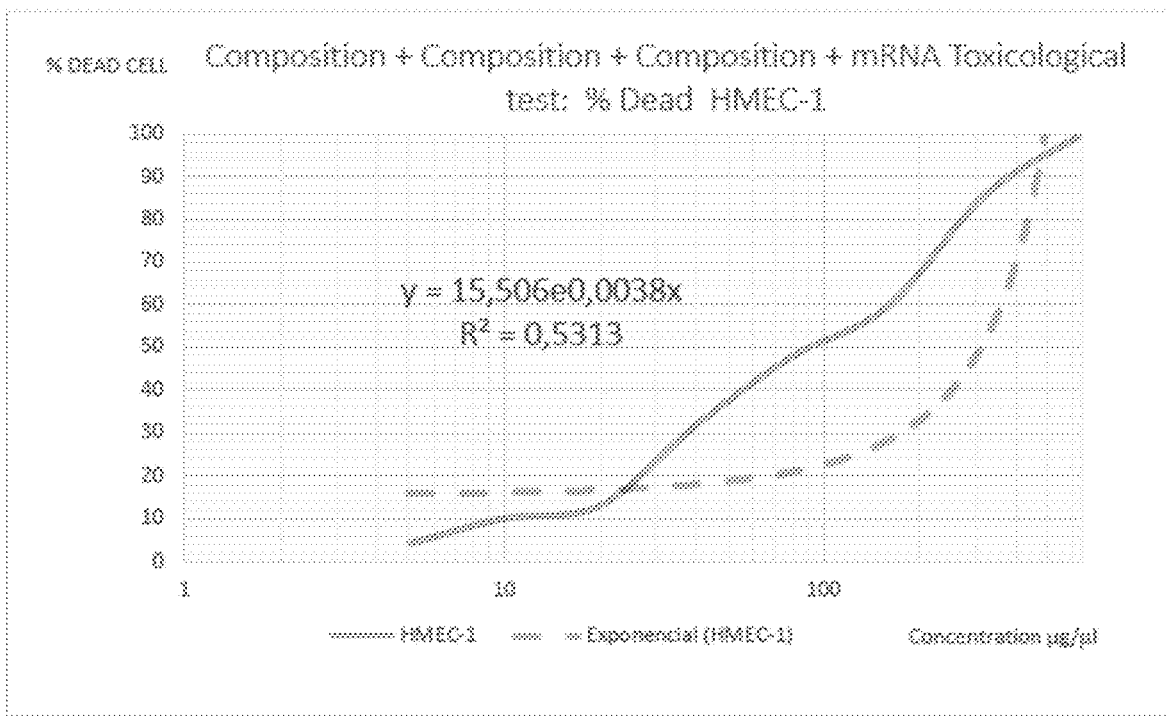
FIG. 72 is a graphic showing the RNA toxicological test in HMEC-1 cell lines after vaccine incubation of 16 hours three times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 73:
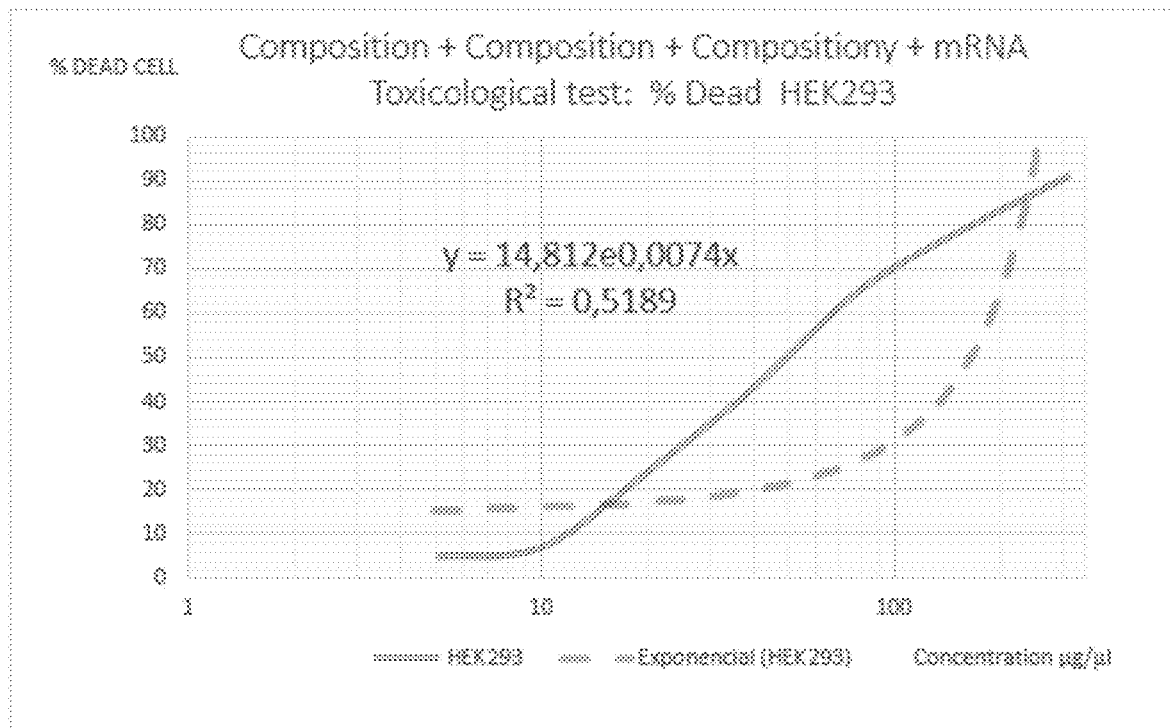
FIG. 73 is a graphic showing the RNA toxicological test in HEK293 cell lines after vaccine incubation of 16 hours three times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 74:
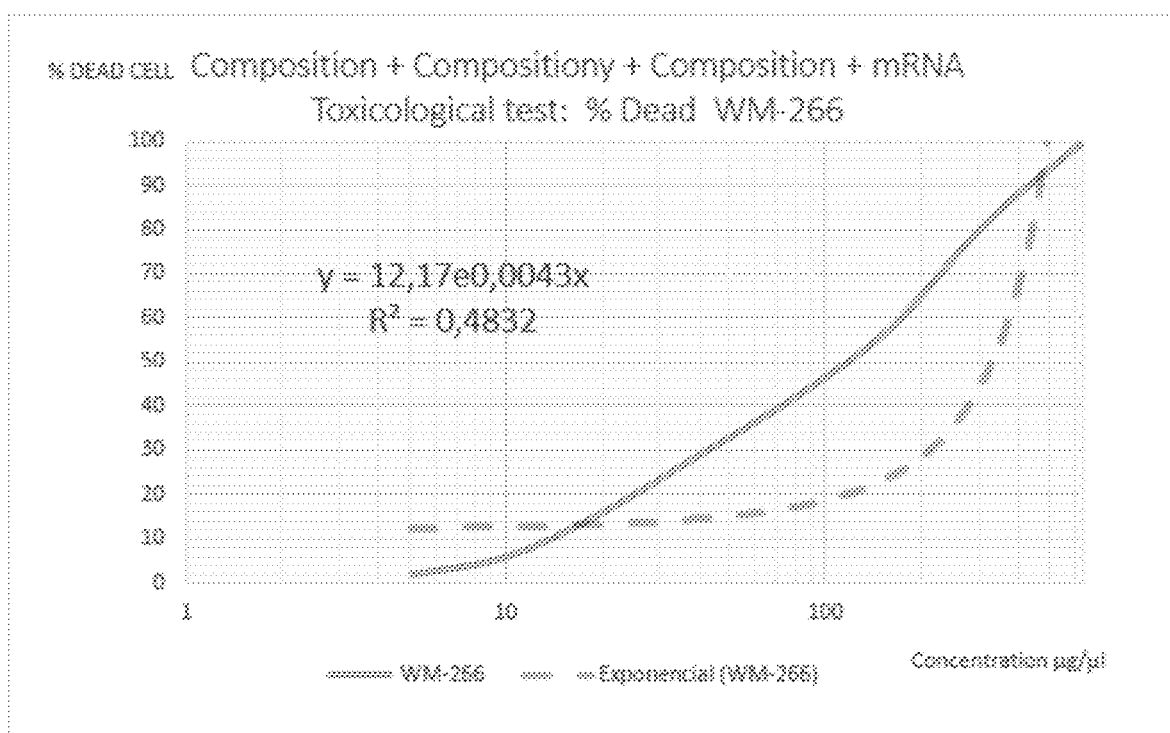
FIG. 74 is a graphic showing the RNA toxicological test in WM-266 cell lines after vaccine incubation of 16 hours three times. The dashed curve represents the exponential dead cell according to serial concentration of RNA (5 µg/µL, 10 µg/µL, 20 µg/µL, 40 µg/µL, 80 µg/µL, 160 µg/µL, 320 µg/µL and 640 µg/µL.
Figure 75:
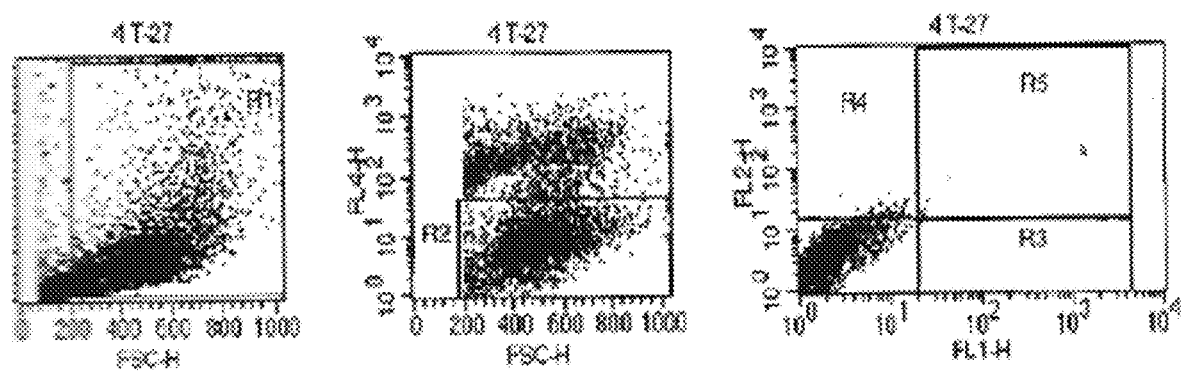
FIG. 75 is a graphic showing the toxicological analysis of RNA-peptide-AB (vaccine) at $LC_{50}=280$ µg/µL in HUVEC cells after 16 hours of incubation. The flux cytometry monitored the dead cells number (R4) 50% of total cell culture.
Figure 76:
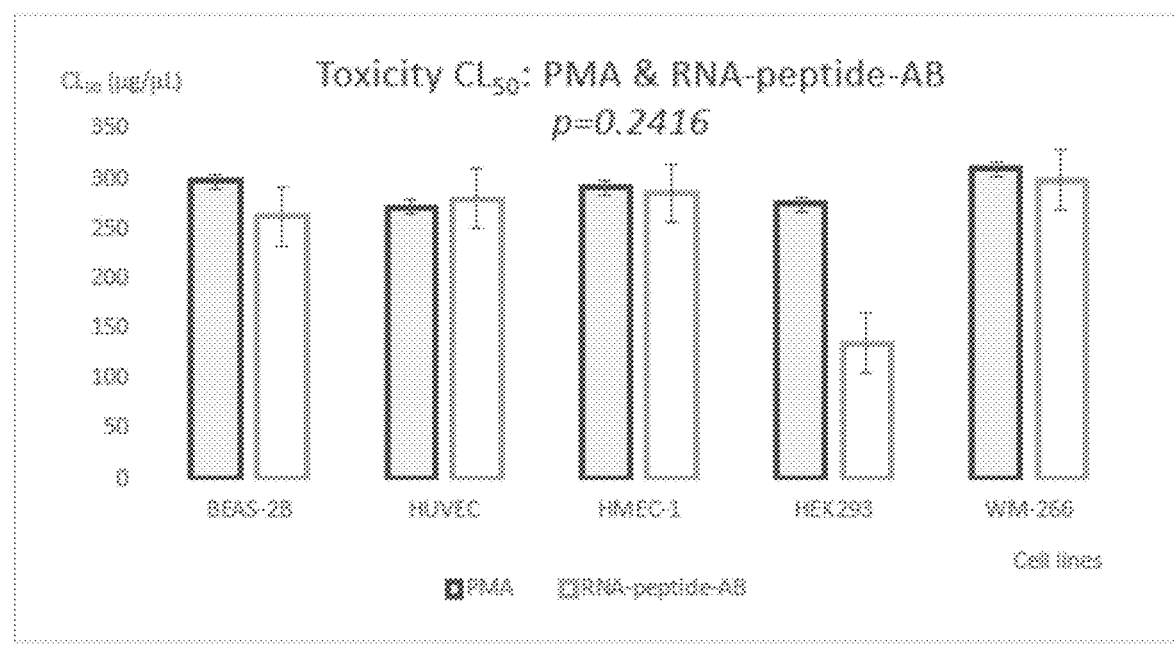
FIG. 76 is a graphic showing the statistical error of $LC_{50}$ in each cell lines (BEAS-2B, HUVEC, HMEC-1, HEK293 and WM-266) according to the action of PMA and RNA-peptide-AB. In order to understand the statistical difference in toxicity action in these cells, the Student's t-test with n=6 is made; and the results is p=0.2416.
Figure 77:
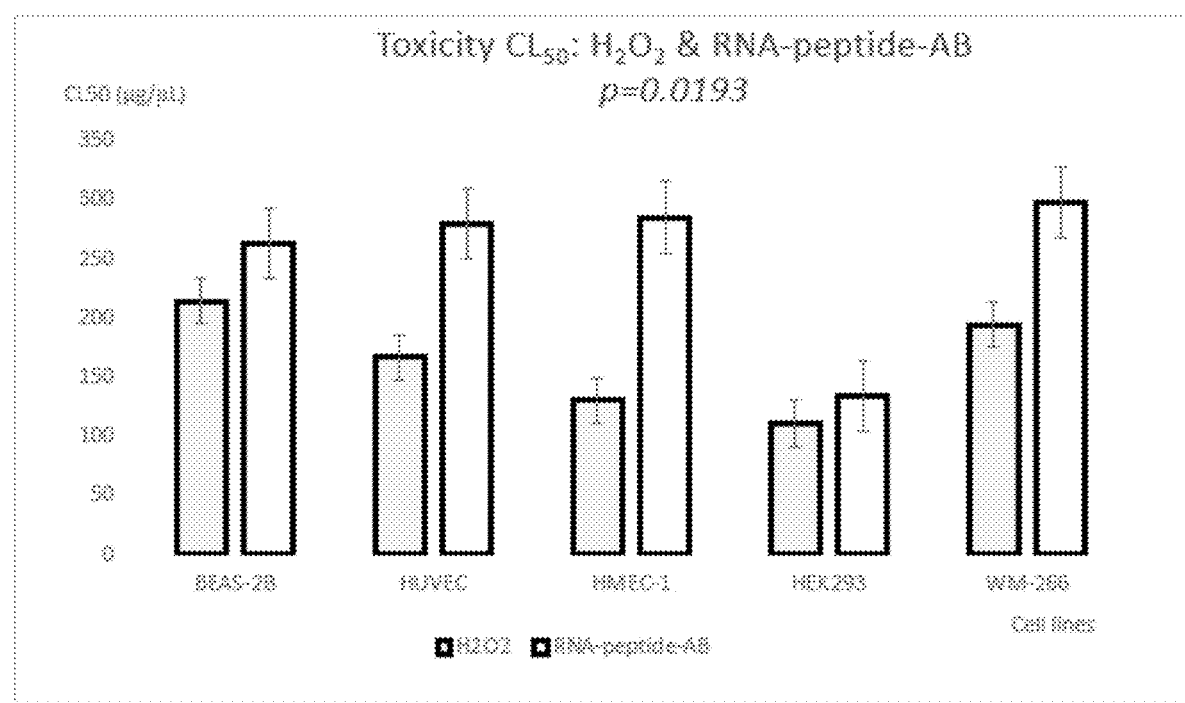
FIG. 77 is a graphic showing the statistical error of $LC_{50}$ in each cell lines (BEAS-2B, HUVEC, HMEC-1, HEK293 and WM-266) according to the action of $H_2O_2$ and RNA-peptide-AB. In order to understand the statistical difference in toxicity action in these cells, the Student's t-test with n=6 is made; and the results is p=0.0193.
Figure 78:
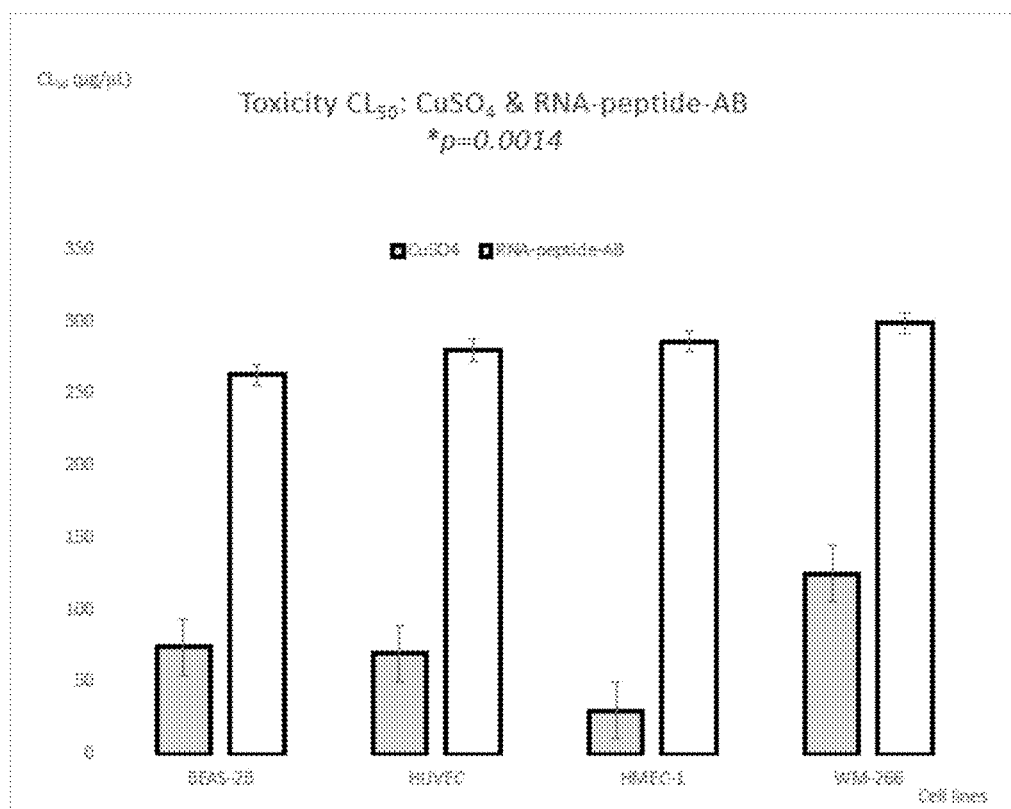
FIG. 78 is a graphic showing the statistical error of $LC_{50}$ in each cell lines (BEAS-2B, HUVEC, HMEC-1 and WM-266) according to the action of $CuSO_4$ and RNA-peptide-AB. In order to understand the statistical difference in toxicity action in these cells, the Student's t-test with n=6 is made; and the results is *p=0.0014.
Figure 79:
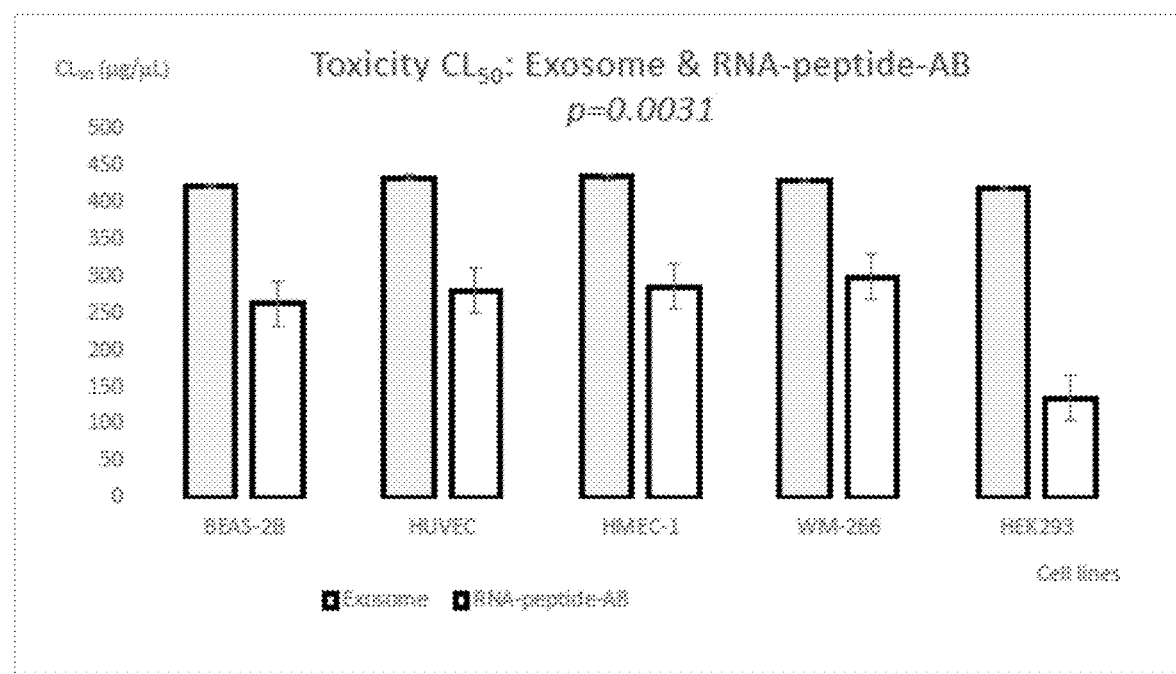
FIG. 79 is a graphic showing the statistical error of $LC_{50}$ in each cell lines (BEAS-2B, HUVEC, HMEC-1, HEK293 and WM-266) according to the action of exosome and RNA-peptide-AB. In order to understand the statistical difference in toxicity action in these cells, the Student's t-test with n=6 is made; and the results is p=0.0031.
Figure 80:
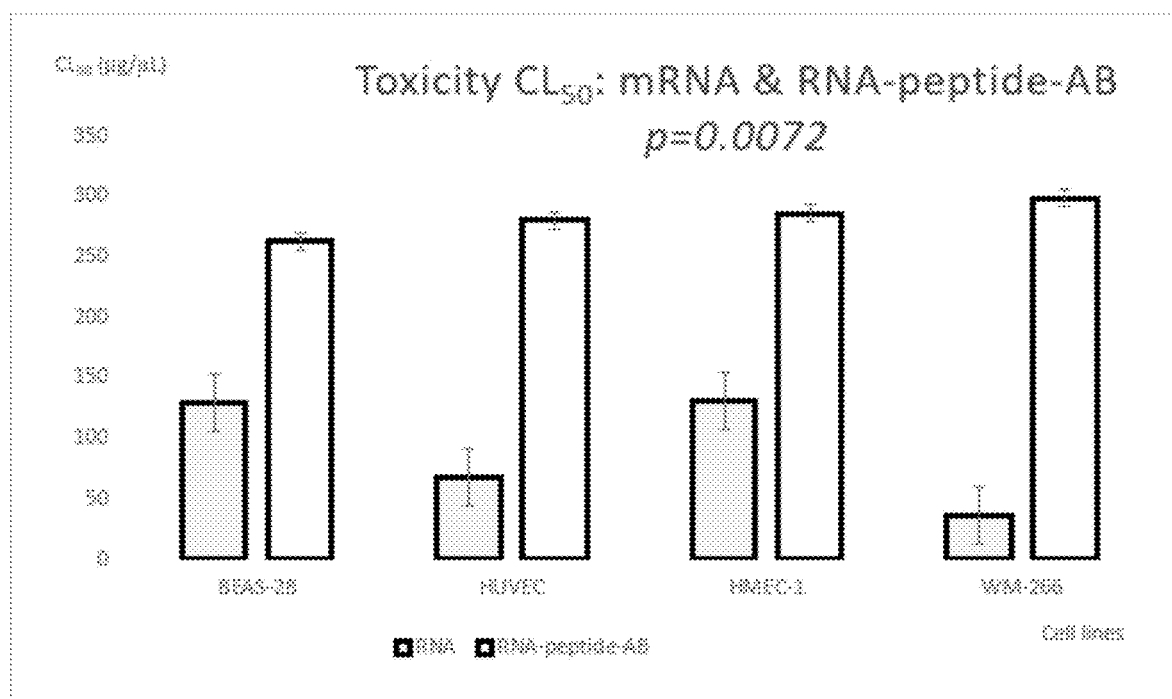
FIG. 80 is a graphic showing the statistical error of $LC_{50}$ in each cell lines (BEAS-2B, HUVEC, HMEC-1 and WM-266) according to the action of RNA and RNA-peptide-AB. In order to understand the statistical difference in toxicity action in these cells, the Student's t-test with n=6 is made; and the results is p=0.0072.
Figure 81:
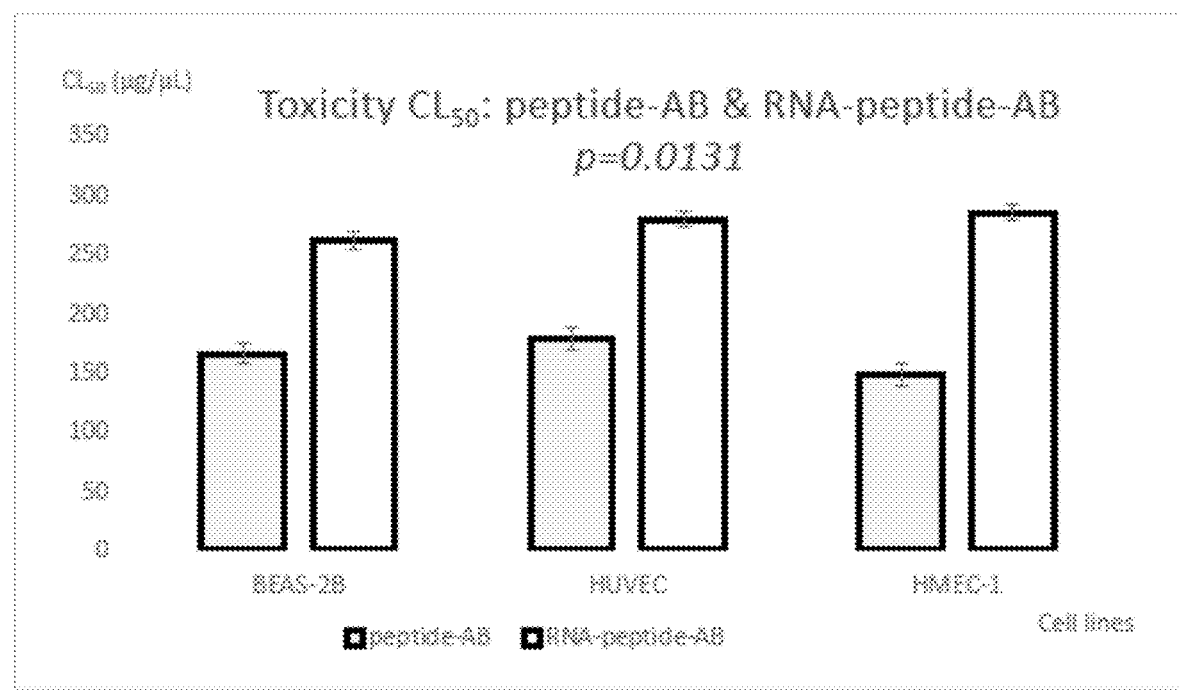
FIG. 81 is a graphic showing the statistical error of $LC_{50}$ in each cell lines (BEAS-2B, HUVEC and HMEC-1) according to the action of peptide-AB and RNA-peptide-AB. In order to understand the statistical difference in toxicity action in these cells, the Student's t-test with n=6 is made; and the results is p=0.0131.
Figure 82:
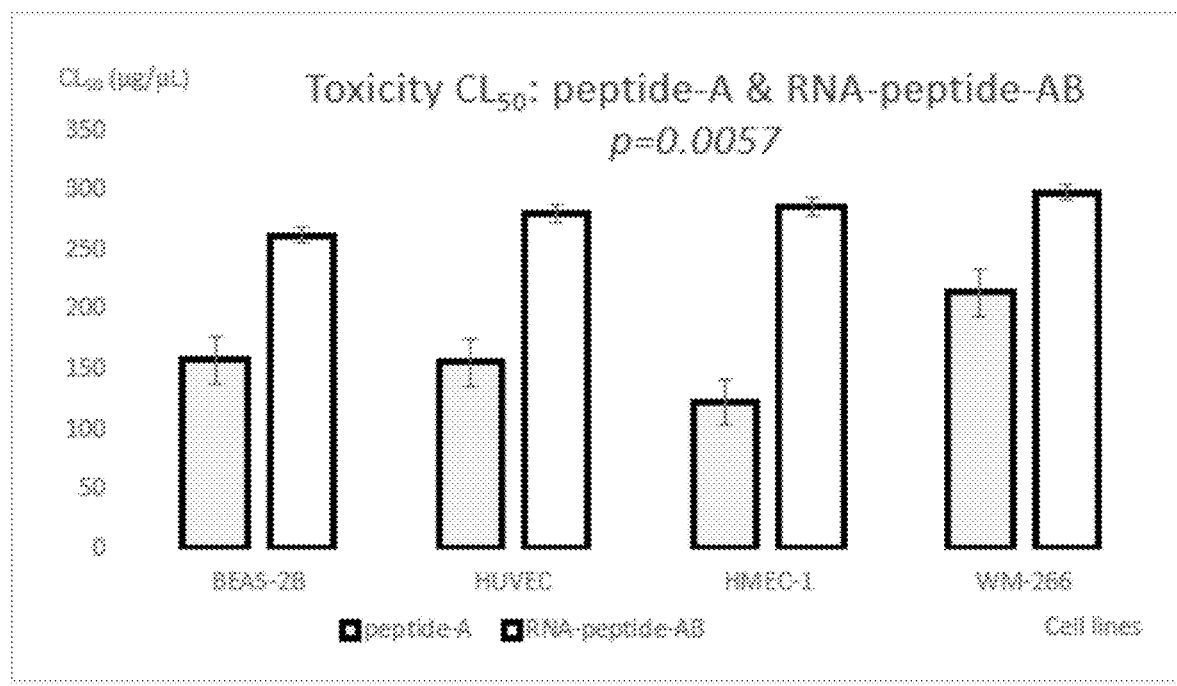
FIG. 82 is a graphic showing the statistical error of $LC_{50}$ in each cell lines (BEAS-2B, HUVEC, HMEC-1 and WM-266) according to the action of peptide-A and RNA-peptide-AB. In order to understand the statistical difference in toxicity action in these cells, the Student's t-test with n=6 is made; and the results is p=0.0057.
Figure 83:
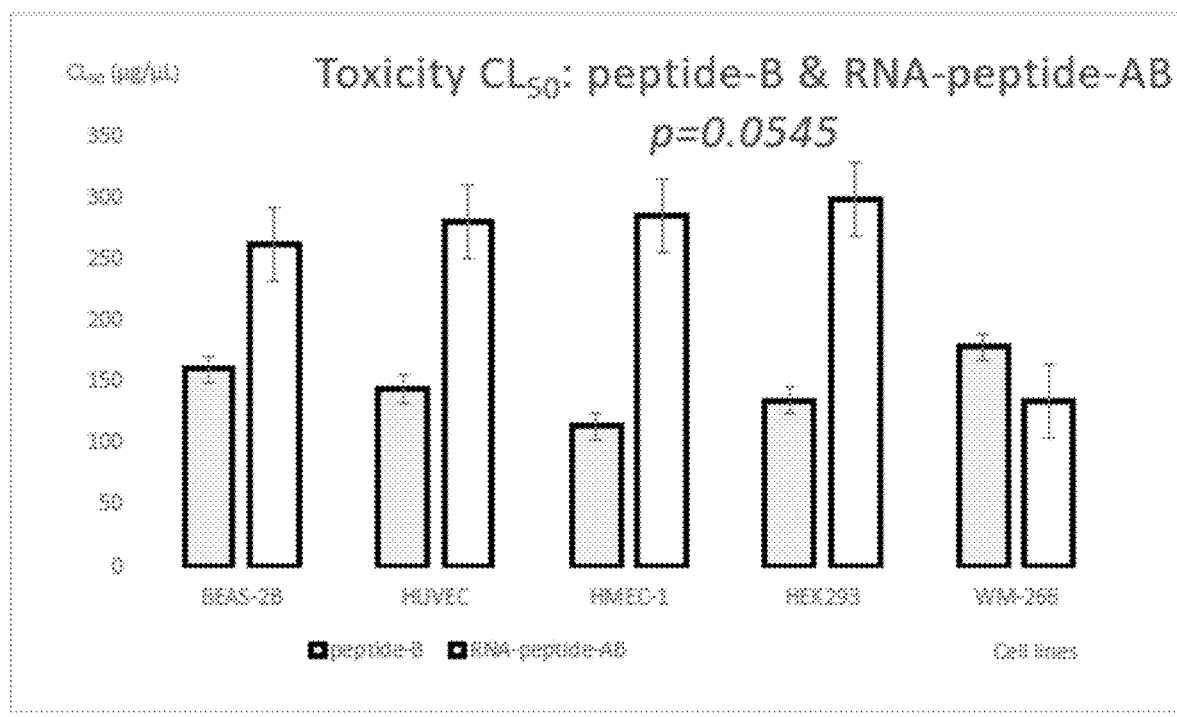
FIG. 83 is a graphic showing the statistical error of $LC_{50}$ in each cell lines (BEAS-2B, HUVEC, HMEC-1, HEK293 and WM-266) according to the action of peptide-B and RNA-peptide-AB. In order to understand the statistical difference in toxicity action in these cells, the Student's t-test with n=6 is made; and the results is p=0.0545.
Figure 84:
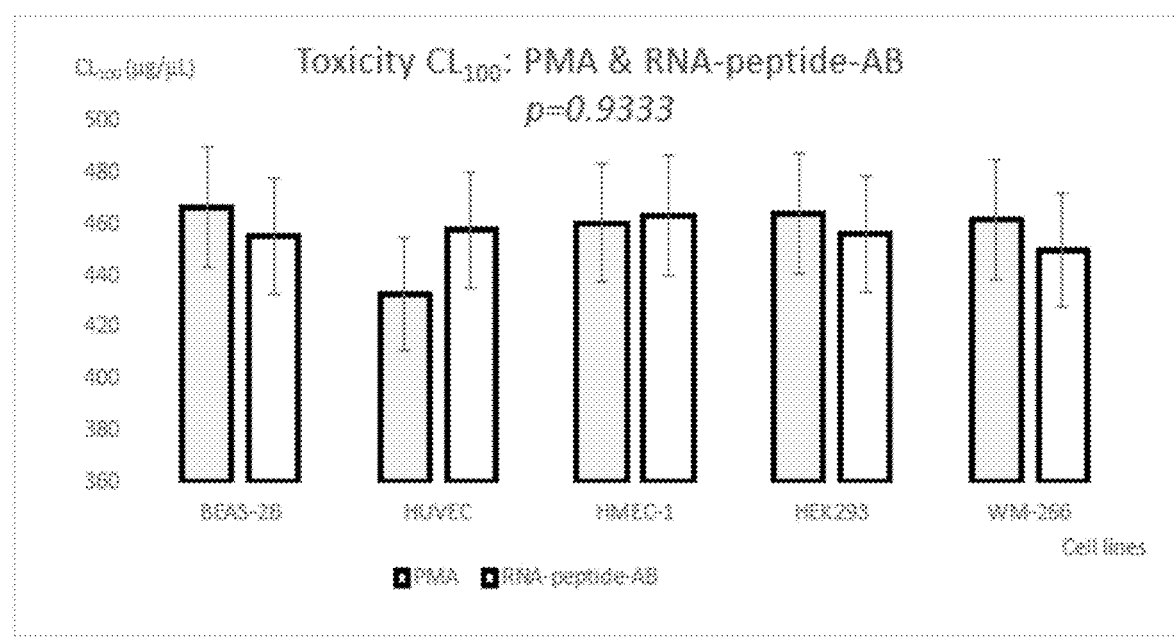
FIG. 84 is a graphic showing the statistical error of $LC_{100}$ in each cell lines (BEAS-2B, HUVEC, HMEC-1, HEK293 and WM-266) according to the action of PMA and RNA-peptide-AB. In order to understand the statistical difference in toxicity action in these cells, the Student's t-test with n=6 is made; and the result is p=0.9333.
Figure 85:
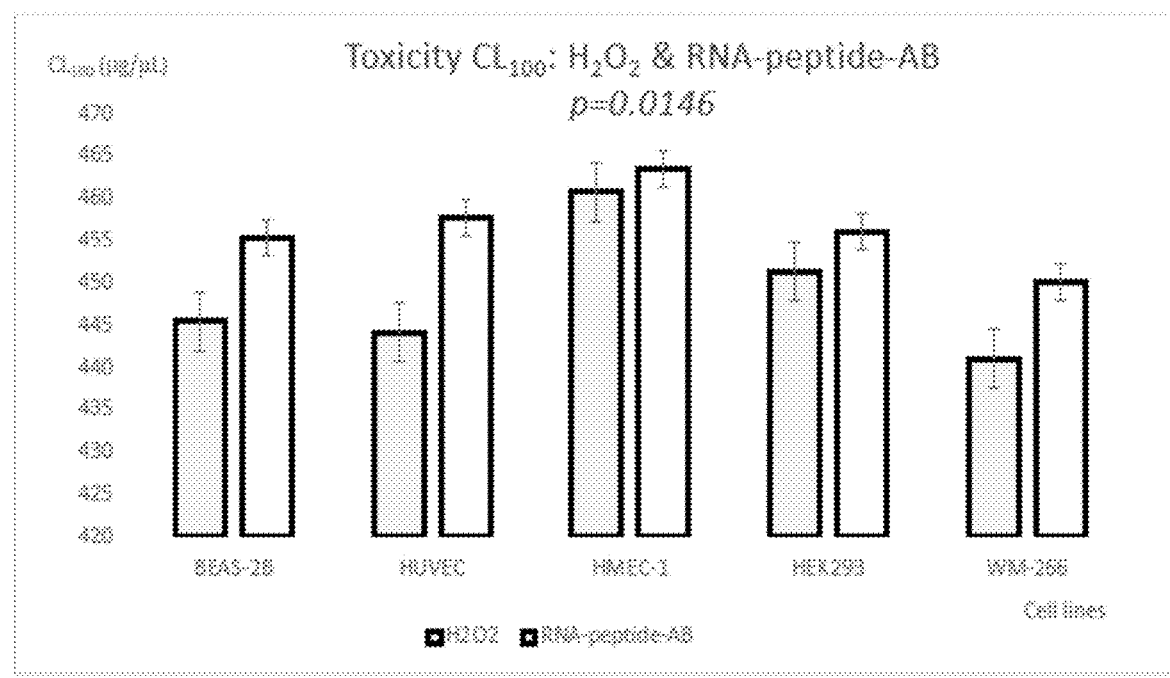
FIG. 85 is a graphic showing the statistical error of $LC_{100}$ in each cell lines (BEAS-2B, HUVEC, HMEC-1, HEK293 and WM-266) according to the action of $H_2O_2$ and RNA-peptide-AB. In order to understand the statistical difference in toxicity action in these cells, the Student's t-test with n=6 is made; and the results is p=0.0146.
Figure 86:
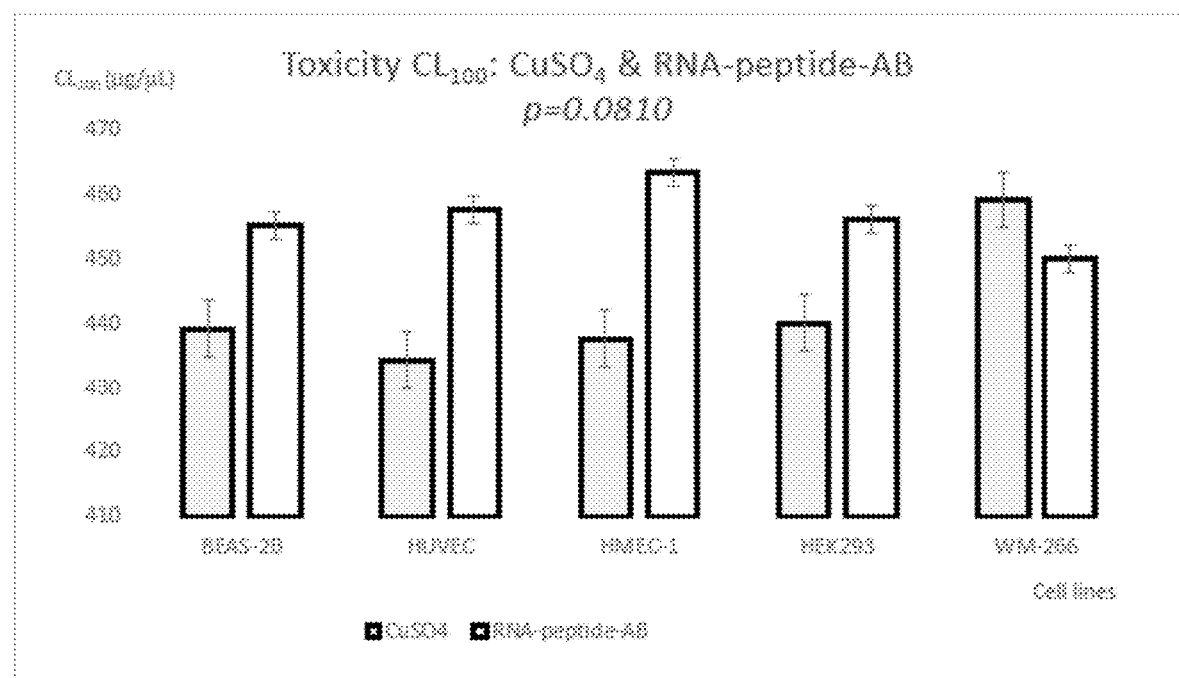
FIG. 86 is a graphic showing the statistical error of $LC_{100}$ in each cell lines (BEAS-2B, HUVEC, HMEC-1, HEK293 and WM-266) according to the action of $CuSO_4$ and RNA-peptide-AB. In order to understand the statistical difference in toxicity action in these cells, the Student's t-test with n=6 is made; and the result is p=0.0810.
Figure 87:
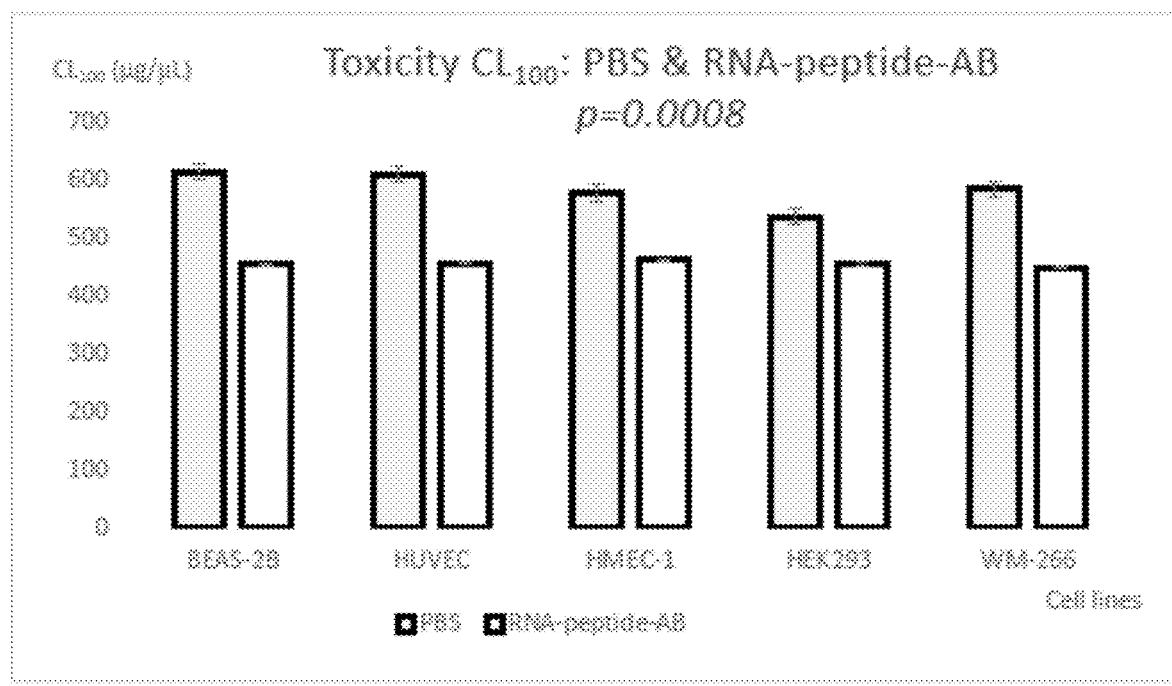
FIG. 87 is a graphic showing the statistical error of $LC_{100}$ in each cell lines (BEAS-2B, HUVEC, HMEC-1, HEK293 and WM-266) according to the action of PBS and RNA-peptide-AB. In order to understand the statistical difference in toxicity action in these cells, the Student's t-test with n=6 is made; and the results is p=0.0008.
Figure 88:
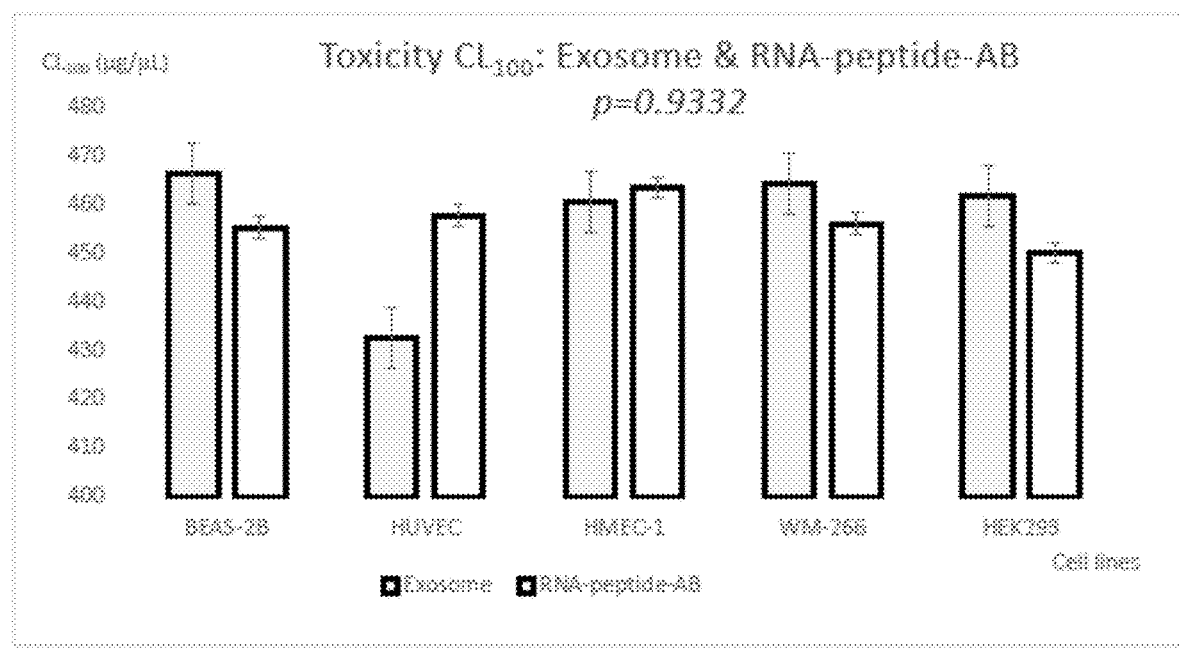
FIG. 88 is a graphic showing the statistical error of $LC_{100}$ in each cell lines (BEAS-2B, HUVEC, HMEC-1, HEK293 and WM-266) according to the action of exosome and RNA-peptide-AB. In order to understand the statistical difference in toxicity action in these cells, the Student's t-test with n=6 is made; and the result is p=0.9332.
Figure 89:
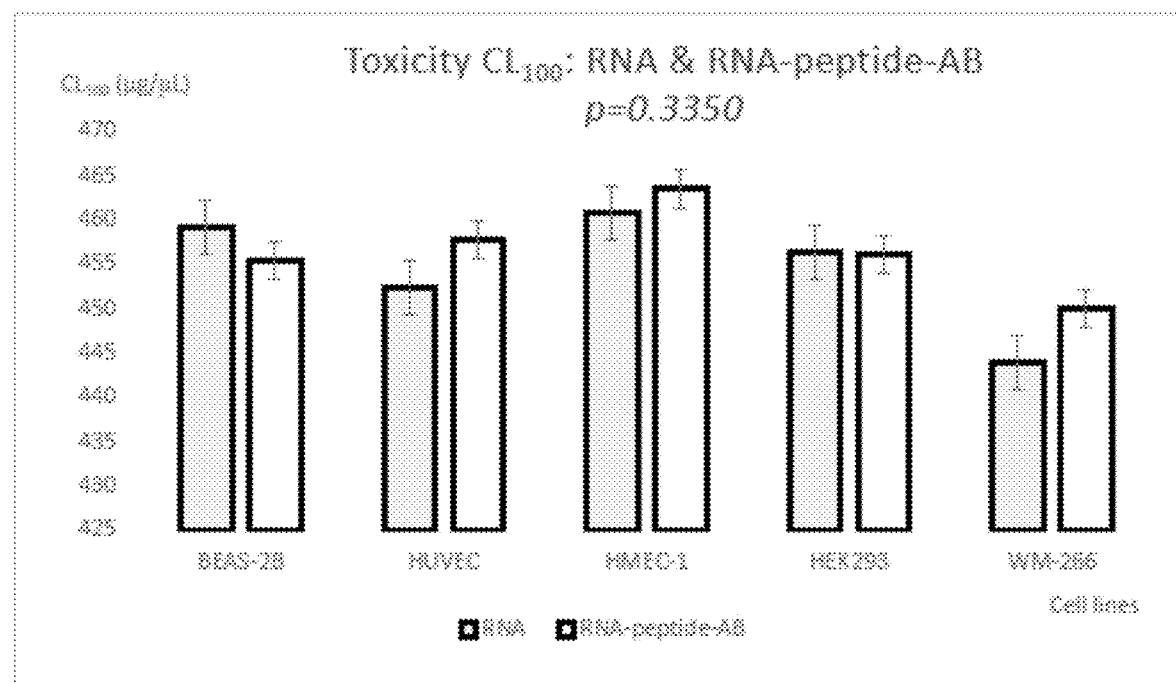
FIG. 89 is a graphic showing the statistical error of $LC_{100}$ in each cell lines (BEAS-2B, HUVEC, HMEC-1, HEK293 and WM-266) according to the action of RNA and RNA-peptide-AB. In order to understand the statistical difference in toxicity action in these cells, the Student's t-test with n=6 is made; and the results is p=0.3350.
Figure 90:
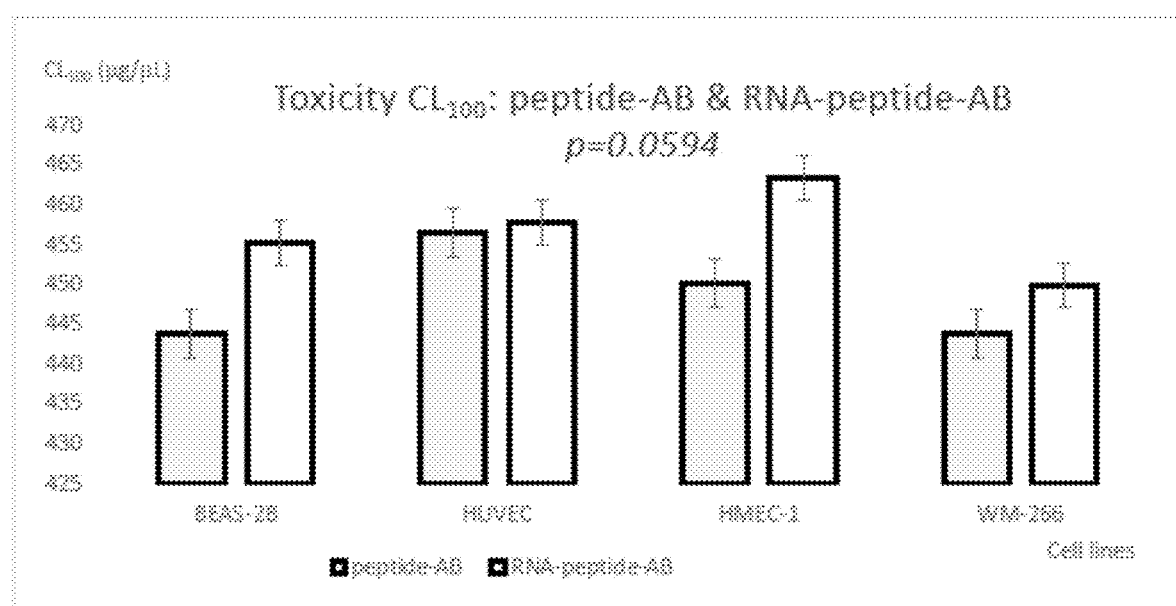
FIG. 90 is a graphic showing the statistical error of $LC_{100}$ in each cell lines (BEAS-2B, HUVEC, HMEC-1 and WM-266) according to the action of peptide-AB and RNA-peptide-AB. In order to understand the statistical difference in toxicity action in these cells, the Student's t-test with n=6 is made; and the results is p=0.0594.
Figure 91:
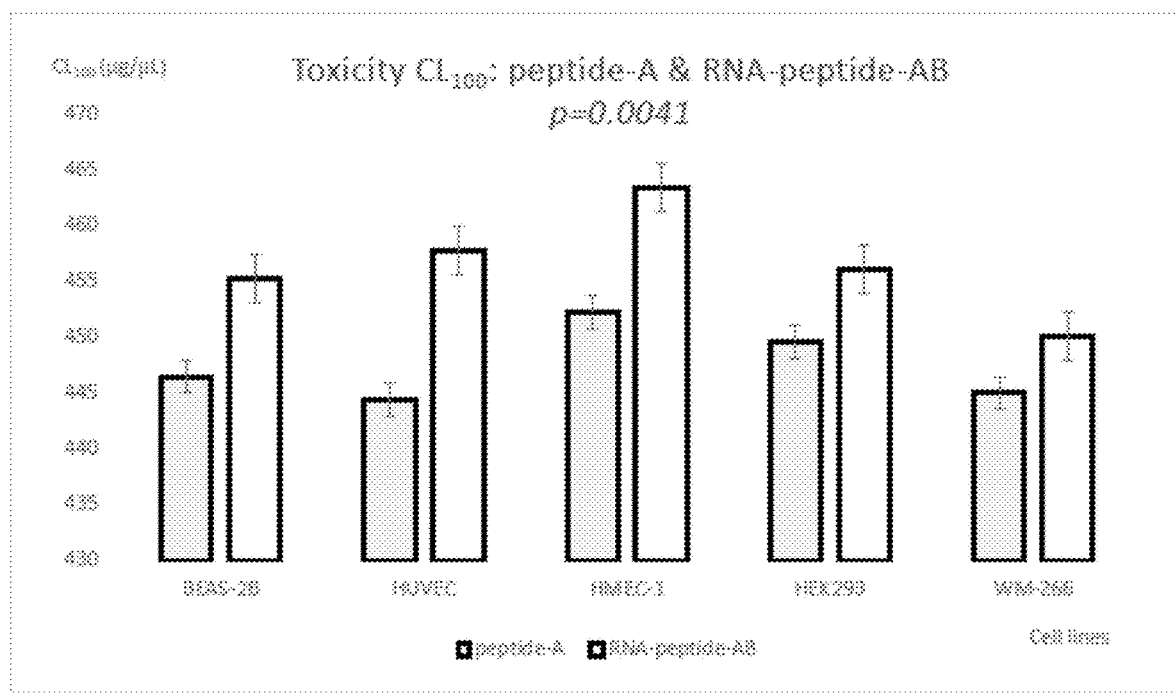
FIG. 91 is a graphic showing the statistical error of $LC_{100}$ in each cell line (BEAS-2B, HUVEC, HMEC-1, HEK293 and WM-266) according to the action of peptide-A and RNA-peptide-AB. In order to understand the statistical difference in toxicity action in these cells, the Student's t-test with n=6 is made; and the results is p=0.0041.
Figure 92:
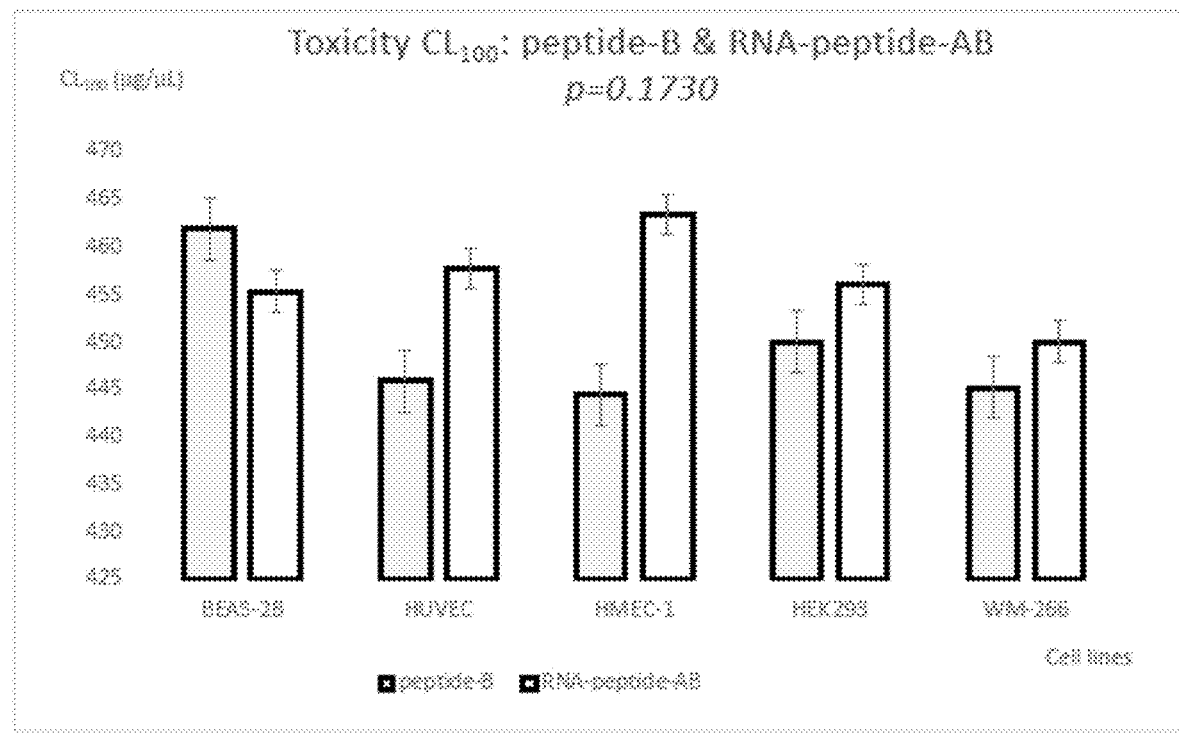
FIG. 92 is a graphic showing the statistical error of $LC_{100}$ in each cell line (BEAS-2B, HUVEC, HMEC-1, HEK293 and WM-266) according to the action of peptide-B and RNA-peptide-AB. In order to understand the statistical difference in toxicity action in these cells, the Student's t-test with n=6 is made; and the result is p=0.1730.

Present invention is a vaccine RNA-peptide against SARS-CoV-2 with therapeutic action using endogenous exosomes as carrier adjuvant.

In one embodiment, the vaccine RNA-peptide against SARS-CoV-2 comprises a micro ribonucleic acid (mRNA) fused to a peptide of a Severe Acute Respiratory Syndrome Coronavirus 2 (SARS-CoV-2) surface protein wherein endogenous exosomes act as carrier.

The vaccine RNA-peptide against SARS-CoV-2 comprising the micro ribonucleic acid (miRNA) fused to the peptide of a Severe Acute Respiratory Syndrome Coronavirus 2 (SARS-CoV-2) surface protein is here also referred as "RNA-peptide-A" vaccine.

The peptide of a Severe Acute Respiratory Syndrome Coronavirus 2 (SARS-CoV-2) surface protein is also here referred as peptide SARS-CoV-2 (peptide A), which has SEQ ID No: 2.

The mRNA comprises a poly-A sequence. In a preferred embodiment, the poly-A sequence is about 10 adenosine nucleotides.

In a preferred embodiment, the miRNA comprises the nucleic acid sequence of SEQ ID NO: 1.

```
                              SEQ ID NO: 1
AAAAAAAAAACUCCUAGAACUAGCAUUACAGAUG
```

Poly-A sequence about 10 adenosine nucleotides is related with a better affinity of the mRNA to endogenous exosomes acting as carrier according to the present invention.

The peptide of the SARS-CoV-2 surface protein is chemically modified.

The term "chemically modified" refers to a modification to the polyprotein of Severe acute respiratory syndrome coronavirus 2 (SARS-CoV-2) sequence, wherein a fragment of the sequence is modified to CVN-DTF-AGSTFIS<u>DEV-D</u> (SEQ ID NO: 2).

The CVN-DTF-AGSTFISDEV-D (SEQ ID NO: 2) is selected as peptide of a Severe Acute Respiratory Syndrome Coronavirus 2 (SARS-CoV-2) surface protein (peptide SARS-CoV-2) target.

In a preferred embodiment, the peptide of the SARS-CoV-2 surface protein, also referred as peptide SARS-CoV-2, and peptide A, comprises the amino acid sequence of SEQ ID NO: 2.

```
                              SEQ ID NO: 2
              CVNDTFAGSTFISDEVD
Size = 17 aa, MW = 1819.91 daltons
```

In another preferred embodiment, the peptide of the SARS-CoV-2 surface protein is fused to a synthetic poly ADP-ribose polymerase peptide also here referred as PARP1 peptide (peptide B).

Example 1, shows a preferred realization of the synthesis process of the peptide A, peptide B, and peptide AB according to the present invention.

In another embodiment, present invention is referred to a vaccine RNA-peptide against SARS-CoV-2 comprising a micro ribonucleic acid (miRNA) fused to a peptide of a Severe Acute Respiratory Syndrome Coronavirus 2 (SARS-CoV-2) surface protein fused to a synthetic poly ADP-ribose polymerase peptide.

The mRNA comprises a poly-A sequence, wherein the poly-A sequence is about 10 adenosine nucleosides.

In a preferred embodiment, the mRNA comprises the nucleic acid sequence of SEQ ID NO: 1.

In a preferred embodiment, the peptide of the SARS-CoV-2 surface protein comprises the amino acid sequence of SEQ ID NO: 2.

The vaccine RNA-peptide against SARS-CoV-2 comprising the micro ribonucleic acid (miRNA) fused to the peptide of a Severe Acute Respiratory Syndrome Coronavirus 2 (SARS-CoV-2) surface protein fused to the synthetic poly ADP-ribose polymerase peptide is also here referred as "RNA-peptide-AB" vaccine.

MHC class I molecules bind the synthetic poly ADP-ribose polymerase peptide, also referred as, peptide-B (SEQ ID NO: 3) GVDEVAKKKSK (Size=11 aa) generated by hydrolysis of RNA-peptide after apoptosis induction for caspase 3 or caspase 7 in infected cell with SARS-CoV-2. The sequence of origin was from RNA-peptide-AB:

```
                    SEQ ID NO: 1 and SEQ ID NO: 4
5'AAAAAAAAAACUCCUAGAACUAGCAUUACAGAUG-Cys-Val- Asn-Asp-Thr-Phe-Ala-Gly-Ser-Thr-Phe-Ile-Ser-Asp- Glu-Val-Asp-Gly-Val-Asp Glu-Val-Ala-Lys-Lys-Lys- Ser-Lys
(Size = 34 nt, Size = 28 aa)
```

In a preferred embodiment, the open reading frame encodes a peptide comprising the amino acid sequence of SEQ ID NO: 4.

```
                              SEQ ID NO: 4
              CVNDTFAGSTFISDEVDGVDEVAKKKSK
```

In a preferred embodiment, the vaccine RNA-peptide against SARS-CoV-2 comprises endogenous exosomes as carrier.

In one embodiment, a method for treating of SARS-CoV-2 in a subject in need thereof comprises administering an effective amount of the RNA-peptide-AB vaccine.

In a preferred embodiment, an effective amount of the composition of the vaccine RNA-peptide comprising micro ribonucleic acid (miRNA) fused to a peptide of a Severe Acute Respiratory Syndrome Coronavirus 2 (SARS-COV2) surface protein fused to a synthetic poly ADP-ribose polymerase peptide is between about 135 µg/µL and 299 µg/µL.

In one embodiment, a method for treating SARS-CoV-2 in a subject in need thereof comprises administering to the subject an effective amount of a vaccine RNA-peptide against SARS-CoV-2 comprising a micro ribonucleic acid (miRNA) comprising an open reading frame encoding the peptide of the Severe Acute Respiratory Syndrome Coronavirus 2 (SARS-CoV-2) surface protein fused to a synthetic poly ADP-ribose polymerase peptide, wherein endogenous exosomes are the carrier. In a preferred embodiment, the miRNA comprises the nucleic acid sequence of SEQ ID NO: 1 and the open reading frame encodes the peptide comprising the amino acid sequence of SEQ ID NO: 4.

The results and efficacy of the vaccine RNA-peptide-A and RNA-peptide-AB of the present invention are showed in Example 9 tables 52 to 59.

In one embodiment, a method for preventing/treating SARS-CoV-2 in a subject comprises administering to the subject a single dose of the RNA-peptide-A/RNA-peptide-AB vaccine of the present invention.

In one embodiment, a method for preventing/treating SARS-CoV-2 in a subject comprises administering to the subject a second dose of the RNA-peptide-A/RNA-peptide-AB vaccine of the present invention.

In one embodiment, a method for preventing/treating SARS-CoV-2 in a subject comprises administering to the subject a third dose of the RNA-peptide-A/RNA-peptide-AB vaccine of the present invention.

As seen in FIG. 1, a schema of structure of RNA-peptide vaccine shows the antigen presentation pathway for peptide B in MHC class I and the RNA-peptide-A presentation in MHC class II.

Given the role that the MHC class I antigen presentation pathway plays in the detection of virally infected cells by CTLs, cell infected by SARS-CoV-2 in MHC class I expose the peptide-B, size 11 aa, and active the elimination of infected cells.

In addition, MHC class II proteins usually accommodate peptides of 13-25 amino acids in length in their open binding groove.

Present invention is also related with a method of stimulating an immune response against SARS-CoV-2 in a subject administering the RNA-peptide-A vaccine. The results and efficacy of the RNA-peptide-A vaccine of the present invention are showed in Example 9 tables 52 to 59.

MHC class II molecules bind the peptide of the SARS-CoV-2 surface protein, also referred as peptide-A (SEQ ID NO: 2), generated by hydrolysis of RNA-peptide after apoptosis induction for caspase 3 or caspase 7 in infected cell with SARS-CoV-2.

```
                        SEQ ID NO: 1 and SEQ ID NO: 2
     5'AAAAAAAAAACUCCUAGAACUAGCAUUACAGAUG- Cys-Val-Asn-Thr-Phe-Ala-Gly-Ser-Phe-Ser- Glu-Val-Asp
(Size = 17 aa)
```

Given the role that the MHC Class II molecules normally found only on professional antigen-presenting cells such as dendritic cells, mononuclear phagocytes, some endothelial cells, thymic epithelial cells, and B cells. These cells are important in initiating immune responses. Cell infected by SARS-CoV-2 in MHC class II expose the RNA-peptide-A, size 17 aa, and active the pathways action of immune system.

Another object of the present invention is the algorithm by which vaccine RNA-peptide of the present invention was achieved.

The algorithms of present invention are a tool that allows predicting the stability of hybrid oligonucleotide and protein molecules in their most simplified expression of cDNA/RNA and peptide. This hybrid molecule has a high affinity for exosomes, allowing its extracellular transport from cell to cell. These chimeras in cDNA-peptide or RNA-peptide have a specific biological action with antiviral efficacy due to their chemical structure, since they participate in the viral pathway's replication. On the other hand, they present specific antigenic structures that can involve immune responses.

The target peptide and the oligonucleotide are molecules selected according to the three following parameters:

1. Fusion Stability (FS); where FS>80%

$FS = a*b*c*d(\text{cruz})$ $a$ = Size poly $A$/Size poly Cys $b$ = MW mRNA/MW peptide $c$ = Size peptide/Size mRNA $d = [\text{mRNA}(2*(A+U)+3*(C+G))/(\text{PI peptide}^2)]$ 2. Exosome Affinity (EA); where EA>95%

$EA = FS*[(\text{MW peptide/mMW RNA})+(\text{Size peptide/Size Poly } A+\text{RNA primer})]$ $EA = (ro)$ 3. Biological Action (BA); where 0.5<BA<2.0

$BA = EA/FS$ $BA = (ro/\text{cruz})$ 3.1. Optimal Biological Action (OBA); where 0.8<OBA<1.3

$OBA = (ro/\text{cruz})$ value for antiviral efficacy to RNA-peptide with exosome as carrier are 0.8<OBA<1.3

1) How to Design the Target RNA

The polyadenylation of RNA primer gives it larger molecular stability and a longer half-life due to the action of oligonuclease enzymes. It has been selected as target RNA that may implication in the metabolic pathways of SARS-CoV-2 virogenesis.

Avian infectious bronchitis virus (IBV) is an enveloped virus with a positive-stranded RNA genome. IBV is a member of the genus *Gammacoronavirus*, family Coronaviridae and is an important viral pathogen in the poultry industry. It causes a highly contagious disease in chickens, mainly affecting the respiratory and reproductive tract.

After research in literature (Table 1) the avian infectious bronchitis virus was selected as target in RNA primers as immune representative model of SARS-CoV-2.

TABLE 1

| miRNA | Species | Cell type/tissue | Infection | Findings |
|---|---|---|---|---|
| MiR-34c | Human | CD4+ T-cells | HIV | T-cell activation, facilitates virus replication [17] |
| | Human | HeLa | Flaviviruses | Inhibits virus replication, Wnt/Notch/ IFN-mediated [18] |
| | Chicken | Trachea | Influenza A virus | Upregulated upon H5N3 infection [19] |
| | Human | A549 | Influenza A virus | Enhances virus replication [20] |
| MiR-34b | Chicken | Spleen | ALV | Promotes virus replication by targeting MDA5 [37] |
| | Human | Throat swab | Influenza B virus | Upregulated upon Influenza B virus infection [21] |
| | Chicken | Spleen | Marek's disease | Upregulated in virus-resistant line [22] |
| | Human | Huh7.5 HCV | HCV | Facilitates virus replication [23] |
| | Chicken | Trachea | Influenza A virus | Upregulated upon H5N3 infection [19] |
| MiR-1788 | Chicken | Cecum | *Salmonella* | Upregulated upon *S. Typhimurium* infection [24] |
| MiR-203a | Chicken | DF-1 & embryo | NDV | Enhances virus replication and embryonic death [25] |

TABLE 1-continued

| miRNA | Species | Cell type/tissue | Infection | Findings |
|---|---|---|---|---|
| | Pig | LFBK-avβ6 | FMDV | Inhibits FMDV replication [26] |
| | Human | HEPG2 | HBV | Upregulated upon infection, induces inflammation [27] |
| | Human | HEPG2 | HCV | Downregulated → EMT & carcinogenesis [28] |
| | Human | Nasal mucosa | RSV | Upregulated in RSV-positive infants [29] |
| MiR-200a | Human | HEPG2 | HBV | Downregulated upon infection → cell division & invasion [30] |
| | Chicken | Intestine | Marek's disease | Upregulated in virus-susceptible line [22] |
| MiR-200b | Human | CNE1AKATA | EBV | Induces EBV lytic reactivation [38] |
| | Chicken | Intestine | Marek's disease | Upregulated in virus-susceptible line [29] |
| MiR-429 | Human | EBV-293 | EBV | Induces EBV lytic reactivation [31] |
| | Human | Nasal mucosa | RSV | Downregulated in RSV-positive infants [29] |
| | Chicken | Intestine | Marek's disease | Upregulated in virus-susceptible line [22] |
| MiR-1b | Chicken | Trachea & lung | Influenza A virus | Upregulated upon H5N3 infection [19] |
| MiR-133c | Chicken | Cecum | *Salmonella* | Upregulated upon *S. enterica* infection [32] |
| MiR-133a | Monkey | Vero | DENV | Suppresses viral replication [33] |
| MiR-1a | Chicken | Kidney | IBV | Upregulated upon viral infection [38] |
| | Chicken | Trachea & lung | Influenza A virus | Upregulated upon H5N3 infection [19] |
| MiR-133b | Dog | Lung | Influenza A virus | May inhibit innate immunity, increasing pathogenicity [34] |
| MiR-206 | Chicken | Lung | Influenza A virus | Downregulated upon infection [35] |
| | Pig | Lung | Influenza A virus | Upregulated upon H1N2 infection [36] |
| | Chicken | Trachea & lung | Influenza A virus | Upregulated in lung; downregulated in trachea (upon H5N3 infection) [19] |
| MiR-499 | Chicken | Spleen | Marek's disease | Upregulated in virus-resistant line [22] |
| | Chicken | Trachea | Influenza A virus] | Upregulated upon H5N3 infection [19] |

Identification of RNA Target

Potential target genes of DE miRNAs were identified using the TargetScan 7.1 and miRBD web platforms. Only targets identified by both programs were considered significant.

A novel insight into the complex interaction between IBV and the chicken host, and specifically the factors that could modulate the human immune response to IBV infection is studied. The results contribute with ribonucleic acid (RNA) involved in IBV infection and pathogenesis.

Based on published data on COVID-19, a preventive vaccine is designed in Silico aimed to protect against COVID-19 infection and transmission. One aim of this is to better understand potential dormant repositories of outbreaks and potential spread of those repositories, together with potential geogenic terrain factors. As mRNA target, are used primers from Kemp V. "miRNA repertoire and host immune factor regulation upon avian coronavirus infection in eggs": primers Biolegio, Nijmegen, The Netherlands.

The analysis identified a miRNA-peptide with theoretical fusion value stability FS=84.81 cruz, EA=99.15 ro and BA=1.17 to treat COVID-19.

The miRNA selected comprises the nucleic acid sequence as seen in Table 2.

TABLE 2

| SEQ ID NO. | Sequence |
|---|---|
| SEQ ID NO: 1 | AAAAAAAAAACUCCUAGAACUAGCAUUACAGAUG |

2) How to Select the Target Protein (Peptide)

Search the epitope that starts with C and finishes with DEV (aa)
Sequence: QQX03240.1
Length: 7101aa
QQX03240.1 ORF1ab polyprotein [Severe acute respiratory syndrome coronavirus 2]

SEQ ID NO: 5

MESLVPGFNEKTHVQLSLPVLQVRDVLVRGFGDSVEEVLSEARQHLKDG

TCGLVEVEKGVLPQLEQPYVFIKRSDARTAPHGHVMVELVAELEGIQYG

RSGETLGVLVPHVGEIPVAYRKVLLRKNGNKGAGGHSYGADLKSFDLGD

ELGTDPYEDFQENWNTKHSSGVTRELMRELNGGAYTRYVDNNFCGPDGY

PLECIKDLLARAGKASCTLSEQLDFIDTKRGVYCCREHEHEIAWYTERS

EKSYELQTPFEIKLAKKFDIFNGECPNFVFPLNSIIKTIQPRVEKKKLD

GFMGRIRSVYPVASPNECNQMCLSTLMKCDHCGETSWQTGDFVKATCEF

CGTENLTKEGATTCGYLPQNAVVKIYCPACHNSEVGPEHSLAEYHNESG

LKTILRKGGRTIAFGGCVFSYVGCHNKCAYWVPRASANIGCNHTGVVGE

GSEGLNDNLLEILQKEKVNINIVGDFKLNEEIAIILASFSASTSAFVET

VKGLDYKAFKQIVESCGNFKVTKGKAKKGAWNIGEQKSILSPLYAFASE

AARVVRSIFSRTLETAQNSVRVLQKAAITILDGISQYSLRLIDAMMFTS

DLATNNLVVMAYITGGVVQLTSQWLTNIFGTVYEKLKPVLDWLEEKFKE

GVEFLRDGWEIVKFISTCACEIVGGQIVTCAKEIKESVQTFFKLVNKFL

ALCADSIIIGGAKLKALNLGETFVTHSKGLYRKCVKSREETGLLMPLKA

PKEIIFLEGETLPTEVLTEEVVLKTGDLQPLEQPTSEAVEAPLVGTPVC

INGLMLLEIKDTEKYCALAPNMMVTNNTFTLKGGAPTKVTFGDDTVIEV

QGYKSVNITFELDERIDKVLNEKCSAYTVELGTEVNEFACVVADAVIKT

LQPVSELLTPLGIDLDEWSMATYYLFDESGEFKLASHMYCSFYPPDEDE

EEGDCEEEEFEPSTQYEYGTEDDYQGKPLEFGATSAALQPENPHLEEEQ

EEDWLDDDSQQTVGQQDGSEDNQTTTIQTIVEVQPQLEMELTPVVQTIE

VNSFSGYLKLTDNVYIKNADIVEEAKKVKPTVVVNAANVYLKHGGGVAG

ALNKATNNAMQVESDDYIATNGPLKVGGSCVLSGHNLAKHCLHVVGPNV

NKGEDIQLLKSAYENFNQHEVLLAPLLSAGIFGADPIHSLRVCVDTVRT

NVYLAVFDKNLYDKLVSSFLEMKSEKQVEQKIAEIPKEEVKPFITESKP

SVEQRKQDDKKIKACVEEVTTTLEETKFLTENLLLYIDINGNLHPDSAT

LVSDIDITFLKKDAPYIVGDVVQEGVLTAVVIPTKKAGGTTEMLAKALR

-continued

KVPTDNYMYPGQGLNGYTVEEAKTVLKKCKSAFYILPSIISNEKQEILG
TVSWNLREMLAHAEETRKLMPVCVETKAIVSTIQRKYKGIKIQEGVVDY
GARFYFYTSKTTVASLINTLNDLNETLVTMPLGYVTHGLNLEEAARYMR
SLKVPATVSVSSPDAVTAYNGYLTSSSKTPEEHFIETISLAGSYKDWSY
SGQSTQLGIEFLKRGDKSVYYTSNPTTFHLDGEVITFDNLKTLLSLREV
RTIKVFTTVDNINLHTQVVDMSMTYGQQFGPTYLDGADVTKIKPHNSHE
GKTFYVLPNDDTLRVEAFEYYHTTDPSFLGRYMSALNHTKKWKYPQVNG
LTSIKWADNNCYLATALLTLQQIELKFNPPALQDAYYRARAGEAANFCA
LILAYCNKTVGELGDVRETMSYLFQHANLDSCKRVLNVVCKTCGQQQTT
LKGVEAVMYMGTLSYEQFKKGVQIPCTCGKQATKYLVQQESPFVMMSAP
PAQYELKHGTFTCASEYTGNYQCGHYKHITSKETLYCIDGALLTKSSEY
KGPITDVFYKENSYTTTIKPVTYKLDGVVCTEIDPKLDNYYKKDNSYFT
EQPIDLVPNQPYPNASFDNFKFVCDNIKFADDLNQLTGYKKPASRELKV
TFFPDLNGDVVAIDYKHYTPSFKKGAKLLHKPIVWHVNNATNKATYKPN
TWCIRCLWSTKPVETSNSFDVLKSEDAQGMDNLACEDLKPVSEEVVENP
TIQKDVLECNVKTTEVVGDIILKPANNSLKITEEVGHTDLMAAYVDNSS
LTIKKPNELSRVLGLKTLATHGLAAVNSVPWDTIANYAKPFLNKVVSTT
TNIVTRCLNRVCTNYMPYFFTLLLQLCTFTRSTNSRIKASMPTTIAKNT
VKSVGKFCLEASFNYLKSPNFSKLINIIIWFLLLSVCLGSLIYSTAALG
VLMSNLGMPSYCTGYREGYLNSTNVTIATYCTGSIPCSVCLSGLDSLDT
YPSLETIQITISSFKWDLTAFGLVAEWFLAYILFTRFFYVLGLAAIMQL
FFSYFAVHFISNSWLMWLIINLVQMAPISAMVRMYIFFASFYYVWKSYV
HVVDGCNSSTCMMCYKRNRATRVECTTIVNGVRRSFYVYANGGKGFCKL
HNWNCVNCDTFCAGSTFISDEVARDLSLQFKRPINPTDQSSYIVDSVTV
KNGSIHLYFDKAGQKTYERHSLSHFVNLDNLRANNTKGSLPINVIVFDG
KSKCEESSAKSASVYYSQLMCQPILLLDQALVSDVGDSAEVAVKMFDAY
VNTFSSTFNVPMEKLKTLVATAEAELAKNVSLDNVLSTFISAARQGFVD
SDVETKDVVECLKLSHQSDIEVTGDSCNNYMLTYNKVENMTPRDLGACI
DCSARHINAQVAKSHNIALIWNVKDFMSLSEQLRKQIRSAAKKNNLPFK
LTCATTRQVVNVVTTKIALKGGKIVNNWLKQLIKVTLVFLFVAAIFYLI
IPVHVMSKHTDFSSEIIGYKAIDGGVTRDIASTDTCFANKHADFDTWFS
QRGGSYTNDKACPLIAAVITREVGFVVPGLPGTILRTTNGDFLHFLPRV
FSAVGNICYTPSKLIEYTDFATSACVLAAECTIFKDASGKPVPYCYDTN
VLEGSVAYESLRPDTRYVLMDGSIIQFPNTYLEGSVRVVWFDSEYCRHG
TCERSEAGVCVSTSGRWVLNNDYYRSLPGVFCGVDAVNLLTNMFTPLIQ
PIGALDISASIVAGGIVAIVVTCLAYYFMRFRRAFGEYSHVVAFNTLLF
LMSFTVLCLTPVYSFLPGVYSVIYLYLTFYLTNDVSFLAHIQWMVMFTP
LVPFWITIAYIICISTKHFYWFFSNYLKRRVVFNGVSFSTFEEAALCTF
LLNKEMYLKLRSDVLLPLTQYNRYLALYNKYKYFSGAMDTTSYREAACC
HLAKALNDFSNSGSDVLYQPPQTSITSAVLQSGFRKMAFPSGKVEGCMV
QVTCGTTTLNGLWLDDVVYCPRHVICTSEDMLNPNYEDLLIRKSNHNFL

-continued

VQAGNVQLRVIGHSMQNCVLKFKVDTANPKTPKYKFVRIQPGQTFSVLA
CYNGSPSGVYQCAMRPNFTIKGSFLNGSCGSVGFNIDYDCVSFCYMHHM
ELPTGVHAGTDLEGNFYGPFVDRQTAQAAGTDTTITVNVLAWLYAAVIN
GDRWFLNRFTITLNDFNLVAMKYNYEPLTQDHVDILGPLSAQTGIAVLD
MCASLKELLQNGMNGRTILGSALLEDEFTPFDVVRQCSGVTFQSAVKRT
IKGTHHWLLLTILTSLLVLVQSTQWSLFFFLYENAFLPFAMGIIAMSAF
AMMFVKHKHAFLCLFLLPSLATVAYFNMVYMPASWVMRIMTWLDMVDTS
LSGFKLKDCVMYASAVVLLILMTARTVYDDGARRVWTLMNVLTLVYKVY
YGNALDQAISMWALIISVTSNYSGVVTTVMFLARGIVFMCVEYCPIFFI
TGNTLQCIMLVYCFLGYFCTCYFGLFCLLNRYFRLTLGVYDYLVSTQEF
RYMNSQGLLPPKNSIDAFKLNIKLLGVGGKPCIKVATVQSKMSDVKCTS
VVLLSVLQQLRVESSSKLWAQCVQLHNDILLAKDTTEAFEKMVSLLSVL
LSMQGAVDINKLCEEMLDNRATLQAIASEFSSLPSYAAFATAQEAYEQA
VANGDSEVVLKKLKKSLNVAKSEFDRDAAMQRKLEKMADQAMTQMYKQA
RSEDKRAKVTSAMQIMLFTMLRKLDNDALNNIINNARDGCVPLNIIPLT
TAAKLMVVIPDYNTYKNTCDGTTFTYASALWEIQQVVDADSKIVQLSEI
SMDNSPNLAWPLIVTALRANSAVKLQNNELSPVALRQMSCAAGTTQTAC
TDDNALAYYNTTKGGRFVLALLSDLQDLKWARFPKSDGTGTIYTELEPP
CRFVTDTPKGPKVKYLYFIKGLNNLNRGMVLGSLAATVRLQAGNATEVP
ANSTVLSFCAFAVDAAKAYKDYLASGGQPITNCVKMLCTHTGTGQAITV
TPEANMDQESFGGASCCLYCRCHIDHPNPKGFCDLKGKYVQIPTTCAND
PVGFTLKNTVCTVCGMWKGYGCSCDQLREPMLQSADAQSFLNRVCGVSA
ARLTPCGTGTSTDVVYRAFDIYNDKVAGFAKFLKTNCCRFQEKDEDDNL
IDSYFVVKRHTFSNYQHEETIYNLLKDCPAVAKHDFFKFRIDGDMVPHI
SRQRLTKYTMADLVYALRHFDEGNCDTLKEILVTYNCCDDDYFNKKDWY
DFVENPDILRVYANLGERVRQALLKTVQFCDAMRNAGIVGVLTLDNQDL
NGNWYDFGDFIQTTPGSGVPVVDSYYSLLMPILTLTRALTAESHVDTDL
TKPYIKWDLLKYDFTEERLKLFDRYFKYWDQTYHPNCVNCLDDRCILHC
ANFNVLFSTVFPLTSFGPLVRKIFVDGVPFVVSTGYHFRELGVVHNQDV
NLHSSRLSFKELLVYAADPAMHAASGNULDKRTTCFSVAALTNNVAFQT
VKPGNFNKDFYDFAVSKGFFKEGSSVELKHFFFAQDGNAAISDYDYYRY
NLPTMCDIRQLLFVVEVVDKYFDCYDGGCINANQVIVNNLDKSAGFPFN
KWGKARLYYDSMSYEDQDALFAYTKRNVIPTITQMNLKYAISAKNRART
VAGVSICSTMTNRQFHQKLLKSIAATRGATVVIGTSKFYGGWHNMLKTV
YSDVENPHLMGWDYPKCDRAMPNMLRIMASLVLARKHTTCCSLSHRFYR
LANECAQVLSEMVMCGGSLYVKPGGTSSGDATTAYANSVFNICQAVTAN
VNALLSTDGNKIADKYVRNLQHRLYECLYRNRDVDTDFVNEFYAYLRKH
FSMMILSDDAVVCFNSTYASQGLVASIKNFKSVLYYQNNVFMSEAKCWT
ETDLTKGPHEFCSQHTMLVKQGDDYVYLPYPDPSRILGAGCFVDDIVKT
DGTLMIERFVSLAIDAYPLTKHPNQEYADVFHLYLQYIRKLHDELTGHM

-continued

```
LDMYSVMLTNDNTSRYWEPEFYEAMYTPHTVLQAVGACVLCNSQTSLRC
GACIRRPFLCCKCCYDHVISTSHKLVLSVNPYVCNAPGCDVTDVTQLYL
GGMSYYCKSHKPPISFPLCANGQVFGLYKNTCVGSDNVTDFNAIATCDW
TNAGDYILANTCTERLKLFAAETLKATEETFKLSYGIATVREVLSDREL
HLSWEVGKPRPPLNRNYVFTGYRVTKNSKVQIGEYTFEKGDYGDAVVYR
GTTTYKLNVGDYFVLTSHTVMPLSAPTLVPQEHYVRITGLYPTLNISDE
FSSNVANYQKVGMQKYSTLQGPPGTGKSHFAIGLALYYPSARIVYTACS
HAAVDALCEKALKYLPIDKCSRIIPARARVECFDKFKVNSTLEQYVFCT
VNALPETTADIVVFDEISMATNYDLSVVNARLRAKHYVYIGDPAQLPAP
RTLLTKGTLEPEYFNSVCRLMKTIGPDMFLGTCRRCPAEIVDTVSALVY
DNKLKAHKDKSAQCFKMFYKGVIMHDVSSAINRPQIGVVREFLTRNPAW
RKAVFISPYNSQNAVASKILGLPTQTVDSSQGSEYDYVIFTQTTETAHS
CNVNRFNVAITRAKVGILCIMSDRDLYDKLQFTSLEIPRRNVATLQAEN
VTGLFKDCSKVITGLHPTQAPTHLSVDTKFKTEGLCVDIPGIPKDMTYR
RLISMMGFKMNYQVNGYPNMFITREEAIRHVRAWIGFDVEGCHATREAV
GTNLPLQLGFSTGVNLVAVPTGYVDTPDNTDFSRVSAKPPPGDQFKHLI
PLMYKGLPWNVVRIKIVQMLSDTLKNLSDRVVFVLWAHGFELTSMKYFV
KIGPERTCCLCDRRATCFSTASDTYACWHHSIGFDYVYNPFMIDVQQWG
FTGNLQSNHDLYCQVHGNAHVASCDAIMTRCLAVHECFVKRVDWTIEYP
IIGDELKINAACRKVQHMVVKAALLADKFPVLHDIGNPKAIKCVPQADV
EWKFYDAQPCSDKAYKIEELFYSYATHSDKFTDGVCLFWNCNVDRYPAN
SIVCRFDTRVLSNLNLPGCDGGSLYVNKHAFHTPAFDKSAFVNLKQLPF
FYYSDSPCESHGKQVVSDIDYVPLKSATCITRCNLGGAVCRHHANEYRL
YLDAYNMMISAGFSLWVYKQFDTYNLWNTFTRLQSLENVAFNVVNKGHF
DGQQGEVPVSIINNTVYTKVDGVDVELFENKTTLPVNVAFELWAKRNIK
PVPEVKILNNLGVDIAANTVIWDYKRDAPAHISTIGVCSMTDIAKKPTE
TICAPLTVFFDGRVDGQVDLFRNARNGVLITEGSVKGLQPSVGPKQASL
NGVTLIGEAVKTQFNYYKKVDGVVQQLPETYFTQSRNLQEFKPRSQMEI
DFLELAMDEFIERYKLEGYAFEHIVYGDFSHSQLGGLHLLIGLAKRFKE
SPFELEDFIPMDSTVKNYFITDAQTGSSKCVCSVIDLLLDDFVEIIKSQ
DLSVVSKVVKVTIDYTEISFMLWCKDGHVETFYPKLQSSQAWQPGVAMP
NLYKMQRMLLEKCDLQNYGDSATLPKGIMMNVAKYTQLCQYLNTLTLAV
PYNMRVIHFGAGSDKGVAPGTAVLRQWLPTGTLLVDSDLNDFVSDADST
LIGDCATVHTANKWDLIISDMYDPKTKNVTKENDSKEGFFTYICGFIQQ
KLALGGSVAIKITEHSWNADLYKLMGHFAWWTAFVTNVNASSSEAFLIG
CNYLGKPCEQIDGYVMHANYIFWRNTNPIQLSSYSLFDMSKFPLKLRGT
AVMSLKEGQINDMILSLLSKGRLIIRENNRVVISSDVLVNN
```

The fragment of sequence, marked in bold, was modified to CVN-DTF-AGSTFISDEV-D (SEQ ID NO: 2).

Sequence CVN-DTF-AGSTFISDEV-D (SEQ ID NO: 2) was selected as peptide of a Severe Acute Respiratory Syndrome Coronavirus 2 (SARS-CoV-2) surface protein (peptide SARS-CoV-2) target, peptide A.

Poly [ADP-Ribose] Polymerase-1 Partial [Synthetic Construct]-Human PARP1

Human PARP1 Sequence: 1014 aa

SEQ ID NO: 6
```
MAESSDKLYRVEYAKSGRASCKKCSESIPKDSLRMAIMVQSPMFDGKVP
HWYHFSCFWKVGHSIRHPDVEVDGFSELRWDDQQKVKKTAEAGGVTGKG
QDGIGSKAEKTLGDFAAEYAKSNRSTCKGCMEKIEKGQVRLFKKMVDPE
KPQLGMIDRWYHPGCFVKNREELGFRPEYSASQLKGFSLLATEDKEALK
KQLPGVKSEGKRKGDEVDGVDEVAKKKSKKEKDKDSKLEKALKAQNDLI
WNIKDELKKVCSTNDLKELLIFNKQQVPSGESAILDRVADGMVFGALLP
CEECSGQLVFKSDAYYCTGDVTAWTKCMVKTQTPNRKEWVTPKEFREIS
YLKKLKVKKQDRIFPPETSASVAATPPPSTASAPAAVNSSASADKPLSN
MKILTLGKLSRNKDEVKAMIEKLGGKLTGTANKASLCISTKKEVEKMNK
KMEEVKEANIRVVSEDFLQDVSASTKSLQELFLAHILSPWGAEVKAEPV
EVVAPRGKSGAALSKKSKGQVKEEGINKSEKRMKLTLKGGAAVDPDSGL
EHSAHVLEKGGKVFSATLGLVDIVKGTNSYYKLQLLEDDKENRYWIFRS
WGRVGTVIGSNKLEQMPSKEDAIEHFMKLYEEKTGNAWHSKNFTKYPKK
FYPLEIDYGQDEEAVKKLTVNPGTKSKLPKPVQDLIKMIFDVESMKKAM
VEYEIDLQKMPLGKLSKRQIQAAYSILSEVQQAVSQGSSDSQILDLSNR
FYTLIPHDFGMKKPPLLNNADSVQAKVEMLDNLLDIEVAYSLLRGGSDD
SSKDPIDVNYEKLKTDIKVVDRDSEEAEIIRKYVKNTHATTHNAYDLEV
IDIFKIEREGECQRYKPFKQLHNRRLLWHGSRTTNFAGILSQGLRIAPP
EAPVTGYMFGKGIYFADMVSKSANYCHTSQGDPIGLILLGEVALGNMYE
LKHASHISKLPKGKHSVKGLGKTTPDPSANISLDGVDVPLGTGISSGVN
DTSLLYNEYIVYDIAQVNLKYLLKLKFNFKTSLW
```

The sequence DEVDGVDEVAKKKSKK (SEQ ID NO: 3) was selected as human PARP1 peptide target, also referred as peptide B.

Peptide of a Severe Acute Respiratory Syndrome Coronavirus 2 Surface Protein (Peptide SARS-Cov-2) and Peptide Human PARP1 Fusion The peptide SARS-CoV-2 and peptide Human PARP1 are fused with DEVD site junction.

Peptide of a Severe Acute Respiratory Syndrome Coronavirus 2 surface protein (Peptide SARS-CoV-2) and Peptide Human PARP1 are fused obtaining Peptide AB with SEQ ID NO: 4.

TABLE 3

| SEQ ID NO. | Sequence |
| --- | --- |
| SEQ ID NO: 2 | CVN-DTF-AGSTFISDEVD |
| SEQ ID NO: 3 | DEVDGVDEVAKKKSK |
| SEQ ID NO: 4 | CVNDTFAGSTFISDEVDGVDEVAKKKSK |

Peptide of a Severe Acute Respiratory Syndrome Coronavirus 2 (SARS-CoV-2) surface protein (Peptide SARS-CoV-2)/Peptide Human PARP1 (SEQ ID No: 4) is used as target using ProtParam.

$C_{125}H_{200}N_{32}O_{46}$ Formula:

Total number of atoms: 403
Atomic Composition:
Carbon C 125
Hydrogen H 200
Nitrogen N 32
Oxygen O 46
Sulfur S 0
Number of amino acids: 27
Molecular weight: 2887.15
Theoretical pI: 4.53
Amino Acid Composition:
Ala (A) 2 7.4%
Arg (R) 0 0.0%
Asn (N) 1 3.7%
Asp (D) 4 14.8%
Cys (C) 0 0.0%
Gin (Q) 0 0.0%
Glu (E) 2 7.4%
Gly (G) 2 7.4%
His (H) 0 0.0%
Ile (I) 1 3.7%
Leu (L) 0 0.0%
Lys (K) 4 14.8%
Met (M) 0 0.0%
Phe (F) 2 7.4%
Pro (P) 0 0.0%
Ser (S) 3 11.1%
Thr (T) 2 7.4%
Trp (W) 0 0.0%
Tyr (Y) 0 0.0%
Val (V) 4 14.8%
Pyl (O) 0 0.0%
Sec (U) 0 0.0%
(B) 0 0.0%
(Z) 0 0.0%
(X) 0 0.0%
Total number of negatively charged residues (Asp+Glu): 6
Total number of positively charged residues (Arg+Lys): 4
Extinction Coefficients:
As there are no Trp; Tyr or Cys in the region considered, protein should not be visible by UV spectrophotometry.
Estimated Half-Life:
The N-terminal of the sequence considered is V (Val).
The estimated half-life is: 100 hours (mammalian reticulocytes, in vitro).
>20 hours (yeast, in vivo).
>10 hours (*Escherichia coli*, in vivo).
Instability Index:
The instability index (II) is computed to be 2.07
This classifies the protein as stable.
Aliphatic index: 64.81.
Grand average of hydropathicity (GRAVY): −0.526
IFNepitope Prediction—peptide-AB
SEQ ID No: 4 CVNDTFAGSTFISDEVDGVDE-VAKKKSK is positive using the method SVM with score 3.1106915.

IFNepitope Score is a webserver that allows users to identify IFN-gamma inducing MHC class II binding peptides in a peptide/antigen. This server permits the user to predict and design IFN-gamma inducing regions in their protein of interest. This prediction method has been trained on 10433 experimentally validated IFN-gamma inducing and non-inducing MHC class II binders/peptides. The prediction server has three major tools, and the algorithm of the prediction is based on three models (motif based, SVM based and hybrid approach). User can select the method of prediction for all the three module.

According to the Algorithms of the Present Invention

Vaccine RNA-peptide-AB according to the present invention, here referred as "Melody"

Fusion Stability (FS)

$$FS = a*b*c*d(\text{cruz})$$

$a$ = Size poly $A$/Size poly Cys $b$ = MW mRNA/MW peptide $c$ = Size peptide/Size mRNA $d = [\text{mRNA}(2*(A+U)+3*(C+G))/(\text{PI peptide}^2)]$ $a = 10/1 = 10$ $b = 7701/2887.15 = 2.6673$ $c = 27/24 = 1.125$ $d = [(2*(8+6)+3*(6+4))/(4.53^2)] = 2.8264$ $FS = 10*2.6673*1.125*2.8264(\text{cruz})$ $FS = 84.81$ cruz Exosome Affinity (EA)

$$EA = FS*[(\text{MW peptide/mMW RNA}) + (\text{Size peptide/Size primer})]$$

$EA = (ro)$ $EA = 84.81*[(2887.15/7701)+(27/34)] = 84.81*[(0.374905)+(0.794117)] = 84.81*1.169 = 99.14$ $EA = 99.15 ro$

Biological Action (BA)

$BA = EA/FS$ $BA = 99.14/84.81$ $BA = 1.17 ro/\text{cruz}$

Optimal Biological Action (OBA)

$OBA = (ro/\text{cruz})$ value for antiviral efficacy to RNA-peptide with exosome as carrier are $0.8 < OBA < 1.3$ Meloyd Fusion Stability (FS)

$$FS = a*b*c*d(\text{cruz})$$

$a$ = Size poly $A$/Size poly Cys $b$ = MW mRNA/MW peptide $c$ = Size peptide/Size mRNA $d = [\text{mRNA}(2*(A+U)+3*(C+G))/(\text{PI peptide}^2)]$ $a = 10/1 = 10$ $b = 6951/2887.15 = 2.4076$ $c = 27/21 = 1.28571$ $d = [(2*(5+4)+3*(2+10))/(4.53^2)] = [(2*9+3*12)/(20.5209)] = [(18+36)/(20.5209)] = 2.6315$ FS=10*2.4076*1.28571*2.6315(cruz)

FS=81.46 cruz

Exosome Affinity (EA)

EA=FS*[(MW peptide/MW mRNA)+(Size peptide/Size primer)]

EA=(ro)

EA=81.46*[(2887.15/6951)+(27/31)]=81.46*[(0.415357)+(0.87096)]=81.45*1.2863=104.77ro

EA=104.77ro

Biological Action (BA)

BA=EA/FS

BA=104.77/81.45

BA=1.29ro/cruz

Optimal Biological Action (OBA)

OBA=(ro/cruz)

value for antiviral efficacy to RNA-peptide with exosome as carrier are 0.8<OBA<1.3

Moledy

Fusion Stability (FS)

FS=$a*b*c*d$(cruz)

$a$=Size poly A/Size poly Cys $b$=MW mRNA/MW peptide $c$=Size peptide/Size mRNA $d$=[mRNA(2*(A+U)+3*(C+G))/(PI peptide^2)]

$a$=10/1=10

$b$=6775/2887.15=2.3466

$c$=27/21=1.28571

$d$=[(2*(6+4)+3*(5+6))/(4.53^2)]=2.5827

FS=10*2.3466*1.28571*2.5827(cruz)

FS=77.92 cruz

Exosome Affinity (EA)

EA=FS*[(MW peptide/mMW RNA)+(Size peptide/Size primer)]

EA=(ro)

EA=77.92*[(2887.15/6775)+(27/31)]=77.92*[(0.4261)+(0.87096)]=77.92*1.29706=101.07ro

EA=101.07ro

Biological Action (BA)

BA=EA/FS

BA=101.07/77.92

BA=1.30ro/cruz

Optimal Biological Action (OBA)

OBA=(ro/cruz)

value for antiviral efficacy to RNA-peptide with exosome as carrier are 0.8<OBA<1.3

Myledo

Fusion Stability (FS)

FS=$a*b*c*d$(cruz)

$a$=Size poly A/Size poly Cys $b$=MW mRNA/MW peptide $c$=Size peptide/Size mRNA $d$=[mRNA(2*(A+U)+3*(C+G))/(PI peptide^2)]

$a$=10/1=10

$b$=6701/2887.15=2.3210

$c$=27/21=1.2857

$d$=[(2*(1+10)+3*(4+6))/(4.53^2)]=2.534

FS=10*2.321*1.2857*2.534(cruz)

FS=75.62 cruz

Exosome Affinity (EA)

EA=FS*[(MW peptide/mMW RNA)+(Size peptide/Size primer)]

EA=(ro)

EA=75.62*[(2887.15/6701)+(27/31)]=98.44ro

EA=98.44ro

Biological Action (BA)

BA=EA/FS

BA=98.44/75.62

BA=1.30ro/cruz

Optimal Biological Action (OBA)

OBA=(ro/cruz)

value for antiviral efficacy to RNA-peptide with exosome as carrier are 0.8<OBA<1.3

Lodyme

Fusion Stability (FS)

FS=$a*b*c*d$(cruz)

$a$=Size poly A/Size poly Cys $b$=MW mRNA/MW peptide $c$=Size peptide/Size mRNA $d$=[mRNA(2*(A+U)+3*(C+G))/(PI peptide^2)]

$a$=10/1=10

$b$=7082/2887.15=2.4529

$c$=27/22=1.2273

$d$=[(2*(6+6)+3*(5+5))/(4.53^2)]=2.6315

FS=10*2.453*1.2273*2.6315(cruz)

FS=79.22 cruz

Exosome Affinity (EA)

$$EA = FS*[(MW\ peptide/mMW\ RNA) + (Size\ peptide/Size\ primer)]$$

$$EA = (ro)$$

$$EA = 79.22*[(2887.15/7082) + (27/32)] = 99.14 ro$$

$$EA = 99.14 ro$$

Biological Action (BA)

$$BA = EA/FS$$

$$BA = 99.14/79.22$$

$$BA = 1.25 ro/cruz$$

Optimal Biological Action (OBA)

$$OBA = (ro/cruz)$$

value for antiviral efficacy to RNA-peptide with exosome as carrier are 0.8<OBA<1.3

Ledymo

Fusion Stability (FS)

FS=*a*b*c***d*(cruz)

*a*=Size poly *A*/Size poly Cys

*b*=MW mRNA/MW peptide

*c*=Size peptide/Size mRNA

*d*=[mRNA(2*(*A*+*U*)+3*(*C*+*G*))/(PI peptide^2)]

*a*=10/1=10

*b*=7059/2887.15=2.4450

*c*=27/22=1.2273

*d*=[(2*(5+7)+3*(5+5))/(4.53^2)]=2.6315

FS=10*2.445*1.227*2.631(cruz)

FS=78.96 cruz

Exosome Affinity (EA)

EA=FS*[(MW peptide/mMW RNA)+(Size peptide/Size primer)]

EA=(*ro*)

EA=78.96*[(2887.15/7059)+(27/32)]=98.92*ro*

EA=98.92*ro*

Biological Action (BA)

BA=EA/FS

BA=98.92/78.96

BA=1.25*ro*/cruz

Optimal Biological Action (OBA)

OBA=(*ro*/cruz)

value for antiviral efficacy to RNA-peptide with exosome as carrier are 0.8<OBA<1.3

Modyle

Fusion Stability (FS)

FS=*a*b*c***d*(cruz)

*a*=Size poly *A*/Size poly Cys

*b*=MW mRNA/MW peptide

*c*=Size peptide/Size mRNA

*d*=[mRNA(2*(*A*+*U*)+3*(*C*+*G*))/(PI peptide^2)]

*a*=10/1=10

*b*=7453/2887.15=2.5814

*c*=27/23=1.1739

*d*=[(2*(7+7)+3*(6+7))/(4.53^2)]=2.6802

FS=10*2.5814*1.1739*2.6802(cruz)

FS=81.22 cruz

Exosome Affinity (EA)

EA=FS*[(MW peptide/mMW RNA)+(Size peptide/Size primer)]

EA=(*ro*)

EA=81.22*[(2887.15/7453)+(27/33)]=97.92*ro*

EA=97.92*ro*

Biological Action (BA)

BA=EA/FS

BA=97.92/81.22

BA=1.21*ro*/cruz

Optimal Biological Action (OBA)

OBA=(*ro*/cruz)

value for antiviral efficacy to RNA-peptide with exosome as carrier are 0.8<OBA<1.3

Medylo

Fusion Stability (FS)

FS=*a*b*c***d*(cruz)

*a*=Size poly *A*/Size poly Cys

*b*=MW mRNA/MW peptide

*c*=Size peptide/Size mRNA

*d*=[mRNA(2*(*A*+*U*)+3*(*C*+*G*))/(PI peptide^2)]

*a*=10/1=10

*b*=6358/2887.15=2.2022

*c*=27/20=1.350

*d*=[(2*(8+4)+3*(7+1))/(4.53^2)]=2.3391

FS=10*2.2022*1.35*2.3391(cruz)

FS=69.54 cruz

Exosome Affinity (EA)

EA=FS*[(MW peptide/mMW RNA)+(Size peptide/Size primer)]

EA=(*ro*)

EA=69.54*[(2887.15/6358)+(27/30)]=94.16*ro*

EA=94.16*ro*

Biological Action (BA)

BA=EA/FS

BA=94.16/69.54

BA=1.35$ro$/cruz

Optimal Biological Action (OBA)

OBA=($ro$/cruz)

value for antiviral efficacy to RNA-peptide with exosome as carrier are 0.8<OBA<1.3
Dylome Fusion Stability (FS)

FS=$a$*$b$*$c$*$d$(cruz)

$a$=Size poly $A$/Size poly Cys $b$=MW mRNA/MW peptide $c$=Size peptide/Size mRNA $d$=[mRNA(2*($A+U$)+3*($C+G$))/(PI peptide^2)]

$a$=10/1=10

$b$=7159/2887.15=2.4796

$c$=27/22=1.2273

$d$=[(2*(6+3)+3*(6+7))/(4.53^2)]=2.7777

FS=10*2.4796*1.2273*2.7777(cruz)

FS=84.53 cruz

Exosome Affinity (EA)

EA=FS*[(MW peptide/mMW RNA)+(Size peptide/Size primer)]

EA=($ro$)

EA=84.53*[(2887.15/7159)+(27/32)]=105.41$ro$

EA=105.41$ro$

Biological Action (BA)

BA=EA/FS

BA=105.41/84.53

BA=1.25$ro$/cruz

Optimal Biological Action (OBA)

OBA=($ro$/cruz)

value for antiviral efficacy to RNA-peptide with exosome as carrier are 0.8<OBA<1.3
Lomedy Fusion Stability (FS)

FS=$a$*$b$*$c$*$d$(cruz)

$a$=Size poly $A$/Size poly Cys $b$=MW mRNA/MW peptide $c$=Size peptide/Size mRNA $d$=[mRNA(2*($A+U$)+3*($C+G$))/(PI peptide^2)]

$a$=10/1=10

$b$=6377/2887.15=2.2088

$c$=27/20=1.350

$d$=[(2*(2+7)+3*(6+5))/(4.53^2)]=2.4853

FS=10*2.2088*1.35*2.4853(cruz)

FS=74.11 cruz

Exosome Affinity (EA)

EA=FS*[(MW peptide/mMW RNA)+(Size peptide/Size primer)]

EA=($ro$)

EA=74.11*[(2887.15/6377)+(27/30)]=133.59$ro$

EA=133.59$ro$

Biological Action (BA)

BA=EA/FS

BA=133.59/74.11

BA=1.80$ro$/cruz

Optimal Biological Action (OBA)

OBA=($ro$/cruz)

value for antiviral efficacy to RNA-peptide with exosome as carrier are 0.8<OBA<1.3
Lemody Fusion Stability (FS)

FS=$a$*$b$*$c$*$d$(cruz)

$a$=Size poly $A$/Size poly Cys $b$=MW mRNA/MW peptide $c$=Size peptide/Size mRNA $d$=[mRNA(2*($A+U$)+3*($C+G$))/(PI peptide^2)]

$a$=10/1=10

$b$=5767/2887.15=1.9975

$c$=27/18=1.50

$d$=[(2*(2+7)+3*(4+5))/(4.53^2)]=2.1929

FS=10*1.9975*1.5*2.1929(cruz)

FS=65.70 cruz

Exosome Affinity (EA)

EA=FS*[(MW peptide/mMW RNA)+(Size peptide/Size primer)]

EA=($ro$)

EA=65.70*[(2887.15/5767)+(27/28)]=131.45$ro$

EA=131.45$ro$

Biological Action (BA)

BA=EA/FS

BA=131.45/65.7

BA=2.00$ro$/cruz

Optimal Biological Action (OBA)

$OBA=(ro/cruz)$ value for antiviral efficacy to RNA-peptide with exosome as carrier are 0.8<OBA<1.3

Modyle

Fusion Stability (FS)

$FS=a*b*c*d(cruz)$ $a$=Size poly $A$/Size poly Cys $b$=MW mRNA/MW peptide $c$=Size peptide/Size mRNA $d=[mRNA(2*(A+U)+3*(C+G))/(PI\ peptide^2)]$ $a=10/1=10$ $b=7013/2887.15=2.4290$ $c=27/22=1.2273$ $d=[(2*(3+9)+3*(5+5))/(4.53^2)]=2.6315$ $FS=10*2.429*1.2273*2.6315(cruz)$ $FS=78.45\ cruz$ Exosome Affinity (EA)

$EA=FS*[(MW\ peptide/mMW\ RNA)+(Size\ peptide/Size\ primer)]$ $EA=(ro)$ $EA=78.45*[(2887.15/7013)+(27/32)]=98.48ro$ $EA=98.48ro$ Biological Action (BA)

$BA=EA/FS$ $BA=98.48/78.45$ $BA=1.26ro/cruz$

Optimal Biological Action (OBA)

$OBA=(ro/cruz)$ value for antiviral efficacy to RNA-peptide with exosome as carrier are 0.8<OBA<1.3

Medylo

Fusion Stability (FS)

$FS=a*b*c*d(cruz)$ $a$=Size poly $A$/Size poly Cys $b$=MW mRNA/MW peptide $c$=Size peptide/Size mRNA $d=[mRNA(2*(A+U)+3*(C+G))/(PI\ peptide^2)]$ $a=10/1=10$ $b=6213/2887.15=2.1519$ $c=27/22=1.4211$ $d=[(2*(3+4)+3*(4+8))/(4.53^2)]=2.4365$ $FS=10*2.1519*1.4211*2.4365(cruz)$ $FS=74.51\ cruz$ Exosome Affinity (EA)

$EA=FS*[(MW\ peptide/mMW\ RNA)+(Size\ peptide/Size\ primer)]$ $EA=(ro)$ $EA=74.51*[(2887.15/6213)+(27/32)]=104.0ro$ $EA=104.0ro$ Biological Action (BA)

$BA=EA/FS$ $BA=104.0/74.51$ $BA=1.4ro/cruz$

Optimal Biological Action (OBA)

$OBA=(ro/cruz)$ value for antiviral efficacy to RNA-peptide with exosome as carrier are 0.8<OBA<1.3

Dyolem

Fusion Stability (FS)

$FS=a*b*c*d(cruz)$ $a$=Size poly $A$/Size poly Cys $b$=MW mRNA/MW peptide $c$=Size peptide/Size mRNA $d=[mRNA(2*(A+U)+3*(C+G))/(PI\ peptide^2)]$ $a=10/1=10$ $b=6214/2887.15=2.1523$ $c=27/19=1.4211$ $d=[(2*(3+5)+3*(3+8))/(4.53^2)]=2.4365$ $FS=10*2.1523*1.4211*2.4365(cruz)$ $FS=73.03\ cruz$ Exosome Affinity (EA)

$EA=FS*[(MW\ peptide/mMW\ RNA)+(Size\ peptide/Size\ primer)]$ $EA=(ro)$ $EA=73.03*[(2887.15/6214)+(27/29)]=137.71$ $EA=137.71ro$ Biological Action (BA)

$BA=EA/FS$ $BA=137.71/73.03$ $BA=1.89ro/cruz$

Optimal Biological Action (OBA)

$OBA=(ro/cruz)$ value for antiviral efficacy to RNA-peptide with exosome as carrier are 0.8<OBA<1.3

Ylomed
Fusion Stability (FS)

$FS=a*b*c*d(cruz)$ $a$=Size poly $A$/Size poly Cys $b$=MW mRNA/MW peptide $c$=Size peptide/Size mRNA $d$=[mRNA(2*($A+U$)+3*($C+G$))/(PI peptide^2)]

$a=10/1=10$ $b=7444/2887.15=2.5783$ $c=27/23=1.1739$ $d=[(2*(5+6)+3*(5+7))/(4.53^2)]=2.8264$ $FS=10*2.5783*1.1739*2.8264(cruz)$ $FS=85.55$ cruz Exosome Affinity (EA)

EA=FS*[(MW peptide/mMW RNA)+(Size peptide/Size primer)]

$EA=(ro)$ $EA=85.55*[(2887.15/7444)+(27/33)]=103.17ro$ $EA=103.17ro$

Biological Action (BA)

BA=EA/FS $BA=103.17/85.55$ $BA=1.21ro/cruz$

Optimal Biological Action (OBA)

OBA=($ro$/cruz)

value for antiviral efficacy to RNA-peptide with exosome as carrier are 0.8<OBA<1.3

Lomedy
Fusion Stability (FS)

$FS=a*b*c*d(cruz)$ $a$=Size poly $A$/Size poly Cys $b$=MW mRNA/MW peptide $c$=Size peptide/Size mRNA $d$=[mRNA(2*($A+U$)+3*($C+G$))/(PI peptide^2)]

$a=10/1=10$ $b=7278/2887.15=2.5208$ $c=27/23=1.1739$ $d=[(2*(3+8)+3*(8+4))/(4.53^2)]=2.8264$ $FS=10*2.5208*1.1739*2.8264(cruz)$ $FS=83.64$ cruz Exosome Affinity (EA)

EA=FS*[(MW peptide/mMW RNA)+(Size peptide/Size primer)]

$EA=(ro)$ $EA=83.64*[(2887.15/7278)+(27/33)]=101.61ro$ $EA=101.61ro$

Biological Action (BA)

BA=EA/FS $BA=101.61/83.64$

Optimal Biological Action (OBA)

OBA=($ro$/cruz)

value for antiviral efficacy to RNA-peptide with exosome as carrier are 0.8<OBA<1.3

According to the algorithms of the present invention, the following table (table 4) shows Fusion Stability, Affinity and Biological Action of the sixteen vaccines candidates.

TABLE 4

| Code | FS | EA | BA |
| --- | --- | --- | --- |
| Melody | 84.81 | 99.15 | 1.17 |
| Meloyd | 81.46 | 104.78 | 1.29 |
| Moledy | 77.92 | 101.07 | 1.30 |
| Myledo | 75.62 | 98.44 | 1.30 |
| Lodyme | 79.22 | 99.14 | 1.25 |
| Ledymo | 78.96 | 98.92 | 1.25 |
| Modyle | 81.22 | 97.92 | 1.21 |
| Medylo | 69.54 | 94.16 | 1.35 |
| Dylome | 84.53 | 105.41 | 1.25 |
| Lomedy | 74.11 | 133.59 | 1.80 |
| Lemody | 65.70 | 131.45 | 2.00 |
| Modyle | 78.45 | 98.48 | 1.26 |
| Medylo | 74.51 | 104.00 | 1.40 |
| Dyolem | 73.03 | 137.71 | 1.89 |
| Ylomed | 85.55 | 103.17 | 1.21 |
| Lomedy | 83.64 | 101.61 | 1.21 |

Results by Stages of the Invention:

Vaccine RNA-peptide against SARS-CoV-2: Exosomes as carrier according to the algorithms of the present invention.

A) Design and Selection of Candidate Isoforms from the Application of the Algorithms of the Present Invention.

The following table (Table 5) shows more significant values of Fusion Stability, Exosome Affinity and Biological Action of the four vaccines candidates:

TABLE 5

|  | FS | EA | BA |
| --- | --- | --- | --- |
| Melody (RNA-peptide-AB) | 84.81 | 99.15 | 1.17 |
| Lodyme | 79.22 | 99.14 | 1.25 |
| Ledymo | 78.96 | 98.92 | 1.25 |
| Modyle | 78.45 | 98.48 | 1.26 |

B) Validation of IFNepitope Score for the Four Vaccines Candidates

The following table (Table 6) shows the RNA-peptide-AB vaccine object of the present invention (referred as Melody) as best candidate vaccine according to its highest value of IFNepitope Score=3.21

TABLE 6

| Code | FS | EA | BA | IFNepitope score |
|---|---|---|---|---|
| Melody | 84.81 | 99.15 | 1.17 | 3.21 |
| Lodyme | 79.22 | 99.14 | 1.25 | 3.09 |
| Ledymo | 78.96 | 98.92 | 1.25 | 3.09 |
| Modyle | 78.45 | 98.48 | 1.26 | 3.02 |

According to IFNepitope Score from Tox21 program, four candidates were studied (Table 3) and selected melody as the best vaccine candidate. These studies were In silico using "in vitro assays" that evaluate key biological pathways and molecular mechanisms linked to human disease.

Vaccine Candidate (RNA-Peptide-A/RNA-Peptide-AB): Compositions of the Present Invention.

RNA vaccine of the present invention comprises a ribonucleic acid polynucleotide fused to at least one peptide. In a preferred embodiment, the peptide, referred as peptide A, is a surface protein peptide from Severe Acute Respiratory Syndrome Coronavirus 2 (SARS-CoV-2).

In a preferred embodiment, a ribonucleic acid polynucleotide fragment comprises the following sequence:

```
                                    SEQ ID NO: 1
AAAAAAAAAACUCCUAGAACUAGCAUUACAGAUG
```

In another preferred embodiment, a peptide of the Severe Acute Respiratory Syndrome Coronavirus 2 (SARS-CoV-2) surface protein, peptide SARS-CoV-2 (peptide A), comprises the following sequence:

```
                                    SEQ ID NO: 2
CVNDTFAGSTFISDEVD
```

(Number of amino acids: 17 aa; MW=1819.91 daltons, Theoretical pI: 3.37)

In another preferred embodiment, poly ADP-ribose polymerase peptide (peptide B) comprises the following sequence:

```
                                    SEQ ID NO: 3
GVDEVAKKKSK
```

(Number of amino acids: 11 aa; MW=1188.39 daltons, Theoretical pI: 9.53).

In a preferred embodiment, RNA vaccine of the present invention is RNA-peptide-A vaccine comprising SEQ ID NO: 1 fused to SEQ ID NO: 2.

```
                          SEQ ID NO: 1 and SEQ ID NO: 2
AAAAAAAAAACUCCUAGAACUAGCAUUACAGAUG- Cys- Val- Asn -Asp- Thr- Phe- Ala- Gly- Ser -Thr- Phe -Ile- Ser -Asp- Glu- Val -Asp
```

In a preferred embodiment, peptide of a Severe Acute Respiratory Syndrome Coronavirus 2 surface protein (Peptide A) and Peptide Human PARP1 (Peptide B) are fused obtaining Peptide-AB with SEQ ID NO: 4.

```
                                    SEQ ID NO: 4
CVNDTFAGSTFISDEVDGVDEVAKKKSK
```

In preferred embodiment, RNA vaccine of the present invention is RNA-peptide-AB vaccine comprising SEQ ID NO: 1 fused to SEQ ID NO: 4.

```
                          SEQ ID NO: 1 and SEQ ID NO: 4
AAAAAAAAAACUCCUAGAACUAGCAUUACAGAUG- Cys- Val -Asn -Asp- Thr- Phe- Ala- Gly- Ser -Thr Phe- Ile -Ser -Asp- Glu -Val- Asp- Gly Asp Glu -Val- Ala- Lys- Lys- Lys- Ser- Lys
```

EXAMPLES

Example 1

Synthesis and Validation of Peptides Targets

```
                                    SEQ ID NO: 4
CVNDTFAGSTFISDEVDGVDEVAKKKSK
(Size 28 = aa)

SEQ ID NO: 2
CVNDTFAGSTFISDEVD
(Size 17 = aa)

SEQ ID NO: 3
GVDEVAKKKSK
(Size 11 = aa)
```

Synthesis of Peptides

According to the present invention peptides were synthesized on ChemMatrix Rink Amide resin, using standard Fmoc synthesis protocol with DIC/Cl-HOBt coupling, on an APEX 396 automatic synthesizer. The resin was swollen in DMF for 30 min, treated with 20 volume (v) % Piperidine-DMF for 8 minutes to remove the Fmoc protecting group, at 50° C., and washed with DMF for three times. For the coupling reaction, the resin was added with Fmoc-protected amino acid, Cl-HOBt, DIC and NMP. The mixture was vortexed for 20 minutes at 50° C. Afterwards, the resin was washed with DMF once. The cycle of deprotection and coupling steps was repeated until the last amino acid residue was assembled. After the final Fmoc protecting group was removed, the resin was treated with 20 v % acetic Anhydride-NMP for 20 minutes. The resin was then washed with DMF, DCM and dried with air. The peptides were cleaved using a TFA cocktail (95 v % TFA, 2.5 v % water and 2.5 v % TIS) for three hours. Crude peptides were precipitated by adding ice-chilled anhydrous ethyl ether, washed with anhydrous ethyl ether for three times, and dried in vacuum. After the synthesis, we use the conventional prep-HPLC for peptide purification. Peptide synthesis is robust and fool proof; however, there are a few things that can really mess up the reproducibility of these protocols. Probably chief amongst them is the quality of DMF.

Solid Supports

The first step in solid-phase peptide synthesis was choose cysteine as amino acid with functional group C-terminus to be a carboxylic acid use 2-chlorotrityl resin in order to load Cysteine amino acid onto the resin.

Loading 2-Chlorotrityl Chloride

The purpose of this step was to covalently link the cysteine amino acid onto the resin.

Prep time: 30 min

Reaction time: 8-24 h

The process comprises the following steps:

1) Weigh out appropriate amount of resin. Generally, we use 300 mg for a 0.1 mmol scale. Transfer the resin into a PolyPrep chromatography column (BioRad).
2) Swell resin for at least 30 min at room temperature in dry $CH_2Cl_2$.
3) Weigh out an appropriate amount of the cysteine amino acid and dissolve it in 8 mL $CH_2Cl_2$ w/0.3 ml 2,4,6-collidine. When making a macrocyclic peptide cysteine amino acid is preferably Boc-Orn(Fmoc)-OH. Use 100 mg of Boc-Orn(Fmoc)-OH.
4) Using a flow of nitrogen gas, push out all $CH_2Cl_2$ from the column that contains the swelled resin and add the amino acid/$CH_2Cl_2$/collidine mixture.
5) Rock for at least 8 hours.
6) Move on to Capping 2-chlorotrityl resin.

Capping 2-Chlorotrityl Chloride Resin

The purpose of this step is to covalently link a small nucleophile (methanol) to the unreacted carbocations on the 2-chlorotrityl chloride resin.

Prep time: 10 mins
Reaction time: 60 mins
The process comprises the following steps:

1) Wash the loaded resin 3× with $CH_2Cl_2$. The loaded resin was washed 3× with $CH_2Cl_2$.
2) capping solution. The capping solution is $CH_2Cl_2$:MeOH:DIPEA (17:2:1). It was made fresh each time by adding 1 mL MeOH and 0.5 mL diisopropylethylamine (DIPEA, or DIEA) to 9 mL of $CH_2Cl_2$.
3) capping solution is dumped on to the loaded resin and rock for 1 hour at room temperature. It is not recommended to extend the reaction time, as exchange of the loaded amino acid with MeOH is a possibility.
4) After 1 hour, push out the capping solution with nitrogen and wash the resin 2× with $CH_2Cl_2$ and 1× with DMF.
5) The loaded resin goes through repeated Fmoc-deprotections and amino acid couplings to build the rest of your peptide. These deprotections and couplings can be done manually (hand coupling) or on an automatic synthesizer.

Capping Rink Amide Resin

The purpose of this step is to cap unreacted amines on rink amide so that the amino acids are not attached to the resin.

Prep time: 5 min
Reaction time: 30 minutes (mins)
1) capping solution is prepared by combining acetic anhydride and pyridine in a 3:2 ratio of acetic anhydride:pyridine. Crudely by using a Pasteur pipette to combine 3 "squirts" of acetic anhydride with 2 "squirts" of pyridine in a scintillation vial.
2) Dump the capping solution on the resin and rock for 30 mins at room temperature.
3) After the resin is done capping push out the capping solution with nitrogen and wash the resin 4× with DMF.
4) loaded resin goes through repeated Fmoc-deprotections and amino acid couplings to build the rest of the peptide. These deprotections and couplings are done on APEX 396 automatic synthesizer.

Checking Resin Loading

The purpose of this step is to determine the mmol of amino acid that are on resin. The procedure is the same regardless of the resin are using.

Prep time: 20 mins
Reaction time: 5 mins
1) Take a small portion (1-2 mg) of resin and transfer it to a new polyprep column. Dry the resin by blowing nitrogen through it.
2) While the resin drying, it is added 3 mL of 20% piperidine in DMF in a 3-mL quartz cuvette. Blank the UV/Vis with the 20% piperidine at 290 nm.
3) Add approximately 1 mg of dried resin to 3 mL 20% piperidine in DMF in the quartz cuvette.
4) Allow the resin to sit in the 20% piperidine for at least 5 min.
5) Take a UV/Vis reading at 290 nm against the 20% piperidine blank.
6) Use Ryan's Excel mass spec calculator to determine the loading percentage. This will dictate the mmol of each amino acid should be used when synthesizing the peptide. Good loading percentages fall between 50-70%.

Solid-Phase Peptide Synthesis

The purpose of this step is to sequentially add amino acids to the resin to build a peptide chain. The first step is deprotecting Fmoc from the amino on the resin to expose an amine. The second step is coupling an activated amino acid to the exposed amine. These steps are done the same on 2-chlorotrityl chloride and rink amide resin.

Alloc Deprotection

Alloc protected groups are removed during peptide synthesis

SEQ ID NO: 4
C-V-N-D-T-F-A-G-S-T-F-I-S-D-E-V-D-G-V-D-E-V-A-K-K-K-S-K

Prep time: 5 min
Reaction time: 40 min
1) Wash the resin in a polyprep column 3× with $CH_2Cl_2$.
2) Based on loading, weigh out 0.1 equiv. of tetrakis (triphenylphosphine) palladium and dissolve in $CH_2Cl_2$ (6 mL).
3) Add 20 equiv. of phenylsilane (density 0.878 g/cm3) to the resulting solution.
4) Transfer the solution to resin in a poly-prep column.
5) Put it on the rocker for 20 minutes.
6) Repeat steps 1-5.
7) Wash the resin in a poly-prep column 3× with $CH_2Cl_2$.
8) Check alloc deprotection by cleaving small portion of resin with 20% HFIP in $CH_2Cl_2$ (15 min).
9) Rotovap the cleaved solution and re-dissolve in MeCN.
10) Using the ESI-MS, search for the alloc deprotected mass.

Dde Deprotection

The purpose of this step is to remove Dde protecting groups during peptide synthesis.

Prep time: 5 min
Reaction time: 30 min
1) Wash the resin in a poly-prep column 3× with DMF.
2) Add 5 mL of 2% hydrazine in DMF.
3) Put it on the rocker for 15 min.
4) Repeat steps 1-3.
5) Wash the resin in a poly-prep column 3× with DMF.
6) Check Dde deprotection by cleaving small portion of resin with 20% HFIP in $CH_2Cl_2$ (15 min).
7) Rotovap the cleaved solution and re-dissolve in MeCN.
8) Using the ESI-MS, search for Dde deprotected mass.

Automated Synthesis-APEX 396 Automatic Synthesizer

The peptides are synthesized on ChemMatrix Rink Amide resin, using standard Fmoc synthesis protocol with DIC/Cl-HOBt coupling, on an APEX 396 automatic synthesizer.

To use the APEX 396 automatic synthesizer, firstly it is weigh out 4 equivalents of each amino acid to couple along with 4 equivalents of coupling agent (HCTU or HATU/HOAt) and add the amino acid and coupling agent to amino acid vials.

Prep time: 1-3 h
Reaction time: variable, typically less than 24 h

1) Transfer the resin to the appropriate reaction vessel and attach it to the synthesizer.
2) Check the solvent levels and waste levels on the instrument. If the waste is more than halfway full attach a new waste container.
3) Program the sequence into the APEX 396 automatic synthesizer.
4) When the peptide finishes synthesizing, the reaction vessel is removed from the synthesizer and the resin is transfered to the poly-prep column.

Cleavage Form Solid Support

Cleavage of side chain protected linear peptide from 2-chlorotrityl chloride resin. The purpose of the step is to cleave the peptide from 2-chlorotrityl resin to expose a free carboxy terminus and maintain the protecting groups on the amino acid side chains Prep time: 10 min
Reaction time: 1.5 h 1) Prepare the cleavage solution. The cleavage solution is 20% hexafluoroisopropanol (HFIP) in $CH_2Cl_2$. This fresh is prepared by adding 3.5 mL HFIP to 11.5 mL $CH_2Cl_2$ in a small graduated cylinder. Alternatively, 1 squirt of HFIP into 4 squirts of $CH_2Cl_2$ with a Pasteur pipette.
2) Add about half of the cleavage solution to the resin in the polyprep column. If the resin is washed with $CH_2Cl_2$ before add the cleavage solution, it will turn red. Rock for 1 h at room temperature, and then drain into a clean round bottom flask.
3) Add the other half of the cleavage solution to the resin and rock for an additional 30 min. After the 30 min is complete drain into the same round bottom flask.
4) Use the rotovap to evaporate the HFIP and $CH_2Cl_2$.
5) Make a linear peptide proceeds to Global Deprotection of Acid Labile Protecting Groups.

Cleavage of Linear Peptide from Rink Amide Resin

Prep time: 1 h
Reaction time: 1.5 h

1) Wash the completed peptide on resin 3× with $CH_2Cl_2$, and transfer it into a poly prep column.
2) Dry resin under a stream on $N_2$ gas for ca-X 1 h.
3) Add 10 mL of an 18:1:1 TFA:$H_2O$:TIPS (prepared by adding 9 mL TFA and 0.5 mL of both $H_2O$ and TIPS) to the resin. Let rock for 1-1.5 hours.
4) Collect solution in a 250 mL round bottom flask.
5) Remove TFA with the use of a rotovap.

Purification of Peptides

Reverse-Phase HPLC Purification

1) Dissolve the deprotected peptide in the round bottom flask in a small amount of MeCN (2 mL) and transfer to a 15-mL conical tube. Wash the round bottom flask with ca. 3 mL $H_2O$ to collect the residual peptide in the round bottom flask and transfer to the 15-mL conical. The volume transferred to the 15-mL conical should not exceed 10 mL.
2) To remove particulates, centrifuge 15-mL conical at 10,000 rpm for 5 min.
3) Pass through a 0.2-µm syringe filter into a new 15-mL falcon tube. Inject the peptide on to the preparative RP-HPLC column. Before inject, it is advisable to obtain analytical HPLC trace to gauge what percentage of MeCN your peptide will come out. General operation of the semi-preparative RP-HPLCs Procedure:

1) Make sure that the solvent bottles are full.
2) Turn on lamp and flow (10 mL/min) on HPLC. The absorbance should be set to 214 nm.
30 Wash column at 95% MeCN over 5 min.
4) Go to 20% MeCN over 5 min at 10 mL/min.
5) Inject peptide and allow the peptide to load onto the column for 10 min.
6) Go to 30% MeCN over 20 min at 15 mL/min.
7) Go to 50% MeCN over 60 min at 15 mL/min. Peptide is likely to come out when going from 30% to 50%.
8) Collect fractions. Typically count 20 sec for each fraction.
9) After the peptide comes out, wash the column with 95% MeCN for at least 15 min. Then return the MeCN percentage to 50%.
10) The column is stored at 50% MeCN.
11) Turn off flow and UV lamp.

The following table (Table 7) shows the compounds synthesized:

TABLE 7

CUSTOM PEPTIDES CERTIFICATE OF ANALYSIS

| Cat. No. | Name | Sequence | Weight | Purity | Formula | M.W. |
|---|---|---|---|---|---|---|
| 360662873 #1 primer | primer | 1.0 mg | HPLC | C328H403 | | 10912.7 |
| 847361 #2 Peptide AB | Peptide AB | 1.0 mg | 98.25% | N140 O224P33 C128H205 | | 2990.25 |
| 847362 #3 Peptide A | Peptide A | 1.0 mg | 98.76% | N33O47S C77H114N | | 1819.89 |
| 847363 #4 Peptide B | Peptide B | 1.0 mg | 98.62% | 18O31S C51H93N1 | | 1188.37 |
| 36305 #5 primer -Peptide AB | primer Peptide AB | 1.4 mg | HPLC | 5O17 C492H648 N180 O282P34S1 | | 14680.75 |

The following table (Table 8) shows the ITEM Sequence, Quantity and Purity of each compound synthesized

TABLE 8

| ITEM # | SEQUENCE AND MODIFICATION | QUANTITY | PURITY |
|---|---|---|---|
| 1. primer | primer | 1 mg | HPLC |
| 2. Peptide AB | Peptide AB | 1 mg | >98% |
| 3. Peptide A | Peptide A | 1 mg | >98% |
| 4. Peptide B | Peptide B | 1 mg | >98% |
| 5. primer-peptide AB | primer-peptide AB | 1 mg | HPLC |

Checking Fractions, and Lyophilizing
1. To assess the purity of the fractions check them on the analytical HPLC. If there are impurities, an additional preparative HPLC was necessary.
2. Combine the pure fractions and take a "combined HPLC" and a "combined mass spec".
3. Evaporate the MeCN/H2O using a rotovap.
4. Re-dissolve the peptide film on the side of the flask in H2O and transfer to a clean polypropylene 15-mL conical.
5. Freeze your peptide in dry ice and then transfer the peptide to a lyophilization vessel. Detach the lid of the 15-mL conical, and use a kimwipe and rubber band to cover the top of the 15-mL conical.
6. Attach the lyophilization vessel to the lyophilizer. 12-48 hours later you will have a dry powder of your peptide as a TFA salt.

Oligonucleotide (RNA) and RNA-Peptide Conjugation

Example 2

Oligonucleotide (RNA) Synthesis

```
The miRNA
                                    SEQ ID NO: 1
5'AAAAAAAAAACUCCUAGAACUAGCAUUACAGAUG3'
``` was synthesized according to Phosphoramidite Method.

The RNA with azide group are synthesized by the oligo vendors following the Phosphoramidite method, a solid-phase synthesis like peptide synthesis, including detritylation of the support-bound 3'-nucleoside, activation and coupling, capping, oxidation and detritylation.

The phosphoramidite method is followed according to the next four steps:
1. Detritylation,
2. Coupling,
3. Capping
4. Oxidation Step 1 (Detritylation)

The cycle is initiated by removal of the 5'-DMT (4,4'-dimethoxytrityl) protecting group of the solid-support-linked nucleoside adenine (A), contains the terminal 3' base of the oligonucleotide RNA. The 5'-DMT prevents polymerization of the nucleoside (A) during functionalization of the solid support resin. The detritylation mechanism. The 5'-DMT protecting group is removed by TCA (trichloroacetic acid) in the solvent. The products include the 3' terminal (A) nucleoside with a free 5'-OH and a DMT carbocation. The nucleoside A proceeds to step 2 in the synthesis while the DMT carbocation absorbs at 495 nm and thereby produces an orange color (used to monitor coupling efficiency).

Step 2 (Coupling)

Once the DMT has been removed, the free 5'-OH of the solid-support-linked A nucleoside is able to react with the next nucleoside A, which is added as a phosphoramidite monomer. (made nine times this step in order to develop the polyadenine arm of ten nucleosides AAAAAAAAAA)

The coupling mechanism. The diisopropylamino group of the incoming phosphoramidite monomer in the solvent acetonitrile is 'activated' (protonated) by the acidic catalyst ETT [5-(ethylthio)-1H-tetrazole]. The mixing is carried out in the fluid lines of the synthesis instrument as the reagents are delivered to the solid support. The activated phosphoramidite is delivered in a many-fold excess over the solid-support-linked nucleoside to drive the reaction to as close to completion as possible. The products include a dinucleoside with a phosphite triester linkage and a free diisopropylamino group.

Step 3 (Oxidation)

The phosphite triester formed during the coupling reaction is unnatural and unstable; therefore, it must be converted to a more stable phosphorus species prior to the start of the next cycle. Oxidation converts the phosphite triester to the stable phosphate triester.

The oxidation mechanism. Oxidation of the phosphite triester is achieved with iodine in the presence of water and pyridine. The product is the phosphate triester, which is essentially a standard DNA backbone with a β-cyanoethyl protecting group on the free oxygen.

Step 4 (Capping)

Since 100% coupling efficiency is impossible, there are always some solid-support-linked nucleosides with unreacted 5'-OH. If not blocked, these hydroxyl groups will react during the next cycle, and hence, lead to a missing base. The accumulation of these deletion mutations through successive cycles would create a complex mixture of 'shortmers' that are difficult to purify and therefore could render the oligonucleotide useless in the subsequent application. Capping is required to prevent shortmer accumulation.

Acetic anhydride and N-methylimidazole react to form an intermediate in the solvent tetrahydrofuran, which contains a small quantity of pyridine. The mixing is carried out in the fluid lines of the synthesis instrument as the reagents are delivered to the solid support. The product is the solid-support-linked nucleoside with an acetylated 5'-OH (pyridine maintains a basic pH thereby preventing detritylation of the phosphoramidite monomer by the free acetate/acetic acid).

Successive Cycles

The second cycle begins by starting with step 1, detritylation, followed by each of the remaining three steps. The number of cycles repeated equals the desired number of bases. We synthesized oligonucleotide RNA from 2 to 34 bases.

Cleavage

The proprietary solid support/linker is stable to all phosphoramidite reagents but is cleavable from the oligonucleotide at the end of synthesis. Cleavage is necessary so that the free 3'-OH may take part in biochemical reactions, such as extension by DNA Polymerase during PCR when the oligonucleotide serves as a primer.

Deprotection

After cleavage, the solution of oligonucleotide in concentrated aqueous ammonia is heated to remove protecting groups from the bases and phosphates.

Bases

While thymine does not require a protecting group, adenine, cytosine, and guanine do since they contain exocyclic primary amino groups. The protecting groups must be removed so that proper hydrogen bonds between the oligonucleotide and the target nucleic acid may form.

The oligonucleotide in concentrated aqueous ammonia is heated. The protecting groups include: N(6)-benzoyl A, N(4)-benzoyl C, and N(2)-isobutyryl G. The product of the reaction is fully-deprotected A, C, and G bases.

In addition to the standard protecting groups, the labile dimethylformamidyl G and the 'ultramild' protecting groups can be used for modified oligonucleotides that are sensitive to ammonia.

Labile and Ultramild Protecting Groups.

The dimethylformamidyl protecting group is typically removed in concentrated aqueous ammonia via heating but in significantly less time than is the isbutyryl group. The ultramild protecting groups include: N(6)-phenoxyacetyl A, N(2)-acetyl C, and N(2)-isopropylphenoxyacetyl G. They are typically removed at room temperature in a concentrated aqueous ammonia/methylamine solution.

Phosphodiester Formation

The β-cyanoethyl group on the free oxygen of the phosphate must be removed to convert it from a phosphate triester to a phosphate diester (phosphodiester).

The mechanism of phosphodiester formation via deprotection.

The cyanoethyl groups are removed in concentrated aqueous ammonia via β-elimination. The reaction is quick because the hydrogen atoms on the carbon adjacent to the electron-withdrawing cyano group are highly acidic. The products are the oligonucleotide with a native phosphodiester backbone and acrylonitrile.

Yield of 5'AAAAAAAAAACUCCUAGAACUAG-CAUUACAGAUG 3' (SEQ ID NO: 1)

The RNA oligos were pre-made with azide group and the peptides were pre-made with the diarylcyclooctyne moiety (DBCO). Mix DBCO-NHS ester labeled peptide with 2-4 times molar excess of azide-modified Oligos. The peptides and oligos were incubated at room temperature for 30 min or 2 hours on ice. Validation of conjugation and purification by HPLC.

Example 3

Method to Prepare RNA-Peptide-AB Conjugate
RNA-peptide-AB

SEQ ID NO: 1 with SEQ ID NO: 4
AAAAAAAAAACUCCUAGAACUAGCAUUACAGAUG- Cys- Val -Asn -Asp- Thr- Phe- Ala- Gly- Ser -Thr- Phe- Ile -Ser -Asp- Glu -Val- Asp- Gly -Val- Asp Glu -Val- Ala- Lys- Lys- Lys- Ser- Lys Conjugation is based on alkyne-azide cycloaddition. This Cu-free click reaction starts from the dibenzocyclooctyne (DBCO) moiety-activated peptide

SEQ ID NO: 4
(CVNDTFAGSTFISDEVDGVDEVAKKKSK)

and subsequently linked covalently with an azide-modified RNA

SEQ ID NO: 1
(AAAAAAAAAACUCCUAGAACUAGCAUUACAGAUG).

The reaction is performed under physiological conditions and has no adverse effects on peptide target. This can also be used as the click chemistry fluorescence labeling and the click chemistry in peptide-based antiviral SARS-CoV-2 vaccine design.

1. Conjugation of DBCO to the peptide. The DBCO-PEGS-NHS was used to react with the $NH_2$ groups on the peptide. The inclusion of a PEGS linker improves the water solubility of the hydrophobic DBCO, introduces a spacer and flexibility between the cysteine from peptide molecule and the RNA molecule. This will alleviate the steric effect of the peptide on the enzymatic reactions.

2. Prepare the azido-peptide or azido-oligonucleotide. The laboratory provides click chemistry modified peptide synthesis: C-terminal peptide/oligo-azide.

3. Covalent attachment of the peptide/RNA to the peptide. The reaction between DBCO and azide is slow compared to CuAAC reaction. The reaction time of 16-18 h in PBS at 4° C. is ideal to increase the final product yield. The DBCO-peptide in the intermediate reaction is stable.

Copper-Free Click Chemistry RNA-Peptide Conjugation

Typically, there are three biological functional groups on the peptide for the further conjugation: amino (—NH2), carboxyl (—COOH), and thiol (—SH). The most effective way is to utilize the free thiol groups from cysteine. The reaction of maleimides with thiols is widely used for bioconjugation and labeling of biomolecules.

Cysteine (—SH) was used as the first amino acid of peptide:

SEQ ID NO: 4
CVNDTFAGSTFISDEVDGVDEVAKKKSK

The click chemistry is another efficient method to conjugate the peptide with other biomolecules as DNA. Also, the peptide can be modified with azide groups (—$N_3$). One example of the peptide vaccine conjugation is the RNA-peptide against SARS-CoV-2 codified as a biomolecules fusion according to the present invention.

A Simple Protocol: Conjugation of the Vaccine of the Present Invention

Pre-conjugation considerations

1) Remove all additives from peptide solutions using dialysis or desalting.

2) Remove BSA and gelatin from peptide solutions.

3) Concentrate the peptide after dialysis or purification.

Activation of Peptide with DBCO-NHS Ester

1) Mix peptide with 20-30 fold molar excess over peptide of DBCO-NHS ester dissolved in DMSO.

2) Incubates at room temperature for 30 min or 2 hours on ice.

Quenching Activation Reaction

1) Add Tis-HCl (50-100 mM, pH 8) to the reaction.

2) Incubate at RT for 5 min or 15 minutes on ice.

Equilibration and Removal of Non-Reactive DBCO-NHS Ester by Zeba Column

Copper-Free Click Reaction

1) Mix DBCO-NHS ester labeled peptide with 2-4 times molar excess of azide-modified RNA.

2) Incubated overnight (around 10-12 hours) at 4° C. or 3-4 hours at room temperature.

Validation of conjugation and purification by HPLC

Example 4

In Vitro Assays of Cell Viability

In order to test the toxicity level of RNA-peptide are carried out studies of this target in five cell cultures monitoring dead cell number. Lethal Concentration (LC) at 50% and 100% ($LC_{50}$ and $LC_{100}$) are calculated in each study.

1) Bronchial Epithelium obtained from Autopsy of non-cancerous individual cells (BEAS-2Bs). It was originally used as an in vitro non-tumorigenic lung epithelial model in a large variety of studies in association with lung carcinogenesis and more recently with lung virologic diseases.

2) Human Umbilical Vein Endothelial Cells (HUVECs) are cells derived from the endothelium of veins from the umbilical cord. They are used as a laboratory model system for the study of the function and pathology of endothelial cells.

3) Human Microvascular Endothelial Cell line (HMEC-1) specifically bind lymphocytes in cell adhesion assays. Thus HMEC-1 is the first immortalized that retains the morphologic, phenotypic, and functional characteristics of normal human microvascular endothelial cells. HMEC-1 possess characteristics of endothelial cells, like HUVECs.

4) Human Embryonic Kidney 293 cells, (HEK 293), are a specific cell line originally derived from human embryonic kidney cells grown in tissue culture taken from a female fetus.

5) Human Malignant Melanoma cell lines, (WM-266) used in this study were derived from biopsy of malignant primary or metastatic melanoma.

Study the Toxicological Action of Control Assay:

A) Phorbol myristate acetate (PMA; phorbol ester) activates protein kinase C, which then activates a wide range of signaling pathways, including ERK via effects on the upstream kinase Raf. ERK then activates a wide range of downstream targets, including S6 ribosomal protein. PMA, through its activation of PKC, can activate T-cells and stimulate low-level production of IL-2.

B) Hydrogen peroxide solution ($H_2O_2$), Oxygen free radicals generated by $H_2O_2$ are involved in the multistage carcinogenic process; mechanisms include carcinogen activation, oxidative DNA damage, and tumor promotion. In this study, we have evaluated another potential mechanism of $H_2O_2$ in carcinogenesis modulation of DNA repair activities.

C) Phosphate-buffered saline (PBS) is a buffer solution commonly used in biological. PBS has many uses because it is isotonic and non-toxic to most cells.

D) Exosomes are a type of extracellular vesicle that contain constituents (protein, DNA, and RNA) of the cells that secrete them.

The following table (Table 9) shows the Name, Code, Sigma-Aldrich No, and function pathology of five cell lines such as: BEAS-2B, HUVEC, HMEC-1, HEK293 and WM-266.

TABLE 9

TOXICOLOGICAL ANALYSIS CELL

| Name | Code | Sigma-Aldrich No | Study of the function and pathology |
|---|---|---|---|
| Human Bronchial Epithelium cells | BEAS-2B | 95102433 | with lung cells |
| Human Umbilical vein Endothelial Cells | HUVEC | C-12203 | with endothelial cells |
| Human Microvascular Endothelial Cells | HMEC-1 | S100-05A | with endothelial cells |
| Human embryonic kidney 293 cells | HEK293 | EJH014 | with embryonic kidney cells |
| Human Metastatic Melanoma cell line | WM-266 | 91061232 | with Melanoma cell line |

The following table (Table 10) shows the Name, Code, provider Cat. No and function of the proliferation controls such as: PMA, $H_2O_2$, $CuSO_4$; and assay control such as PBS and exosome and as targets: RNA, peptide-AB, peptide-A, peptide-B and RNA-peptide-AB.

TABLE 10

TOXICOLOGICAL ANALYSIS

| Name | Code | Cat. No | Function |
|---|---|---|---|
| Proliferation control | | | |
| Phorbol 12-myristate 13-acetate | PMA | P8139 | activates a wide range of downstream targets |
| Hydrogen peroxide solution | $H_2O_2$ | H1009 | involved in the multistage carcinogenic process |
| Copper(II) sulfate | $CuSO_4$ | 451657 | increase in DNA damage |
| Assay control | | | |
| Phosphate-buffered saline | PBS | P5493 | buffer solution |
| Exosome | HEK293 Exosomes | 300192exo | vesicle carrier of protein, DNA and RNA |
| Target | | | |
| RNA | RNA | LCR-008rna | RNA candidate vaccine |
| peptide-AB | peptide-AB | LCR-008pab | peptide-AB candidate vaccine |
| peptide-A | peptide-A | LCR-008pa | peptide-A candidate vaccine |
| peptide-B | peptide-B | LCR-008pb | Peptide-B candidate vaccine |
| RNA-peptide-AB | RNA-peptide-AB | RNA-peptide-AB | RNA-peptide-AB candidate vaccine |

PMA Toxicological Test: % DEAD CELLS (Flow Cytometry)

In order to test the toxicity level of PMA we made our studies in the five-cell cultures. We monitored dead cell number using flow cytometry according to the manufacturer's recommendations. LC50 and LC100 are calculated, and LC50 values are used as a general indicator of a target's acute toxicity.

1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

Flow Cytometry of Cell Surface Receptor Staining (FACS)

The five-cell cultures are the following:
1. BEAS-2B
2. HUVEC
3. HMEC-1
4. HEK 293
5. WM-266

Protocol FACS

After confluency stage of the five cell lines, wash each cell (single cell suspension) and adjust cell number to a concentration of 1-5×10⁶ cells/ml in ice cold FACS Buffer (PBS, 0.5-1% BSA or 5-10% FBS, 0.1% $NaN_3$ sodium azide).

The five-cell cultures are usually stained in polystyrene round-bottom 12×75 mm BD polystyrene tube (cat #Z376787). It is convenient to check the viability of the cells, which should be around 95% but not less than 90%. (Important for HUVEC and HMEC-1 cell lines)

Add 100 µL of each cell lines suspension to each tube.
Add 0.1-10 µg/ml of the primary labeled antibody.
Dilutions, if necessary, should be made in FACS buffer.
Incubate for at least 30 min at room temperature or 4° C. in the dark.

Wash the cells 3 times by centrifugation at 1500 rpm for 5 minutes and resuspend them in 200 μL to 1 ml of ice cold FACS buffer*. Keep the cells in the dark on ice or at 4° C. in a fridge until your scheduled time for analysis.

Resuspend cells in this solution and incubate for at least 20-30 minutes at room temperature or 4° C. in the dark. Wash the cells 3 times by centrifugation at 1500 rpm for 5 minutes and resuspend them in 200 μL to 1 ml of ice cold FACS buffer. Keep the cells in the dark on ice or at 4° C. in a fridge until the scheduled time for analysis.

the cells were Analyzed on the flow cytometer within 24 hours.

The following table shows a) the percentage of dead cells (BEAS-2B, HUVEC, HMEC-1, HEK293 and WM-266) according to serial concentration of PMA (5 μg/μL, 10 μg/μL, 20 μg/μL, 40 μg/μL, 80 μg/μL, 160 μg/μL, 320 μg/μL and 640 μg/μL. It was made using in serial dilution ½ starting from 640 μg/μL). b) Shows the values of PMA $LC_{50}$ (μg/μL). c) Shows the values of PMA $LC_{100}$ (μg/μL). The number of dead cells was monitored using the flow cytometry.

TABLE 11

PMA Toxicological test: % DEAD CELLS (Flow Cytometry)

a)

| Concentration μg/μL | BEAS-2B | HUVEC | HMEC-1 | HEK293 | WM-266 |
|---|---|---|---|---|---|
| 5 | 2 | 2 | 3 | 4 | 1 |
| 10 | 7 | 6 | 8 | 7 | 9 |
| 20 | 14 | 13 | 11 | 14 | 12 |
| 40 | 42 | 33 | 29 | 42 | 38 |
| 80 | 63 | 65 | 72 | 85 | 53 |
| 160 | 86 | 82 | 91 | 98 | 76 |
| 320 | 95 | 100 | 100 | 100 | 98 |
| 640 | 100 | 100 | 100 | 100 | 100 |

| b) | | c) | |
|---|---|---|---|
| Cell lines | PMA $LC_{50}$ (μg/μL) | Cell lines | PMA $LC_{100}$ (μg/μL) |
| BEAS-2B | 297 | BEAS-2B | 466 |
| HUVEC | 272 | HUVEC | 433 |
| HMEC-1 | 291 | HMEC-1 | 461 |
| HEK293 | 275 | HEK293 | 462 |
| WM-266 | 310 | WM-266 | 464 |

$H_2O_2$ Toxicological Test: % DEAD CELLS (Flow Cytometry)

In order to test the toxicity level of $H_2O_2$ studies were made in the five cell culture. Dead cell number was monitored using flow cytometry. $LC_{50}$ and $LC_{100}$, were $LC_{50}$ values were calculated as general indicator of a target's acute toxicity.

1) Bronchial Epithelium obtained from Autopsy of non-cancerous individual cells (BEAS-2Bs)
2) Human umbilical vein endothelial cells (HUVECs)
3) Human Microvascular Endothelial Cell line (HMEC-1)
4) Human embryonic kidney 293 cells, (HEK 293)
5) Human malignant melanoma cell lines, (WM-266)

In the following table (table 12) is showed a) the percentage of dead cells (BEAS-2B, HUVEC, HMEC-1, HEK293 and WM-266) according to serial concentration of $H_2O_2$ (5 μg/μL, 10 μg/μL, 20 μg/μL, 40 μg/μL, 80 μg/μL, 160 μg/μL, 320 μg/μL and 640 μg/μL is showed in the following table. It was made using in serial dilution ½ starting from 640 μg/μL). b) Shows the values of $H_2O_2$ $LC_{50}$ (μg/μL). c) Shows the values of $H_2O_2$ $LC_{100}$ (μg/μL). The number of dead cells was monitored using the flow cytometry.

TABLE 12

$H_2O_2$ Toxicological test: % DEAD CELLS (Flow Cytometry)

a)

| Concentration μg/μL | BEAS-2B | HUVEC | HMEC-1 | HEK293 | WM-266 |
|---|---|---|---|---|---|
| 5 | 4 | 6 | 9 | 5 | 3 |
| 10 | 9 | 16 | 24 | 36 | 27 |
| 20 | 41 | 38 | 44 | 59 | 42 |
| 40 | 72 | 91 | 77 | 84 | 66 |
| 80 | 96 | 100 | 92 | 96 | 82 |
| 160 | 100 | 100 | 100 | 100 | 98 |
| 320 | 100 | 100 | 100 | 100 | 100 |
| 640 | 100 | 100 | 100 | 100 | 100 |

| b) | | c) | |
|---|---|---|---|
| Cell lines | $H_2O_2$ $LC_{50}$ (μg/μL) | Cell lines | $H_2O_2$ $LC_{100}$ (μg/μL) |
| BEAS-2B | 214 | BEAS-2B | 446 |
| HUVEC | 167 | HUVEC | 444 |
| HMEC-1 | 131 | HMEC-1 | 461 |
| HEK293 | 111 | HEK293 | 441 |
| WM-266 | 195 | WM-266 | 451 |

$CuSO_4$ Toxicological Test: % DEAD CELLS (Flow Cytometry)

In order to test the toxicity level of $CuSO_4$ studies were made in the five cell culture. Dead cell number was monitored using flow cytometry. $LC_{50}$ and $LC_{100}$ are calculated and $LC_{50}$ value is calculated as a general indicator of a target's acute toxicity.

1) Bronchial epithelium obtained from autopsy of non-cancerous individual cells (BEAS-2Bs)
2) Human umbilical vein endothelial cells (HUVECs)
3) Human microvascular endothelial Cell line (HMEC-1)
4) Human embryonic kidney 293 cells, (HEK 293)
5) Human malignant melanoma cell lines, (WM-266)

In the following table (table 13) a) Shows the percentage of dead cells (BEAS-2B, HUVEC, HMEC-1, HEK293 and WM-266) according to serial concentration of $CuSO_4$ (5 μg/μL, 10 μg/μL, 20 μg/μL, 40 μg/μL, 80 μg/μL, 160 μg/μL, 320 μg/μL and 640 μg/μL. It was made using in serial dilution ½ starting from 640 μg/μL). b) Shows the values of $CuSO_4$ $LC_{50}$ (μg/μL). c) Shows the values of $CuSO_4$ $LC_{100}$ (μg/μL). The number of dead cells was monitored using the flow cytometry.

TABLE 13

$CuSO_4$ Toxicological test: % DEAD CELLS (Flow Cytometry)

a)

| Concentration μg/μL | BEAS-2B | HUVEC | HMEC-1 | HEK293 | WM-266 |
|---|---|---|---|---|---|
| 5 | 10 | 9 | 13 | 15 | 8 |
| 10 | 25 | 28 | 36 | 44 | 17 |
| 20 | 64 | 69 | 60 | 55 | 63 |
| 40 | 86 | 83 | 77 | 79 | 81 |
| 80 | 100 | 100 | 100 | 100 | 100 |
| 160 | 100 | 100 | 100 | 100 | 100 |
| 320 | 100 | 100 | 100 | 100 | 100 |
| 640 | 100 | 100 | 100 | 100 | 100 |

TABLE 13-continued

CuSO₄ Toxicological test: % DEAD CELLS (Flow Cytometry)

| b) | | c) | |
|---|---|---|---|
| P Cell lines | CuSO₄ LC$_{50}$ (µg/µL) | Cell lines | CuSO₄ LC$_{100}$ (µg/µL) |
| BEAS-2B | 74 | BEAS-2B | 439 |
| HUVEC | 70 | HUVEC | 434 |
| HMEC-1 | 30 | HMEC-1 | 438 |
| HEK293 | — | HEK293 | 459 |
| WM-266 | 125 | WM-266 | 440 |

PBS Toxicological Test: % DEAD CELLS (Flow Cytometry)

In order to test the toxicity level of PBS studies are made in the five cell culture. Dead cell number is monitored using flow cytometry. LC$_{50}$ and LC$_{100}$, are calculated and LC$_{50}$ values are general indicator of a target's acute toxicity.

1. Bronchial epithelium obtained from autopsy of non-cancerous individual cells (BEAS-2Bs)
2. Human umbilical vein endothelial cells (HUVECs)
3. Human microvascular endothelial Cell line (HMEC-1)
4. Human embryonic kidney 293 cells, (HEK 293)
5. Human malignant melanoma cell lines, (WM-266)

In the following table (Table 14), a) Shows the percentage of dead cells (BEAS-2B, HUVEC, HMEC-1, HEK293 and WM-266) according to serial concentration of PBS (5 µg/µL, 10 µg/µL, 20 µg/µL, 40 µg/µL, 80 µg/µL, 160 µg/µL, 320 µg/µL and 640 µg/µL. It was made using in serial dilution ½ starting from 640 µg/µL). b) Shows the values of PBS LC$_{50}$ (µg/µL). c) Shows the values of PBS LC$_{100}$ (µg/µL). The number of dead cells was monitored using the flow cytometry.

TABLE 14

PBS Toxicological test: % DEAD CELLS (Flow Cytometry)

a)

| Concentration µg/µL | BEAS-2B | HUVEC | HMEC-1 | HEK293 | WM-266 |
|---|---|---|---|---|---|
| 5 | 1 | 2 | 1 | 3 | 1 |
| 10 | 2 | 3 | 3 | 9 | 2 |
| 20 | 3 | 6 | 5 | 14 | 4 |
| 40 | 5 | 8 | 7 | 25 | 9 |
| 80 | 12 | 15 | 15 | 33 | 17 |
| 160 | 22 | 21 | 25 | 49 | 38 |
| 320 | 44 | 48 | 45 | 79 | 46 |
| 640 | 56 | 66 | 77 | 86 | 62 |

| b) | | c) | |
|---|---|---|---|
| Cell lines | PBS LC$_{50}$ (µg/µL) | Cell lines | PBS LC$_{100}$ (µg/µL) |
| BEAS-2B | 490 | BEAS-2B | 616 |
| HUVEC | 468 | HUVEC | 612 |
| HMEC-1 | 451 | HMEC-1 | 580 |
| HEK293 | 356 | HEK293 | 539 |
| WM-266 | 456 | WM-266 | 587 |

Exosome Toxicological Test: % DEAD CELLS (Flow Cytometry)

In order to test the toxicity level of exosome studies are made in the five cell cultures. Dead cells number are monitored using flow cytometry. LC$_{50}$ and LC$_{100}$ are calculated and LC$_{50}$ values are used as a general indicator of a target's acute toxicity.

1. Bronchial epithelium obtained from autopsy of non-cancerous individual cells (BEAS-2Bs)
2. Human umbilical vein endothelial cells (HUVECs)
3. Human microvascular endothelial Cell line (HMEC-1)
4. Human embryonic kidney 293 cells, (HEK 293)
5. Human malignant melanoma cell lines, (WM-266)

In the following table (Table 15) a) Shows the percentage of dead cells (BEAS-2B, HUVEC, HMEC-1, HEK293 and WM-266) according to serial concentration of exosome (5 µg/µL, 10 µg/µL, 20 µg/µL, 40 µg/µL, 80 µg/µL, 160 µg/µL, 320 µg/µL and 640 µg/µL. It was made using in serial dilution ½ starting from 640 µg/µL). b) Shows the values of exosome LC$_{50}$ (µg/µL). c) Shows the values of exosome LC$_{100}$ (µg/µL). The number of dead cells was monitored using the flow cytometry.

TABLE 15 a)

Exosome Toxicological test: % DEAD CELLS (Flow Cytometry)

| Concentration µg/µL | BEAS-2B | HUVEC | HMEC-1 | HEK293 | WM-266 |
|---|---|---|---|---|---|
| 5 | 1 | 1 | 1 | 1 | 1 |
| 10 | 1 | 1 | 1 | 1 | 1 |
| 20 | 1 | 1 | 1 | 1 | 1 |
| 40 | 3 | 4 | 3 | 3 | 3 |
| 80 | 8 | 9 | 8 | 8 | 8 |
| 160 | 21 | 16 | 23 | 20 | 21 |
| 320 | 74 | 56 | 56 | 89 | 65 |
| 640 | 100 | 100 | 100 | 100 | 100 |

| b) | | c) | |
|---|---|---|---|
| Cell lines | Exosome LC$_{50}$ (µg/µL) | Cell lines | Exosome LC$_{100}$ (µg/µL) |
| BEAS-2B | 423 | BEAS-2B | 516 |
| HUVEC | 434 | HUVEC | 528 |
| HMEC-1 | 434 | HMEC-1 | 530 |
| HEK293 | 420 | HEK293 | 510 |
| WM-266 | 430 | WM-266 | 524 |

RNA Toxicological Test: % DEAD CELLS (Flow Cytometry)

In order to test the toxicity level of RNA studies are made in the five cell culture. Dead cells number are monitored using flow cytometry. LC$_{50}$ and LC$_{100}$ are calculated, and LC$_{50}$ values are used as a general indicator of a target's acute toxicity.

1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following table (Table 16) a) Shows the percentage of dead cells (BEAS-2B, HUVEC, HMEC-1, HEK293 and WM-266) according to serial concentration of RNA (5 µg/µL, 10 µg/µL, 20 µg/µL, 40 µg/µL, 80 µg/µL, 160 µg/µL, 320 µg/µL and 640 µg/µL. It was made using in serial dilution ½ starting from 640 µg/µL). b) Shows the values of RNA LC$_{50}$ (µg/µL). c) Shows the values of RNA LC$_{100}$ (µg/µL). The number of dead cells was monitored using the flow cytometry.

TABLE 16 a)
RNA Toxicological test: % DEAD CELLS (Flow Cytometry)

| Concentration µg/µL | BEAS-2B | HUVEC | HMEC-1 | HEK293 | WM-266 |
|---|---|---|---|---|---|
| 5 | 13 | 15 | 16 | 19 | 11 |
| 10 | 26 | 35 | 42 | 51 | 39 |
| 20 | 38 | 49 | 61 | 64 | 61 |
| 40 | 63 | 69 | 76 | 79 | 80 |
| 80 | 85 | 82 | 89 | 95 | 98 |
| 160 | 94 | 98 | 100 | 100 | 100 |
| 320 | 100 | 100 | 100 | 100 | 100 |
| 640 | 100 | 100 | 100 | 100 | 100 |

| b) | | c) | |
|---|---|---|---|
| Cell lines | RNA $LC_{50}$ (µg/µL) | Cell lines | RNA $LC_{100}$ (µg/µL) |
| BEAS-2B | 129 | BEAS-2B | 459 |
| HUVEC | 67 | HUVEC | 452 |
| HMEC-1 | 131 | HMEC-1 | 461 |
| HEK293 | — | HEK293 | 456 |
| WM-266 | 36 | WM-266 | 444 |

Peptide-AB Toxicological Test: % DEAD CELLS (Flow Cytometry)

In order to test the toxicity level of Peptide AB studies are made in the five cell cultures. Dead cells number are monitored using flow cytometry. $LC_{50}$ and $LC_{100}$ are calculated, and $LC_{50}$ values are used as a general indicator of a target's acute toxicity.
1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following table (Table 17), a) Shows the percentage of dead cells (BEAS-2B, HUVEC, HMEC-1, HEK293 and WM-266) according to serial concentration of Peptide-AB (5 µg/µL, 10 µg/µL, 20 µg/µL, 40 µg/µL, 80 µg/µL, 160 µg/µL, 320 µg/µL and 640 µg/µL. It was made using in serial dilution ½ starting from 640 µg/µL). b) Shows the values of Peptide-AB $LC_{50}$ (µg/µL). c) Shows the values of Peptide-AB $LC_{100}$ (µg/µL). The number of dead cells was monitored using the flow cytometry.

TABLE 17 a)
Peptide-AB Toxicological test: % DEAD CELLS (Flow Cytometry)

| Concentration µg/µL | BEAS-2B | HUVEC | HMEC-1 | HEK293 | WM-266 |
|---|---|---|---|---|---|
| 5 | 8 | 7 | 6 | 13 | 4 |
| 10 | 12 | 11 | 12 | 28 | 9 |
| 20 | 54 | 52 | 75 | 88 | 46 |
| 40 | 72 | 76 | 92 | 96 | 85 |
| 80 | 86 | 91 | 100 | 100 | 96 |
| 160 | 100 | 100 | 100 | 100 | 100 |
| 320 | 100 | 100 | 100 | 100 | 100 |
| 640 | 100 | 100 | 100 | 100 | 100 |

| b) | | c) | |
|---|---|---|---|
| Cell lines | Peptide-AB, $LC_{50}$ (µg/µL) | Cell lines | Peptide-AB, $LC_{100}$ (µg/µL) |
| BEAS-2B | 167 | BEAS-2B | 444 |
| HUVEC | 179 | HUVEC | 456 |
| HMEC-1 | 149 | HMEC-1 | 450 |
| HEK293 | 6 | HEK293 | 7 |
| WM-266 | 36 | WM-266 | 444 |

Peptide-A Toxicological Test: % DEAD CELLS (Flow Cytometry)

In order to test the toxicity level of Peptide A studies are made in the five cell cultures. Dead cells number are monitored using flow cytometry. $LC_{50}$ and $LC_{100}$ are calculated, and $LC_{50}$ values are used as a general indicator of a target's acute toxicity.
1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following table (Table 18), a) Shows the percentage of dead cells (BEAS-2B, HUVEC, HMEC-1, HEK293 and WM-266) according to serial concentration of Peptide-A (5 µg/µL, 10 µg/µL, 20 µg/µL, 40 µg/µL, 80 µg/µL, 160 µg/µL, 320 µg/µL and 640 µg/µL. It was made using in serial dilution ½ starting from 640 µg/µL). b) Shows the values of Peptide-A $LC_{50}$ (µg/µL). c) Shows the values of Peptide-A $LC_{100}$ (µg/µL). The number of dead cells was monitored using the flow cytometry.

TABLE 18 a)
Peptide-A Toxicological test: % DEAD CELLS (Flow Cytometry)

| Concentration µg/µL | BEAS-2B | HUVEC | HMEC-1 | HEK293 | WM-266 |
|---|---|---|---|---|---|
| 5 | 5 | 6 | 7 | 11 | 3 |
| 10 | 16 | 19 | 21 | 33 | 12 |
| 20 | 66 | 51 | 61 | 75 | 39 |
| 40 | 83 | 74 | 85 | 92 | 74 |
| 80 | 92 | 95 | 100 | 100 | 100 |
| 160 | 100 | 100 | 100 | 100 | 100 |
| 320 | 100 | 100 | 100 | 100 | 100 |
| 640 | 100 | 100 | 100 | 100 | 100 |

| b) | | c) | |
|---|---|---|---|
| Cell lines | Peptide-A, $LC_{50}$ (µg/µL) | Cell lines | Peptide-A, $LC_{100}$ (µg/µL) |
| BEAS-2B | 158 | BEAS-2B | 447 |
| HUVEC | 156 | HUVEC | 445 |
| HMEC-1 | 122 | HMEC-1 | 452 |
| HEK293 | 16 | HEK293 | 450 |
| WM-266 | 214 | WM-266 | 445 |

Peptide-B Toxicological Test: % DEAD CELLS (Flow Cytometry)

In order to test the toxicity level of Peptide B studies are made in the five cell cultures. Dead cells number are monitored using flow cytometry. $LC_{50}$ and $LC_{100}$ are calculated, and $LC_{50}$ values are used as a general indicator of a target's acute toxicity.
1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following table a) Shows the percentage of dead cells (BEAS-2B, HUVEC, HMEC-1, HEK293 and WM-266) according to serial concentration of Peptide-B (5 µg/µL, 10 µg/µL, 20 µg/µL, 40 µg/µL, 80 µg/µL, 160 µg/µL, 320 µg/µL and 640 µg/µL. It was made using in serial dilution ½ starting from 640 µg/µL). b) Shows the values of Peptide-B $LC_{50}$ (µg/µL). c) Shows the values of Peptide-B $LC_{100}$ (µg/µL). The number of dead cells was monitored using the flow cytometry

TABLE 19 a)
Peptide-B Toxicological test: % DEAD CELLS (Flow Cytometry)

| Concentration µg/µL | BEAS-2B | HUVEC | HMEC-1 | HEK293 | WM-266 |
|---|---|---|---|---|---|
| 5 | 7 | 7 | 8 | 9 | 6 |
| 10 | 21 | 23 | 31 | 27 | 14 |
| 20 | 49 | 49 | 45 | 41 | 44 |
| 40 | 67 | 68 | 77 | 71 | 74 |
| 80 | 86 | 93 | 94 | 86 | 93 |
| 160 | 97 | 100 | 100 | 95 | 100 |
| 320 | 100 | 100 | 100 | 100 | 100 |
| 640 | 100 | 100 | 100 | 100 | 100 |

| b) | | c) | |
|---|---|---|---|
| Cell lines | Peptide-B, $LC_{50}$ (µg/µL) | Cell lines | Peptide-B, $LC_{100}$ (µg/µL) |
| BEAS-2B | 161 | BEAS-2B | 462 |
| HUVEC | 145 | HUVEC | 446 |
| HMEC-1 | 114 | HMEC-1 | 444 |
| HEK293 | 135 | HEK293 | 450 |
| WM-266 | 179 | WM-266 | 445 |

RNA-peptide-AB Toxicological Test: % DEAD CELLS (Flow Cytometry)

In order to test the toxicity level of RNA-peptide-AB, studies are made in the five cell cultures. Dead cells number are monitored using flow cytometry. $LC_{50}$ and $LC_{100}$ are calculated, and $LC_{50}$ values are used as a general indicator of a target's acute toxicity.

1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following table (table 20), a) Shows the percentage of dead cells (BEAS-2B, HUVEC, HMEC-1, HEK293 and WM-266) according to serial concentration of vaccine RNA-peptide-AB (5 µg/µL, 10 µg/µL, 20 µg/µL, 40 µg/µL, 80 µg/µL, 160 µg/µL, 320 µg/µL and 640 µg/µL. It was made using in serial dilution ½ starting from 640 µg/µL). b) Shows the values of vaccine $LC_{50}$ (µg/µL). c) Shows the values of vaccine $LC_{100}$ (µg/µL). The number of dead cells was monitored using the flow cytometry.

TABLE 20 a)
RNA-peptide-AB (melody) Toxicological test:
% DEAD CELLS (Flow Cytometry)

| Concentration µg/µL | BEAS-2B | HUVEC | HMEC-1 | HEK293 | WM-266 |
|---|---|---|---|---|---|
| 5 | 3 | 4 | 3 | 3 | 2 |
| 10 | 11 | 7 | 7 | 6 | 5 |
| 20 | 18 | 12 | 14 | 11 | 14 |
| 40 | 45 | 35 | 36 | 39 | 33 |
| 80 | 78 | 79 | 81 | 92 | 65 |
| 160 | 92 | 96 | 93 | 100 | 91 |
| 320 | 100 | 100 | 100 | 100 | 100 |
| 640 | 100 | 100 | 100 | 100 | 100 |

| b) | | c) | |
|---|---|---|---|
| Cell lines | vaccine $LC_{50}$ (µg/µL) | Cell lines | vaccine $LC_{100}$ (µg/µL) |
| BEAS-2B | 263 | BEAS-2B | 455 |
| HUVEC | 280 | HUVEC | 458 |
| HMEC-1 | 286 | HMEC-1 | 463 |
| HEK293 | 135 | HEK293 | 450 |
| WM-266 | 299 | WM-266 | 456 |

According to the previous studies, in a preferred embodiment, an effective amount of the composition of the RNA-peptide-AB according to the present invention is between about 135 µg/µL and 299 µg/µL.

Example 5

Efficacy Studies of the Composition of the Present Invention

1) RNA Toxicological Test: % DEAD CELLS (Flow Cytometry)

In order to test the toxicity level of RNA after vaccine incubation 16 hours, we made our studies in the five cell cultures. We monitored dead cell number using flow cytometry. $LC_{50}$ and $LC_{100}$ are calculated and $LC_{50}$ values are used as a general indicator of a target's acute toxicity.

1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following Table (Table 21), a) Shows the percentage of dead cells (BEAS-2B, HUVEC, HMEC-1, HEK293 and WM-266) according to serial concentration of RNA (5 µg/µL, 10 µg/µL, 20 µg/µL, 40 µg/µL, 80 µg/µL, 160 µg/µL, 320 µg/µL and 640 µg/µL after vaccine incubation 16 hours. It was made using in serial dilution ½ starting from 640 µg/µL). b) Shows the values of vaccine $LC_{50}$ (µg/µL). c) Shows the values of vaccine $LC_{100}$ (µg/µL). The number of dead cells was monitored using the flow cytometry.

TABLE 21 a)
RNA Toxicological test: % DEAD CELL (Flow Cytometry)

| Concentration µg/µL | BEAS-2B | HUVEC | HMEC-1 | HEK293 | WM-266 |
|---|---|---|---|---|---|
| 5 | 8 | 7 | 5 | 6 | 6 |
| 10 | 12 | 14 | 18 | 16 | 9 |
| 20 | 21 | 29 | 24 | 33 | 20 |
| 40 | 39 | 42 | 38 | 44 | 46 |
| 80 | 66 | 63 | 68 | 61 | 60 |
| 160 | 85 | 83 | 77 | 72 | 74 |
| 320 | 98 | 92 | 89 | 86 | 94 |
| 640 | 100 | 100 | 100 | 100 | 100 |

TABLE 21-continued

| | b) | | c) |
|---|---|---|---|
| Cell lines | RNA LC$_{50}$ (µg/µL) | Cell lines | RNA LC$_{100}$ (µg/µL) |
| BEAS-2B | 249 | BEAS-2B | 472 |
| HUVEC | 243 | HUVEC | 482 |
| HMEC-1 | 259 | HMEC-1 | 490 |
| HEK293 | 251 | HEK293 | 499 |

RNA Toxicological Test: % DEAD CELLS (Flow Cytometry)

In order to test the toxicity level of RNA after incubation of the composition of the present invention, two times of 16 hours each incubation, studies are in the five-cell cultures. Dead cells number are monitored using flow cytometry. LC$_{50}$ and LC$_{100}$ are calculated and LC$_{50}$ values are used as an indicator of a target's acute toxicity.
1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following Table: a) Shows the percentage of dead cells (BEAS-2B, HUVEC, HMEC-1, HEK293 and WM-266) according to serial concentration of RNA (5 µg/µL, 10 µg/µL, 20 µg/µL, 40 µg/µL, 80 µg/µL, 160 µg/µL, 320 µg/µL and 640 µg/µL after vaccine incubation 16 hours two times. It was made using in serial dilution ½ starting from 640 µg/µL). b) Shows the values of vaccine LC$_{50}$ (µg/µL). c) Shows the values of vaccine LC$_{100}$ (µg/µL). The number of dead cells was monitored using the flow cytometry.

TABLE 22 a)
Composition+ Composition + RNA Toxicological test:
% DEAD CELLS (Flow Cytometry)

| Concentration µg/µL | BEAS-2B | HUVEC | HMEC-1 | HEK293 | WM-266 |
|---|---|---|---|---|---|
| 5 | 4 | 3 | 5 | 4 | 2 |
| 10 | 9 | 7 | 11 | 9 | 7 |
| 20 | 16 | 18 | 14 | 25 | 15 |
| 40 | 31 | 35 | 33 | 44 | 30 |
| 80 | 49 | 48 | 45 | 66 | 43 |
| 160 | 68 | 63 | 59 | 80 | 57 |
| 320 | 89 | 84 | 87 | 92 | 83 |
| 640 | 100 | 100 | 100 | 100 | 100 |

| | b) | | c) |
|---|---|---|---|
| Cell lines | RNA LC$_{50}$ (µg/µL) | Cell lines | RNA LC$_{100}$ (µg/µL) |
| BEAS-2B | 299 | BEAS-2B | 482 |
| HUVEC | 311 | HUVEC | 489 |
| HMEC-1 | 306 | HMEC-1 | 498 |
| HEK293 | 270 | HEK293 | 474 |
| WM-266 | 330 | WM-266 | 495 |

RNA Toxicological Test: % DEAD CELLS (Flow Cytometry)

In order to test the toxicity level of RNA after vaccine incubation three times of 16 hours each incubation, we made our studies in the five-cell cultures. We monitored dead cell number using flow cytometry. We calculated LC$_{50}$ and LC$_{100}$, were LC$_{50}$ values are frequently used as a general indicator of a target's acute toxicity.
1) Bronchial epithelium obtained from autopsy of non-cancerous individual cells (BEAS-2Bs)
2) Human umbilical vein endothelial cells (HUVECs)
3) Human microvascular endothelial cell line (HMEC-1)
4) Human embryonic kidney 293 cells, (HEK 293)
5) Human malignant melanoma cell lines, (WM-266)

In the following table (Table 23), a) Shows the percentage of dead cells (BEAS-2B, HUVEC, HMEC-1, HEK293 and WM-266) according to serial concentration of RNA (5 µg/µL, 10 µg/µL, 20 µg/µL, 40 µg/µL, 80 µg/µL, 160 µg/µL, 320 µg/µL and 640 µg/µL after vaccine incubation 16 hours three times. It was made using in serial dilution ½ starting from 640 µg/µL). b) Shows the values of vaccine LC$_{50}$ (µg/µL). c) Shows the values of vaccine LC$_{100}$ (µg/µL). The number of dead cells was monitored.

TABLE 23 a)
vaccine + vaccine + vaccine + RNA Toxicological test:
% DEAD CELLS (Flow Cytometry)

| Concentration µg/µL | BEAS-2B | HUVEC | HMEC-1 | HEK293 | WM-266 |
|---|---|---|---|---|---|
| 5 | 4 | 4 | 4 | 5 | 2 |
| 10 | 8 | 6 | 10 | 7 | 6 |
| 20 | 14 | 15 | 13 | 24 | 16 |
| 40 | 32 | 33 | 32 | 43 | 29 |
| 80 | 48 | 45 | 48 | 65 | 42 |
| 160 | 68 | 62 | 60 | 79 | 58 |
| 320 | 88 | 83 | 86 | 91 | 82 |
| 640 | 100 | 100 | 100 | 100 | 100 |

| | b) | | c) |
|---|---|---|---|
| Cell lines | RNA LC$_{50}$ (µg/µL) | Cell lines | RNA LC$_{100}$ (µg/µL) |
| BEAS-2B | 303 | BEAS-2B | 481 |
| HUVEC | 319 | HUVEC | 497 |
| HMEC-1 | 308 | HMEC-1 | 491 |
| HEK293 | 164 | HEK293 | 258 |
| WM-266 | 329 | WM-266 | 490 |

The following table shows the comparison of lethal concentration 50% (LC$_{50}$ µg/µL) of dead cells (BEAS-2B, HUVEC, HMEC-1, HEK293 and WM-266) according to the action of PMA and RNA-peptide-AB. The number of dead cells was monitored using the flow cytometry.

TABLE 24

| Cell lines | PMA | RNA-peptide-AB LC$_{50}$ µg/µL |
|---|---|---|
| BEAS-2B | 297 | 263 |
| HUVEC | 272 | 280 |
| HMEC-1 | 291 | 286 |
| HEK293 | 275 | 135 |
| WM-266 | 310 | 299 |

The following table (Table 25) shows the comparison of lethal concentration 50% (LC$_{50}$ µg/µL) of dead cells (BEAS-2B, HUVEC, HMEC-1, HEK293 and WM-266) according to the action of H$_2$O$_2$ and RNA-peptide-AB. The number of dead cells was monitored using the flow cytometry.

TABLE 25

| Cell lines | H$_2$O$_2$ | RNA-peptide-AB LC$_{50}$ µg/µL |
|---|---|---|
| BEAS-2B | 214 | 263 |
| HUVEC | 167 | 280 |
| HMEC-1 | 131 | 286 |
| HEK293 | 111 | 135 |
| WM-266 | 195 | 299 |

The following table (Table 26) Shows the comparison of lethal concentration 50% (LC$_{50}$ µg/µL) of dead cells (BEAS-2B, HUVEC, HMEC-1, HEK293 and WM-266) according to the action of CuSO$_4$ and RNA-peptide-AB. The number of dead cells was monitored using the flow cytometry.

TABLE 26

| Cell lines | CuSO$_4$ | RNA-peptide-AB LC$_{50}$ µg/µL |
|---|---|---|
| BEAS-2B | 74 | 263 |
| HUVEC | 70 | 280 |
| HMEC-1 | 30 | 286 |
| WM-266 | 125 | 299 |
| HEK293 | — | 135 |

The following table (table 27) shows the comparison of lethal concentration 50% (LC$_{50}$ µg/µL) of dead cells (BEAS-2B, HUVEC, HMEC-1, HEK293 and WM-266) according to the action of PBS and RNA-peptide-AB. The number of dead cells was monitored using the flow cytometry.

TABLE 27

| Cell lines | PBS | RNA-peptide-AB LC$_{50}$ µg/µL |
|---|---|---|
| BEAS-2B | 490 | 263 |
| HUVEC | 468 | 280 |
| HMEC-1 | 451 | 286 |
| HEK293 | 356 | 299 |
| WM-266 | 456 | 135 |

The following Table (Table 28), shows the comparison of lethal concentration 50% (LC$_{50}$ µg/µL) of dead cells (BEAS-2B, HUVEC, HMEC-1, HEK293 and WM-266) according to the action of Exosome and RNA-peptide-AB. The number of dead cells was monitored using the flow cytometry.

TABLE 28

| Cell lines | Exosome | RNA-peptide-AB LC$_{50}$ µg/µL |
|---|---|---|
| BEAS-2B | 423 | 263 |
| HUVEC | 434 | 280 |
| HMEC-1 | 434 | 286 |
| WM-266 | 430 | 299 |
| HEK293 | 420 | 135 |

The following Table (Table 29), shows the comparison of lethal concentration 50% (LC$_{50}$ µg/µL) of dead cells (BEAS-2B, HUVEC, HMEC-1, HEK293 and WM-266) according to the action of RNA and RNA-peptide-AB. The number of dead cells was monitored using the flow cytometry. (The LC$_{50}$ of RNA in HEK290 cell lines was not detected)

TABLE 29

| Cell lines | RNA | RNA-peptide-AB LC$_{50}$ µg/µL |
|---|---|---|
| BEAS-2B | 129 | 263 |
| HUVEC | 67 | 280 |
| HMEC-1 | 131 | 286 |
| WM-266 | 36 | 299 |
| HEK293 | — | 135 |

The following Table (Table 30), shows the comparison of lethal concentration 50% (LC$_{50}$ µg/µL) of dead cells (BEAS-2B, HUVEC, HMEC-1, HEK293 and WM-266) according to the action of peptide-AB and RNA-peptide-AB. The number of dead cells was monitored using the flow cytometry. (The LC$_{50}$ of peptide-AB in WM-266 and HEK293 cell lines were not detected)

TABLE 30

| Cell lines | peptide-AB | RNA-peptide-AB LC$_{50}$ µg/µL |
|---|---|---|
| BEAS-2B | 167 | 263 |
| HUVEC | 179 | 280 |
| HMEC-1 | 149 | 286 |
| WM-266 | — | 299 |
| HEK293 | — | 135 |

The following Table (Table 31), shows the comparison of lethal concentration 50% (LC$_{50}$ µg/µL) of dead cells (BEAS-2B, HUVEC, HMEC-1, HEK293 and WM-266) according to the action of peptide-A and RNA-peptide-AB. The number of dead cells was monitored using the flow cytometry. (The LC$_{50}$ of peptide-A in HEK293 cell lines was not detected)

TABLE 31

| Cell lines | peptide-A | RNA-peptide-AB LC$_{50}$ µg/µL |
|---|---|---|
| BEAS-2B | 158 | 263 |
| HUVEC | 156 | 280 |
| HMEC-1 | 122 | 286 |
| WM-266 | 214 | 299 |
| HEK293 | — | 135 |

The following Table (Table 32), shows the comparison of lethal concentration 50% (LC$_{50}$ µg/µL) of dead cells (BEAS-2B, HUVEC, HMEC-1, HEK293 and WM-266) according to the action of peptide-B and RNA-peptide-AB. The number of dead cells was monitored using the flow cytometry.

TABLE 32

| Cell lines | peptide-B | RNA-peptide-AB LC$_{50}$ µg/µL |
|---|---|---|
| BEAS-2B | 161 | 263 |
| HUVEC | 145 | 280 |
| HMEC-1 | 114 | 286 |
| HEK293 | 135 | 299 |
| WM-266 | 179 | 135 |

The following Table (Table 33) shows the statistical values of probability (p). Where, we compared the LC$_{50}$ from vaccine candidate RNA-peptide-AB (vaccine) with target such as: PMA, H$_2$O$_2$, CuSO$_4$, PBS, Exosome, RNA, peptide-AB, peptide-A and peptide-B. It is used the Student's t-test with n=6 in order to calculate p value. Our conclusion was focused to understand the statistical difference in toxicity action between vaccine and each target.

TABLE 33

TOXICOLOGICAL ANALYSIS (Student's t-test)

| Code | | student T (n = 6) | Toxicological analysis |
|---|---|---|---|
| Control Proliferation $LC_{50}$ | | | |
| PMA | RNA-peptide-AB | p = 0,2416 | Not statistical difference |
| $H_2O_2$ | RNA-peptide-AB | p = 0,0193 | Statistical difference |
| $CuSO_4$ | RNA-peptide-AB | *p = 0,0014 | Significative (*) Statistical difference |
| Control assay | | | |
| PBS | RNA-peptide-AB | p = 0,0110 | Statistical difference |
| Exosome | RNA-peptide-AB | p = 0,0031 | Statistical difference |
| Targets assay | | | |
| RNA | RNA-peptide-AB | p = 0,0072 | Statistical difference |
| peptide-AB | RNA-peptide-AB | p = 0,0131 | Statistical difference |
| peptide-A | RNA-peptide-AB | p = 0,0057 | Statistical difference |
| peptide-B | RNA-peptide-AB | p = 0,0545 | Statistical difference |

Results

The studies of cell proliferation action of this invention were carried out at concentrations lethal of 50% ($LC_{50}$) in cell lines such as: BEAS-2B, HUVEC, HMEC-1, HEK293 and WM-266. The result obtained shows that the vaccine RNA-peptide against SARS-CoV-2 of the present invention does not present a statistical difference in toxicity values with PMA (positive inductor of cell proliferation). Meanwhile, the vaccine of the present invention presents a statistical difference with the negative controls of proliferation such as: $H_2O_2$ and $CuSO_4$. Being a statistically significant difference with sulfate of copper (II).

In addition, the vaccine RNA-peptide against SARS-CoV-2 of the present invention shows in the five cell lines (BEAS-2B, HUVEC, HMEC-1, HEK293 and WM-266) a statistical difference between the toxicity values $LC_{50}$ with the controls assay such as: PBS and Exosomes.

Finally, the vaccine RNA-peptide against SARS-CoV-2 of the present invention shows in the five cell lines (BEAS-2B, HUVEC, HMEC-1, HEK293 and WM-266) a statistical difference between the toxicity values at $LC_{50}$ with the test targets: RNA, peptide-AB, peptide-A, and peptide-B.

Conclusion

The vaccine RNA-peptide against SARS-CoV-2 of the present invention has no equivalent mechanisms of toxicity comparing with the toxicity mechanisms different from the inducers of oxidation and DNA damage such as $H_2O_2$ and $CuSO_4$. The vaccine candidate does not present a significant difference between the toxicity values at $LC_{50}$ with the assay controls and targets statistically. These targets that are the substrate in its chemical construction (fusion between RNA and peptide-AB).

Example 6

The following Table (Table 34), shows the comparison of lethal concentration 100% ($LC_{100}$ µg/µL) of dead cells (BEAS-2B, HUVEC, HMEC-1, HEK293 and WM-266) according to the action of PMA and RNA-peptide-AB. The number of dead cells was monitored using the flow cytometry.

TABLE 34

| Cell lines | PMA | RNA-peptide-AB $LC_{100}$ µg/µL |
|---|---|---|
| BEAS-2B | 466 | 455 |
| HUVEC | 433 | 458 |
| HMEC-1 | 461 | 463 |
| HEK293 | 464 | 456 |
| WM-266 | 462 | 450 |

The following Table (Table 35), shows the comparison of lethal concentration 100% ($LC_{100}$ µg/µL) of dead cells (BEAS-2B, HUVEC, HMEC-1, HEK293 and WM-266) according to the action of $H_2O_2$ and RNA-peptide-AB. The number of dead cells was monitored using the flow cytometry.

TABLE 35

| Cell lines | $H_2O_2$ | RNA-peptide-AB $LC_{100}$ µg/µL |
|---|---|---|
| BEAS-2B | 446 | 455 |
| HUVEC | 444 | 458 |
| HMEC-1 | 461 | 463 |
| HEK293 | 451 | 456 |
| WM-266 | 441 | 450 |

The following Table (Table 36) shows the comparison of lethal concentration 100% ($LC_{100}$ µg/µL) of dead cells (BEAS-2B, HUVEC, HMEC-1, HEK293 and WM-266) according to the action of $CuSO_4$ and RNA-peptide-AB. The number of dead cells was monitored using the flow cytometry.

TABLE 36

| Cell lines | $CuSO_4$ | RNA-peptide-AB $LC_{100}$ µg/µL |
|---|---|---|
| BEAS-2B | 439 | 455 |
| HUVEC | 434 | 458 |
| HMEC-1 | 438 | 463 |
| HEK293 | 440 | 456 |
| WM-266 | 459 | 450 |

The following Table (Table 37) shows the comparison of lethal concentration 100% ($LC_{100}$ µg/µL) of dead cells (BEAS-2B, HUVEC, HMEC-1, HEK293 and WM-266) according to the action of PBS and RNA-peptide-AB. The number of dead cells was monitored using the flow cytometry.

TABLE 37

| Cell lines | PBS | RNA-peptide-AB $LC_{100}$ µg/µL |
|---|---|---|
| BEAS-2B | 616 | 455 |
| HUVEC | 612 | 458 |
| HMEC-1 | 580 | 463 |
| HEK293 | 539 | 456 |
| WM-266 | 587 | 450 |

The following Table (Table 38) shows the comparison of lethal concentration 100% ($LC_{100}$ µg/µL) of dead cells (BEAS-2B, HUVEC, HMEC-1, HEK293 and WM-266) according to the action of exosome and RNA-peptide-AB. The number of dead cells was monitored using the flow cytometry.

TABLE 38

| Cell lines | Exosome | RNA-peptide-AB $LC_{100}$ µg/µL |
|---|---|---|
| BEAS-2B | 466 | 455 |
| HUVEC | 433 | 458 |
| HMEC-1 | 461 | 463 |
| WM-266 | 464 | 456 |
| HEK293 | 462 | 450 |

The following Table (Table 39) shows the comparison of lethal concentration 100% ($LC_{100}$ µg/µL) of dead cells (BEAS-2B, HUVEC, HMEC-1, HEK293 and WM-266) according to the action of RNA and RNA-peptide-AB. The number of dead cells was monitored using the flow cytometry.

TABLE 39

| Cell lines | RNA | RNA-peptide-AB $LC_{100}$ µg/µL |
|---|---|---|
| BEAS-2B | 459 | 455 |
| HUVEC | 452 | 458 |
| HMEC-1 | 461 | 463 |
| HEK293 | 456 | 456 |
| WM-266 | 444 | 450 |

The following Table (Table 40) shows the comparison of lethal concentration 100% ($LC_{100}$ µg/µL) of dead cells (BEAS-2B, HUVEC, HMEC-1, HEK293 and WM-266) according to the action of peptide-AB and RNA-peptide-AB. The number of dead cells was monitored using the flow cytometry. (The $LC_{100}$ of peptide-AB in HEK293 cell lines was not detected)

TABLE 40

| Cell lines | peptide-AB | RNA-peptide-AB $LC_{100}$ µg/µL |
|---|---|---|
| BEAS-2B | 444 | 455 |
| HUVEC | 456 | 458 |
| HMEC-1 | 450 | 463 |
| WM-266 | 444 | 450 |
| HEK293 | — | 456 |

The following Table (Table 41) shows the comparison of lethal concentration 100% ($LC_{100}$ µg/µL) of dead cells (BEAS-2B, HUVEC, HMEC-1, HEK293 and WM-266) according to the action of peptide-A and RNA-peptide-A. The number of dead cells was monitored using the flow cytometry.

TABLE 41

| Cell lines | peptide-A | RNA-peptide-AB $LC_{100}$ µg/µL |
|---|---|---|
| BEAS-2B | 447 | 455 |
| HUVEC | 445 | 458 |
| HMEC-1 | 452 | 463 |
| HEK293 | 450 | 456 |
| WM-266 | 445 | 450 |

The following Table (Table 42), shows the comparison of lethal concentration 100% ($LC_{100}$ µg/µL) of dead cells (BEAS-2B, HUVEC, HMEC-1, HEK293 and WM-266) according to the action of peptide-B and RNA-peptide-A. The number of dead cells was monitored using the flow cytometry.

TABLE 42

| Cell lines | peptide-B | RNA-peptide-AB $LC_{100}$ µg/µL |
|---|---|---|
| BEAS-2B | 462 | 455 |
| HUVEC | 446 | 458 |
| HMEC-1 | 444 | 463 |
| HEK293 | 450 | 456 |
| WM-266 | 445 | 450 |

The following Table (Table 42) shows the statistical values of probability (p). Where, we compared the $LC_{100}$ from vaccine candidate RNA-peptide-AB (vaccine) with target such as: PMA, $H_2O_2$, $CuSO_4$, PBS, exosome, RNA, peptide-AB, peptide-A and peptide-B. We are using the Student's t-test with n=6 to calculate p value. Our conclusion was focused to understand the statistical difference in toxicity action between vaccine and each target.

TABLE 43

TOXICOLOGICAL ANALYSIS (student Test)

| Code | | student T (n = 6) | Toxicological analysis |
|---|---|---|---|
| Control Proliferation $LC_{100}$ | | | |
| PMA | RNA-peptide-AB | p = 0,9333 | Not statistical difference |
| $H_2O_2$ | RNA-peptide-AB | p = 0,0146 | Statistical difference |
| $CuSO_4$ | RNA-peptide-AB | p = 0,0810 | Not statistical difference |
| Control assay | | | |
| PBS | RNA-peptide-AB | *p = 0,0008 | Significative (*) Statistical difference |
| Exosome | RNA-peptide-AB | p = 0,9332 | Not statistical difference |
| Targets assay | | | |
| RNA | RNA-peptide-AB | p = 0,3350 | Not statistical difference |
| peptide-AB | RNA-peptide-AB | p = 0,0594 | Not statistical difference |
| peptide-A | RNA-peptide-AB | p = 0,0041 | Statistical difference |
| peptide-B | RNA-peptide-AB | p = 0,1730 | Not statistical difference |

Results

The studies of cell proliferation action of this invention were carried out at concentrations lethal of 100% ($LC_{100}$) in cell lines such as: BEAS-2B, HUVEC, HMEC-1, HEK293 and WM-266. Results obtained are that: The vaccine does not present a statistical difference in toxicity values with PMA and $CuSO_4$. Meanwhile, the vaccine RNA-peptide against SARS-CoV-2 of the present invention has a statistical difference with the $H_2O_2$.

In addition the RNA-peptide against SARS-CoV-2 of the present invention shows in the five cell lines (BEAS-2B, HUVEC, HMEC-1, HEK293 and WM-266) a significative statistical difference in the toxicity values $LC_{100}$ with the control assay PBS and not presents significant difference in the toxicity values with the exosomes.

Finally, the vaccine RNA-peptide against SARS-CoV-2 of the present invention shows in the five cell lines (BEAS-2B, HUVEC, HMEC-1, HEK293 and WM-266) a not statistical difference between the toxicity values at $LC_{100}$ with the test targets: RNA, peptide-AB, and peptide-B. The vaccine RNA-peptide against SARS-CoV-2 of the present invention has statistical difference in the toxicity values with the peptide-A.

Conclusion

This invention at $LC_{100}$, comprises equivalents mechanisms of toxicity comparing with the inductor of cell proliferation (PMA) and $CuSO_4$, as well as do not has equivalents mechanisms of toxicity comparing with $H_2O_2$. The present invention does not have a significant difference between the toxicity values at $LC_{100}$ with the assay controls and targets.

Example 7

The following table (Table 44) shows the comparison of lethal concentration 50% ($LC_{50}$ μg/μL) of dead cells (BEAS-2B, HUVEC, HMEC-1, HEK293 and WM-266) according to the RNA action after one incubation of 16 hours with RNA-peptide-AB (vaccine). The number of dead cells was monitored using the flow cytometry. (The $LC_{50}$ of RNA in HEK293 cell lines was not detected)

TABLE 44

| Cell lines | RNA | vaccine (1 dose) + RNA $LC_{100}$ μg/μL |
|---|---|---|
| BEAS-2B | 129 | 249 |
| HUVEC | 67 | 243 |
| HMEC-1 | 131 | 259 |
| WM-266 | 36 | 272 |
| HEK293 | — | 251 |

The following table (Table 45) shows the comparison of lethal concentration 50% ($LC_{50}$ μg/μL) of dead cells (BEAS-2B, HUVEC, HMEC-1, HEK293 and WM-266) according to the RNA action after two incubations of 16 hours with RNA-peptide-AB (vaccine). The number of dead cells was monitored using the flow cytometry. (The $LC_{50}$ of RNA in HEK293 cell lines was not detected)

TABLE 45

| Cell lines | RNA | vaccine(2 doses) + RNA $LC_{50}$ (μg/μL) |
|---|---|---|
| BEAS-2B | 129 | 299 |
| HUVEC | 67 | 311 |
| HMEC-1 | 131 | 306 |
| WM-266 | 36 | 330 |
| HEK293 | — | 270 |

The following table (Table 46) shows the comparison of lethal concentration 50% ($LC_{50}$ μg/μL) of dead cells (BEAS-2B, HUVEC, HMEC-1, HEK293 and WM-266) according to RNA action after three incubations of 16 hours with RNA-peptide-AB (vaccine). The number of dead cells was monitored using the flow cytometry. (The $LC_{50}$ of RNA in HEK293 cell lines was not detected)

TABLE 46

| Cell lines | RNA | vaccine (3 doses) + RNA $LC_{50}$ (μg/μL) |
|---|---|---|
| BEAS-2B | 129 | 303 |
| HUVEC | 67 | 319 |
| HMEC-1 | 131 | 308 |
| WM-266 | 36 | 329 |
| HEK293 | — | 164 |

The following table (Table 47) shows the statistical values of probability (p). The Student's t-test with n=6 is used to calculate p value. According to RNA action after one, two and three serial incubations of 16 hours with RNA-peptide-AB (vaccine). The conclusion was focused to understand the statistical difference in $LC_{50}$ to estimate the vaccine efficacy as vaccine in "In vitro" test in cell lines such as: BEAS-2B, HUVEC, HMEC-1 and WM-266.

TABLE 47

EFFICACY ANALYSIS
Efficacy of Control Proliferation $LC_{50}$

| Code | student T (n = 6) | Efficacy analysis |
|---|---|---|
| RNA vaccine incubation 16 hours (1 time) + RNA One dose | p = 0,0086 | Statistical difference |
| RNA vaccine incubation 16 hours (2 times) + RNA Two doses | p = 0,0050 | Statistical difference |
| RNA vaccine incubation 16 hours (3 times) + RNA Three doses | p = 0,0045 | Statistical difference |

Results

The studies of efficacy of the vaccine RNA-peptide against SARS-CoV-2 of the present invention were monitored by flux cytometry (cell viability) at concentrations lethal of 50% ($LC_{50}$) in cell lines such as: BEAS-2B, HUVEC, HMEC-1, HEK293 and WM-266. Results obtained are that: The five-cell lines after vaccine incubation of 16 hours before treatment with RNA induced metabolic adaptation and keep this behavior in new adapting cellular pathways as "temporal memory". The present invention shows statistical difference in the toxicity values between the five cell lines incubated with vaccine vaccine (one, two and three times of incubation or doses) RNA and placebo groups of cells (without vaccine incubation).

Conclusion

The vaccine RNA-peptide against SARS-CoV-2 of the present invention shows not equivalents mechanisms of toxicity at $LC_{50}$ comparing the cell lines (BEAS-2B, HUVEC, HMEC-1, HEK293 and WM-266) incubated with the vaccine and the same cell lines with placebo assay. Three doses of the vaccine RNA-peptide against SARS-CoV-2 of the present invention can induce temporal memory in adapting pathway against RNA infection.

Example 8

The following table (Table 48) shows the comparison of lethal concentration 100% ($LC_{100}$ μg/μL) of dead cells (BEAS-2B, HUVEC, HMEC-1, HEK293 and WM-266) according to the action of RNA and RNA after one incubation of 16 hours with RNA-peptide-AB (vaccine).

TABLE 48

| Cell lines | RNA | vaccine (1 dose) + RNA $LC_{100}$ (µg/µL) |
|---|---|---|
| BEAS-2B | 459 | 472 |
| HUVEC | 452 | 482 |
| HMEC-1 | 461 | 490 |
| HEK293 | 456 | 499 |
| WM-266 | 444 | 482 |

The following table (Table 49) shows the comparison of lethal concentration 100% ($LC_{100}$ µg/µL) of dead cells (BEAS-2B, HUVEC, HMEC-1, HEK293 and WM-266) according to the action of RNA and RNA after two incubations of 16 hours with RNA-peptide-AB.

TABLE 49

| Cell lines | RNA | vaccine (2 doses) + RNA $LC_{100}$ (µg/µL) |
|---|---|---|
| BEAS-2B | 459 | 482 |
| HUVEC | 452 | 489 |
| HMEC-1 | 461 | 498 |
| HEK293 | 456 | 474 |
| WM-266 | 444 | 495 |

The following table (Table 50) shows the comparison of lethal concentration 100% ($LC_{100}$ µg/µL) of dead cells (BEAS-2B, HUVEC, HMEC-1, HEK293 and WM-266) according to the action of RNA and RNA after three incubations of 16 hours with RNA-peptide-AB (vaccine).

TABLE 50

| Cell lines | RNA | vaccine (3 doses) + RNA $LC_{100}$ (µg/µL) |
|---|---|---|
| BEAS-2B | 459 | 481 |
| HUVEC | 452 | 497 |
| HMEC-1 | 461 | 491 |
| HEK293 | 456 | 258 |
| WM-266 | 444 | 490 |

The following table (Table 51) shows the statistical values of probability (p). We are using the Student's t-test with n=6 to calculate p value. According to RNA action after one, two and three serial incubations of 16 hours with RNA-peptide-AB (vaccine). Our conclusion was focused to understand the statistical difference in $LC_{100}$ in order to estimate the vaccine efficacy as vaccine in "In vitro" test in cell lines such as: cells (BEAS-2B, HUVEC, HMEC-1 and WM-266).

TABLE 51

EFFICACY ANALYSIS
Efficacy of Control Proliferation $LC_{100}$

| Code | student T (n = 6) | Efficacy analysis |
|---|---|---|
| RNA<br>vaccine incubation 16 hours (1 time) + RNA<br>One dose | p = 0,0038 | Statistical difference |
| RNA<br>vaccine incubation 16 hours (2 times) + RNA<br>Two doses | p = 0,0052 | Statistical difference |
| RNA<br>vaccine incubation 16 hours (3 times) + RNA<br>Three doses | p = 0,8232 | Not statistical difference |

Results

The studies of the efficacy of the vaccine RNA-peptide against SARS-CoV-2 of the present invention were monitored by flux cytometry (cell viability) at concentrations lethal of 100% ($LC_{100}$) in cell lines such as: BEAS-2B, HUVEC, HMEC-1, HEK293 and WM-266. Result obtained are that: The five cell lines after vaccine RNA-peptide against SARS-CoV-2 incubation of 16 hours before treatment with RNA induced metabolic adaptation and keep this behavior in new adapting cellular pathways as "temporal memory". The present invention shows statistical difference in the toxicity values between the five cell lines incubated with vaccine RNA-peptide against SARS-CoV-2 one or two doses and the placebo groups of cells (without vaccine incubation). With three doses of vaccine the five cell lines and placebo not shows statistical difference in the toxicity values.

Conclusion

The vaccine RNA-peptide against SARS-CoV-2 of the present invention at $LC_{100}$, comprises equivalents mechanisms of toxicity comparing the cell lines (BEAS-2B, HUVEC, HMEC-1, HEK293 and WM-266) incubated with the vaccine and placebo assay. Two doses of the vaccine RNA-peptide against SARS-CoV-2 induces temporal memory in adapting pathway against RNA infection.

Example 9

Studies of the efficacy of the vaccine RNA-peptide against SARS-CoV-2 were made in five cell cultures, in vitro assay, where dead cell number was monitored using flow cytometry in percentages of: BEAS-2B, HUVEC, HMEC-1, HEK293 and WM-266 cells.

The efficacy of the vaccine RNA-peptide against SARS-CoV-2 was tested by incubating vaccine RpA (RNA-peptide A) and vaccine RpAB (RNA-peptide AB). Both incubations were pending 16 hours with vaccine $LC_{50}$ (μg/μL), which was determined in a toxicological assay in the 5 cell cultures previously described.

The incubation of the vaccine RNA-peptide against SARS-CoV-2, also referred as vaccine, was made 1, 2 and 3 times of 16 hours of incubation in the five cell cultures. "Placebo" is used as control in each cell culture without incubation to determinate the percentage of dead cells by comparing incubated cells and placebo dead cells.

In one embodiment, RNA-peptide-A vaccine, as preventive vaccine, comprises an efficacy of about 78.95%.

1. Studies of Efficacy with a Single Incubation Dose of $LC_{50}$ of RNA-Peptide A. (Preventive Vaccine with a Single Dose)

The Table 52 shows the efficacy studies to face mRNA avian coronavirus (16 hours of incubation with $LC_{50}$ mRNA) with a single dose of $LC_{50}$ incubation of the vaccine pending 16 hours in cell cultures (BEAS-2B, HUVEC, HMEC-1, HEK293 and WM-266).

TABLE 52

| Cell lines confluence | Dead cell % (1) (1 incubation with vaccine + incubation with viral mRNA) Both incubation were with LC50 (µg/µL) | Dead cell % (2) Placebo: (0 incubation with vaccine + incubation with viral mRNA) Both incubation were with LC50 (µg/µL)) | Efficacy: [100 − (Dead cell % (1)/ Dead cell % (2)] % |
|---|---|---|---|
| BEAS-2B | 44 | 249 | 82.3 |
| HUVEC | 58 | 243 | 76.13 |
| HMEC-1 | 49 | 259 | 81.08 |
| HEK293 | 56 | 251 | 77.69 |
| WM-266 | 61 | 272 | 77.57 |
| Media value | | | 78.95 |

2. Studies of Vaccine Efficacy with a Single Incubation Dose of $LC_{50}$ of RNA-Peptide AB.

The Table 53 shows the efficacy studies to face mRNA avian coronavirus (16 hours of incubation with $LC_{50}$ mRNA) with a single dose of $LC_{50}$ incubation of therapeutic vaccine pending 16 hours in cell cultures (BEAS-2B, HUVEC, HMEC-1, HEK293 and WM-266). We are showing the vaccine therapeutic efficacy value for each cell culture and the media value.

TABLE 53

| Cell lines confluence | (1 incubation with Vaccine + incubation with viral mRNA) Both incubation were with $LC_{50}$ (µg/µL) | Placebo: (0 incubation with Vaccine + incubation with viral mRNA) Both incubation were with $LC_{50}$ (µg/µL) | Vaccine Efficacy: [100 − (Dead cell % (1)/ Dead cell % (2)] % |
|---|---|---|---|
| BEAS-2B | 22 | 255 | 91.37 |
| HUVEC | 19 | 266 | 92.86 |
| HMEC-1 | 15 | 288 | 94.79 |
| HEK293 | 16 | 275 | 94.18 |
| WM-266 | 12 | 293 | 95.90 |
| Media value | | | 93.82 |

3. Studies of Efficacy with Two Incubation Doses of $LC_{50}$ of RNA-Peptide A. (Preventive Vaccine with Two Doses)

The Table 54 shows the efficacy studies to face mRNA avian coronavirus (16 hours of incubation with $LC_{50}$ mRNA) with two doses of $LC_{50}$ incubation of preventive vaccine pending 16 hours in cell cultures (BEAS-2B, HUVEC, HMEC-1, HEK293 and WM-266).

TABLE 54

| Cell lines confluence | Dead cell % (1) (2 incubation with vaccine + incubation with viral mRNA) Both incubation were with $LC_{50}$ (µg/µL) | Dead cell % (2) Placebo: (0 incubation with vaccine + incubation with viral mRNA) Both incubation were with $LC_{50}$ (µg/µL)) | vaccine Efficacy: [100 − (Dead cell % (1)/ Dead cell % (2)] % |
|---|---|---|---|
| BEAS-2B | 27 | 317 | 91.48 |
| HUVEC | 25 | 340 | 92.65 |
| HMEC-1 | 29 | 344 | 91.57 |
| HEK293 | 22 | 298 | 92.62 |
| WM-266 | 17 | 301 | 94.35 |
| Media value | | | 92.53 |

4. Studies of Efficacy with 2 Incubation Doses of $LC_{50}$ of RNA-Peptide AB. (Therapeutic Vaccine with Two Doses).

The Table 55 shows the efficacy studies to face mRNA avian coronavirus (16 hours of incubation with $LC_{50}$ mRNA) with two doses of $LC_{50}$ incubation of vaccine therapeutic vaccine pending 16 hours in cell cultures (BEAS-2B, HUVEC, HMEC-1, HEK293 and WM-266).

TABLE 55

| Cell lines confluence | (2 incubation with vaccine + incubation with viral mRNA) Both incubation were with $LC_{50}$ (µg/µL) | Placebo: (0 incubation with vaccine + incubation with viral mRNA) Both incubation were with $LC_{50}$ (µg/µL) | vaccine Efficacy: [100 − (Dead cell % (1)/ Dead cell % (2)] % |
|---|---|---|---|
| BEAS-2B | 24 | 266 | 90.98 |
| HUVEC | 27 | 273 | 90.10 |
| HMEC-1 | 31 | 282 | 89.00 |
| HEK293 | 22 | 259 | 91.51 |
| WM-266 | 29 | 254 | 88.58 |
| Media value | | | 90.03 |

5. Studies of Vaccine Efficacy with Three Incubation Doses of $LC_{50}$ of RNA-Peptide A. (Preventive Vaccine with Three Doses)

The Table 56 shows the vaccine efficacy studies to face mRNA avian coronavirus (16 hours of incubation with $LC_{50}$ mRNA) with three doses of $LC_{50}$ incubation of preventive vaccine pending 16 hours in cell cultures (BEAS-2B, HUVEC, HMEC-1, HEK293 and WM-266).

TABLE 56

| Cell lines confluence | Dead cell % (1) (3 incubation with Vaccine + incubation with viral mRNA) Both incubation were with $LC_{50}$ (µg/µL) | Dead cell % (2) Placebo: (0 incubation with Vaccine + incubation with viral mRNA) Both incubation were with $LC_{50}$ (µg/µL)) | Vaccine Efficacy: [100 − (Dead cell % (1)/ Dead cell % (2)] % |
|---|---|---|---|
| BEAS-2B | 60 | 317 | 81.07 |
| HUVEC | 87 | 354 | 75.42 |
| HMEC-1 | 56 | 342 | 83.63 |
| HEK293 | 49 | 298 | 83.56 |
| WM-266 | 65 | 319 | 79.62 |
| Media value | | | 80.66 |

6) Studies of Vaccine Efficacy with Three Incubation Doses of $LC_{50}$ of RNA-Peptide AB. (Therapeutic Vaccine with Three Doses)

The Table 57 shows the vaccine efficacy studies to face mRNA avian coronavirus (16 hours of incubation with $LC_{50}$ mRNA) with three doses of $LC_{50}$ incubation of preventive vaccine pending 16 hours in cell cultures (BEAS-2B, HUVEC, HMEC-1, HEK293 and WM-266).

TABLE 57

| Cell lines confluence | (3 incubation with Vaccine + incubation with viral mRNA) Both incubation were with $LC_{50}$ (μg/μL) | Placebo: (0 incubation with Vaccine + incubation with viral mRNA) Both incubation were with $LC_{50}$ (μg/μL) | Vaccine Efficacy: [100 − (Dead cell % (1)/ Dead cell % (2)] % |
|---|---|---|---|
| BEAS-2B | 15 | 238 | 93.70 |
| HUVEC | 11 | 245 | 95.51 |
| HMEC-1 | 17 | 263 | 93.54 |
| HEK293 | 24 | 278 | 91.37 |
| WM-266 | 19 | 299 | 93.65 |
| Media value | | | 93.55 |

7. Preventive Efficacy

The Table 58 shows the Efficacy studies to face mRNA avian coronavirus (16 hours of incubation with $LC_{50}$ mRNA) with one, two and three doses of $LC_{50}$ incubation of vaccine therapeutic vaccine pending 16 hours in cell cultures (BEAS-2B, HUVEC, HMEC-1, HEK293 and WM-266).

The Statistical Values of Probability (p).

Student's t-test with n=6 to calculate p value was used. According to mRNA avian coronavirus action after one, two and three doses incubations of 16 hours with mRNA-peptide-A (vaccine preventive). The conclusion was focused to understand the statistical difference in $LC_{50}$ in order to estimate the vaccine preventive efficacy as vaccine in "In vitro" test in cell lines such as: cells (BEAS-2B, HUVEC, HMEC-1 and WM-266). In the present study, the preventive efficacy values obtained in the five cell lines differ statistically between the value of two doses when compared with a single or three doses, p=5.321. These results suggested that the application of two doses is more effective.

TABLE 58

| Cell lines confluence | Vaccine Efficacy: [100 − (Dead cell % (1)/Dead cell % (2)] 1 dose | Vaccine Efficacy: [100 − (Dead cell % (1)/Dead cell % (2)] 2 doses | Vaccine Efficacy: [100 − (Dead cell % (1)/ Dead cell % (2)] 3 doses |
|---|---|---|---|
| BEAS-2B | 82.3 | 91.48 | 81.07 |
| HUVEC | 76.13 | 92.65 | 75.42 |
| HMEC-1 | 81.08 | 91.57 | 83.63 |
| HEK293 | 77.69 | 92.62 | 83.56 |
| WM-266 | 77.57 | 94.35 | 79.62 |
| Media value | 78.95 | 92.53 | 80.66 |

8. Therapeutic Efficacy

The Table 59 shows the Efficacy studies to face mRNA avian coronavirus (16 hours of incubation with $LC_{50}$ mRNA) with one, two and three doses of $LC_{50}$ incubation of vaccine therapeutic vaccine pending 16 hours in cell cultures (BEAS-2B, HUVEC, HMEC-1, HEK293 and WM-266).

The Statistical Values of Probability (p).

Student's t-test with n=6 to calculate p value was used. According to mRNA avian coronavirus action after one, two and three doses incubations of 16 hours with mRNA-peptide-A (vaccine therapeutic). The conclusion was focused to understand the statistical difference in $LC_{50}$ in order to estimate the vaccine therapeutic efficacy as vaccine in "In vitro" test in cell lines such as: cells (BEAS-2B, HUVEC, HMEC-1 and WM-266). In the present study, the therapeutic efficacy values obtained in the five cell lines do not differ statistically significantly between the three doses applied, p**=0.004. As a result, the application of single doses is recommended.

TABLE 59

| Cell lines confluence | Vaccine Efficacy: [100 − (Dead cell % (1)/ Dead cell % (2)] 1 dose | Vaccine Efficacy: [100 − (Dead cell % (1)/ Dead cell % (2)] 2 doses | Vaccine Efficacy: [100 − (Dead cell % (1)/ Dead cell % (2)] 3 doses |
|---|---|---|---|
| BEAS-2B | 91.37 | 90.98 | 93.70 |
| HUVEC | 92.86 | 90.10 | 95.51 |
| HMEC-1 | 94.79 | 89.00 | 93.54 |
| HEK293 | 94.18 | 91.51 | 91.37 |
| WM-266 | 95.90 | 88.58 | 93.65 |
| Media value | 93.82 | 90.03 | 93.55 |

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

REFERENCES

Cruz-Rodriguez L, Dilsiz N, Barea R, Ziarati P, Hochwimmer B, Zayas Tamayo A and Lambert Brown D. "*The Algorithms Cruz Rodriguez (CR) are Proposing A Novel Vaccine RNA Peptide against Breast, Ovarian, and Lung Cancers Disease: Exosomes as Carrier in Cancer Progression and Metastasis*". *J Med-Clin Res & Rev.* 2021; 5(2): 1-16

Cruz-Rodriguez L., Zayas Tamayo A M., Sanchez Batista L., Lambert Brown D., Hochwimmer B. and Ziarati P.; "*A Novel vaccine candidate with double antiviral activity against the HIV-1 and Covid-19*": *International Journal of Infectious Diseases and Research, I J Infectious Disea;* 2020. DOI: doi.org/10.47485/2693-2326.1002

Cruz-Rodriguez L., Ziarati P, Hochwimmer B., Kaabar M. K. A., Bin Zhao, N., Dilsiz N., Sanchez Batista L., Barea R., Pelaez Figueroa Y. (2020). "*A DNA-Peptide Fusion as a Vaccine Candidate against Breast and Ovarian Cancer Metastasis*": *Consequent Benefit in Certain Lung Cancers. Journal of Bioscience & Biomedical Engineering*1 (3), 1-11, doi.org/10.47485/2693-2504.1021

Na Zhu, et. al, China Novel Coronavirus Investigating and Research Team: "*A Novel Coronavirus from Patients with Pneumonia in China*", 2019. *N Engl J Med.* 2020 Feb. 20; 382(8):727-733. doi: 10.1056/NEJMoa2001017.

Youdfil Ophinni, Anshari Saifuddin Hasibuan, Alvina Widhani, Suzy Maria, Sukamto Koesnoe, Evy Yunihastuti, Teguh H Karjadi, Iris Rengganis, Samsuridjal Djauzi: "*COVID-19 Vaccines: Current Status and Implication for Use in Indonesia*" *Acta Med Indones*". 2020 October; 52(4):388-412.

Kizzmekia S Corbett, et al. "*SARS-CoV-2 mRNA vaccine design enabled by prototype pathogen preparedness*". *Nature.* 2020 October; 586(7830):567-571. doi: 10.1038/s41586-020-2622-0.

Cruz-Rodriguez L, Cruz-Rodriguez L D, Sanchez Batista L, Hochwimmer B. (2020). "Calculation of Fusion Stability of [DNA or RNA]—Peptide (FS) Algorithm "Cruz-Rodriguez" Journal of Bioscience & Biomedical Engineering, Vol 2, issue 1. doi.org/10.47485/2693-2504.1003

Cruz-Rodriguez L, Sanchez Batista L, Hochwimmer B, Bin Zhao and Ziarati P. (2020). "The mathematical formula to estimate the Exosome Affinity between miRNA-peptide and Exosome: ALGORITHM CRUZRODRIGUEZ (EA)", Journal of Bioscience & Biomedical Engineering, Volume 1, Issue 2, doi.org/10.47485/2693-2504.1012.

Cruz-Rodriguez L." The algorithms "CRUZ-RODRIGUEZ" (CR) as tool to design of multiepitope RNA peptide as novel vaccine against Breast/Ovarian and Lung cancer Diseases. Evaluation of Fusion Stability (FS), Exosome Affinity (EA) and Optimal Biological Action (OBA). U.S. Copyright number. TXu "2-229-629 Registered: Dec. 4, 2020

Cavanagh D. "Coronavirus avian infectious bronchitis virus". 2007. Vet Res 38(2):281-297.

D Krewski, M E Andersen, et. al, "Toxicity testing in the 21st century: progress in the past decade and future perspectives"; Arch Toxicol. 2020 January; 94(1):1-58. doi: 10.1007/s00204-019-02613-4. Epub 2019 Dec. 17.

Zhirong Mou, Yujun He, Yuzhang Wu. "Immunoproteomics to identify tumor-associated antigens eliciting humoral response" Cancer Lett. 2009 Jun. 18; 278(2):123-129. doi: 10.1016/j.canlet. 2008.09.009.

Raymond R Tice, Christopher P Austin, Robert J Kavlock, John R Bucher. "Improving the human hazard characterization of chemicals: a Tox21 update" Environ Health Perspect. 2013 July; 121(7):756-65. doi: 10.1289/ehp.1205784.

Ann M Richard, et al, "The Tox21l0K Compound Library: Collaborative Chemistry Advancing Toxicology". Chem Res Toxicol. 2021 Feb. 15; 34(2):189-216. doi: 10.1021/acs.chemrestox. 0c00264.

Rory B Conolly, "Toxicity testing in the 21st century: implications for human health risk assessment" by Krewski et al". Risk Anal 2009 Apr.; 29(4):480-1; discussion 492-7. doi: 10.1111/j.1539-6924.2008.01165.

Qiaozhu Tan, Ming Zhang, Lujing Geng, Zhenghua Xia, Cen Li, Muhammad Usman, Yuzhi Du, Lixin Wei, Hongtao Bi. "Hormesis of methylmercury-human serum albumin conjugate on N9 microglia via ERK/MAPKs and STATS signaling pathways". Toxicol Appl Pharmacol. 2019 Jan. 1; 362:59-66. doi: 10.1016/j.taap.2018.10.017.

Amaral A J, Andrade J, Foxall R B, Matoso P, Matos A M, Soares R S, Rocha C, Ramos C G, Tendeiro R, Serra-Caetano A, GuerraAssuncao J A, Santa-Marta M, Goncalves J, Gama-Carvalho M, Sousa A E (2017). "miRNA profling of human naive CD4 T cells links miR-34c-5p to cell activation and HIV replication". EMBO J 36(3):346-360. https://doi.org/10.15252/embj.201694335

Smith J L, Jeng S, McWeeney S K, Hirsch A J (2017). "A microRNA screen identifes the wnt signaling pathway as a regulator of the interferon response during favivirus infection". J Virol.

Wang Y, Brahmakshatriya V, Zhu H, Lupiani B, Reddy S M, Yoon B J, Gunaratne P H, Kim J H, Chen R, Wang J, Zhou H (2009). "Identifcation of deferentially expressed miR-NAs in chicken lung and trachea with avian infuenza virus infection by a deep sequencing approach". BMC Genom 10:512.

Bakre A, Andersen L E, Meliopoulos V, Coleman K, Yan X, Brooks P, Crabtree J, Tompkins S M, Tripp R A (2013). "Identification of host kinase genes required for influenza virus replication and the regulatory role of microRNAs". PLoS One8(6): e66796.

Peng F, et al., "Identification of microRNAs in throat swab as the biomarkers for diagnosis of influenza". Int J Med Sci13(1):77-84.

[22] Dinh H, Hong Y H, Lillehoj H S (2014). "Modulation of microRNAs in two genetically disparate chicken lines showing different necrotic enteritis disease susceptibility". Vet Immunol Immunopathol 159(1-2):74-82.

Kamada K, Shoji I, Deng L, Aoki C, Ratnoglik S L, Wakita T, Hotta H (2012). "Generation of a recombinant reporter hepatitis C virus useful for the analyses of virus entry, intra-cellular replication and virion production". Microbes Infect 14(1):69-78.

Chen Q, Tong C, Ma S, Zhou L, Zhao L, Zhao X (2017). "Involvement of microRNAs in probiotics-induced reduction of the cecal infammation by Salmonella typhimurium". Front Immunol 8:704.

Jia Y Q, Wang X L, Wang X W, Yan C Q, Lv C J, Li X Q, Chu Z L, Adam F E A, Xiao S, Zhang S X, Yang Z Q (2018). "Common microRNA(-)mRNA interactions in different new castle disease virus-infected chicken embryonic visceral tissues". Int J Mol Sci.

Gutkoska J, LaRocco M, Ramirez-Medina E, de Los Santos T, Lawrence P (2017). "Host microRNA-203a is antagonistic to the progression of foot-and-mouth disease virus infection". Virology 504:52-62.

Wu A, Chen H, Xu C, Zhou J, Chen S, Shi Y, Xu J, Gan J, Zhang J (2016). "miR-203a is involved in HBx-induced inflammation by targeting Rap1a". Exp Cell Res 349(1): 191-197.

Liu D, Wu J, Liu M, Yin H, He J, Zhang B (2015). "Downregulation of miRNA-30c and miR-203a is associated with hepatitis C virus core protein-induced epithelial-mesenchymal transition in normal hepatocytes and hepatocellular carcinoma cells". Biochem Biophys Res Commun 464(4):1215-1221.

Inchley C S, Sonerud T, Fjaerli H O, Nakstad B (2015). "Nasal mucosal microRNA expression in children with respiratory syncytial virus infection". BMC Infect Dis 15:150. https://doi.org/10.1186/s12879-015-0878-z Shi T, Hua Q, Ma Z, Lv Q (2017). "Downregulation of miR200a-3p induced by hepatitis B Virus X (HBx) Protein promotes cell proliferation and invasion in HBV-infection-associated hepatocarcinoma". Pathol Res Pract 213 (12):1464-1469.

Ellis-Connell A L, Iempridee T, Xu I, Mertz J E (2010). "Cellular microRNAs 200b and 429 regulate the Epstein-Barr virus switch between latency and lytic replication". J Virol 84(19):10329-10343. https://doi.org/10.1128/JVI.00923-10

Wu G, Qi Y, Liu X, Yang N, Xu G, Liu L, Li X (2017). "Cecal microRNAome response to Salmonella enterica serovar Enteritidis infection in White Leghorn Layer". BMC Genom 18(1):77. https://doi.org/10.1186/s12864-016-3413-8

[Castillo J A, Castrillon J C, Diosa-Toro M, Betancur J G, St Laurent G 3rd, Smit J M, Urcuqui-Inchima S (2016). "Complex interaction between dengue virus replication and expression of miRNA133a". BMC Infect Dis 16:29.

Zheng Y, Fu X, Wang L, Zhang W, Zhou P, Zhang X, Zeng W, Chen J, Cao Z, Jia K, Li S (2018). "Comparative analysis of MicroRNA expression in dog lungs infected with the H3N2 and H5N1 canine influenza viruses". Microb Pathog 121:252-261.

Wang Y, Brahmakshatriya V, Lupiani B, Reddy S M, Soibam B, Benham A L, Gunaratne P, Liu H C, Trakooljul N, Ing N, Okimoto R, Zhou H (2012). "Integrated analysis of microRNA expression and mRNA transcriptome in lungs of avian infuenza virus infected broilers". BMC Genomics 13:278. https://doi.org/10.1186/1471-2164-13-278

Skovgaard K, Cirera S, Vasby D, Podolska A, Breum S O, Durrwald R, Schlegel M, Heegaard P M (2013). "Expression of innate immune genes, proteins and microRNAs in lung tissue of pigs infected experimentally with influenza virus (H1N2)". Innate Immun 19(5):531-544.

Li Z, Luo Q, Xu H, Zheng M, Abdalla B A, Feng M, Cai B, Zhang X, Nie Q, Zhang X (2017). "MiR-34b-5p suppresses melanoma diferentiation-associated gene (MDA5) signaling pathway to promote avian leukosis virus subgroup J (ALV-J)-infected cells proliferaction and ALV-J replication". Front Cell Infect Microbiol 7:17

Cruz-Rodriguez L, Zayas Tamayo A. Dilsiz N, and Lambert Brown D. "New Drug/Vaccine RNA-Peptide Named Melody Against SARS-CoV-2: Adapting Antiviral Pathways in Cell Culture WM-266 As Temporal Memory of "In Vitro Cell*"". *I J Infectious Disea;* 2021. *Volume* 2, *Issue* 2.

Cruz-Rodriguez L, Dilsiz N, Ziarati P, Hochwimmer B, Zayas Tamayo A. and Lambert Brown D. "*The Algorithms Cruz Rodriguez* (*CR*) *are Proposing a Novel Vaccine RNA Peptide Against Liver Cancer Disease: Exosomes as Carrier in Cancer* 19 *Progression*". *Acta Scientific Medical Sciences* 5.5 (2021): 31-38.

Cruz-Rodriguez L, Zayas Tamayo A. Dilsiz N, and Lambert Brown D. "*A Novel Vaccine RNA peptide against HIV*-1: *Exosomes as Carrier in Viral Progression*". *I J* 23 *Infectious Disea;* 2021. *Volume* 2, *Issue* 2. *I J Infectious Disea;* 2021. *Vol* 2, *Issue* 2.

Yang X, Gao W, Liu H, Li J, Chen D, Yuan F, Zhang Z, Wang H (2017). "*MicroRNA transcriptome analysis in chicken kidneys in response to difering virulent infectious bronchitis virus infections*". *Arch Virol* 162(11):3397-3405. https://doi.org/10.1007/s00705-017-3502-2

Nagase, T., Yamakawa, H., Tadokoro, S., Nakajima, D., Inoue, S., Yamaguchi, K., Itokawa, Y., Kikuno, R. F., Koga, H. and Ohara, O. "*Exploration of human ORFeome: high-throughput preparation of ORF clones and efficient characterization of their protein products JOURNAL DNA Res.* 15 (3), 137-149 (2008)

Nagase, T., Yamakawa, H., Kikuno, R. F. and Ohara, O. Direct Submission JOURNAL Submitted (15 Feb. 2008) *DNA Research Institute, Huamn Genome Research; Kazusa-Kamatari* 2-6-7, Kisarazu, Chiba 292-0818, Japan

What is claimed is:

1. A composition against SARS-CoV-2, comprising a micro ribonucleic acid (miRNA) fused to a peptide of a Severe Acute Respiratory Syndrome Coronavirus 2 (SARS-CoV-2) surface protein having an amino acid sequence of SEQ ID NO: 2 wherein endogenous exosomes act as carrier.

2. The composition against SARS-CoV-2 according to claim 1, wherein the miRNA comprises a poly-A sequence.

3. The composition against SARS-CoV-2 according to claim 1, wherein the poly-A sequence is about 10 adenosine nucleotides.

4. The composition against SARS-CoV-2 according to claim 1, wherein the miRNA comprises the nucleic acid sequence of SEQ ID NO: 1.

5. The composition against SARS-CoV-2 according to claim 1, wherein the peptide of the SARS-CoV-2 surface protein of SEQ ID: 2 is fused to a synthetic poly ADP-ribose polymerase peptide.

6. A method for stimulating an immune response against SARS-CoV-2 in a subject comprising administering to said subject an effective amount of the composition of claim 1.

7. A composition against SARS-CoV-2, comprising a micro ribonucleic acid (miRNA) fused to a peptide of a Severe Acute Respiratory Syndrome Coronavirus 2 (SARS-CoV-2) surface protein having the amino acid sequence of SEQ ID NO: 2 fused to a synthetic poly ADP-ribose polymerase peptide.

8. The composition against SARS-CoV-2 according to claim 7, wherein the miRNA comprises a poly-A sequence.

9. The composition against SARS-CoV-2 according to claim 7, wherein the poly-A sequence is about 10 adenosine nucleosides.

10. The composition against SARS-CoV-2 according to claim 7, wherein the miRNA comprises the nucleic acid sequence of SEQ ID NO: 1.

11. The composition against SARS-CoV-2 according to claim 7, wherein the synthetic poly ADP-ribose polymerase peptide comprises the amino acid sequence of SEQ ID NO: 3.

12. The composition against SARS-CoV-2 according to claim 7, wherein the micro ribonucleic acid (miRNA) is fused to a peptide that comprises the amino acid sequence of SEQ ID NO: 4.

13. A method for stimulating an immune response against SARS-CoV-2 in a subject in need thereof comprising administering to said subject an effective amount of the composition of claim 7.

14. A composition against SARS-CoV-2 comprising a micro ribonucleic acid (miRNA) having a nucleic acid sequence of SEQ ID NO: 1 fused to a peptide of a Severe Acute Respiratory Syndrome Coronavirus 2 (SARS-CoV-2) surface protein fused to a synthetic poly ADP-ribose polymerase peptide that comprises the amino acid sequence of SEQ ID NO: 4, wherein endogenous exosomes act as carrier.

* * * * *